US012666543B2

(12) United States Patent
Halac et al.

(10) Patent No.: US 12,666,543 B2
(45) Date of Patent: Jun. 23, 2026

(54) PRE-CONNECTED ANALYTE SENSORS

(71) Applicant: DexCom, Inc., San Diego, CA (US)

(72) Inventors: Jason Halac, San Diego, CA (US); John Charles Barry, San Diego, CA (US); Becky L. Clark, San Diego, CA (US); Chris W. Dring, Fremont, CA (US); John Michael Gray, San Diego, CA (US); Kris Elliot Higley, Ramona, CA (US); Jeff Jackson, Poway, CA (US); David A. Keller, Encinitas, CA (US); Ted Tang Lee, San Diego, CA (US); Jason Mitchell, San Diego, CA (US); Kenneth Pirondini, San Diego, CA (US); David Rego, San Diego, CA (US); Ryan Everett Schoonmaker, Oceanside, CA (US); Peter C. Simpson, Cardiff, CA (US); Craig Thomas Gadd, Lemon Grove, CA (US); Kyle Thomas Stewart, San Diego, CA (US); John Stanley Hayes, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 64 days.

(21) Appl. No.: 18/205,365

(22) Filed: Jun. 2, 2023

(65) Prior Publication Data

US 2023/0328893 A1 Oct. 12, 2023

Related U.S. Application Data

(63) Continuation of application No. 17/719,181, filed on Apr. 12, 2022, now Pat. No. 11,706,876, which is a
(Continued)

(51) Int. Cl.
*H05K 3/32* (2006.01)
*A61B 5/00* (2006.01)
(Continued)

(52) U.S. Cl.
CPC ......... *H05K 3/321* (2013.01); *A61B 5/14532* (2013.01); *A61B 5/14546* (2013.01);
(Continued)

(58) Field of Classification Search
None
See application file for complete search history.

(56) References Cited

U.S. PATENT DOCUMENTS 52,641 A 2/1866 Gates
62,334 A 2/1867 Holmes
(Continued)

FOREIGN PATENT DOCUMENTS

CA 2127172 C 7/1998
CN 101091114 A 12/2007
(Continued)

OTHER PUBLICATIONS

US 7,530,950 B2, 05/2009, Brister et al. (withdrawn)
(Continued)

*Primary Examiner* — Manuel A Mendez
(74) *Attorney, Agent, or Firm* — Snell & Wilmer LLP

(57) ABSTRACT

Pre-connected analyte sensors are provided. A pre-connected analyte sensor includes a sensor carrier attached to an analyte sensor. The sensor carrier includes a substrate configured for mechanical coupling of the sensor to testing, calibration, or wearable equipment. The sensor carrier also includes conductive contacts for electrically coupling sensor electrodes to the testing, calibration, or wearable equipment.

15 Claims, 42 Drawing Sheets

Related U.S. Application Data continuation of application No. 17/464,547, filed on Sep. 1, 2021, now Pat. No. 11,350,862, which is a continuation of application No. 17/369,535, filed on Jul. 7, 2021, now Pat. No. 11,160,926, which is a continuation of application No. 16/167,976, filed on Oct. 23, 2018, now Pat. No. 11,382,540.

(60) Provisional application No. 62/576,560, filed on Oct. 24, 2017.

(51) Int. Cl.

| | |
|---|---|
| A61B 5/145 | (2006.01) |
| A61B 5/1459 | (2006.01) |
| A61B 5/1473 | (2006.01) |
| A61B 5/1486 | (2006.01) |
| A61B 5/1495 | (2006.01) |
| A61M 5/142 | (2006.01) |
| A61M 5/172 | (2006.01) |
| A61M 5/20 | (2006.01) |
| A61M 11/00 | (2006.01) |
| A61M 15/00 | (2006.01) |
| A61M 35/00 | (2006.01) |
| G01N 27/327 | (2006.01) |
| G01N 33/66 | (2006.01) |
| G16H 20/17 | (2018.01) |
| G16H 40/63 | (2018.01) |
| H05K 3/321 | (2026.01) |
| A61M 5/00 | (2006.01) |
| A61M 5/178 | (2006.01) |
| A61M 5/30 | (2006.01) |

(52) U.S. Cl.
CPC .......... *A61B 5/1459* (2013.01); *A61B 5/1473* (2013.01); *A61B 5/14865* (2013.01); *A61B 5/1495* (2013.01); *A61B 5/6801* (2013.01); *A61B 5/6849* (2013.01); *A61M 5/14244* (2013.01); *A61M 5/14276* (2013.01); *A61M 5/1723* (2013.01); *A61M 5/20* (2013.01); *A61M 11/00* (2013.01); *A61M 15/0065* (2013.01); *A61M 15/0068* (2014.02); *A61M 15/008* (2014.02); *A61M 15/0083* (2014.02); *A61M 35/00* (2013.01); *G01N 27/3273* (2013.01); *G01N 27/3274* (2013.01); *G01N 33/66* (2013.01); *G16H 20/17* (2018.01); *G16H 40/63* (2018.01); *A61B 5/0031* (2013.01); *A61B 2560/0468* (2013.01); *A61B 2562/043* (2013.01); *A61B 2562/08* (2013.01); *A61B 2562/085* (2013.01); *A61B 2562/12* (2013.01); *A61B 2562/125* (2013.01); *A61B 2562/16* (2013.01); *A61M 5/003* (2013.01); *A61M 2005/14296* (2013.01); *A61M 5/178* (2013.01); *A61M 5/30* (2013.01); *A61M 15/00* (2013.01); *A61M 2205/3569* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/587* (2013.01); *A61M 2205/8206* (2013.01); *A61M 2230/201* (2013.01); *Y10T 29/49169* (2015.01)

(56) References Cited

U.S. PATENT DOCUMENTS

| | | |
|---|---|---|
| 65,604 A | 6/1867 | Reynolds |
| 1,954,643 A | 4/1934 | Neuhaus |
| 2,719,797 A | 10/1955 | Rosenblatt et al. |
| 3,210,578 A | 10/1965 | Sherer |
| 3,219,533 A | 11/1965 | Mullins |
| 3,381,371 A | 5/1968 | Russell |
| 3,506,032 A | 4/1970 | Eveleigh et al. |
| 3,556,950 A | 1/1971 | Dahms et al. |
| 3,581,062 A | 5/1971 | Aston |
| 3,610,226 A | 10/1971 | Albisser |
| 3,775,182 A | 11/1973 | Patton et al. |
| 3,780,727 A | 12/1973 | King |
| 3,826,244 A | 7/1974 | Salcman et al. |
| 3,837,339 A | 9/1974 | Aisenberg et al. |
| 3,838,682 A | 10/1974 | Clark et al. |
| 3,874,850 A | 4/1975 | Sorensen et al. |
| 3,898,984 A | 8/1975 | Mandel et al. |
| 3,910,256 A | 10/1975 | Clark et al. |
| 3,926,760 A | 12/1975 | Allen et al. |
| 3,929,971 A | 12/1975 | Roy |
| 3,933,593 A | 1/1976 | Sternberg |
| 3,943,918 A | 3/1976 | Lewis |
| 3,949,388 A | 4/1976 | Fuller |
| 3,957,613 A | 5/1976 | Macur |
| 3,960,497 A | 6/1976 | Acord |
| 3,964,974 A | 6/1976 | Banauch et al. |
| 3,978,856 A | 9/1976 | Michel |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,036,749 A | 7/1977 | Anderson |
| 4,040,908 A | 8/1977 | Clark, Jr. |
| 4,052,754 A | 10/1977 | Homsy |
| 4,055,175 A | 10/1977 | Clemens et al. |
| 4,073,713 A | 2/1978 | Newman |
| 4,076,656 A | 2/1978 | White et al. |
| 4,109,505 A | 8/1978 | Clark et al. |
| 4,119,406 A | 10/1978 | Clemens |
| 4,129,128 A | 12/1978 | McFarlane |
| 4,136,250 A | 1/1979 | Mueller et al. |
| 4,151,845 A | 5/1979 | Clemens |
| 4,172,770 A | 10/1979 | Semersky et al. |
| 4,176,659 A | 12/1979 | Rolfe |
| 4,197,840 A | 4/1980 | Beck et al. |
| 4,197,852 A | 4/1980 | Schindler et al. |
| 4,206,755 A | 6/1980 | Klein |
| 4,215,703 A | 8/1980 | Willson |
| 4,240,438 A | 12/1980 | Updike et al. |
| 4,240,889 A | 12/1980 | Yoda et al. |
| 4,245,634 A | 1/1981 | Albisser et al. |
| 4,253,469 A | 3/1981 | Aslan |
| 4,255,500 A | 3/1981 | Hooke |
| 4,259,540 A | 3/1981 | Sabia |
| 4,265,249 A | 5/1981 | Schindler et al. |
| 4,319,578 A | 3/1982 | Enger |
| 4,327,725 A | 5/1982 | Cortese et al. |
| 4,344,438 A | 8/1982 | Schultz |
| 4,349,728 A | 9/1982 | Phillips et al. |
| 4,366,040 A | 12/1982 | Marsoner et al. |
| 4,367,967 A | 1/1983 | Albert, Jr. |
| 4,369,785 A | 1/1983 | Rehkopf et al. |
| 4,373,527 A | 2/1983 | Fischell |
| 4,374,013 A | 2/1983 | Enfors |
| 4,388,166 A | 6/1983 | Suzuki et al. |
| 4,392,849 A | 7/1983 | Petre et al. |
| 4,403,984 A | 9/1983 | Ash et al. |
| 4,415,666 A | 11/1983 | D'Orazio et al. |
| 4,425,920 A | 1/1984 | Bourland et al. |
| 4,431,004 A | 2/1984 | Bessman et al. |
| 4,432,366 A | 2/1984 | Margules |
| 4,436,094 A | 3/1984 | Cerami |
| 4,441,968 A | 4/1984 | Emmer et al. |
| 4,442,841 A | 4/1984 | Uehara et al. |
| 4,454,295 A | 6/1984 | Wittmann et al. |
| 4,457,339 A | 7/1984 | Juan et al. |
| 4,462,048 A | 7/1984 | Ross |
| 4,477,314 A | 10/1984 | Richter et al. |
| 4,478,222 A | 10/1984 | Koning et al. |
| 4,478,976 A | 10/1984 | Goertz et al. |
| 4,486,290 A | 12/1984 | Cahalan et al. |

(56)     References Cited

U.S. PATENT DOCUMENTS

| 4,492,575 A | 1/1985 | Mabille |
| 4,494,950 A | 1/1985 | Fischell |
| 4,506,680 A | 3/1985 | Stokes |
| 4,509,531 A | 4/1985 | Ward |
| 4,519,973 A | 5/1985 | Cahalan et al. |
| RE31,916 E | 6/1985 | Oswin et al. |
| 4,526,569 A | 7/1985 | Bernardi |
| 4,527,240 A | 7/1985 | Kvitash |
| 4,534,825 A | 8/1985 | Koning et al. |
| 4,535,786 A | 8/1985 | Kater |
| 4,538,616 A | 9/1985 | Rogoff |
| 4,545,382 A | 10/1985 | Higgins et al. |
| 4,554,927 A | 11/1985 | Fussell |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,577,642 A | 3/1986 | Stokes |
| 4,583,976 A | 4/1986 | Ferguson |
| 4,592,824 A | 6/1986 | Smith et al. |
| 4,600,495 A | 7/1986 | Fogt |
| 4,614,514 A | 9/1986 | Carr et al. |
| 4,619,793 A | 10/1986 | Lee |
| 4,625,730 A | 12/1986 | Fountain et al. |
| 4,626,104 A | 12/1986 | Pointon et al. |
| 4,632,968 A | 12/1986 | Yokota et al. |
| RE32,361 E | 2/1987 | Duggan |
| 4,655,880 A | 4/1987 | Liu |
| 4,663,824 A | 5/1987 | Kenmochi |
| 4,671,288 A | 6/1987 | Gough |
| 4,672,734 A | 6/1987 | Kawada et al. |
| 4,672,970 A | 6/1987 | Uchida et al. |
| 4,680,268 A | 7/1987 | Clark, Jr. |
| 4,685,463 A | 8/1987 | Williams |
| 4,685,903 A | 8/1987 | Cable et al. |
| 4,694,861 A | 9/1987 | Goodale et al. |
| 4,702,732 A | 10/1987 | Powers et al. |
| 4,703,756 A | 11/1987 | Gough et al. |
| 4,705,503 A | 11/1987 | Dorman et al. |
| 4,711,245 A | 12/1987 | Higgins et al. |
| 4,711,251 A | 12/1987 | Stokes |
| 4,721,677 A | 1/1988 | Clark, Jr. |
| 4,726,381 A | 2/1988 | Jones |
| 4,731,051 A | 3/1988 | Fischell |
| 4,731,726 A | 3/1988 | Allen, III |
| 4,736,748 A | 4/1988 | Nakamura et al. |
| 4,747,822 A | 5/1988 | Peabody |
| 4,749,985 A | 6/1988 | Corsberg |
| 4,750,496 A | 6/1988 | Reinhart et al. |
| 4,753,652 A | 6/1988 | Langer et al. |
| 4,755,168 A | 7/1988 | Romanelli et al. |
| 4,757,022 A | 7/1988 | Shults et al. |
| 4,759,366 A | 7/1988 | Callaghan |
| 4,759,828 A | 7/1988 | Young et al. |
| 4,763,648 A | 8/1988 | Wyatt |
| 4,763,658 A | 8/1988 | Jones |
| 4,777,953 A | 10/1988 | Ash et al. |
| 4,777,954 A * | 10/1988 | Keusch .................... A61B 5/25 |
| | | 600/397 |
| 4,779,618 A | 10/1988 | Mund et al. |
| 4,781,798 A | 11/1988 | Gough |
| 4,784,157 A | 11/1988 | Halls et al. |
| 4,786,394 A | 11/1988 | Enzer et al. |
| 4,787,398 A | 11/1988 | Garcia et al. |
| 4,789,467 A | 12/1988 | Lindsay et al. |
| 4,791,932 A | 12/1988 | Margules |
| 4,803,243 A | 2/1989 | Fujimoto et al. |
| 4,805,624 A | 2/1989 | Yao et al. |
| 4,805,625 A | 2/1989 | Wyler |
| 4,807,632 A | 2/1989 | Liess et al. |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,810,470 A | 3/1989 | Burkhardt et al. |
| 4,815,471 A | 3/1989 | Stobie |
| 4,820,281 A | 4/1989 | Lawler, Jr. |
| 4,822,336 A | 4/1989 | DiTraglia |
| 4,823,808 A | 4/1989 | Clegg et al. |
| 4,828,544 A | 5/1989 | Lane et al. |
| 4,830,013 A | 5/1989 | Maxwell |
| 4,831,070 A | 5/1989 | McInally et al. |
| 4,832,005 A | 5/1989 | Takamiya et al. |
| 4,832,034 A | 5/1989 | Pizziconi et al. |
| 4,834,101 A | 5/1989 | Collison et al. |
| 4,838,281 A | 6/1989 | Rogers et al. |
| 4,841,974 A | 6/1989 | Gumbrecht et al. |
| 4,849,458 A | 7/1989 | Reed et al. |
| 4,852,573 A | 8/1989 | Kennedy |
| 4,854,322 A | 8/1989 | Ash et al. |
| 4,858,615 A | 8/1989 | Meinema |
| 4,867,741 A | 9/1989 | Portnoy |
| 4,871,351 A | 10/1989 | Feingold |
| 4,871,440 A | 10/1989 | Nagata et al. |
| 4,874,363 A | 10/1989 | Abell |
| 4,883,057 A | 11/1989 | Broderick |
| 4,883,467 A | 11/1989 | Franetzki et al. |
| 4,889,528 A | 12/1989 | Nadai et al. |
| 4,889,744 A | 12/1989 | Quaid |
| 4,890,620 A | 1/1990 | Gough |
| 4,890,621 A | 1/1990 | Hakky |
| 4,900,305 A | 2/1990 | Smith et al. |
| 4,902,294 A | 2/1990 | Gosserez |
| 4,907,857 A | 3/1990 | Giuliani et al. |
| 4,908,208 A | 3/1990 | Lee et al. |
| 4,909,786 A | 3/1990 | Gijselhart et al. |
| 4,919,114 A | 4/1990 | Miyazaki |
| 4,919,141 A | 4/1990 | Zier et al. |
| 4,919,649 A | 4/1990 | Timothy et al. |
| 4,921,477 A | 5/1990 | Davis |
| 4,921,480 A | 5/1990 | Sealfon |
| 4,925,268 A | 5/1990 | Iyer et al. |
| 4,925,444 A | 5/1990 | Orkin et al. |
| 4,927,407 A | 5/1990 | Dorman |
| 4,927,516 A | 5/1990 | Yamaguchi et al. |
| 4,928,694 A | 5/1990 | Maxwell |
| 4,934,369 A | 6/1990 | Maxwell |
| 4,934,375 A | 6/1990 | Cole et al. |
| 4,935,345 A | 6/1990 | Guilbeau et al. |
| 4,944,299 A | 7/1990 | Silvian |
| 4,946,439 A | 8/1990 | Eggers |
| 4,947,845 A | 8/1990 | Davis |
| 4,950,246 A | 8/1990 | Muller |
| 4,951,657 A | 8/1990 | Pfister et al. |
| 4,951,669 A | 8/1990 | Maxwell et al. |
| 4,953,552 A | 9/1990 | DeMarzo |
| 4,957,483 A | 9/1990 | Gonser et al. |
| 4,963,595 A | 10/1990 | Ward et al. |
| 4,966,579 A | 10/1990 | Polaschegg |
| 4,967,940 A | 11/1990 | Blette et al. |
| 4,970,145 A | 11/1990 | Bennetto et al. |
| 4,973,320 A | 11/1990 | Brenner et al. |
| 4,974,592 A | 12/1990 | Branco |
| 4,974,929 A | 12/1990 | Curry |
| 4,975,636 A | 12/1990 | Desautels |
| 4,976,687 A | 12/1990 | Martin |
| 4,979,509 A | 12/1990 | Hakky |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,989,607 A | 2/1991 | Keusch et al. |
| 4,992,794 A | 2/1991 | Brouwers |
| 4,994,026 A | 2/1991 | Fecondini |
| 4,994,167 A | 2/1991 | Shults et al. |
| 4,995,402 A | 2/1991 | Smith et al. |
| 4,997,627 A | 3/1991 | Bergkuist et al. |
| 5,000,180 A | 3/1991 | Kuypers et al. |
| 5,002,054 A | 3/1991 | Ash et al. |
| 5,002,055 A | 3/1991 | Merki et al. |
| 5,002,572 A | 3/1991 | Picha |
| 5,006,050 A | 4/1991 | Cooke et al. |
| 5,006,111 A | 4/1991 | Inokuchi et al. |

(56)                References Cited

U.S. PATENT DOCUMENTS

| | | |
|---|---|---|
| 5,007,929 A | 4/1991 | Quaid |
| 5,009,251 A | 4/1991 | Pike et al. |
| 5,019,974 A | 5/1991 | Beckers |
| 5,026,348 A | 6/1991 | Venegas |
| 5,030,199 A | 7/1991 | Barwick et al. |
| 5,030,333 A | 7/1991 | Clark, Jr. |
| 5,034,112 A | 7/1991 | Murase et al. |
| 5,035,711 A | 7/1991 | Aoki et al. |
| 5,041,092 A | 8/1991 | Barwick |
| 5,045,057 A | 9/1991 | Van Driessche et al. |
| 5,046,496 A | 9/1991 | Betts et al. |
| 5,048,525 A | 9/1991 | Maxwell |
| 5,050,612 A | 9/1991 | Matsumura |
| 5,055,171 A | 10/1991 | Peck |
| 5,055,198 A | 10/1991 | Shettigar |
| 5,059,654 A | 10/1991 | Hou et al. |
| 5,067,491 A | 11/1991 | Taylor, II et al. |
| 5,068,536 A | 11/1991 | Rosenthal |
| 5,070,169 A | 12/1991 | Robertson et al. |
| 5,077,476 A | 12/1991 | Rosenthal |
| 5,082,550 A | 1/1992 | Rishpon et al. |
| 5,088,981 A | 2/1992 | Howson et al. |
| 5,089,421 A | 2/1992 | Dieffenbach |
| 5,096,669 A | 3/1992 | Lauks et al. |
| 5,097,834 A | 3/1992 | Skrabal |
| 5,098,377 A | 3/1992 | Borsanyi et al. |
| 5,101,814 A | 4/1992 | Palti |
| 5,106,365 A | 4/1992 | Hernandez |
| 5,108,819 A | 4/1992 | Heller et al. |
| 5,109,850 A | 5/1992 | Blanco et al. |
| 5,112,301 A | 5/1992 | Fenton, Jr. et al. |
| 5,112,455 A | 5/1992 | Cozzette et al. |
| 5,113,869 A | 5/1992 | Nappholz et al. |
| 5,116,313 A | 5/1992 | McGregor |
| 5,122,925 A | 6/1992 | Inpyn |
| 5,127,405 A | 7/1992 | Alcala et al. |
| 5,135,004 A | 8/1992 | Adams et al. |
| 5,137,028 A | 8/1992 | Nishimura |
| 5,140,985 A | 8/1992 | Schroeder et al. |
| 5,145,565 A | 9/1992 | Kater et al. |
| 5,148,812 A | 9/1992 | Verrier et al. |
| 5,152,746 A | 10/1992 | Atkinson et al. |
| 5,160,418 A | 11/1992 | Mullen |
| 5,161,532 A | 11/1992 | Joseph |
| 5,165,406 A | 11/1992 | Wong |
| 5,165,407 A | 11/1992 | Wilson et al. |
| 5,174,291 A | 12/1992 | Schoonen et al. |
| 5,176,632 A | 1/1993 | Bernardi |
| 5,176,658 A | 1/1993 | Ranford |
| 5,178,142 A | 1/1993 | Harjunmaa et al. |
| 5,182,004 A | 1/1993 | Kohno |
| 5,188,591 A | 2/1993 | Dorsey, III |
| 5,190,041 A | 3/1993 | Palti |
| 5,195,963 A | 3/1993 | Yafuso et al. |
| 5,196,025 A | 3/1993 | Ranalletta et al. |
| 5,198,771 A | 3/1993 | Fidler et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer |
| 5,208,147 A | 5/1993 | Kagenow et al. |
| 5,208,313 A | 5/1993 | Krishnan |
| 5,210,778 A | 5/1993 | Massart |
| 5,220,917 A | 6/1993 | Cammilli et al. |
| 5,220,920 A | 6/1993 | Gharib |
| 5,224,929 A | 7/1993 | Remiszewski |
| 5,225,063 A | 7/1993 | Gumbrecht et al. |
| 5,231,988 A | 8/1993 | Wernicke et al. |
| 5,232,434 A | 8/1993 | Inagaki et al. |
| 5,235,003 A | 8/1993 | Ward et al. |
| 5,237,123 A | 8/1993 | Miller |
| 5,243,982 A | 9/1993 | Mostl et al. |
| 5,243,983 A | 9/1993 | Tarr et al. |
| 5,246,867 A | 9/1993 | Lakowicz et al. |
| 5,249,576 A | 10/1993 | Goldberger et al. |
| 5,251,126 A | 10/1993 | Kahn et al. |
| 5,254,102 A | 10/1993 | Ogawa |
| 5,262,035 A | 11/1993 | Gregg et al. |
| 5,262,305 A | 11/1993 | Heller et al. |
| 5,264,105 A | 11/1993 | Gregg et al. |
| 5,265,594 A | 11/1993 | Olsson et al. |
| 5,266,179 A | 11/1993 | Nankai et al. |
| 5,269,891 A | 12/1993 | Colin |
| 5,271,736 A | 12/1993 | Picha |
| 5,271,815 A | 12/1993 | Wong |
| 5,279,294 A | 1/1994 | Anderson et al. |
| 5,281,319 A | 1/1994 | Kaneko et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,285,792 A | 2/1994 | Sjoquist et al. |
| 5,287,753 A | 2/1994 | Routh et al. |
| 5,293,877 A | 3/1994 | O'Hara et al. |
| 5,298,022 A | 3/1994 | Bernardi |
| 5,299,571 A | 4/1994 | Mastrototaro |
| 5,302,093 A | 4/1994 | Owens et al. |
| 5,304,468 A | 4/1994 | Phillips et al. |
| 5,307,263 A | 4/1994 | Brown |
| 5,310,469 A | 5/1994 | Cunningham et al. |
| 5,311,908 A | 5/1994 | Barone et al. |
| 5,312,361 A | 5/1994 | Zadini et al. |
| 5,313,953 A | 5/1994 | Yomtov et al. |
| 5,314,441 A | 5/1994 | Cusack et al. |
| 5,314,471 A | 5/1994 | Brauker et al. |
| 5,316,008 A | 5/1994 | Suga et al. |
| 5,316,452 A | 5/1994 | Bogen et al. |
| 5,318,511 A | 6/1994 | Riquier et al. |
| 5,318,583 A | 6/1994 | Rabenau et al. |
| 5,320,715 A | 6/1994 | Berg |
| 5,320,725 A | 6/1994 | Gregg et al. |
| 5,322,063 A | 6/1994 | Allen et al. |
| 5,324,322 A | 6/1994 | Grill, Jr. et al. |
| 5,326,356 A | 7/1994 | Della Valle et al. |
| 5,326,449 A | 7/1994 | Cunningham |
| 5,328,460 A | 7/1994 | Lord et al. |
| 5,330,521 A | 7/1994 | Cohen |
| 5,330,634 A | 7/1994 | Wong et al. |
| 5,331,555 A | 7/1994 | Hashimoto et al. |
| 5,335,658 A | 8/1994 | Bedingham |
| 5,337,747 A | 8/1994 | Neftel |
| 5,340,722 A | 8/1994 | Wolfbeis et al. |
| 5,342,409 A | 8/1994 | Mullett |
| 5,342,789 A | 8/1994 | Chick et al. |
| 5,343,869 A | 9/1994 | Pross et al. |
| 5,344,454 A | 9/1994 | Clarke et al. |
| 5,345,932 A | 9/1994 | Yafuso et al. |
| 5,348,788 A | 9/1994 | White |
| 5,352,348 A | 10/1994 | Young et al. |
| 5,352,349 A | 10/1994 | Inamoto et al. |
| 5,352,351 A | 10/1994 | White et al. |
| 5,354,272 A | 10/1994 | Swendson et al. |
| 5,354,449 A | 10/1994 | Band et al. |
| 5,356,217 A | 10/1994 | Sheffield |
| 5,356,375 A | 10/1994 | Higley |
| 5,356,378 A | 10/1994 | Doan |
| 5,356,786 A | 10/1994 | Heller et al. |
| 5,360,404 A | 11/1994 | Novacek et al. |
| 5,360,405 A | 11/1994 | Yoon |
| 5,365,426 A | 11/1994 | Siegel et al. |
| 5,368,028 A | 11/1994 | Palti |
| 5,368,224 A | 11/1994 | Richardson et al. |
| 5,368,562 A | 11/1994 | Blomquist et al. |
| 5,372,133 A | 12/1994 | Hogen Esch |
| 5,372,135 A | 12/1994 | Mendelson et al. |
| 5,372,427 A | 12/1994 | Padovani et al. |
| 5,372,709 A | 12/1994 | Hood |
| 5,376,070 A | 12/1994 | Purvis et al. |
| 5,378,229 A | 1/1995 | Layer et al. |
| 5,379,238 A | 1/1995 | Stark |
| 5,380,268 A | 1/1995 | Wheeler |
| 5,380,491 A | 1/1995 | Carver, Jr. et al. |
| 5,380,536 A | 1/1995 | Hubbell et al. |
| 5,380,665 A | 1/1995 | Cusack et al. |

(56) References Cited

U.S. PATENT DOCUMENTS

| | | |
|---|---|---|
| 5,384,028 A | 1/1995 | Ito |
| 5,384,547 A | 1/1995 | Lynk, Jr. et al. |
| 5,390,671 A | 2/1995 | Lord et al. |
| 5,391,250 A | 2/1995 | Cheney, II et al. |
| 5,397,848 A | 3/1995 | Yang et al. |
| 5,400,795 A | 3/1995 | Murphy et al. |
| 5,405,510 A | 4/1995 | Betts et al. |
| 5,408,999 A | 4/1995 | Singh et al. |
| 5,411,052 A | 5/1995 | Murray |
| 5,411,647 A | 5/1995 | Johnson et al. |
| 5,411,866 A | 5/1995 | Luong et al. |
| 5,417,206 A | 5/1995 | Kaneyoshi |
| 5,421,328 A | 6/1995 | Bedingham |
| 5,421,923 A | 6/1995 | Clarke et al. |
| 5,422,829 A | 6/1995 | Pollock |
| 5,423,738 A | 6/1995 | Robinson et al. |
| 5,423,749 A | 6/1995 | Merte et al. |
| 5,425,749 A | 6/1995 | Adams |
| 5,425,868 A | 6/1995 | Pedersen |
| 5,428,123 A | 6/1995 | Ward et al. |
| 5,429,485 A | 7/1995 | Dodge |
| 5,429,602 A | 7/1995 | Hauser |
| 5,429,735 A | 7/1995 | Johnson et al. |
| 5,431,160 A | 7/1995 | Wilkins |
| 5,431,174 A | 7/1995 | Knute |
| 5,431,921 A | 7/1995 | Thombre |
| 5,434,412 A | 7/1995 | Sodickson et al. |
| 5,437,635 A | 8/1995 | Fields et al. |
| 5,438,983 A | 8/1995 | Falcone |
| 5,438,984 A | 8/1995 | Schoendorfer |
| 5,443,508 A | 8/1995 | Giampapa |
| 5,445,610 A | 8/1995 | Evert |
| 5,448,992 A | 9/1995 | Kupershmidt |
| 5,451,260 A | 9/1995 | Versteeg et al. |
| 5,453,278 A | 9/1995 | Chan et al. |
| 5,458,631 A | 10/1995 | Xavier |
| 5,462,051 A | 10/1995 | Oka et al. |
| 5,462,064 A | 10/1995 | D'Angelo et al. |
| 5,462,645 A | 10/1995 | Albery et al. |
| 5,466,356 A | 11/1995 | Schneider et al. |
| 5,469,846 A | 11/1995 | Khan |
| 5,472,317 A | 12/1995 | Field et al. |
| 5,474,552 A | 12/1995 | Palti |
| 5,476,776 A | 12/1995 | Wilkins |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,508,203 A | 4/1996 | Fuller et al. |
| 5,509,410 A | 4/1996 | Hill et al. |
| 5,509,888 A | 4/1996 | Miller |
| 5,512,046 A | 4/1996 | Pusinelli et al. |
| 5,512,055 A | 4/1996 | Domb et al. |
| 5,512,248 A | 4/1996 | Van |
| 5,513,636 A | 5/1996 | Palti |
| 5,514,253 A | 5/1996 | Davis et al. |
| 5,514,718 A | 5/1996 | Lewis et al. |
| 5,515,851 A | 5/1996 | Goldstein |
| 5,518,601 A | 5/1996 | Foos et al. |
| 5,520,191 A | 5/1996 | Karlsson et al. |
| 5,527,288 A | 6/1996 | Gross et al. |
| 5,527,334 A | 6/1996 | Kanner et al. |
| 5,531,679 A | 7/1996 | Schulman et al. |
| 5,531,878 A | 7/1996 | Vadgama et al. |
| 5,538,511 A | 7/1996 | Van Antwerp |
| 5,540,828 A | 7/1996 | Yacynych |
| 5,543,326 A | 8/1996 | Heller et al. |
| 5,545,220 A | 8/1996 | Andrews et al. |
| 5,545,223 A | 8/1996 | Neuenfeldt et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |
| 5,551,850 A | 9/1996 | Williamson et al. |
| 5,552,997 A | 9/1996 | Massart |
| 5,553,616 A | 9/1996 | Ham et al. |
| 5,554,339 A | 9/1996 | Cozzette et al. |
| 5,561,615 A | 10/1996 | Kuo et al. |
| 5,562,614 A | 10/1996 | O'Donnell |
| 5,562,615 A | 10/1996 | Nassif |
| 5,564,439 A | 10/1996 | Picha |
| 5,567,740 A * | 10/1996 | Free ........................ C08J 9/0028 |
| | | 252/500 |
| 5,568,400 A | 10/1996 | Stark et al. |
| 5,568,806 A | 10/1996 | Cheney, II et al. |
| 5,569,186 A | 10/1996 | Lord et al. |
| 5,569,188 A | 10/1996 | Mackool |
| 5,569,219 A | 10/1996 | Hakki et al. |
| 5,569,462 A | 10/1996 | Martinson et al. |
| 5,575,293 A | 11/1996 | Miller et al. |
| 5,575,930 A | 11/1996 | Tietje-Girault et al. |
| 5,577,499 A | 11/1996 | Teves |
| 5,582,184 A | 12/1996 | Erickson et al. |
| 5,582,593 A | 12/1996 | Hultman |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,590,651 A | 1/1997 | Shaffer et al. |
| 5,593,440 A | 1/1997 | Brauker et al. |
| 5,593,852 A | 1/1997 | Heller et al. |
| 5,601,435 A | 2/1997 | Quy |
| 5,609,572 A | 3/1997 | Lang |
| 5,609,575 A | 3/1997 | Larson et al. |
| 5,611,900 A | 3/1997 | Worden et al. |
| 5,624,409 A | 4/1997 | Seale |
| 5,624,537 A | 4/1997 | Turner et al. |
| 5,626,563 A | 5/1997 | Dodge et al. |
| 5,628,310 A | 5/1997 | Rao et al. |
| 5,628,619 A | 5/1997 | Wilson |
| 5,628,890 A | 5/1997 | Carter et al. |
| 5,637,083 A | 6/1997 | Bertrand et al. |
| 5,640,470 A | 6/1997 | Iyer et al. |
| 5,640,954 A | 6/1997 | Pfeiffer et al. |
| 5,643,195 A | 7/1997 | Drevet et al. |
| 5,645,077 A | 7/1997 | Foxlin |
| 5,651,767 A | 7/1997 | Schulman et al. |
| 5,653,239 A | 8/1997 | Pompei et al. |
| 5,653,756 A | 8/1997 | Clarke et al. |
| 5,653,863 A | 8/1997 | Genshaw et al. |
| 5,658,250 A | 8/1997 | Blomquist et al. |
| 5,660,163 A | 8/1997 | Schulman et al. |
| 5,660,565 A | 8/1997 | Williams |
| 5,665,061 A | 9/1997 | Antwiler |
| 5,665,065 A | 9/1997 | Colman et al. |
| 5,665,222 A | 9/1997 | Heller et al. |
| 5,667,504 A | 9/1997 | Baumann et al. |
| 5,673,694 A | 10/1997 | Rivers |
| 5,674,289 A | 10/1997 | Fournier et al. |
| 5,676,651 A | 10/1997 | Larson, Jr. et al. |
| 5,676,820 A | 10/1997 | Wang et al. |
| 5,681,572 A | 10/1997 | Seare, Jr. |
| 5,682,884 A | 11/1997 | Hill et al. |
| 5,683,562 A | 11/1997 | Schaffar et al. |
| 5,686,829 A | 11/1997 | Girault |
| 5,688,239 A | 11/1997 | Walker |
| 5,688,244 A | 11/1997 | Lang |
| 5,695,623 A | 12/1997 | Michel et al. |
| 5,696,314 A | 12/1997 | McCaffrey et al. |
| 5,697,366 A | 12/1997 | Kimball et al. |
| 5,697,899 A | 12/1997 | Hillman et al. |
| 5,704,354 A | 1/1998 | Preidel et al. |
| 5,706,807 A | 1/1998 | Picha |
| 5,711,001 A | 1/1998 | Bussan et al. |
| 5,711,861 A | 1/1998 | Ward et al. |
| 5,713,888 A | 2/1998 | Neuenfeldt et al. |

(56) References Cited

U.S. PATENT DOCUMENTS

| | | |
|---|---|---|
| 5,720,295 A | 2/1998 | Greenhut et al. |
| 5,730,654 A | 3/1998 | Brown |
| 5,733,259 A | 3/1998 | Valcke et al. |
| 5,733,336 A | 3/1998 | Neuenfeldt et al. |
| 5,735,285 A | 4/1998 | Albert et al. |
| 5,741,211 A | 4/1998 | Renirie et al. |
| 5,743,262 A | 4/1998 | Lepper, Jr. et al. |
| 5,749,832 A | 5/1998 | Vadgama et al. |
| 5,749,907 A | 5/1998 | Mann |
| 5,755,692 A | 5/1998 | Manicom |
| 5,756,632 A | 5/1998 | Ward et al. |
| 5,758,643 A | 6/1998 | Wong et al. |
| 5,763,760 A | 6/1998 | Gumbrecht et al. |
| 5,771,890 A | 6/1998 | Tamada |
| 5,772,586 A | 6/1998 | Heinonen et al. |
| 5,773,286 A | 6/1998 | Dionne et al. |
| 5,776,324 A | 7/1998 | Usala |
| 5,779,665 A | 7/1998 | Mastrototaro et al. |
| 5,781,455 A | 7/1998 | Hyodo |
| 5,782,880 A | 7/1998 | Lahtinen et al. |
| 5,782,912 A | 7/1998 | Brauker et al. |
| 5,785,660 A | 7/1998 | Van Lake et al. |
| 5,787,900 A | 8/1998 | Butler et al. |
| 5,791,344 A | 8/1998 | Schulman et al. |
| 5,791,880 A | 8/1998 | Wilson |
| 5,792,065 A | 8/1998 | Xue et al. |
| 5,795,453 A | 8/1998 | Gilmartin |
| 5,795,774 A | 8/1998 | Matsumoto et al. |
| 5,798,065 A | 8/1998 | Picha |
| 5,800,383 A | 9/1998 | Chandler et al. |
| 5,800,420 A | 9/1998 | Gross et al. |
| 5,800,529 A | 9/1998 | Brauker et al. |
| 5,806,517 A | 9/1998 | Gerhardt et al. |
| 5,807,274 A | 9/1998 | Henning et al. |
| 5,807,312 A | 9/1998 | Dzwonkiewicz |
| 5,807,375 A | 9/1998 | Gross et al. |
| 5,807,406 A | 9/1998 | Brauker et al. |
| 5,810,770 A | 9/1998 | Chin et al. |
| 5,811,487 A | 9/1998 | Schulz, Jr. et al. |
| 5,814,599 A | 9/1998 | Mitragotri et al. |
| 5,820,551 A | 10/1998 | Hill et al. |
| 5,820,589 A | 10/1998 | Torgerson et al. |
| 5,820,622 A | 10/1998 | Gross et al. |
| 5,822,715 A | 10/1998 | Worthington et al. |
| 5,836,887 A | 11/1998 | Oka et al. |
| 5,836,989 A | 11/1998 | Shelton |
| 5,837,454 A | 11/1998 | Cozzette et al. |
| 5,837,728 A | 11/1998 | Purcell |
| 5,840,026 A | 11/1998 | Uber, III et al. |
| 5,840,148 A | 11/1998 | Campbell et al. |
| 5,848,991 A | 12/1998 | Gross et al. |
| 5,851,197 A | 12/1998 | Marano et al. |
| 5,851,229 A | 12/1998 | Lentz et al. |
| 5,858,365 A | 1/1999 | Faller |
| 5,858,747 A | 1/1999 | Schinstine et al. |
| 5,861,019 A | 1/1999 | Sun et al. |
| 5,863,400 A | 1/1999 | Drummond et al. |
| 5,871,514 A | 2/1999 | Wiklund et al. |
| 5,873,862 A | 2/1999 | Lopez |
| 5,879,713 A | 3/1999 | Roth et al. |
| 5,882,494 A | 3/1999 | Van Antwerp |
| 5,891,047 A | 4/1999 | Lander et al. |
| 5,891,048 A | 4/1999 | Nigam et al. |
| 5,895,235 A | 4/1999 | Droz |
| 5,897,525 A | 4/1999 | Dey et al. |
| 5,897,578 A | 4/1999 | Wiklund et al. |
| 5,899,855 A | 5/1999 | Brown |
| 5,904,666 A | 5/1999 | DeDecker et al. |
| 5,904,708 A | 5/1999 | Goedeke |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,917,346 A | 6/1999 | Gord |
| 5,918,603 A | 7/1999 | Brown |
| 5,919,215 A | 7/1999 | Wiklund et al. |
| 5,919,216 A | 7/1999 | Houben et al. |
| 5,921,951 A | 7/1999 | Morris |
| 5,925,021 A | 7/1999 | Castellano et al. |
| 5,928,155 A | 7/1999 | Eggers et al. |
| 5,928,182 A | 7/1999 | Kraus et al. |
| 5,928,189 A | 7/1999 | Phillips et al. |
| 5,928,195 A | 7/1999 | Malamud et al. |
| 5,931,814 A | 8/1999 | Alex et al. |
| 5,932,175 A | 8/1999 | Knute et al. |
| 5,933,136 A | 8/1999 | Brown |
| 5,935,224 A | 8/1999 | Svancarek et al. |
| 5,935,785 A | 8/1999 | Reber et al. |
| 5,938,636 A | 8/1999 | Kramer et al. |
| 5,942,979 A | 8/1999 | Luppino |
| 5,944,661 A | 8/1999 | Swette et al. |
| 5,947,911 A | 9/1999 | Wong et al. |
| 5,954,643 A | 9/1999 | Vanantwerp et al. |
| 5,954,954 A | 9/1999 | Houck et al. |
| 5,957,854 A | 9/1999 | Besson et al. |
| 5,957,903 A | 9/1999 | Mirzaee et al. |
| 5,960,797 A | 10/1999 | Kramer et al. |
| 5,961,451 A | 10/1999 | Reber et al. |
| 5,963,132 A | 10/1999 | Yoakum |
| 5,964,745 A | 10/1999 | Lyles et al. |
| 5,964,993 A | 10/1999 | Blubaugh, Jr. et al. |
| 5,965,125 A | 10/1999 | Mineau-Hanschke |
| 5,965,380 A | 10/1999 | Heller et al. |
| 5,971,922 A | 10/1999 | Arita et al. |
| 5,972,369 A | 10/1999 | Roorda et al. |
| 5,976,085 A | 11/1999 | Kimball et al. |
| 5,980,728 A | 11/1999 | Farber et al. |
| 5,984,940 A | 11/1999 | Davis et al. |
| 5,987,352 A | 11/1999 | Klein et al. |
| 5,990,422 A | 11/1999 | Komori et al. |
| 5,995,208 A | 11/1999 | Sarge et al. |
| 5,995,860 A | 11/1999 | Sun et al. |
| 5,997,501 A | 12/1999 | Gross et al. |
| 5,999,848 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,007,845 A | 12/1999 | Domb et al. |
| 6,011,984 A | 1/2000 | Van Antwerp et al. |
| 6,014,577 A | 1/2000 | Henning et al. |
| 6,016,443 A | 1/2000 | Ekwall et al. |
| 6,016,448 A | 1/2000 | Busacker et al. |
| 6,017,435 A | 1/2000 | Hassard et al. |
| 6,021,350 A | 2/2000 | Mathson |
| 6,023,629 A | 2/2000 | Tamada |
| 6,024,699 A | 2/2000 | Surwit et al. |
| 6,024,720 A | 2/2000 | Chandler et al. |
| 6,027,445 A | 2/2000 | Von Bahr |
| 6,027,479 A | 2/2000 | Alei et al. |
| 6,032,059 A | 2/2000 | Henning et al. |
| 6,032,667 A | 3/2000 | Heinonen |
| 6,036,924 A | 3/2000 | Simons et al. |
| 6,038,469 A | 3/2000 | Karlsson et al. |
| 6,043,328 A | 3/2000 | Domschke et al. |
| 6,045,671 A | 4/2000 | Wu et al. |
| 6,048,691 A | 4/2000 | Maracas |
| 6,049,727 A | 4/2000 | Crothall |
| 6,059,946 A | 5/2000 | Yukawa et al. |
| 6,063,637 A | 5/2000 | Arnold et al. |
| 6,066,088 A | 5/2000 | Davis |
| 6,066,448 A | 5/2000 | Wohlstadter et al. |
| 6,071,391 A | 6/2000 | Gotoh et al. |
| 6,073,031 A | 6/2000 | Helstab et al. |
| 6,077,299 A | 6/2000 | Adelberg et al. |
| 6,080,583 A | 6/2000 | Von Bahr |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,090,087 A | 7/2000 | Tsukada et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,099,511 A | 8/2000 | Devos et al. |

(56) References Cited

U.S. PATENT DOCUMENTS

| | | | |
|---|---|---|---|
| 6,102,896 A | 8/2000 | Roser | |
| 6,103,033 A | 8/2000 | Say et al. | |
| 6,103,533 A | 8/2000 | Hassard et al. | |
| 6,107,083 A | 8/2000 | Collins et al. | |
| 6,108,577 A | 8/2000 | Benser | |
| 6,112,116 A | 8/2000 | Fischell et al. | |
| 6,115,622 A | 9/2000 | Minoz | |
| 6,115,628 A | 9/2000 | Stadler et al. | |
| 6,115,634 A | 9/2000 | Donders et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,122,536 A | 9/2000 | Sun et al. | |
| 6,123,827 A | 9/2000 | Wong et al. | |
| 6,127,154 A | 10/2000 | Mosbach et al. | |
| 6,128,519 A | 10/2000 | Say | |
| 6,128,526 A | 10/2000 | Stadler et al. | |
| 6,129,891 A | 10/2000 | Rolander et al. | |
| 6,134,461 A | 10/2000 | Say et al. | |
| 6,135,978 A | 10/2000 | Houben et al. | |
| 6,142,939 A | 11/2000 | Eppstein et al. | |
| 6,143,164 A | 11/2000 | Heller et al. | |
| 6,144,837 A | 11/2000 | Quy | |
| 6,144,869 A | 11/2000 | Berner et al. | |
| 6,159,147 A | 12/2000 | Lichter et al. | |
| 6,159,186 A | 12/2000 | Wickham et al. | |
| 6,161,095 A | 12/2000 | Brown | |
| 6,162,201 A | 12/2000 | Cohen et al. | |
| 6,162,611 A | 12/2000 | Heller et al. | |
| 6,163,720 A | 12/2000 | Gyory et al. | |
| 6,164,921 A | 12/2000 | Moubayed et al. | |
| 6,165,154 A | 12/2000 | Gray et al. | |
| 6,167,614 B1 | 1/2001 | Tuttle et al. | |
| 6,168,568 B1 | 1/2001 | Gavriely | |
| 6,169,155 B1 | 1/2001 | Alvarez et al. | |
| 6,171,276 B1 | 1/2001 | Lippe et al. | |
| 6,175,752 B1 | 1/2001 | Say et al. | |
| 6,180,416 B1 | 1/2001 | Kurnik et al. | |
| 6,183,437 B1 | 2/2001 | Walker | |
| 6,186,982 B1 | 2/2001 | Gross et al. | |
| 6,187,062 B1 | 2/2001 | Oweis et al. | |
| 6,189,536 B1 | 2/2001 | Martinez et al. | |
| 6,191,860 B1 | 2/2001 | Klinger et al. | |
| 6,192,891 B1 | 2/2001 | Gravel et al. | |
| 6,200,265 B1 | 3/2001 | Walsh et al. | |
| 6,201,980 B1 | 3/2001 | Darrow et al. | |
| 6,201,993 B1 | 3/2001 | Kruse et al. | |
| 6,206,856 B1 | 3/2001 | Mahurkar | |
| 6,208,894 B1 | 3/2001 | Schulman et al. | |
| 6,212,416 B1 | 4/2001 | Ward et al. | |
| 6,212,424 B1 | 4/2001 | Robinson | |
| 6,213,739 B1 | 4/2001 | Phallen et al. | |
| 6,214,185 B1 | 4/2001 | Offenbacher et al. | |
| 6,219,574 B1 | 4/2001 | Cormier et al. | |
| 6,223,080 B1 | 4/2001 | Thompson | |
| 6,223,083 B1 | 4/2001 | Rosar | |
| 6,223,283 B1 | 4/2001 | Chaiken et al. | |
| 6,224,562 B1 | 5/2001 | Lurie et al. | |
| 6,230,059 B1 | 5/2001 | Duffin | |
| 6,231,879 B1 | 5/2001 | Li et al. | |
| 6,232,783 B1 | 5/2001 | Merrill | |
| 6,233,080 B1 | 5/2001 | Brenner et al. | |
| 6,233,486 B1 | 5/2001 | Ekwall et al. | |
| 6,234,964 B1 | 5/2001 | Iliff | |
| 6,241,863 B1 | 6/2001 | Monbouquette | |
| 6,248,067 B1 | 6/2001 | Causey, III et al. | |
| 6,248,077 B1 | 6/2001 | Elson et al. | |
| 6,248,093 B1 | 6/2001 | Moberg | |
| 6,249,705 B1 | 6/2001 | Snell | |
| 6,254,586 B1 | 7/2001 | Mann et al. | |
| 6,256,522 B1 | 7/2001 | Schultz | |
| 6,256,538 B1 | 7/2001 | Ekwall | |
| 6,259,937 B1 | 7/2001 | Schulman et al. | |
| 6,263,222 B1 | 7/2001 | Diab et al. | |
| 6,264,606 B1 | 7/2001 | Ekwall et al. | |
| 6,264,825 B1 | 7/2001 | Blackburn et al. | |
| 6,270,455 B1 | 8/2001 | Brown | |
| 6,270,478 B1 | 8/2001 | Mernoee | |
| 6,271,332 B1 | 8/2001 | Lohmann et al. | |
| 6,272,364 B1 | 8/2001 | Kurnik | |
| 6,272,379 B1 | 8/2001 | Fischell et al. | |
| 6,272,382 B1 | 8/2001 | Faltys et al. | |
| 6,272,480 B1 | 8/2001 | Tresp et al. | |
| 6,274,285 B1 | 8/2001 | Gries et al. | |
| 6,275,717 B1 | 8/2001 | Gross et al. | |
| 6,280,408 B1 | 8/2001 | Sipin | |
| 6,281,015 B1 | 8/2001 | Mooney et al. | |
| 6,283,761 B1 | 9/2001 | Joao | |
| 6,284,478 B1 | 9/2001 | Heller et al. | |
| 6,288,537 B1 * | 9/2001 | Viertl | G01N 27/904 |
| | | | 324/229 |
| 6,293,925 B1 | 9/2001 | Safabash et al. | |
| 6,295,506 B1 | 9/2001 | Heinonen et al. | |
| 6,298,254 B2 | 10/2001 | Tamada | |
| 6,299,578 B1 | 10/2001 | Kurnik et al. | |
| 6,299,583 B1 | 10/2001 | Eggers et al. | |
| 6,299,757 B1 | 10/2001 | Feldman et al. | |
| 6,300,002 B1 | 10/2001 | Webb et al. | |
| 6,302,855 B1 | 10/2001 | Lav et al. | |
| 6,306,104 B1 | 10/2001 | Cunningham et al. | |
| 6,309,351 B1 | 10/2001 | Kurnik et al. | |
| 6,309,384 B1 | 10/2001 | Harrington et al. | |
| 6,309,884 B1 | 10/2001 | Cooper et al. | |
| 6,312,388 B1 | 11/2001 | Marcovecchio et al. | |
| 6,315,738 B1 | 11/2001 | Nishikawa et al. | |
| 6,325,978 B1 | 12/2001 | Labuda et al. | |
| 6,326,160 B1 | 12/2001 | Dunn et al. | |
| 6,329,161 B1 | 12/2001 | Heller et al. | |
| 6,329,929 B1 | 12/2001 | Weijand et al. | |
| 6,330,464 B1 | 12/2001 | Colvin, Jr. et al. | |
| 6,338,790 B1 | 1/2002 | Feldman et al. | |
| 6,343,225 B1 | 1/2002 | Clark, Jr. | |
| 6,348,640 B1 | 2/2002 | Navot et al. | |
| 6,356,776 B1 | 3/2002 | Berner et al. | |
| 6,358,225 B1 | 3/2002 | Butterfield | |
| 6,359,444 B1 | 3/2002 | Grimes | |
| 6,360,888 B1 | 3/2002 | McIvor et al. | |
| 6,361,503 B1 | 3/2002 | Starobin et al. | |
| 6,365,670 B1 | 4/2002 | Fry | |
| 6,366,794 B1 | 4/2002 | Moussy et al. | |
| 6,368,141 B1 | 4/2002 | Vanantwerp et al. | |
| 6,368,274 B1 | 4/2002 | Van Antwerp et al. | |
| 6,370,941 B2 | 4/2002 | Nakamura et al. | |
| 6,372,244 B1 | 4/2002 | Antanavich et al. | |
| 6,377,828 B1 | 4/2002 | Chaiken et al. | |
| 6,377,852 B1 | 4/2002 | Bornzin et al. | |
| 6,377,894 B1 | 4/2002 | Deweese et al. | |
| 6,379,301 B1 | 4/2002 | Worthington et al. | |
| 6,379,317 B1 | 4/2002 | Kintzig et al. | |
| 6,381,493 B1 | 4/2002 | Stadler et al. | |
| 6,383,478 B1 | 5/2002 | Prokop et al. | |
| 6,387,048 B1 | 5/2002 | Schulman et al. | |
| 6,387,709 B1 | 5/2002 | Mason et al. | |
| 6,391,019 B1 | 5/2002 | Ito | |
| 6,400,974 B1 | 6/2002 | Lesho | |
| 6,402,703 B1 | 6/2002 | Kensey et al. | |
| 6,403,944 B1 | 6/2002 | MacKenzie et al. | |
| 6,405,066 B1 | 6/2002 | Essenpreis et al. | |
| 6,406,066 B1 | 6/2002 | Uegane | |
| 6,407,195 B2 | 6/2002 | Sherman et al. | |
| 6,409,674 B1 | 6/2002 | Brockway et al. | |
| 6,413,393 B1 | 7/2002 | Van Antwerp et al. | |
| 6,416,651 B1 | 7/2002 | Millar | |
| 6,424,847 B1 | 7/2002 | Mastrototaro et al. | |
| 6,427,088 B1 | 7/2002 | Bowman, IV et al. | |
| 6,430,437 B1 | 8/2002 | Marro | |
| 6,438,397 B1 * | 8/2002 | Bosquet | A61B 5/14532 |
| | | | 600/344 |
| 6,440,068 B1 | 8/2002 | Brown et al. | |
| 6,447,448 B1 | 9/2002 | Ishikawa et al. | |
| 6,447,542 B1 | 9/2002 | Weadock | |

(56) References Cited

U.S. PATENT DOCUMENTS

| | | | |
|---|---|---|---|
| 6,459,917 B1 | 10/2002 | Gowda et al. |
| 6,461,496 B1 | 10/2002 | Feldman et al. |
| 6,464,849 B1 | 10/2002 | Say et al. |
| 6,466,810 B1 | 10/2002 | Ward et al. |
| 6,467,480 B1 | 10/2002 | Meier et al. |
| 6,471,689 B1 | 10/2002 | Joseph et al. |
| 6,474,360 B1 | 11/2002 | Ito |
| 6,475,750 B1 | 11/2002 | Han et al. |
| 6,477,392 B1 | 11/2002 | Honigs et al. |
| 6,477,395 B2 | 11/2002 | Schulman et al. |
| 6,478,736 B1 | 11/2002 | Mault |
| 6,481,440 B2 | 11/2002 | Gielen et al. |
| 6,484,045 B1 | 11/2002 | Holker et al. |
| 6,484,046 B1 | 11/2002 | Say et al. |
| 6,485,449 B2 | 11/2002 | Ito |
| 6,486,661 B2 | 11/2002 | Chia et al. |
| 6,488,652 B1 | 12/2002 | Weijand et al. |
| 6,494,830 B1 | 12/2002 | Wessel |
| 6,494,879 B2 | 12/2002 | Lennox et al. |
| 6,497,729 B1 | 12/2002 | Moussy et al. |
| 6,498,043 B1 | 12/2002 | Schulman et al. |
| 6,498,941 B1 | 12/2002 | Jackson |
| 6,501,976 B1 | 12/2002 | Sohrab |
| 6,501,983 B1 | 12/2002 | Natarajan et al. |
| 6,503,381 B1 | 1/2003 | Gotoh et al. |
| 6,510,239 B1 | 1/2003 | Wieres et al. |
| 6,510,329 B2 | 1/2003 | Heckel |
| 6,512,939 B1 | 1/2003 | Colvin et al. |
| 6,514,460 B1 | 2/2003 | Fendrock |
| 6,514,718 B2 | 2/2003 | Heller et al. |
| 6,517,508 B1 | 2/2003 | Utterberg et al. |
| 6,520,326 B2 | 2/2003 | McIvor et al. |
| 6,520,477 B2 | 2/2003 | Trimmer |
| 6,520,937 B2 | 2/2003 | Hart et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,534,711 B1 | 3/2003 | Pollack |
| 6,536,433 B1 | 3/2003 | Cewers |
| 6,537,318 B1 | 3/2003 | Ita et al. |
| 6,540,891 B1 | 4/2003 | Stewart et al. |
| 6,541,266 B2 | 4/2003 | Modzelewski et al. |
| 6,542,765 B1 | 4/2003 | Guy et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,549,796 B2 | 4/2003 | Sohrab |
| 6,551,494 B1 | 4/2003 | Heller et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,805 B2 | 4/2003 | Hiejima |
| 6,554,822 B1 | 4/2003 | Holschneider et al. |
| 6,558,320 B1 | 5/2003 | Causey, III et al. |
| 6,558,321 B1 | 5/2003 | Burd et al. |
| 6,558,347 B1 | 5/2003 | Jhuboo et al. |
| 6,558,351 B1 | 5/2003 | Steil et al. |
| 6,558,955 B1 | 5/2003 | Kristal et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,565,535 B2 | 5/2003 | Zaias et al. |
| 6,565,807 B1 | 5/2003 | Patterson et al. |
| 6,569,195 B2 | 5/2003 | Yang et al. |
| 6,569,521 B1 | 5/2003 | Sheridan et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,575,905 B2 | 6/2003 | Knobbe et al. |
| 6,576,101 B1 | 6/2003 | Heller et al. |
| 6,577,899 B2 | 6/2003 | Lebel et al. |
| 6,579,257 B1 | 6/2003 | Elgas et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,705 B1 | 7/2003 | Kim et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,594,514 B2 | 7/2003 | Berner et al. |
| 6,595,756 B2 | 7/2003 | Gray et al. |
| 6,595,919 B2 | 7/2003 | Berner et al. |
| 6,600,997 B2 | 7/2003 | Deweese et al. |
| 6,602,221 B1 | 8/2003 | Saravia et al. |
| 6,605,072 B2 | 8/2003 | Struys et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,609,071 B2 | 8/2003 | Shapiro et al. |
| 6,610,012 B2 | 8/2003 | Mault |
| 6,612,984 B1 | 9/2003 | Kerr, II |
| 6,613,379 B2 | 9/2003 | Ward et al. |
| 6,615,061 B1 | 9/2003 | Khalil et al. |
| 6,615,078 B1 | 9/2003 | Burson et al. |
| 6,616,819 B1 | 9/2003 | Liamos et al. |
| 6,618,603 B2 | 9/2003 | Varalli et al. |
| 6,618,934 B1 | 9/2003 | Feldman et al. |
| 6,620,138 B1 | 9/2003 | Marrgi et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,650,471 B2 | 11/2003 | Doi |
| 6,653,091 B1 | 11/2003 | Dunn et al. |
| 6,654,625 B1 | 11/2003 | Say et al. |
| 6,656,114 B1 | 12/2003 | Poulsen et al. |
| 6,656,157 B1 | 12/2003 | Duchon et al. |
| 6,658,396 B1 | 12/2003 | Tang et al. |
| 6,659,948 B2 | 12/2003 | Lebel et al. |
| 6,663,615 B1 | 12/2003 | Madou et al. |
| 6,668,196 B1 | 12/2003 | Villegas et al. |
| 6,673,022 B1 | 1/2004 | Bobo et al. |
| 6,673,596 B1 | 1/2004 | Sayler et al. |
| 6,675,030 B2 | 1/2004 | Ciurczak et al. |
| 6,676,816 B2 | 1/2004 | Mao et al. |
| 6,679,865 B2 | 1/2004 | Shekalim |
| 6,679,872 B2 | 1/2004 | Turovskiy et al. |
| 6,683,535 B1 | 1/2004 | Utke |
| 6,684,904 B2 | 2/2004 | Ito |
| 6,685,668 B1 | 2/2004 | Cho et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,689,089 B1 | 2/2004 | Tiedtke et al. |
| 6,689,265 B2 | 2/2004 | Heller et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,699,218 B2 | 3/2004 | Flaherty et al. |
| 6,699,383 B2 | 3/2004 | Lemire et al. |
| 6,702,249 B2 | 3/2004 | Ito |
| 6,702,857 B2 | 3/2004 | Brauker et al. |
| 6,702,972 B1 | 3/2004 | Markle |
| 6,711,424 B1 | 3/2004 | Fine et al. |
| 6,712,796 B2 | 3/2004 | Fentis et al. |
| 6,721,582 B2 | 4/2004 | Trepagnier et al. |
| 6,721,587 B2 | 4/2004 | Gough |
| 6,723,086 B2 | 4/2004 | Bassuk et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |

(56)                References Cited

U.S. PATENT DOCUMENTS

| | | |
|---|---|---|
| 6,736,783 B2 | 5/2004 | Blake et al. |
| 6,736,957 B1 | 5/2004 | Forrow et al. |
| 6,740,072 B2 | 5/2004 | Starkweather et al. |
| 6,740,075 B2 | 5/2004 | Lebel et al. |
| 6,741,877 B1 | 5/2004 | Shults et al. |
| 6,742,635 B2 | 6/2004 | Hirshberg |
| 6,743,635 B2 | 6/2004 | Neel et al. |
| 6,746,582 B2 | 6/2004 | Heller et al. |
| 6,749,587 B2 | 6/2004 | Flaherty |
| 6,749,740 B2 | 6/2004 | Liamos et al. |
| 6,750,055 B1 | 6/2004 | Connelly et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,770,067 B2 | 8/2004 | Lorenzen et al. |
| 6,773,565 B2 | 8/2004 | Kunimoto et al. |
| 6,773,671 B1 | 8/2004 | Lewis et al. |
| 6,780,297 B2 | 8/2004 | Matsumoto et al. |
| 6,790,178 B1 | 9/2004 | Mault et al. |
| 6,793,632 B2 | 9/2004 | Sohrab |
| 6,801,041 B2 | 10/2004 | Karinka et al. |
| 6,802,957 B2 | 10/2004 | Jung et al. |
| 6,804,002 B2 | 10/2004 | Fine et al. |
| 6,805,693 B2 | 10/2004 | Gray et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,548 B2 | 11/2004 | Jeffrey |
| 6,813,519 B2 | 11/2004 | Lebel et al. |
| 6,832,200 B2 | 12/2004 | Greeven et al. |
| 6,850,790 B2 | 2/2005 | Berner et al. |
| 6,850,859 B1 | 2/2005 | Schuh |
| 6,858,020 B2 | 2/2005 | Rusnak |
| 6,862,465 B2 | 3/2005 | Shults et al. |
| 6,865,407 B2 | 3/2005 | Kimball et al. |
| 6,869,413 B2 | 3/2005 | Langley et al. |
| 6,873,268 B2 | 3/2005 | Lebel et al. |
| 6,875,195 B2 | 4/2005 | Choi |
| 6,881,551 B2 | 4/2005 | Heller et al. |
| 6,882,940 B2 | 4/2005 | Potts et al. |
| 6,887,228 B2 | 5/2005 | McKay |
| 6,892,085 B2 | 5/2005 | McIvor et al. |
| 6,893,396 B2 | 5/2005 | Schulze et al. |
| 6,893,545 B2 | 5/2005 | Gotoh et al. |
| 6,893,552 B1 | 5/2005 | Wang et al. |
| 6,895,263 B2 | 5/2005 | Shin et al. |
| 6,895,265 B2 | 5/2005 | Silver |
| 6,902,544 B2 | 6/2005 | Ludin et al. |
| 6,912,413 B2 | 6/2005 | Rantala et al. |
| 6,923,763 B1 | 8/2005 | Kovatchev et al. |
| 6,925,393 B1 | 8/2005 | Kalatz et al. |
| 6,926,691 B2 | 8/2005 | Miethke |
| 6,931,327 B2 | 8/2005 | Goode, Jr. et al. |
| 6,932,584 B2 | 8/2005 | Gray et al. |
| 6,932,892 B2 | 8/2005 | Chen et al. |
| 6,932,894 B2 | 8/2005 | Mao et al. |
| 6,936,006 B2 | 8/2005 | Sabra |
| 6,936,029 B2 | 8/2005 | Mann et al. |
| 6,942,518 B2 | 9/2005 | Liamos et al. |
| 6,945,965 B2 | 9/2005 | Whiting |
| 6,948,492 B2 | 9/2005 | Wermeling et al. |
| 6,950,708 B2 | 9/2005 | Bowman, IV et al. |
| 6,952,604 B2 | 10/2005 | Denuzzio et al. |
| 6,954,662 B2 | 10/2005 | Freger et al. |
| 6,958,705 B2 | 10/2005 | Lebel et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,968,294 B2 | 11/2005 | Gutta et al. |
| 6,971,274 B2 | 12/2005 | Olin |
| 6,974,437 B2 | 12/2005 | Lebel et al. |
| 6,975,893 B2 | 12/2005 | Say et al. |
| 6,979,315 B2 | 12/2005 | Rogers et al. |
| 6,989,891 B2 | 1/2006 | Braig et al. |

| | | |
|---|---|---|
| 6,990,366 B2 | 1/2006 | Say et al. |
| 6,990,422 B2 | 1/2006 | Laletin et al. |
| 6,997,907 B2 | 2/2006 | Safabash et al. |
| 6,997,921 B2 | 2/2006 | Gray et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,008,979 B2 | 3/2006 | Schottman et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,025,727 B2 | 4/2006 | Brockway et al. |
| 7,025,743 B2 | 4/2006 | Mann et al. |
| 7,027,848 B2 | 4/2006 | Robinson et al. |
| 7,029,443 B2 | 4/2006 | Kroll |
| 7,029,444 B2 | 4/2006 | Shin et al. |
| 7,033,322 B2 | 4/2006 | Silver |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,044,911 B2 | 5/2006 | Drinan et al. |
| 7,048,727 B1 | 5/2006 | Moss |
| 7,052,472 B1 | 5/2006 | Miller et al. |
| 7,052,483 B2 | 5/2006 | Wojcik |
| 7,056,302 B2 | 6/2006 | Douglas |
| 7,058,437 B2 | 6/2006 | Buse et al. |
| 7,060,059 B2 | 6/2006 | Keith et al. |
| 7,061,593 B2 | 6/2006 | Braig et al. |
| 7,063,086 B2 | 6/2006 | Shahbazpour et al. |
| 7,066,884 B2 | 6/2006 | Custer et al. |
| 7,070,577 B1 | 7/2006 | Haller et al. |
| 7,074,307 B2 | 7/2006 | Simpson et al. |
| 7,076,300 B1 | 7/2006 | Kroll et al. |
| 7,081,195 B2 * | 7/2006 | Simpson ................ C12Q 1/006 |
| | | 205/792 |
| 7,092,891 B2 | 8/2006 | Maus et al. |
| 7,096,064 B2 | 8/2006 | Deno et al. |
| 7,097,637 B2 | 8/2006 | Triplett et al. |
| 7,097,775 B2 | 8/2006 | Greenberg et al. |
| 7,098,803 B2 | 8/2006 | Mann et al. |
| 7,100,628 B1 | 9/2006 | Izenson et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russell et al. |
| 7,123,950 B2 | 10/2006 | Mannheimer |
| 7,131,967 B2 | 11/2006 | Gray et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,144,404 B2 | 12/2006 | Whitson et al. |
| 7,146,202 B2 | 12/2006 | Ward et al. |
| 7,150,741 B2 | 12/2006 | Erickson et al. |
| 7,150,755 B2 | 12/2006 | Levaughn et al. |
| 7,153,265 B2 | 12/2006 | Vachon |
| 7,162,290 B1 | 1/2007 | Levin |
| 7,166,074 B2 | 1/2007 | Reghabi et al. |
| 7,167,818 B2 | 1/2007 | Brown |
| 7,168,597 B1 | 1/2007 | Jones et al. |
| 7,169,289 B2 | 1/2007 | Schuelein et al. |
| 7,171,274 B2 | 1/2007 | Starkweather et al. |
| 7,183,102 B2 | 2/2007 | Monfre et al. |
| 7,184,810 B2 | 2/2007 | Caduff et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,968 B1 | 4/2007 | Harcinske |
| 7,207,974 B2 | 4/2007 | Safabash et al. |
| 7,211,074 B2 | 5/2007 | Sansoucy |
| 7,221,970 B2 | 5/2007 | Parker |
| 7,223,253 B2 | 5/2007 | Hogendijk |

(56) References Cited

U.S. PATENT DOCUMENTS

| | | | |
|---|---|---|---|
| 7,223,276 | B2 | 5/2007 | List et al. |
| 7,225,535 | B2 | 6/2007 | Feldman et al. |
| 7,226,978 | B2 | 6/2007 | Tapsak et al. |
| 7,228,162 | B2 | 6/2007 | Ward et al. |
| 7,229,288 | B2 | 6/2007 | Stuart et al. |
| 7,238,165 | B2 | 7/2007 | Vincent et al. |
| 7,247,138 | B2 | 7/2007 | Reghabi et al. |
| 7,253,680 | B2 | 8/2007 | Laletin |
| 7,254,450 | B2 | 8/2007 | Christopherson et al. |
| 7,255,690 | B2 | 8/2007 | Gray et al. |
| 7,258,673 | B2 | 8/2007 | Racchini et al. |
| 7,258,681 | B2 | 8/2007 | Houde |
| 7,261,690 | B2 | 8/2007 | Teller et al. |
| 7,266,400 | B2 | 9/2007 | Fine et al. |
| 7,267,665 | B2 | 9/2007 | Steil et al. |
| 7,272,436 | B2 | 9/2007 | Gill et al. |
| 7,276,029 | B2 | 10/2007 | Goode, Jr. et al. |
| 7,278,983 | B2 | 10/2007 | Ireland et al. |
| 7,279,174 | B2 | 10/2007 | Pacetti et al. |
| 7,282,029 | B1 | 10/2007 | Poulsen et al. |
| 7,285,198 | B2 * | 10/2007 | Douglas ................ B82Y 30/00 |
| | | | 204/403.14 |
| 7,288,085 | B2 | 10/2007 | Olsen |
| 7,291,114 | B2 | 11/2007 | Mault |
| 7,295,867 | B2 | 11/2007 | Berner et al. |
| 7,297,114 | B2 | 11/2007 | Gill et al. |
| 7,297,136 | B2 | 11/2007 | Wyrick |
| 7,299,082 | B2 | 11/2007 | Feldman et al. |
| 7,303,549 | B2 | 12/2007 | Flaherty et al. |
| 7,310,544 | B2 | 12/2007 | Brister et al. |
| 7,311,690 | B2 | 12/2007 | Burnett |
| 7,313,425 | B2 | 12/2007 | Finarov et al. |
| 7,314,452 | B2 | 1/2008 | Madonia |
| 7,315,767 | B2 | 1/2008 | Caduff et al. |
| 7,316,662 | B2 | 1/2008 | Delnevo et al. |
| 7,317,938 | B2 | 1/2008 | Lorenz et al. |
| 7,317,939 | B2 | 1/2008 | Fine et al. |
| 7,318,814 | B2 | 1/2008 | Levine et al. |
| 7,318,816 | B2 | 1/2008 | Bobroff et al. |
| 7,327,273 | B2 | 2/2008 | Hung et al. |
| 7,329,234 | B2 | 2/2008 | Sansoucy |
| 7,329,239 | B2 | 2/2008 | Safabash et al. |
| 7,334,594 | B2 | 2/2008 | Ludin |
| 7,335,179 | B2 | 2/2008 | Burnett |
| 7,335,195 | B2 | 2/2008 | Mehier |
| 7,335,294 | B2 | 2/2008 | Heller et al. |
| 7,338,464 | B2 | 3/2008 | Blischak et al. |
| 7,338,639 | B2 | 3/2008 | Burke et al. |
| 7,344,500 | B2 | 3/2008 | Talbot et al. |
| 7,354,420 | B2 | 4/2008 | Steil et al. |
| 7,357,793 | B2 | 4/2008 | Pacetti |
| 7,359,723 | B2 | 4/2008 | Jones |
| 7,361,155 | B2 | 4/2008 | Sage, Jr. et al. |
| 7,364,562 | B2 | 4/2008 | Braig et al. |
| 7,364,592 | B2 | 4/2008 | Carr-Brendel et al. |
| 7,366,556 | B2 | 4/2008 | Brister et al. |
| 7,367,942 | B2 | 5/2008 | Grage et al. |
| 7,379,765 | B2 | 5/2008 | Petisce et al. |
| 7,381,184 | B2 | 6/2008 | Funderburk et al. |
| 7,390,667 | B2 | 6/2008 | Burke et al. |
| 7,396,353 | B2 | 7/2008 | Lorenzen et al. |
| 7,399,277 | B2 | 7/2008 | Saidara et al. |
| 7,402,153 | B2 | 7/2008 | Steil et al. |
| 7,407,493 | B2 | 8/2008 | Cane' |
| 7,407,811 | B2 | 8/2008 | Burke et al. |
| 7,417,164 | B2 | 8/2008 | Suri |
| 7,424,318 | B2 | 9/2008 | Brister et al. |
| 7,426,408 | B2 | 9/2008 | Denuzzio et al. |
| 7,433,727 | B2 | 10/2008 | Ward et al. |
| 7,455,663 | B2 | 11/2008 | Bikovsky |
| 7,460,898 | B2 | 12/2008 | Brister et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,474,992 | B2 | 1/2009 | Ariyur |
| 7,481,819 | B2 | 1/2009 | Koeppel et al. |
| 7,488,601 | B2 | 2/2009 | Burke et al. |
| 7,494,465 | B2 | 2/2009 | Brister et al. |
| 7,494,816 | B2 | 2/2009 | Burke et al. |
| 7,497,827 | B2 | 3/2009 | Brister et al. |
| 7,499,002 | B2 | 3/2009 | Blasko et al. |
| 7,502,644 | B2 | 3/2009 | Gill et al. |
| 7,519,408 | B2 | 4/2009 | Rasdal et al. |
| 7,519,478 | B2 | 4/2009 | Bartkowiak et al. |
| 7,523,004 | B2 | 4/2009 | Bartkowiak et al. |
| 7,524,287 | B2 | 4/2009 | Bharmi |
| 7,530,964 | B2 | 5/2009 | Lavi et al. |
| 7,547,281 | B2 | 6/2009 | Hayes et al. |
| 7,569,030 | B2 | 8/2009 | Lebel et al. |
| 7,572,237 | B2 | 8/2009 | Saikley et al. |
| 7,582,059 | B2 | 9/2009 | Funderburk et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,604,593 | B2 | 10/2009 | Parris et al. |
| 7,613,491 | B2 | 11/2009 | Boock et al. |
| 7,615,007 | B2 | 11/2009 | Shults et al. |
| 7,618,368 | B2 | 11/2009 | Brown |
| 7,618,369 | B2 | 11/2009 | Hayter et al. |
| 7,620,438 | B2 | 11/2009 | He |
| 7,624,028 | B1 | 11/2009 | Brown |
| 7,630,748 | B2 | 12/2009 | Budiman |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,032 | B2 | 12/2009 | Jones |
| 7,640,048 | B2 | 12/2009 | Dobbles et al. |
| 7,647,237 | B2 | 1/2010 | Malave et al. |
| 7,651,596 | B2 | 1/2010 | Petisce et al. |
| 7,653,425 | B2 | 1/2010 | Hayter et al. |
| 7,654,955 | B2 | 2/2010 | Polidori et al. |
| 7,657,297 | B2 | 2/2010 | Simpson et al. |
| 7,670,288 | B2 | 3/2010 | Sher |
| 7,682,338 | B2 | 3/2010 | Griffin |
| 7,695,434 | B2 | 4/2010 | Malecha |
| 7,697,967 | B2 | 4/2010 | Stafford |
| 7,699,775 | B2 | 4/2010 | Desai et al. |
| 7,699,807 | B2 | 4/2010 | Faust et al. |
| 7,699,964 | B2 | 4/2010 | Feldman et al. |
| 7,711,402 | B2 | 5/2010 | Shults et al. |
| 7,711,493 | B2 | 5/2010 | Bartkowiak et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,731,659 | B2 | 6/2010 | Malecha |
| 7,731,691 | B2 | 6/2010 | Cote et al. |
| 7,736,310 | B2 | 6/2010 | Taub |
| 7,736,338 | B2 | 6/2010 | Kavazov et al. |
| 7,749,445 | B2 | 7/2010 | Masters |
| 7,751,864 | B2 | 7/2010 | Buck, Jr. |
| 7,761,126 | B2 | 7/2010 | Gardner et al. |
| 7,761,130 | B2 | 7/2010 | Simpson et al. |
| 7,766,829 | B2 | 8/2010 | Sloan et al. |
| 7,766,830 | B2 | 8/2010 | Fox et al. |
| 7,771,352 | B2 | 8/2010 | Shults et al. |
| 7,774,038 | B2 | 8/2010 | Wang et al. |
| 7,774,145 | B2 | 8/2010 | Brauker et al. |
| 7,775,975 | B2 | 8/2010 | Brister et al. |
| 7,776,559 | B2 | 8/2010 | Childers et al. |
| 7,778,679 | B2 | 8/2010 | Schulman et al. |
| 7,778,680 | B2 | 8/2010 | Goode, Jr. et al. |
| 7,783,333 | B2 | 8/2010 | Brister et al. |
| 7,789,857 | B2 | 9/2010 | Moberg et al. |
| 7,792,562 | B2 | 9/2010 | Shults et al. |
| 7,797,028 | B2 | 9/2010 | Goode, Jr. et al. |
| 7,826,981 | B2 | 11/2010 | Goode, Jr. et al. |
| 7,828,728 | B2 | 11/2010 | Boock et al. |
| 7,831,287 | B2 | 11/2010 | Brister et al. |
| 7,835,777 | B2 | 11/2010 | Shults et al. |
| 7,838,639 | B2 | 11/2010 | Tschopp et al. |
| 7,846,132 | B2 | 12/2010 | Gravesen et al. |
| 7,850,652 | B2 | 12/2010 | Liniger et al. |
| 7,857,760 | B2 | 12/2010 | Brister et al. |
| 7,860,545 | B2 | 12/2010 | Shults et al. |

(56) References Cited

U.S. PATENT DOCUMENTS

| | | | |
|---|---|---|---|
| 7,866,025 B2 | 1/2011 | James et al. |
| 7,866,026 B1 | 1/2011 | Wang et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,885,698 B2 | 2/2011 | Feldman |
| 7,889,069 B2 | 2/2011 | Fifolt et al. |
| 7,894,870 B1 | 2/2011 | Lucisano et al. |
| 7,896,809 B2 | 3/2011 | Simpson et al. |
| 7,896,844 B2 | 3/2011 | Thalmann et al. |
| 7,899,511 B2 | 3/2011 | Shults et al. |
| 7,901,354 B2 | 3/2011 | Shults et al. |
| 7,901,394 B2 | 3/2011 | Ireland et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode et al. |
| 7,927,274 B2 | 4/2011 | Rasdal et al. |
| 7,933,639 B2 | 4/2011 | Goode et al. |
| 7,935,057 B2 | 5/2011 | Goode, Jr. et al. |
| 7,938,797 B2 | 5/2011 | Estes |
| 7,946,984 B2 | 5/2011 | Brister et al. |
| 7,946,985 B2 | 5/2011 | Mastrototaro et al. |
| 7,949,381 B2 | 5/2011 | Brister et al. |
| 7,955,261 B2 | 6/2011 | Goode et al. |
| 7,955,297 B2 | 6/2011 | Radmer et al. |
| 7,959,569 B2 | 6/2011 | Goode et al. |
| 7,970,448 B2 | 6/2011 | Shults et al. |
| 7,974,672 B2 | 7/2011 | Shults et al. |
| 7,976,492 B2 | 7/2011 | Brauker et al. |
| 7,979,104 B2 | 7/2011 | Kamath et al. |
| 7,985,203 B2 | 7/2011 | Haueter et al. |
| 7,985,330 B2 | 7/2011 | Wang et al. |
| 7,986,986 B2 | 7/2011 | Goode et al. |
| 7,990,828 B2 | 8/2011 | Su et al. |
| 7,996,158 B2 | 8/2011 | Hayter et al. |
| 7,998,071 B2 | 8/2011 | Goode, Jr. et al. |
| 8,000,763 B2 | 8/2011 | Mazza et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,025,658 B2 | 9/2011 | Chong et al. |
| 8,026,104 B2 | 9/2011 | Wu et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,519 B2 | 12/2011 | Goode, Jr. et al. |
| 8,073,520 B2 | 12/2011 | Kamath et al. |
| 8,079,961 B2 | 12/2011 | Saikley et al. |
| 8,103,471 B2 | 1/2012 | Hayter |
| 8,112,240 B2 | 2/2012 | Fennell |
| 8,114,268 B2 | 2/2012 | Wang et al. |
| 8,116,837 B2 | 2/2012 | Huang |
| 8,118,877 B2 | 2/2012 | Brauker et al. |
| 8,128,562 B2 | 3/2012 | Goode, Jr. et al. |
| 8,128,597 B2 | 3/2012 | Cross et al. |
| 8,133,178 B2 | 3/2012 | Brauker et al. |
| 8,140,312 B2 | 3/2012 | Hayter et al. |
| 8,149,117 B2 | 4/2012 | Fennell et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,670 B2 | 4/2012 | Ouyang et al. |
| 8,160,671 B2 | 4/2012 | Kamath et al. |
| 8,160,834 B2 | 4/2012 | Liang et al. |
| 8,160,900 B2 | 4/2012 | Taub et al. |
| 8,167,801 B2 | 5/2012 | Goode, Jr. et al. |
| 8,170,803 B2 | 5/2012 | Kamath et al. |
| 8,172,804 B2 | 5/2012 | Bikovsky |
| 8,172,805 B2 | 5/2012 | Mogensen et al. |
| 8,195,265 B2 | 6/2012 | Goode, Jr. et al. |
| 8,198,569 B2 * | 6/2012 | Krobok ................. B60N 2/002 |
| | | 219/217 |
| 8,202,491 B2 | 6/2012 | Masters et al. |
| 8,206,297 B2 | 6/2012 | Kamath et al. |
| 8,211,016 B2 | 7/2012 | Budiman |
| 8,216,137 B2 | 7/2012 | Budiman |
| 8,216,138 B1 | 7/2012 | McGarraugh |
| 8,216,139 B2 | 7/2012 | Brauker et al. |
| 8,219,173 B2 | 7/2012 | Budiman et al. |
| 8,224,415 B2 | 7/2012 | Budiman |
| 8,226,615 B2 | 7/2012 | Bikovsky |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,239,166 B2 | 8/2012 | Hayter et al. |
| 8,249,683 B2 | 8/2012 | Wang et al. |
| 8,249,684 B2 | 8/2012 | Kamath et al. |
| 8,251,906 B2 | 8/2012 | Brauker et al. |
| 8,255,026 B1 | 8/2012 | Al-Ali |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,260,558 B2 | 9/2012 | Hayter et al. |
| 8,262,618 B2 | 9/2012 | Scheurer |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,292,849 B2 | 10/2012 | Bobroff et al. |
| 8,298,142 B2 | 10/2012 | Simpson et al. |
| 8,298,172 B2 | 10/2012 | Nielsen et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,332,008 B2 | 12/2012 | Goode et al. |
| 8,346,335 B2 | 1/2013 | Harper et al. |
| 8,346,337 B2 | 1/2013 | Heller et al. |
| 8,346,338 B2 | 1/2013 | Goode, Jr. et al. |
| 8,348,923 B2 | 1/2013 | Kanderian, Jr. et al. |
| 8,364,229 B2 | 1/2013 | Simpson et al. |
| 8,366,682 B2 | 2/2013 | Wyrick |
| 8,366,729 B2 | 2/2013 | Levaughn et al. |
| 8,369,919 B2 | 2/2013 | Kamath et al. |
| 8,372,351 B2 | 2/2013 | Ow-Wing |
| 8,374,667 B2 | 2/2013 | Brauker et al. |
| 8,376,945 B2 | 2/2013 | Hayter et al. |
| 8,386,004 B2 | 2/2013 | Kamath et al. |
| 8,394,021 B2 | 3/2013 | Goode et al. |
| 8,409,140 B2 | 4/2013 | Ejlersen et al. |
| 8,409,145 B2 | 4/2013 | Raymond et al. |
| 8,417,312 B2 | 4/2013 | Kamath et al. |
| 8,439,838 B2 | 5/2013 | Mogensen et al. |
| 8,444,560 B2 | 5/2013 | Hayter et al. |
| 8,457,703 B2 | 6/2013 | Al-Ali |
| 8,460,231 B2 | 6/2013 | Brauker et al. |
| 8,461,985 B2 | 6/2013 | Fennell et al. |
| 8,463,350 B2 | 6/2013 | Kamath et al. |
| 8,473,022 B2 | 6/2013 | Hayter et al. |
| 8,475,373 B2 | 7/2013 | Brister et al. |
| 8,475,432 B2 | 7/2013 | Moberg et al. |
| 8,478,557 B2 | 7/2013 | Hayter et al. |
| 8,483,792 B2 | 7/2013 | Slomski et al. |
| 8,484,005 B2 | 7/2013 | Hayter et al. |

(56)        References Cited

U.S. PATENT DOCUMENTS

| | | | |
|---|---|---|---|
| 8,500,654 B2 | 8/2013 | Goldenberg |
| 8,512,245 B2 | 8/2013 | Markle et al. |
| 8,512,276 B2 | 8/2013 | Talbot et al. |
| 8,515,517 B2 | 8/2013 | Hayter et al. |
| 8,527,025 B1 | 9/2013 | Shults et al. |
| 8,532,935 B2 | 9/2013 | Budiman |
| 8,543,354 B2 | 9/2013 | Luo et al. |
| 8,560,037 B2 | 10/2013 | Goode, Jr. et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,593,109 B2 | 11/2013 | He |
| 8,600,681 B2 | 12/2013 | Hayter et al. |
| 8,612,163 B2 | 12/2013 | Hayter et al. |
| 8,615,281 B2 | 12/2013 | Yodfat et al. |
| 8,628,498 B2 | 1/2014 | Safabash et al. |
| 8,641,674 B2 | 2/2014 | Bobroff et al. |
| 8,657,746 B2 | 2/2014 | Roy |
| 8,663,220 B2 | 3/2014 | Wiener et al. |
| 8,665,091 B2 | 3/2014 | Fennell et al. |
| 8,668,645 B2 | 3/2014 | Drucker et al. |
| 8,672,962 B2 | 3/2014 | Brenneman |
| 8,682,615 B2 | 3/2014 | Hayter et al. |
| 8,718,739 B2 | 5/2014 | Harper et al. |
| 8,718,965 B2 | 5/2014 | Hayter et al. |
| 8,721,545 B2 | 5/2014 | Brister et al. |
| 8,721,585 B2 | 5/2014 | Brauker et al. |
| 8,744,547 B2 | 6/2014 | Budiman et al. |
| 8,747,363 B2 | 6/2014 | Nielsen et al. |
| 8,764,657 B2 | 7/2014 | Curry et al. |
| 8,792,956 B2 | 7/2014 | Ouyang et al. |
| 8,808,228 B2 | 8/2014 | Brister et al. |
| 8,828,201 B2 | 9/2014 | Simpson et al. |
| 8,868,151 B2 | 10/2014 | Telson et al. |
| 8,868,161 B2 | 10/2014 | Thierman |
| 8,870,822 B2 | 10/2014 | Thalmann et al. |
| 8,880,138 B2 | 11/2014 | Cho |
| 8,882,741 B2 | 11/2014 | Brauker et al. |
| D719,267 S | 12/2014 | Vaccarella |
| 8,920,401 B2 | 12/2014 | Brauker et al. |
| 8,926,585 B2 | 1/2015 | Brauker et al. |
| 8,932,256 B2 | 1/2015 | Chong et al. |
| 8,933,664 B2 | 1/2015 | He |
| 8,942,778 B2 | 1/2015 | Ocvirk et al. |
| 8,971,983 B2 * | 3/2015 | Gilmore ................. A61B 5/296 |
| | | 600/391 |
| 9,050,413 B2 | 6/2015 | Brauker et al. |
| 9,060,719 B2 | 6/2015 | Hayter et al. |
| 9,060,727 B2 | 6/2015 | Saikley et al. |
| 9,113,828 B2 | 8/2015 | Budiman |
| 9,119,528 B2 | 9/2015 | Cobelli et al. |
| 9,119,529 B2 | 9/2015 | Hampapuram et al. |
| 9,125,548 B2 | 9/2015 | Hayter |
| 9,149,220 B2 | 10/2015 | Bohm et al. |
| 9,155,843 B2 | 10/2015 | Brauker et al. |
| 9,161,714 B2 | 10/2015 | Martini et al. |
| 9,186,098 B2 | 11/2015 | Lee et al. |
| 9,192,717 B2 | 11/2015 | Cote et al. |
| 9,215,992 B2 | 12/2015 | Donnay et al. |
| D746,994 S | 1/2016 | Lewis, Jr. et al. |
| 9,245,221 B2 | 1/2016 | Forster |
| 9,265,453 B2 | 2/2016 | Curry et al. |
| 9,295,786 B2 | 3/2016 | Gottlieb et al. |
| 9,314,196 B2 | 4/2016 | Pryor et al. |
| 9,320,462 B2 | 4/2016 | Harper et al. |
| 9,320,468 B2 | 4/2016 | Hayter et al. |
| 9,326,709 B2 | 5/2016 | Budiman |
| 9,332,934 B2 | 5/2016 | Hayter et al. |
| 9,339,217 B2 | 5/2016 | Harper et al. |
| 9,357,951 B2 | 6/2016 | Simpson et al. |
| 9,357,959 B2 | 6/2016 | Hayter et al. |
| 9,380,971 B2 | 7/2016 | He |
| 9,380,975 B2 | 7/2016 | Karbowniczek et al. |
| 9,392,969 B2 | 7/2016 | Hayter et al. |
| 9,398,872 B2 | 7/2016 | Hayter et al. |
| 9,399,094 B2 | 7/2016 | Krag et al. |
| 9,402,544 B2 | 8/2016 | Yee et al. |
| 9,408,566 B2 | 8/2016 | Hayter et al. |
| 9,451,908 B2 | 9/2016 | Kamath et al. |
| 9,452,258 B2 | 9/2016 | Dobbles et al. |
| 9,452,259 B2 | 9/2016 | Dobbles et al. |
| 9,457,146 B2 | 10/2016 | Dobbles et al. |
| 9,463,277 B2 | 10/2016 | Dobbles et al. |
| 9,483,608 B2 | 11/2016 | Hayter et al. |
| 9,498,159 B2 | 11/2016 | Heller et al. |
| 9,533,092 B2 | 1/2017 | Gyrn |
| 9,558,325 B2 | 1/2017 | Hayter et al. |
| 9,572,935 B2 | 2/2017 | Dobbles et al. |
| 9,572,936 B2 | 2/2017 | Dobbles et al. |
| 9,586,004 B2 | 3/2017 | Dobbles et al. |
| 9,597,453 B2 | 3/2017 | Dobbles et al. |
| 9,615,779 B2 | 4/2017 | Pryor et al. |
| 9,629,578 B2 | 4/2017 | Hayter et al. |
| 9,662,056 B2 | 5/2017 | Budiman et al. |
| 9,675,285 B2 | 6/2017 | Christian |
| 9,675,290 B2 | 6/2017 | Budiman et al. |
| 9,687,183 B2 | 6/2017 | Donnay et al. |
| 9,693,722 B2 | 7/2017 | Shah et al. |
| D794,801 S | 8/2017 | Newhouse et al. |
| 9,724,032 B2 | 8/2017 | Brenneman |
| 9,730,623 B2 | 8/2017 | Harper et al. |
| 9,737,249 B2 | 8/2017 | Hayter et al. |
| 9,743,863 B2 | 8/2017 | He |
| 9,770,211 B2 | 9/2017 | Hayter et al. |
| 9,788,771 B2 | 10/2017 | Stafford |
| 9,797,880 B2 | 10/2017 | Hayter et al. |
| 9,801,571 B2 | 10/2017 | Hayter |
| 9,801,575 B2 | 10/2017 | Bohm et al. |
| 9,801,577 B2 | 10/2017 | Budiman et al. |
| 9,804,148 B2 | 10/2017 | Hayter et al. |
| 9,804,150 B2 | 10/2017 | Hayter et al. |
| 9,808,190 B2 | 11/2017 | Bohm et al. |
| 9,808,574 B2 | 11/2017 | Yodfat et al. |
| 9,814,428 B2 | 11/2017 | Budiman |
| 9,827,372 B2 | 11/2017 | Dobbles et al. |
| 9,833,181 B2 | 12/2017 | Hayter et al. |
| 9,839,383 B2 | 12/2017 | Hayter et al. |
| 9,848,809 B2 | 12/2017 | Bohm et al. |
| D815,289 S | 4/2018 | Evers et al. |
| D816,229 S | 4/2018 | Frick et al. |
| 9,931,065 B2 | 4/2018 | Pryor et al. |
| 9,936,910 B2 | 4/2018 | Hayter et al. |
| 9,937,293 B2 | 4/2018 | Brauker et al. |
| 9,980,670 B2 | 5/2018 | Funderburk et al. |
| 10,002,233 B2 | 6/2018 | Hayter et al. |
| 10,004,442 B2 | 6/2018 | Bohm et al. |
| 10,010,280 B2 | 7/2018 | Donnay et al. |
| 10,031,002 B2 | 7/2018 | Hayter et al. |
| 10,045,720 B2 | 8/2018 | Hayter et al. |
| 10,052,055 B2 | 8/2018 | Li et al. |
| 10,076,606 B2 | 9/2018 | Ambruzs et al. |
| 10,078,380 B2 | 9/2018 | Budiman |
| 10,082,493 B2 | 9/2018 | Harper et al. |
| D829,889 S | 10/2018 | Hwang et al. |
| D831,831 S | 10/2018 | Newhouse et al. |
| 10,089,446 B2 | 10/2018 | Budiman |
| 10,119,956 B2 | 11/2018 | Hayter et al. |
| 10,143,409 B2 | 12/2018 | Hayter |
| 10,182,750 B1 | 1/2019 | Philippine et al. |
| 10,188,334 B2 | 1/2019 | Budiman et al. |
| 10,188,794 B2 | 1/2019 | Hayter et al. |
| 10,194,842 B2 | 2/2019 | Peterson et al. |
| 10,194,843 B2 | 2/2019 | Peterson et al. |
| 10,194,868 B2 | 2/2019 | Budiman |
| D842,996 S | 3/2019 | Frick et al. |
| 10,251,605 B2 | 4/2019 | Liu et al. |
| 10,261,069 B2 | 4/2019 | Hayter et al. |
| 10,278,580 B2 | 5/2019 | Brister et al. |
| 10,278,630 B2 | 5/2019 | Hayter et al. |
| 10,292,632 B2 | 5/2019 | Lee et al. |
| 10,327,679 B2 | 6/2019 | Peterson et al. |
| 10,327,688 B2 | 6/2019 | Bohm et al. |
| 10,335,066 B2 | 7/2019 | Peterson et al. |

(56) References Cited

U.S. PATENT DOCUMENTS

| | | |
|---|---|---|
| 10,335,075 B2 | 7/2019 | Vanslyke et al. |
| 10,376,187 B2 | 8/2019 | Peterson et al. |
| 10,376,637 B2 | 8/2019 | Gyrn et al. |
| 10,413,183 B2 | 9/2019 | Antonio et al. |
| 10,420,508 B2 | 9/2019 | Antonio et al. |
| 10,448,873 B2 | 10/2019 | Bohm et al. |
| 10,456,064 B2 | 10/2019 | Peterson et al. |
| D870,291 S | 12/2019 | Barry et al. |
| 10,492,685 B2 | 12/2019 | Bernstein et al. |
| 10,561,354 B2 | 2/2020 | Bohm et al. |
| 10,610,103 B2 | 4/2020 | Brister et al. |
| 10,610,135 B2 | 4/2020 | Kamath et al. |
| 10,610,136 B2 | 4/2020 | Kamath et al. |
| 10,610,141 B2 | 4/2020 | Böhm et al. |
| 10,624,539 B2 | 4/2020 | Brister et al. |
| 10,624,568 B2 | 4/2020 | Böhm et al. |
| 10,631,787 B2 | 4/2020 | Antonio et al. |
| 10,653,835 B2 | 5/2020 | Dobbles et al. |
| 10,667,729 B2 | 6/2020 | Simpson et al. |
| 10,682,084 B2 | 6/2020 | Bohm et al. |
| 10,682,984 B2 | 6/2020 | Doi |
| 10,687,740 B2 | 6/2020 | Bohm et al. |
| 10,702,193 B2 | 7/2020 | Simpson et al. |
| 10,709,362 B2 | 7/2020 | Simpson et al. |
| 10,709,363 B2 | 7/2020 | Brister et al. |
| 10,709,364 B2 | 7/2020 | Kamath et al. |
| 10,722,152 B2 | 7/2020 | Brister et al. |
| 10,722,162 B2 | 7/2020 | Böhm et al. |
| 10,799,158 B2 | 10/2020 | Brister et al. |
| 10,813,576 B2 | 10/2020 | Brister et al. |
| 10,813,577 B2 | 10/2020 | Brister et al. |
| 10,827,956 B2 | 11/2020 | Brister et al. |
| 10,835,162 B2 | 11/2020 | Bohm et al. |
| D904,629 S | 12/2020 | Debock et al. |
| 10,856,787 B2 | 12/2020 | Pryor et al. |
| 10,863,931 B2 | 12/2020 | Hernandez-Rosas et al. |
| 10,863,944 B2 | 12/2020 | Gray et al. |
| 10,881,340 B2 | 1/2021 | Curry et al. |
| 10,881,341 B1 | 1/2021 | Curry et al. |
| 10,905,377 B2 | 2/2021 | Gray et al. |
| 10,918,313 B2 | 2/2021 | Brister et al. |
| 10,918,314 B2 | 2/2021 | Brister et al. |
| 10,918,316 B2 | 2/2021 | Pryor et al. |
| 10,932,700 B2 | 3/2021 | Simpson et al. |
| 10,952,657 B2 | 3/2021 | Curry et al. |
| 10,959,654 B2 | 3/2021 | Curry et al. |
| 10,980,450 B2 | 4/2021 | Wedekind et al. |
| 10,980,452 B2 | 4/2021 | Simpson et al. |
| 10,980,453 B2 | 4/2021 | Wedekind et al. |
| 10,980,461 B2 | 4/2021 | Simpson et al. |
| 10,985,804 B2 | 4/2021 | Miller et al. |
| 10,993,642 B2 | 5/2021 | Simpson et al. |
| 11,000,216 B2 | 5/2021 | Curry et al. |
| 11,051,725 B2 | 7/2021 | Pace et al. |
| 11,943,876 B2 | 3/2024 | Halac et al. |
| 2001/0007950 A1 | 7/2001 | North et al. |
| 2001/0016682 A1 | 8/2001 | Berner et al. |
| 2001/0021817 A1 | 9/2001 | Brugger et al. |
| 2001/0039053 A1 | 11/2001 | Liseo et al. |
| 2001/0041830 A1 | 11/2001 | Varalli et al. |
| 2001/0041831 A1 | 11/2001 | Starkweather et al. |
| 2001/0044588 A1 | 11/2001 | Mault |
| 2001/0051768 A1 | 12/2001 | Schulman et al. |
| 2002/0009810 A1 | 1/2002 | O'Connor et al. |
| 2002/0016534 A1 | 2/2002 | Trepagnier et al. |
| 2002/0016535 A1 | 2/2002 | Martin et al. |
| 2002/0018843 A1 | 2/2002 | Van Antwerp et al. |
| 2002/0019022 A1 | 2/2002 | Dunn et al. |
| 2002/0019330 A1 | 2/2002 | Murray et al. |
| 2002/0022855 A1 | 2/2002 | Bobroff et al. |
| 2002/0022883 A1 | 2/2002 | Burg |
| 2002/0023852 A1 | 2/2002 | Mcivor et al. |
| 2002/0026110 A1 | 2/2002 | Parris et al. |
| 2002/0026111 A1 | 2/2002 | Ackerman |
| 2002/0029058 A1 | 3/2002 | Levaughn et al. |
| 2002/0038101 A1 | 3/2002 | Avrahami et al. |
| 2002/0042090 A1 | 4/2002 | Heller et al. |
| 2002/0042561 A1 | 4/2002 | Schulman et al. |
| 2002/0043471 A1 | 4/2002 | Ikeda et al. |
| 2002/0045808 A1 | 4/2002 | Ford et al. |
| 2002/0060692 A1 | 5/2002 | Broemmelsiek |
| 2002/0065453 A1 | 5/2002 | Lesho et al. |
| 2002/0065454 A1 | 5/2002 | Lebel et al. |
| 2002/0068860 A1 | 6/2002 | Clark |
| 2002/0071776 A1 | 6/2002 | Bandis et al. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0103499 A1 | 8/2002 | Perez et al. |
| 2002/0106709 A1 | 8/2002 | Potts et al. |
| 2002/0111547 A1 | 8/2002 | Knobbe et al. |
| 2002/0119711 A1 | 8/2002 | Vanantwerp et al. |
| 2002/0120186 A1 | 8/2002 | Keimel |
| 2002/0123048 A1 | 9/2002 | Gau |
| 2002/0128594 A1 | 9/2002 | Das et al. |
| 2002/0133224 A1 | 9/2002 | Bajgar et al. |
| 2002/0143266 A1 | 10/2002 | Bock |
| 2002/0143372 A1 | 10/2002 | Snell et al. |
| 2002/0151796 A1 | 10/2002 | Koulik |
| 2002/0155615 A1 | 10/2002 | Novikov et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0182241 A1 | 12/2002 | Borenstein et al. |
| 2002/0188185 A1 | 12/2002 | Sohrab |
| 2002/0193679 A1 | 12/2002 | Malave et al. |
| 2002/0193885 A1 | 12/2002 | Legeay et al. |
| 2002/0198513 A1 | 12/2002 | Lebel et al. |
| 2003/0004403 A1 | 1/2003 | Drinan et al. |
| 2003/0004432 A1 | 1/2003 | Assenheimer |
| 2003/0006669 A1 | 1/2003 | Pei et al. |
| 2003/0021729 A1 | 1/2003 | Moller et al. |
| 2003/0023171 A1 | 1/2003 | Sato et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028126 A1 | 2/2003 | List |
| 2003/0031699 A1 | 2/2003 | Van Antwerp |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | L. Ruchti et al. |
| 2003/0060753 A1 | 3/2003 | Starkweather et al. |
| 2003/0060765 A1 | 3/2003 | Campbell et al. |
| 2003/0065308 A1 | 4/2003 | Lebel et al. |
| 2003/0070548 A1 | 4/2003 | Clausen |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0091433 A1 | 5/2003 | Tam et al. |
| 2003/0097082 A1 | 5/2003 | Purdy et al. |
| 2003/0099682 A1 | 5/2003 | Moussy et al. |
| 2003/0100040 A1 | 5/2003 | Bonnecaze et al. |
| 2003/0100821 A1 | 5/2003 | Heller et al. |
| 2003/0114836 A1 | 6/2003 | Estes et al. |
| 2003/0117296 A1 | 6/2003 | Seely |
| 2003/0119208 A1 | 6/2003 | Yoon et al. |
| 2003/0120152 A1 | 6/2003 | Omiya |
| 2003/0125612 A1 | 7/2003 | Fox et al. |
| 2003/0125613 A1 | 7/2003 | Enegren et al. |
| 2003/0125669 A1 | 7/2003 | Safabash et al. |
| 2003/0130616 A1 | 7/2003 | Steil et al. |
| 2003/0130619 A1 | 7/2003 | Safabash et al. |
| 2003/0132227 A1 | 7/2003 | Geisler et al. |
| 2003/0134347 A1 | 7/2003 | Heller et al. |
| 2003/0143746 A1 | 7/2003 | Sage |
| 2003/0153821 A1 | 8/2003 | Berner et al. |
| 2003/0158520 A1 | 8/2003 | Safabash et al. |
| 2003/0168338 A1 | 9/2003 | Gao et al. |
| 2003/0175987 A1 | 9/2003 | Verdonk et al. |
| 2003/0176183 A1 | 9/2003 | Drucker et al. |

(56) References Cited

U.S. PATENT DOCUMENTS

| 2003/0176933 A1 | 9/2003 | Lebel et al. |
| 2003/0187338 A1 | 10/2003 | Say et al. |
| 2003/0187470 A1 | 10/2003 | Chelak et al. |
| 2003/0188427 A1 | 10/2003 | Say et al. |
| 2003/0191377 A1 | 10/2003 | Robinson et al. |
| 2003/0199744 A1 | 10/2003 | Buse et al. |
| 2003/0199745 A1 | 10/2003 | Burson et al. |
| 2003/0199790 A1 | 10/2003 | Boecker et al. |
| 2003/0199823 A1 | 10/2003 | Bobroff et al. |
| 2003/0208113 A1 | 11/2003 | Mault et al. |
| 2003/0211050 A1 | 11/2003 | Majeti et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225324 A1 | 12/2003 | Anderson et al. |
| 2003/0225373 A1 | 12/2003 | Bobroff et al. |
| 2003/0225437 A1 | 12/2003 | Ferguson |
| 2003/0231550 A1 | 12/2003 | Macfarlane |
| 2003/0235817 A1 | 12/2003 | Bartkowiak et al. |
| 2004/0002682 A1 | 1/2004 | Kovelman et al. |
| 2004/0006263 A1 | 1/2004 | Anderson et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015063 A1 | 1/2004 | Denuzzio et al. |
| 2004/0015134 A1 | 1/2004 | Lavi et al. |
| 2004/0023253 A1 | 2/2004 | Kunwar et al. |
| 2004/0023317 A1 | 2/2004 | Motamedi et al. |
| 2004/0024327 A1 | 2/2004 | Brodnick |
| 2004/0024553 A1 | 2/2004 | Monfre et al. |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039406 A1 | 2/2004 | Jessen |
| 2004/0040840 A1 | 3/2004 | Mao et al. |
| 2004/0044272 A1 | 3/2004 | Moerman et al. |
| 2004/0045879 A1 | 3/2004 | Shults et al. |
| 2004/0052689 A1 | 3/2004 | Yao |
| 2004/0054263 A1 | 3/2004 | Moerman et al. |
| 2004/0054352 A1 | 3/2004 | Adams et al. |
| 2004/0064068 A1 | 4/2004 | DeNuzzio et al. |
| 2004/0068230 A1 | 4/2004 | Estes et al. |
| 2004/0074785 A1 | 4/2004 | Holker et al. |
| 2004/0077962 A1 | 4/2004 | Kroll |
| 2004/0078065 A1 | 4/2004 | Kroll |
| 2004/0078219 A1 | 4/2004 | Kaylor et al. |
| 2004/0093167 A1 | 5/2004 | Braig et al. |
| 2004/0099529 A1 | 5/2004 | Mao et al. |
| 2004/0106857 A1 | 6/2004 | Gough |
| 2004/0106858 A1 | 6/2004 | Say et al. |
| 2004/0108226 A1 | 6/2004 | Polychronakos et al. |
| 2004/0122297 A1 | 6/2004 | Stahmann et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138543 A1 | 7/2004 | Russell et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0143173 A1 | 7/2004 | Reghabi et al. |
| 2004/0146909 A1 | 7/2004 | Duong et al. |
| 2004/0147819 A1 | 7/2004 | Caduff et al. |
| 2004/0152187 A1 | 8/2004 | Haight et al. |
| 2004/0152622 A1 | 8/2004 | Keith et al. |
| 2004/0158137 A1 | 8/2004 | Eppstein et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0219664 A1 | 11/2004 | Heller et al. |
| 2004/0220517 A1 | 11/2004 | Starkweather et al. |
| 2004/0224001 A1 | 11/2004 | Pacetti et al. |
| 2004/0225338 A1 | 11/2004 | Lebel et al. |
| 2004/0236200 A1 | 11/2004 | Say et al. |
| 2004/0248282 A1 | 12/2004 | Sobha M. et al. |
| 2004/0249253 A1 | 12/2004 | Racchini et al. |
| 2004/0249420 A1 | 12/2004 | Olson et al. |
| 2004/0253365 A1 | 12/2004 | Warren et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003399 A1 | 1/2005 | Blackburn et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010265 A1 | 1/2005 | Baru et al. |
| 2005/0010269 A1 | 1/2005 | Lebel et al. |
| 2005/0016276 A1 | 1/2005 | Guan et al. |
| 2005/0026689 A1 | 2/2005 | Marks |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049472 A1 | 3/2005 | Manda et al. |
| 2005/0049473 A1 | 3/2005 | Desai et al. |
| 2005/0049553 A1 | 3/2005 | Triplett et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0077584 A1 | 4/2005 | Uhland et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096519 A1 | 5/2005 | Denuzzio et al. |
| 2005/0101847 A1 | 5/2005 | Routt et al. |
| 2005/0107677 A1 | 5/2005 | Ward et al. |
| 2005/0112169 A1 | 5/2005 | Brauker et al. |
| 2005/0113653 A1 | 5/2005 | Fox et al. |
| 2005/0113744 A1 | 5/2005 | Donoghue et al. |
| 2005/0114068 A1 | 5/2005 | Chey et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say et al. |
| 2005/0124873 A1 | 6/2005 | Shults et al. |
| 2005/0131305 A1 | 6/2005 | Danielson et al. |
| 2005/0131346 A1 | 6/2005 | Douglas |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0149089 A1 | 7/2005 | Trissel et al. |
| 2005/0154271 A1 | 7/2005 | Rasdal et al. |
| 2005/0176136 A1 | 8/2005 | Burd et al. |
| 2005/0177036 A1 | 8/2005 | Shults et al. |
| 2005/0177398 A1 | 8/2005 | Watanabe et al. |

(56) References Cited

U.S. PATENT DOCUMENTS

| | | |
|---|---|---|
| 2005/0181012 A1 | 8/2005 | Saint et al. |
| 2005/0182306 A1 | 8/2005 | Sloan |
| 2005/0182451 A1 | 8/2005 | Griffin et al. |
| 2005/0183954 A1 | 8/2005 | Hitchcock et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0211571 A1 | 9/2005 | Schulein et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0242479 A1* | 11/2005 | Petisce .............. A61B 5/14865 |
| | | 264/650 |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251083 A1 | 11/2005 | Carr-Brendel et al. |
| 2005/0261563 A1 | 11/2005 | Zhou et al. |
| 2005/0277164 A1 | 12/2005 | Drucker et al. |
| 2005/0277912 A1 | 12/2005 | John |
| 2005/0283114 A1 | 12/2005 | Bresina et al. |
| 2005/0287620 A1 | 12/2005 | Heller et al. |
| 2005/0288596 A1 | 12/2005 | Eigler et al. |
| 2005/0288725 A1 | 12/2005 | Hettrick et al. |
| 2006/0001538 A1 | 1/2006 | Kraft et al. |
| 2006/0001550 A1 | 1/2006 | Mann et al. |
| 2006/0004270 A1 | 1/2006 | Bedard et al. |
| 2006/0007017 A1 | 1/2006 | Mann et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0042353 A1 | 3/2006 | Marquis et al. |
| 2006/0047095 A1 | 3/2006 | Pacetti |
| 2006/0052745 A1 | 3/2006 | Van Antwerp et al. |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0079809 A1 | 4/2006 | Goldberger et al. |
| 2006/0091006 A1 | 5/2006 | Wang et al. |
| 2006/0094946 A1 | 5/2006 | Kellogg et al. |
| 2006/0100588 A1 | 5/2006 | Brunnberg et al. |
| 2006/0134165 A1 | 6/2006 | Pacetti |
| 2006/0142651 A1* | 6/2006 | Brister ................. A61B 5/1495 |
| | | 600/347 |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0171980 A1 | 8/2006 | Helmus et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0177379 A1 | 8/2006 | Asgari |
| 2006/0183871 A1 | 8/2006 | Ward et al. |
| 2006/0183984 A1 | 8/2006 | Dobbles et al. |
| 2006/0183985 A1 | 8/2006 | Brister et al. |
| 2006/0189851 A1 | 8/2006 | Tivig et al. |
| 2006/0189863 A1 | 8/2006 | Peyser et al. |
| 2006/0193375 A1 | 8/2006 | Lee |
| 2006/0195029 A1 | 8/2006 | Shults et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0235285 A1 | 10/2006 | Brister et al. |
| 2006/0241517 A1 | 10/2006 | Fowler et al. |
| 2006/0241669 A1 | 10/2006 | Stout et al. |
| 2006/0247508 A1 | 11/2006 | Fennell |
| 2006/0247671 A1 | 11/2006 | LeVaughn |
| 2006/0247685 A1 | 11/2006 | Bharmi |
| 2006/0247985 A1 | 11/2006 | Liamos et al. |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0253085 A1 | 11/2006 | Geismar et al. |
| 2006/0257995 A1 | 11/2006 | Simpson et al. |
| 2006/0258761 A1 | 11/2006 | Boock et al. |
| 2006/0258929 A1 | 11/2006 | Goode, Jr. et al. |
| 2006/0258939 A1 | 11/2006 | Pesach et al. |
| 2006/0258990 A1 | 11/2006 | Weber |
| 2006/0263763 A1 | 11/2006 | Simpson et al. |
| 2006/0263839 A1 | 11/2006 | Ward et al. |
| 2006/0264785 A1 | 11/2006 | Dring et al. |
| 2006/0269586 A1 | 11/2006 | Pacetti |
| 2006/0270922 A1 | 11/2006 | Brauker et al. |
| 2006/0270923 A1 | 11/2006 | Brauker et al. |
| 2006/0272652 A1 | 12/2006 | Stocker et al. |
| 2006/0275857 A1 | 12/2006 | Kjaer et al. |
| 2006/0281985 A1 | 12/2006 | Ward et al. |
| 2006/0287630 A1 | 12/2006 | Hommann |
| 2007/0007133 A1 | 1/2007 | Mang et al. |
| 2007/0016381 A1 | 1/2007 | Kamath et al. |
| 2007/0027370 A1 | 2/2007 | Brauker et al. |
| 2007/0027381 A1 | 2/2007 | Stafford |
| 2007/0027385 A1 | 2/2007 | Brister et al. |
| 2007/0032706 A1 | 2/2007 | Kamath et al. |
| 2007/0032718 A1 | 2/2007 | Shults et al. |
| 2007/0033074 A1 | 2/2007 | Nitzan et al. |
| 2007/0038044 A1 | 2/2007 | Dobbles et al. |
| 2007/0045902 A1 | 3/2007 | Brauker et al. |
| 2007/0049873 A1 | 3/2007 | Hansen et al. |
| 2007/0056858 A1 | 3/2007 | Chen et al. |
| 2007/0059196 A1 | 3/2007 | Brister et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |

(56)                References Cited

U.S. PATENT DOCUMENTS

| | | |
|---|---|---|
| 2007/0078322 A1 | 4/2007 | Stafford |
| 2007/0078323 A1 | 4/2007 | Reggiardo et al. |
| 2007/0085995 A1 | 4/2007 | Pesach et al. |
| 2007/0095661 A1 | 5/2007 | Wang et al. |
| 2007/0100222 A1 | 5/2007 | Mastrototaro et al. |
| 2007/0106135 A1 | 5/2007 | Sloan et al. |
| 2007/0108048 A1 | 5/2007 | Wang et al. |
| 2007/0112298 A1 | 5/2007 | Mueller, Jr. et al. |
| 2007/0116600 A1 | 5/2007 | Kochar et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129619 A1 | 6/2007 | Ward et al. |
| 2007/0129621 A1 | 6/2007 | Kellogg et al. |
| 2007/0135698 A1 | 6/2007 | Shah et al. |
| 2007/0135699 A1 | 6/2007 | Ward et al. |
| 2007/0149875 A1 | 6/2007 | Ouyang et al. |
| 2007/0151869 A1 | 7/2007 | Heller et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0167907 A1 | 7/2007 | Deslierres et al. |
| 2007/0168224 A1 | 7/2007 | Letzt et al. |
| 2007/0169533 A1 | 7/2007 | Shah et al. |
| 2007/0170073 A1 | 7/2007 | Wang et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173712 A1 | 7/2007 | Shah et al. |
| 2007/0173741 A1 | 7/2007 | Deshmukh et al. |
| 2007/0173761 A1 | 7/2007 | Kanderian, Jr. et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0200254 A1 | 8/2007 | Curry |
| 2007/0200267 A1 | 8/2007 | Tsai |
| 2007/0202562 A1 | 8/2007 | Curry |
| 2007/0203407 A1 | 8/2007 | Hoss et al. |
| 2007/0203410 A1 | 8/2007 | Say et al. |
| 2007/0203966 A1 | 8/2007 | Brauker et al. |
| 2007/0206193 A1 | 9/2007 | Pesach |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213657 A1 | 9/2007 | Jennewine et al. |
| 2007/0218097 A1 | 9/2007 | Heller et al. |
| 2007/0219441 A1 | 9/2007 | Carlin et al. |
| 2007/0224700 A1 | 9/2007 | Masters |
| 2007/0225579 A1 | 9/2007 | Lucassen et al. |
| 2007/0225675 A1 | 9/2007 | Robinson et al. |
| 2007/0227907 A1 | 10/2007 | Shah et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg |
| 2007/0233167 A1 | 10/2007 | Weiss et al. |
| 2007/0235331 A1 | 10/2007 | Simpson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2007/0249916 A1 | 10/2007 | Pesach et al. |
| 2007/0249922 A1 | 10/2007 | Peyser et al. |
| 2007/0255126 A1 | 11/2007 | Moberg et al. |
| 2007/0255302 A1 | 11/2007 | Koeppel et al. |
| 2007/0255321 A1 | 11/2007 | Gerber et al. |
| 2007/0275193 A1 | 11/2007 | Desimone et al. |
| 2007/0293742 A1 | 12/2007 | Simonsen et al. |
| 2007/0293747 A1 | 12/2007 | Douglas et al. |
| 2007/0299409 A1 | 12/2007 | Whitbourne et al. |
| 2007/0299617 A1 | 12/2007 | Willis |
| 2008/0000779 A1 | 1/2008 | Wang et al. |
| 2008/0004515 A1 | 1/2008 | Jennewine |
| 2008/0004601 A1 | 1/2008 | Jennewine et al. |
| 2008/0007141 A1 | 1/2008 | Deck |
| 2008/0009692 A1 | 1/2008 | Stafford |
| 2008/0009805 A1 | 1/2008 | Ethelfeld |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021668 A1 | 1/2008 | Son |
| 2008/0021972 A1 | 1/2008 | Huelskamp et al. |
| 2008/0027301 A1 | 1/2008 | Ward et al. |
| 2008/0027474 A1 | 1/2008 | Curry et al. |
| 2008/0029390 A1 | 2/2008 | Roche et al. |
| 2008/0029391 A1 | 2/2008 | Mao et al. |
| 2008/0031941 A1 | 2/2008 | Pettersson |
| 2008/0033254 A1 | 2/2008 | Kamath et al. |
| 2008/0034972 A1 | 2/2008 | Gough et al. |
| 2008/0039702 A1 | 2/2008 | Hayter et al. |
| 2008/0045824 A1 | 2/2008 | Tapsak et al. |
| 2008/0051714 A1 | 2/2008 | Moberg et al. |
| 2008/0051718 A1 | 2/2008 | Kavazov et al. |
| 2008/0051730 A1 | 2/2008 | Bikovsky |
| 2008/0051738 A1 | 2/2008 | Griffin |
| 2008/0058625 A1 | 3/2008 | McGarraugh et al. |
| 2008/0064937 A1 | 3/2008 | McGarraugh et al. |
| 2008/0064944 A1 | 3/2008 | Vanantwerp et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0072663 A1 | 3/2008 | Keenan et al. |
| 2008/0074270 A1 | 3/2008 | Ashwood-Smith et al. |
| 2008/0081000 A1 | 4/2008 | MacLeod et al. |
| 2008/0081977 A1 | 4/2008 | Hayter et al. |
| 2008/0083617 A1 | 4/2008 | Simpson et al. |
| 2008/0086039 A1 | 4/2008 | Heller et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0097246 A1 | 4/2008 | Stafford |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0114227 A1 | 5/2008 | Haar et al. |
| 2008/0114228 A1 | 5/2008 | McCluskey et al. |
| 2008/0114280 A1 | 5/2008 | Stafford |
| 2008/0115599 A1 | 5/2008 | Masters et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0119708 A1 | 5/2008 | Budiman |
| 2008/0125751 A1 | 5/2008 | Fjield et al. |
| 2008/0139903 A1 | 6/2008 | Bruce et al. |
| 2008/0139910 A1 | 6/2008 | Mastrototaro et al. |
| 2008/0148873 A1 | 6/2008 | Wang |
| 2008/0154101 A1 | 6/2008 | Jain et al. |
| 2008/0154513 A1 | 6/2008 | Kovatchev et al. |
| 2008/0156661 A1 | 7/2008 | Cooper et al. |
| 2008/0161656 A1 | 7/2008 | Bruce et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167641 A1 | 7/2008 | Hansen et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0187655 A1 | 8/2008 | Markle et al. |

(56) References Cited

U.S. PATENT DOCUMENTS

| | | |
|---|---|---|
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0188796 A1 | 8/2008 | Steil et al. |
| 2008/0188798 A1 | 8/2008 | Weber |
| 2008/0189051 A1 | 8/2008 | Goode et al. |
| 2008/0193936 A1 | 8/2008 | Squirrell |
| 2008/0194837 A1 | 8/2008 | Kim et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0210557 A1 | 9/2008 | Heller et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0249383 A1 | 10/2008 | Sass et al. |
| 2008/0249473 A1 | 10/2008 | Rutti et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269683 A1 | 10/2008 | Bikovsky |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278332 A1 | 11/2008 | Fennell et al. |
| 2008/0281270 A1 | 11/2008 | Cross et al. |
| 2008/0287761 A1 | 11/2008 | Hayter et al. |
| 2008/0287762 A1 | 11/2008 | Hayter et al. |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter et al. |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0305009 A1 | 12/2008 | Gamsey et al. |
| 2008/0305506 A1 | 12/2008 | Suri |
| 2008/0306368 A1 | 12/2008 | Goode, Jr. et al. |
| 2008/0306433 A1 | 12/2008 | Cesaroni |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter et al. |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0012376 A1 | 1/2009 | Agus |
| 2009/0012379 A1 | 1/2009 | Goode, Jr. et al. |
| 2009/0012472 A1 | 1/2009 | Ahm et al. |
| 2009/0018418 A1 | 1/2009 | Markle et al. |
| 2009/0018424 A1 | 1/2009 | Kamath et al. |
| 2009/0018425 A1 | 1/2009 | Ouyang et al. |
| 2009/0018426 A1 | 1/2009 | Markle et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine |
| 2009/0054748 A1 | 2/2009 | Feldman |
| 2009/0054749 A1 | 2/2009 | He |
| 2009/0054753 A1 | 2/2009 | Robinson et al. |
| 2009/0054812 A1 | 2/2009 | Mace |
| 2009/0055149 A1 | 2/2009 | Hayter et al. |
| 2009/0061528 A1 | 3/2009 | Suri |
| 2009/0062633 A1 | 3/2009 | Brauker et al. |
| 2009/0062635 A1 | 3/2009 | Brauker et al. |
| 2009/0062645 A1 | 3/2009 | Fehre et al. |
| 2009/0062767 A1 | 3/2009 | Van Antwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0082693 A1 | 3/2009 | Stafford |
| 2009/0082728 A1 | 3/2009 | Bikovsky |
| 2009/0085768 A1 | 4/2009 | Patel et al. |
| 2009/0088689 A1 | 4/2009 | Carter |
| 2009/0099434 A1 | 4/2009 | Liu et al. |
| 2009/0099436 A1 | 4/2009 | Brister et al. |
| 2009/0105569 A1 | 4/2009 | Stafford |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171178 A1 | 7/2009 | He et al. |
| 2009/0177143 A1 | 7/2009 | Markle et al. |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0192366 A1 | 7/2009 | Mensinger et al. |

(56) References Cited

U.S. PATENT DOCUMENTS

| | | |
|---|---|---|
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0221893 A1 | 9/2009 | Herndon |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0257911 A1 | 10/2009 | Thomas et al. |
| 2009/0259147 A1 | 10/2009 | Saikley et al. |
| 2009/0264719 A1 | 10/2009 | Markle et al. |
| 2009/0264825 A1 | 10/2009 | Cote et al. |
| 2009/0264856 A1 | 10/2009 | Lebel et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0306695 A1 | 12/2009 | Brenneman |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0010529 A1 | 1/2010 | Shi |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0023291 A1 | 1/2010 | Hayter et al. |
| 2010/0025174 A1 | 2/2010 | Dayton |
| 2010/0025238 A1 | 2/2010 | Gottlieb et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045231 A1 | 2/2010 | He |
| 2010/0045465 A1 | 2/2010 | Brauker et al. |
| 2010/0049015 A1 | 2/2010 | Martini et al. |
| 2010/0049021 A1 | 2/2010 | Jina et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094111 A1 | 4/2010 | Heller et al. |
| 2010/0096259 A1 | 4/2010 | Zhang et al. |
| 2010/0121167 A1 | 5/2010 | McGarraugh |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145174 A1 | 6/2010 | Alferness et al. |
| 2010/0145377 A1 | 6/2010 | Lai et al. |
| 2010/0152561 A1 | 6/2010 | Goodnow et al. |
| 2010/0160759 A1 | 6/2010 | Celentano et al. |
| 2010/0160761 A1 | 6/2010 | Say et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0169035 A1 | 7/2010 | Liang et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174266 A1 | 7/2010 | Estes |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0185178 A1 | 7/2010 | Sharp et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0213057 A1 | 8/2010 | Feldman et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228226 A1 | 9/2010 | Nielsen |
| 2010/0228497 A1 | 9/2010 | Kamath et al. |
| 2010/0230285 A1 | 9/2010 | Hoss et al. |
| 2010/0234707 A1 | 9/2010 | Goode, Jr. et al. |
| 2010/0234710 A1 | 9/2010 | Budiman et al. |
| 2010/0235106 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0261987 A1 | 10/2010 | Kamath et al. |
| 2010/0265073 A1 | 10/2010 | Harper |
| 2010/0274107 A1 | 10/2010 | Boock et al. |
| 2010/0274515 A1 | 10/2010 | Hoss et al. |
| 2010/0277342 A1 | 11/2010 | Sicurello et al. |
| 2010/0280341 A1 | 11/2010 | Boock et al. |
| 2010/0280441 A1 | 11/2010 | Wilinska et al. |
| 2010/0280782 A1 | 11/2010 | Harper |
| 2010/0286496 A1 | 11/2010 | Simpson et al. |
| 2010/0298684 A1 | 11/2010 | Leach et al. |
| 2010/0313105 A1 | 12/2010 | Nekoomaram et al. |
| 2010/0317935 A1 | 12/2010 | Roe et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0326842 A1 | 12/2010 | Mazza et al. |

(56)        References Cited

U.S. PATENT DOCUMENTS

| | | |
|---|---|---|
| 2010/0331642 A1 | 12/2010 | Bruce et al. |
| 2010/0331644 A1 | 12/2010 | Neale et al. |
| 2010/0331656 A1 | 12/2010 | Mensinger et al. |
| 2010/0331657 A1 | 12/2010 | Mensinger et al. |
| 2010/0331824 A1 | 12/2010 | Moberg et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0029269 A1 | 2/2011 | Hayter et al. |
| 2011/0040163 A1 | 2/2011 | Telson et al. |
| 2011/0040256 A1 | 2/2011 | Bobroff et al. |
| 2011/0046467 A1 | 2/2011 | Simpson et al. |
| 2011/0060287 A1 | 3/2011 | Ambruzs et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman |
| 2011/0082484 A1 | 4/2011 | Saravia et al. |
| 2011/0098656 A1 | 4/2011 | Burnell et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0124992 A1 | 5/2011 | Brauker et al. |
| 2011/0124997 A1 | 5/2011 | Goode, Jr. et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137601 A1 | 6/2011 | Goode, Jr. et al. |
| 2011/0144463 A1 | 6/2011 | Pesach et al. |
| 2011/0144465 A1 | 6/2011 | Shults et al. |
| 2011/0144683 A1 | 6/2011 | Butz et al. |
| 2011/0148905 A1 | 6/2011 | Simmons et al. |
| 2011/0174638 A1 | 7/2011 | Katsuki |
| 2011/0178378 A1 | 7/2011 | Brister et al. |
| 2011/0178461 A1 | 7/2011 | Chong et al. |
| 2011/0184268 A1 | 7/2011 | Taub |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0208155 A1 | 8/2011 | Palerm et al. |
| 2011/0213225 A1 | 9/2011 | Bernstein et al. |
| 2011/0218414 A1 | 9/2011 | Kamath et al. |
| 2011/0224523 A1 | 9/2011 | Budiman |
| 2011/0230735 A1 | 9/2011 | Wolfe et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257597 A1 | 10/2011 | Safabash et al. |
| 2011/0257895 A1 | 10/2011 | Brauker et al. |
| 2011/0263958 A1 | 10/2011 | Brauker et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0288574 A1 | 11/2011 | Curry et al. |
| 2011/0290645 A1 | 12/2011 | Brister et al. |
| 2011/0313317 A1 | 12/2011 | Callicoat et al. |
| 2011/0313543 A1 | 12/2011 | Brauker et al. |
| 2011/0319729 A1 | 12/2011 | Donnay et al. |
| 2011/0319734 A1 | 12/2011 | Gottlieb et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0059673 A1 | 3/2012 | Cohen et al. |
| 2012/0078071 A1 | 3/2012 | Bohm et al. |
| 2012/0083679 A1 | 4/2012 | Saikley et al. |
| 2012/0097289 A1 | 4/2012 | Chun et al. |
| 2012/0097554 A1 | 4/2012 | Shah et al. |
| 2012/0108931 A1 | 5/2012 | Taub et al. |
| 2012/0108934 A1 | 5/2012 | Valdes et al. |
| 2012/0123692 A1 | 5/2012 | Hayter |
| 2012/0130214 A1 | 5/2012 | Brister et al. |
| 2012/0150123 A1 | 6/2012 | Lawrence et al. |
| 2012/0165626 A1 | 6/2012 | Irina et al. |
| 2012/0165640 A1 | 6/2012 | Galley et al. |
| 2012/0172691 A1 | 7/2012 | Brauker et al. |
| 2012/0173200 A1 | 7/2012 | Breton et al. |
| 2012/0179014 A1 | 7/2012 | Shults et al. |
| 2012/0179106 A1 | 7/2012 | Cote et al. |
| 2012/0184909 A1 | 7/2012 | Gyrn |
| 2012/0186581 A1 | 7/2012 | Brauker et al. |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0190951 A1 | 7/2012 | Curry et al. |
| 2012/0190953 A1 | 7/2012 | Brauker et al. |
| 2012/0191063 A1 | 7/2012 | Brauker et al. |
| 2012/0197098 A1 | 8/2012 | Donnay et al. |
| 2012/0197222 A1 | 8/2012 | Donnay et al. |
| 2012/0203467 A1 | 8/2012 | Kamath et al. |
| 2012/0209098 A1 | 8/2012 | Goode, Jr. et al. |
| 2012/0209099 A1 | 8/2012 | Ljuhs et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0220979 A1 | 8/2012 | Brauker et al. |
| 2012/0226121 A1 | 9/2012 | Kamath et al. |
| 2012/0227737 A1 | 9/2012 | Mastrototaro et al. |
| 2012/0228134 A1 | 9/2012 | Simpson et al. |
| 2012/0238852 A1 | 9/2012 | Brauker et al. |
| 2012/0239304 A1 | 9/2012 | Hayter et al. |
| 2012/0245447 A1 | 9/2012 | Karan et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0259278 A1 | 10/2012 | Hayes et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0265042 A1 | 10/2012 | Neinast et al. |
| 2012/0277562 A1 | 11/2012 | Brister et al. |
| 2012/0277564 A1 | 11/2012 | Budiman et al. |
| 2012/0277565 A1 | 11/2012 | Budiman |
| 2012/0277566 A1 | 11/2012 | Kamath et al. |
| 2012/0283541 A1 | 11/2012 | Kamath et al. |
| 2012/0283542 A1 | 11/2012 | McGarraugh |
| 2012/0283543 A1 | 11/2012 | Brauker et al. |
| 2012/0283960 A1 | 11/2012 | Budiman |
| 2012/0291254 A1 | 11/2012 | Say |
| 2012/0291516 A1 | 11/2012 | Hayter et al. |
| 2012/0296311 A1 | 11/2012 | Brauker et al. |
| 2012/0302854 A1 | 11/2012 | Kamath et al. |
| 2012/0302855 A1 | 11/2012 | Kamath et al. |
| 2012/0303043 A1 | 11/2012 | Donnay |
| 2012/0323098 A1 | 12/2012 | Moein et al. |
| 2012/0323100 A1 | 12/2012 | Kamath et al. |
| 2012/0330561 A1 | 12/2012 | Hayter et al. |

(56)        References Cited

U.S. PATENT DOCUMENTS

| | | |
|---|---|---|
| 2013/0006112 A1 | 1/2013 | Vardy |
| 2013/0012798 A1 | 1/2013 | Brister et al. |
| 2013/0018317 A1 | 1/2013 | Bobroff et al. |
| 2013/0030273 A1 | 1/2013 | Tapsak et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0053665 A1 | 2/2013 | Hughes et al. |
| 2013/0053666 A1 | 2/2013 | Hughes et al. |
| 2013/0060105 A1 | 3/2013 | Shah et al. |
| 2013/0060112 A1 | 3/2013 | Pryor et al. |
| 2013/0076531 A1 | 3/2013 | San Vicente et al. |
| 2013/0076532 A1 | 3/2013 | San Vicente et al. |
| 2013/0078912 A1 | 3/2013 | San Vicente et al. |
| 2013/0116527 A1 | 5/2013 | Harper et al. |
| 2013/0131478 A1 | 5/2013 | Simpson et al. |
| 2013/0137953 A1 | 5/2013 | Harper et al. |
| 2013/0150691 A1 | 6/2013 | Pace et al. |
| 2013/0150692 A1 | 6/2013 | Kamath et al. |
| 2013/0162405 A1 | 6/2013 | Forster |
| 2013/0172695 A1 | 7/2013 | Nielsen et al. |
| 2013/0178727 A1 | 7/2013 | Hayter et al. |
| 2013/0184547 A1 | 7/2013 | Taub et al. |
| 2013/0199944 A1 | 8/2013 | Petisce |
| 2013/0231541 A1 | 9/2013 | Hayter et al. |
| 2013/0245412 A1 | 9/2013 | Rong et al. |
| 2013/0253846 A1 | 9/2013 | Hayter et al. |
| 2013/0267809 A1 | 10/2013 | Brister et al. |
| 2013/0267811 A1 | 10/2013 | Pryor et al. |
| 2013/0267812 A1 | 10/2013 | Pryor et al. |
| 2013/0267813 A1 | 10/2013 | Pryor et al. |
| 2013/0281807 A1 | 10/2013 | Hayter et al. |
| 2013/0282322 A1 | 10/2013 | Hayter et al. |
| 2013/0282403 A1 | 10/2013 | Hayter et al. |
| 2013/0303869 A1 | 11/2013 | Rebec et al. |
| 2013/0321425 A1 | 12/2013 | Greene et al. |
| 2013/0324823 A1 | 12/2013 | Koski et al. |
| 2013/0325352 A1 | 12/2013 | Greene et al. |
| 2013/0325504 A1 | 12/2013 | Greene et al. |
| 2013/0338454 A1 | 12/2013 | Hayter et al. |
| 2014/0005492 A1 | 1/2014 | Harttig |
| 2014/0005499 A1 | 1/2014 | Catt et al. |
| 2014/0005505 A1 | 1/2014 | Peyser et al. |
| 2014/0005508 A1 | 1/2014 | Estes et al. |
| 2014/0005968 A1 | 1/2014 | Budiman |
| 2014/0012118 A1 | 1/2014 | Mensinger et al. |
| 2014/0018642 A1 | 1/2014 | Hayter |
| 2014/0041441 A1 | 2/2014 | Hayter et al. |
| 2014/0046155 A1 | 2/2014 | Hayter et al. |
| 2014/0046156 A1 | 2/2014 | Hayter et al. |
| 2014/0046157 A1 | 2/2014 | Hayter et al. |
| 2014/0046160 A1 | 2/2014 | Terashima et al. |
| 2014/0046161 A1 | 2/2014 | Hayter et al. |
| 2014/0058223 A1 | 2/2014 | Markle et al. |
| 2014/0066736 A1 | 3/2014 | Budiman |
| 2014/0088389 A1 | 3/2014 | Simpson et al. |
| 2014/0088390 A1 | 3/2014 | He |
| 2014/0088392 A1 | 3/2014 | Bernstein et al. |
| 2014/0088908 A1 | 3/2014 | Hayter et al. |
| 2014/0094671 A1 | 4/2014 | Boock et al. |
| 2014/0094756 A1 | 4/2014 | Bobroff et al. |
| 2014/0100796 A1 | 4/2014 | Hayter et al. |
| 2014/0107450 A1 | 4/2014 | Simpson et al. |
| 2014/0107581 A1 | 4/2014 | Safabash et al. |
| 2014/0114156 A1 | 4/2014 | Bohm et al. |
| 2014/0121480 A1 | 5/2014 | Budiman et al. |
| 2014/0121488 A1 | 5/2014 | Budiman |
| 2014/0121989 A1 | 5/2014 | Kamath et al. |
| 2014/0129151 A1 | 5/2014 | Bhavaraju et al. |
| 2014/0142604 A1 | 5/2014 | Brenneman |
| 2014/0182350 A1 | 7/2014 | Bhavaraju et al. |
| 2014/0187876 A1 | 7/2014 | Ohkoshi |
| 2014/0188402 A1 | 7/2014 | Garcia et al. |
| 2014/0207400 A1 | 7/2014 | Hayter et al. |
| 2014/0221966 A1 | 8/2014 | Buckingham et al. |
| 2014/0236536 A1 | 8/2014 | Hayter et al. |
| 2014/0243638 A1 | 8/2014 | Harper et al. |
| 2014/0257059 A1 | 9/2014 | Budiman et al. |
| 2014/0276586 A1 | 9/2014 | Swaney et al. |
| 2014/0278189 A1 | 9/2014 | Vanslyke et al. |
| 2014/0336486 A1 | 11/2014 | Ouyang et al. |
| 2015/0005601 A1 | 1/2015 | Hoss et al. |
| 2015/0006109 A1 | 1/2015 | Fennell et al. |
| 2015/0025338 A1 | 1/2015 | Lee et al. |
| 2015/0094555 A1 | 4/2015 | He |
| 2015/0190076 A1 | 7/2015 | Ohkoshi et al. |
| 2015/0216456 A1 | 8/2015 | Budiman |
| 2015/0241407 A1 | 8/2015 | Ou et al. |
| 2015/0282742 A1 | 10/2015 | Hayter et al. |
| 2015/0289788 A1 | 10/2015 | Simpson et al. |
| 2015/0313521 A1 | 11/2015 | Say |
| 2015/0366510 A1 | 12/2015 | Budiman |
| 2015/0374299 A1 | 12/2015 | Hayter |
| 2016/0022221 A1 | 1/2016 | Ou et al. |
| 2016/0058344 A1 | 3/2016 | Peterson et al. |
| 2016/0058470 A1 | 3/2016 | Peterson et al. |
| 2016/0058471 A1 | 3/2016 | Peterson et al. |
| 2016/0058472 A1 | 3/2016 | Peterson et al. |
| 2016/0058473 A1 | 3/2016 | Peterson et al. |
| 2016/0058474 A1 | 3/2016 | Peterson et al. |
| 2016/0073941 A1 | 3/2016 | Bohm et al. |
| 2016/0106349 A1 | 4/2016 | Pryor et al. |
| 2016/0128615 A1 | 5/2016 | Curry et al. |
| 2016/0151006 A1 | 6/2016 | Harper et al. |
| 2016/0157758 A1 | 6/2016 | Bohm et al. |
| 2016/0198986 A1 | 7/2016 | Bohm et al. |
| 2016/0206233 A1 | 7/2016 | Hayter et al. |
| 2016/0220189 A1 | 8/2016 | Hayter et al. |
| 2016/0233632 A1 | 8/2016 | Scruggs et al. |
| 2016/0235346 A1 | 8/2016 | Liu et al. |
| 2016/0235365 A1 | 8/2016 | Liu et al. |
| 2016/0238589 A1 | 8/2016 | Harper et al. |
| 2016/0243302 A1 | 8/2016 | Gyrn |
| 2016/0245791 A1 | 8/2016 | Hayter et al. |
| 2016/0270705 A1 | 9/2016 | He |
| 2016/0287150 A1 | 10/2016 | Yu |
| 2016/0296697 A1 | 10/2016 | Hayter et al. |
| 2016/0317069 A1 | 11/2016 | Hayter et al. |
| 2016/0331283 A1 | 11/2016 | Rao et al. |
| 2017/0003766 A1 | 1/2017 | Budiman |
| 2017/0027484 A1 | 2/2017 | Hayter et al. |
| 2017/0042456 A1 | 2/2017 | Budiman |
| 2017/0042457 A1 | 2/2017 | Pace et al. |
| 2017/0049369 A1 | 2/2017 | Hayter et al. |
| 2017/0055851 A1 | 3/2017 | Al-Ali |
| 2017/0071511 A1 | 3/2017 | Garcia et al. |
| 2017/0112534 A1 | 4/2017 | Schoonmaker et al. |
| 2017/0124287 A1 | 5/2017 | Hayter et al. |
| 2017/0127982 A1 | 5/2017 | Larson et al. |
| 2017/0127985 A1 | 5/2017 | Thompson et al. |
| 2017/0128011 A1 | 5/2017 | Frey et al. |
| 2017/0188909 A1 | 7/2017 | Hayter et al. |
| 2017/0188910 A1 | 7/2017 | Halac et al. |
| 2017/0188911 A1 | 7/2017 | Halac et al. |
| 2017/0188912 A1 | 7/2017 | Halac et al. |
| 2017/0224258 A1 | 8/2017 | Hayter et al. |
| 2017/0258379 A1 | 9/2017 | Budiman et al. |
| 2017/0265790 A1 | 9/2017 | Budiman et al. |
| 2017/0281060 A1 | 10/2017 | Wedekind et al. |
| 2017/0281092 A1 | 10/2017 | Burnette et al. |
| 2017/0290512 A1 | 10/2017 | Antonio et al. |
| 2017/0290532 A1 | 10/2017 | Antonio et al. |
| 2017/0290533 A1 | 10/2017 | Antonio et al. |
| 2017/0290534 A1 | 10/2017 | Antonio et al. |
| 2017/0340250 A1 | 11/2017 | Hayter et al. |
| 2017/0347927 A1 | 12/2017 | He |
| 2018/0000389 A1 | 1/2018 | Harper et al. |
| 2018/0008174 A1 | 1/2018 | Bohm et al. |
| 2018/0008201 A1 | 1/2018 | Hayter et al. |
| 2018/0038844 A1 | 2/2018 | Hayter et al. |
| 2018/0042530 A1 | 2/2018 | Bohm et al. |
| 2018/0042531 A1 | 2/2018 | Budiman et al. |
| 2018/0042534 A1 | 2/2018 | Hayter |
| 2018/0043096 A1 | 2/2018 | Dobbles et al. |

(56)  References Cited

U.S. PATENT DOCUMENTS

| 2018/0045707 A1 | 2/2018 | Hayter et al. |
| 2018/0059093 A1 | 3/2018 | Hayter et al. |
| 2018/0064376 A1 | 3/2018 | Stafford |
| 2018/0064398 A1 | 3/2018 | Budiman |
| 2018/0085037 A1 | 3/2018 | Hayter et al. |
| 2018/0098721 A1 | 4/2018 | Hayter et al. |
| 2018/0146895 A1 | 5/2018 | Biederman et al. |
| 2018/0185587 A1 | 7/2018 | Brauker et al. |
| 2018/0228396 A1 | 8/2018 | Okubo et al. |
| 2018/0271414 A1 | 9/2018 | Deck et al. |
| 2018/0271415 A1 | 9/2018 | Bohm et al. |
| 2018/0328766 A1 | 11/2018 | Hayter et al. |
| 2018/0344220 A1 | 12/2018 | Hayter et al. |
| 2018/0364215 A1 | 12/2018 | Harper et al. |
| 2018/0368771 A1 | 12/2018 | Gray et al. |
| 2018/0368772 A1 | 12/2018 | Gray et al. |
| 2018/0368773 A1 | 12/2018 | Gray et al. |
| 2018/0368774 A1 | 12/2018 | Gray et al. |
| 2019/0035488 A1 | 1/2019 | Budiman |
| 2019/0070360 A1 | 3/2019 | Sloan et al. |
| 2019/0072538 A1 | 3/2019 | Hayter et al. |
| 2019/0076073 A1 | 3/2019 | Donnay et al. |
| 2019/0083012 A1 | 3/2019 | Hayter et al. |
| 2019/0083015 A1 | 3/2019 | Hayter |
| 2019/0117131 A1 | 4/2019 | Halac et al. |
| 2019/0117133 A1 | 4/2019 | Halac et al. |
| 2019/0120784 A1 | 4/2019 | Halac et al. |
| 2019/0120785 A1 | 4/2019 | Halac et al. |
| 2019/0133638 A1 | 5/2019 | Il et al. |
| 2019/0150802 A1 | 5/2019 | Budiman et al. |
| 2019/0151542 A1 | 5/2019 | Hayter et al. |
| 2019/0159734 A1 | 5/2019 | Budiman |
| 2019/0187814 A1 | 6/2019 | Budiman |
| 2019/0192071 A1 | 6/2019 | Taub et al. |
| 2019/0209009 A1 | 7/2019 | Brister et al. |
| 2019/0254575 A1 | 8/2019 | Hayter et al. |
| 2019/0261511 A1 | 8/2019 | Frick et al. |
| 2019/0261902 A1 | 8/2019 | Bohm et al. |
| 2019/0298232 A1 | 10/2019 | Ko et al. |
| 2019/0320948 A1 | 10/2019 | Bohm et al. |
| 2019/0320949 A1 | 10/2019 | Bohm et al. |
| 2019/0336051 A1 | 11/2019 | Bohm et al. |
| 2019/0336055 A1 | 11/2019 | Shah et al. |
| 2019/0350499 A1 | 11/2019 | Bohm et al. |
| 2019/0357817 A1 | 11/2019 | Bohm et al. |
| 2019/0357818 A1 | 11/2019 | Pryor et al. |
| 2019/0380627 A1 | 12/2019 | Bohm et al. |
| 2020/0022626 A1 | 1/2020 | Bohm et al. |
| 2020/0037874 A1 | 2/2020 | Simpson et al. |
| 2020/0037934 A1 | 2/2020 | Bohm et al. |
| 2020/0037935 A1 | 2/2020 | Bohm et al. |
| 2020/0037936 A1 | 2/2020 | Bohm et al. |
| 2020/0178899 A1 | 6/2020 | Chae et al. |
| 2020/0196919 A1 | 6/2020 | Rao et al. |
| 2020/0289748 A1 | 9/2020 | Lanigan et al. |
| 2020/0352480 A1 | 11/2020 | Lucisano et al. |
| 2021/0000399 A1 | 1/2021 | Curry et al. |
| 2021/0000400 A1 | 1/2021 | Curry et al. |
| 2021/0007651 A1 | 1/2021 | Donnay et al. |
| 2021/0022654 A1 | 1/2021 | Curry et al. |
| 2021/0038137 A1 | 2/2021 | Curry et al. |
| 2021/0052224 A1 | 2/2021 | Gray et al. |
| 2021/0113126 A1 | 4/2021 | Donnay et al. |

FOREIGN PATENT DOCUMENTS

| CN | 101711678 A | 5/2010 | | |
| CN | 102469966 A | 5/2012 | | |
| CN | 102473276 A | 5/2012 | | |
| CN | 103781422 A | 5/2014 | | |
| CN | 209606445 U | 11/2019 | | |
| CN | 212438615 U | 2/2021 | | |
| EP | 0098592 A2 | 1/1984 | | |
| EP | 0107634 A2 | 5/1984 | | |
| EP | 0127958 A2 | 12/1984 | | |
| EP | 0286118 A2 | 10/1988 | | |
| EP | 0288793 A2 | 11/1988 | | |
| EP | 0320109 A1 | 6/1989 | | |
| EP | 0352610 A2 | 1/1990 | | |
| EP | 0352631 A2 | 1/1990 | | |
| EP | 0353328 A1 | 2/1990 | | |
| EP | 0390390 A1 | 10/1990 | | |
| EP | 0396788 A1 | 11/1990 | | |
| EP | 0406473 A1 | 1/1991 | | |
| EP | 0440044 A1 | 8/1991 | | |
| EP | 0441252 A2 | 8/1991 | | |
| EP | 0441394 A2 | 8/1991 | | |
| EP | 0467078 A2 | 1/1992 | | |
| EP | 0472411 A1 | 2/1992 | | |
| EP | 0534074 A1 | 3/1993 | | |
| EP | 0535898 A1 | 4/1993 | | |
| EP | 0539751 A1 | 5/1993 | | |
| EP | 0563795 A1 | 10/1993 | | |
| EP | 0323605 B1 | 1/1994 | | |
| EP | 0286118 B1 | 1/1995 | | |
| EP | 0647849 A2 | 4/1995 | | |
| EP | 0424633 B1 | 1/1996 | | |
| EP | 0729366 A1 | 9/1996 | | |
| EP | 0747069 A2 | 12/1996 | | |
| EP | 0776628 A2 | 6/1997 | | |
| EP | 0817809 A1 | 1/1998 | | |
| EP | 0838230 A2 | 4/1998 | | |
| EP | 0867146 A1 | 9/1998 | | |
| EP | 0880936 A2 | 12/1998 | | |
| EP | 0885932 A2 | 12/1998 | | |
| EP | 0967788 A2 | 12/1999 | | |
| EP | 0995805 A1 | 4/2000 | | |
| EP | 1048264 A1 | 11/2000 | | |
| EP | 1077634 A1 | 2/2001 | | |
| EP | 1078258 A1 | 2/2001 | | |
| EP | 1102194 A2 | 5/2001 | | |
| EP | 0789540 B1 | 9/2001 | | |
| EP | 1153571 A1 | 11/2001 | | |
| EP | 0729366 B1 | 7/2002 | | |
| EP | 0817809 B1 | 7/2002 | | |
| EP | 1266607 A2 | 12/2002 | | |
| EP | 1338295 A1 | 8/2003 | | |
| EP | 1419731 A1 | 5/2004 | | |
| EP | 0939602 B1 | 9/2004 | | |
| EP | 1475113 A1 | 11/2004 | | |
| EP | 1498067 A1 | 1/2005 | | |
| EP | 1571582 A2 | 9/2005 | | |
| EP | 1850909 B1 | 4/2010 | | |
| EP | 1677668 B1 | 7/2010 | | |
| EP | 2223710 A1 | 9/2010 | | |
| EP | 2226086 A1 | 9/2010 | | |
| EP | 2228642 A1 | 9/2010 | | |
| EP | 2679156 A1 | 1/2014 | | |
| EP | 2069772 B1 | 5/2014 | | |
| EP | 3170451 A1 | 5/2017 | | |
| EP | 3170453 A1 | 5/2017 | | |
| EP | 3575796 A1 | 12/2019 | | |
| FR | 2656423 A1 | 6/1991 | | |
| FR | 2760962 A1 | 9/1998 | | |
| GB | 1442303 A | 7/1976 | | |
| GB | 2149918 A | 6/1985 | | |
| JP | S6283649 A | 4/1987 | | |
| JP | S6283849 A | 4/1987 | | |
| JP | H0783871 A | 3/1995 | | |
| JP | 2000060826 A | 2/2000 | | |
| JP | 2002515302 A | 5/2002 | | |
| JP | 2002189015 A | 7/2002 | | |
| JP | 2003108679 A | 4/2003 | | |
| JP | 2003522558 A | 7/2003 | | |
| JP | 2004000555 A | 1/2004 | | |
| JP | 2004506468 A | * 3/2004 | ......... A61B 5/14532 |
| JP | 2004524869 A | * 8/2004 | ........ A61M 5/14248 |
| JP | 2006346160 A | 12/2006 | | |
| JP | 2007501028 A | 1/2007 | | |
| JP | 2008506468 A | 3/2008 | | |
| JP | 2008511841 A | 4/2008 | | |
| JP | 2008209219 A | 9/2008 | | |
| JP | 2008246204 A | 10/2008 | | |
| JP | 2008253482 A | 10/2008 | | |

(56)           References Cited

FOREIGN PATENT DOCUMENTS

| | | | | |
|---|---|---|---|---|
| JP | 2009509166 | A | 3/2009 | |
| JP | 2010538745 | A | 12/2010 | |
| JP | 2013502978 | A | 1/2013 | |
| JP | 2014516628 | A | 7/2014 | |
| JP | WO2012131827 | A1 * | 7/2024 | ......... A61B 5/14503 |
| JP | 7612782 | B2 * | 1/2025 | .......... A61B 5/6801 |
| NZ | 573020 | A | 9/2010 | |
| WO | WO-8902720 | A1 | 4/1989 | |
| WO | WO-9000738 | A1 | 1/1990 | |
| WO | WO-9010861 | A1 | 9/1990 | |
| WO | WO-9013021 | A1 | 11/1990 | |
| WO | WO-9116416 | A1 | 10/1991 | |
| WO | WO-9213271 | A1 | 8/1992 | |
| WO | WO-9314693 | A1 | 8/1993 | |
| WO | WO-9323744 | A1 | 11/1993 | |
| WO | WO-9422367 | A1 | 10/1994 | |
| WO | WO-9507109 | A1 | 3/1995 | |
| WO | WO-9513838 | A1 | 5/1995 | |
| WO | WO-9601611 | A1 | 1/1996 | |
| WO | WO-9603117 | A1 | 2/1996 | |
| WO | WO-9614026 | A1 | 5/1996 | |
| WO | WO-9625089 | A1 | 8/1996 | |
| WO | WO-9630431 | A1 | 10/1996 | |
| WO | WO-9632076 | A1 | 10/1996 | |
| WO | WO-9635370 | A1 | 11/1996 | |
| WO | WO-9637246 | A1 | 11/1996 | |
| WO | WO-9701986 | A1 | 1/1997 | |
| WO | WO-9706727 | A1 | 2/1997 | |
| WO | WO-9715227 | A1 | 5/1997 | |
| WO | WO-9719188 | A1 | 5/1997 | |
| WO | WO-9728737 | A1 | 8/1997 | |
| WO | WO-9743633 | A1 | 11/1997 | |
| WO | WO-9824358 | A2 | 6/1998 | |
| WO | WO-9835053 | A2 | 8/1998 | |
| WO | WO-9838906 | A1 | 9/1998 | |
| WO | WO-9907878 | A1 | 2/1999 | |
| WO | WO-9908485 | A1 | 2/1999 | |
| WO | WO-9948419 | A1 | 9/1999 | |
| WO | WO-9956613 | A1 | 11/1999 | |
| WO | WO-9958051 | A1 | 11/1999 | |
| WO | WO-9958973 | A1 | 11/1999 | |
| WO | WO-9959657 | A1 | 11/1999 | |
| WO | WO-0012720 | A2 | 3/2000 | |
| WO | WO-0013002 | A2 | 3/2000 | |
| WO | WO-0013003 | A1 | 3/2000 | |
| WO | WO-0019887 | A1 | 4/2000 | |
| WO | WO-0032098 | A1 | 6/2000 | |
| WO | WO-0033065 | A1 | 6/2000 | |
| WO | WO-0049940 | A2 | 8/2000 | |
| WO | WO-0049941 | A1 | 8/2000 | |
| WO | WO-0059370 | A1 | 10/2000 | |
| WO | WO-0059373 | A1 | 10/2000 | |
| WO | WO-0074753 | A1 | 12/2000 | |
| WO | WO-0078210 | A1 | 12/2000 | |
| WO | WO-0112158 | A1 | 2/2001 | |
| WO | WO-0116579 | A1 | 3/2001 | |
| WO | WO-0120019 | A2 | 3/2001 | |
| WO | WO-0120334 | A1 | 3/2001 | |
| WO | WO-0134243 | A1 | 5/2001 | |
| WO | WO-0143660 | A2 | 6/2001 | |
| WO | WO-0152727 | A1 | 7/2001 | |
| WO | WO-0152935 | A1 | 7/2001 | |
| WO | WO-0154753 | A2 | 8/2001 | |
| WO | WO-0158348 | A2 | 8/2001 | |
| WO | WO-0168901 | A2 | 9/2001 | |
| WO | WO-0169222 | A2 | 9/2001 | |
| WO | WO-0188524 | A1 | 11/2001 | |
| WO | WO-0188534 | A2 | 11/2001 | |
| WO | WO-0205702 | A2 | 1/2002 | |
| WO | WO-0216905 | A2 | 2/2002 | |
| WO | WO-0224065 | A1 | 3/2002 | |
| WO | WO-0078210 | A9 | 5/2002 | |
| WO | WO-02082989 | A1 | 10/2002 | |
| WO | WO-02089666 | A2 | 11/2002 | |
| WO | WO-02100266 | A1 | 12/2002 | |
| WO | WO-03000127 | A2 | 1/2003 | |
| WO | WO-03022125 | A2 | 3/2003 | |
| WO | WO-03022327 | A2 | 3/2003 | |
| WO | WO-03063700 | A1 | 8/2003 | |
| WO | WO-03072269 | A1 | 9/2003 | |
| WO | WO-03076893 | A2 | 9/2003 | |
| WO | WO-03082091 | A2 | 10/2003 | |
| WO | WO-03101862 | A1 | 12/2003 | |
| WO | WO-2004009161 | A1 | 1/2004 | |
| WO | WO-2004060455 | A1 | 7/2004 | |
| WO | WO-2004110256 | A2 | 12/2004 | |
| WO | WO-2005010756 | A2 | 2/2005 | |
| WO | WO-2005011489 | A1 | 2/2005 | |
| WO | WO-2005012873 | A2 | 2/2005 | |
| WO | WO-2005026689 | A2 | 3/2005 | |
| WO | WO-2005032400 | A1 | 4/2005 | |
| WO | WO-2005046780 | A1 | 5/2005 | |
| WO | WO-2005057168 | A2 | 6/2005 | |
| WO | WO-2005057175 | A2 | 6/2005 | |
| WO | WO-2005065542 | A2 | 7/2005 | |
| WO | WO-2005078424 | A1 | 8/2005 | |
| WO | WO-2005026689 | A9 | 10/2005 | |
| WO | WO-2005093629 | A2 | 10/2005 | |
| WO | WO-2006008505 | A1 | 1/2006 | |
| WO | WO-2006017358 | A2 | 2/2006 | |
| WO | WO-2006021430 | A2 | 3/2006 | |
| WO | WO-2006024671 | A1 | 3/2006 | |
| WO | WO-2006026748 | A1 | 3/2006 | |
| WO | WO-2006038044 | A2 | 4/2006 | |
| WO | WO-2006050405 | A1 | 5/2006 | |
| WO | WO-2006067217 | A2 | 6/2006 | |
| WO | WO-2006075016 | A1 | 7/2006 | |
| WO | WO-2006077262 | A1 | 7/2006 | |
| WO | WO-2006081336 | A2 | 8/2006 | |
| WO | WO-2006105146 | A2 | 10/2006 | |
| WO | WO-2006118713 | A1 | 11/2006 | |
| WO | WO-2006131288 | A1 | 12/2006 | |
| WO | WO-2007002209 | A2 | 1/2007 | |
| WO | WO-2007002579 | A1 | 1/2007 | |
| WO | WO-2007031125 | A1 | 3/2007 | |
| WO | WO-2007037970 | A1 | 4/2007 | |
| WO | WO-2007065285 | A2 | 6/2007 | |
| WO | WO-2007097754 | A1 | 8/2007 | |
| WO | WO-2007114943 | A2 | 10/2007 | |
| WO | WO-2007127606 | A1 | 11/2007 | |
| WO | WO-2007137286 | A2 | 11/2007 | |
| WO | WO-2007143225 | A2 | 12/2007 | |
| WO | WO-2008001091 | A1 | 1/2008 | |
| WO | WO-2008021913 | A2 | 2/2008 | |
| WO | WO-2008065646 | A1 | 6/2008 | |
| WO | WO-2008076868 | A2 | 6/2008 | |
| WO | WO-2008078319 | A1 | 7/2008 | |
| WO | WO-2008083379 | A1 | 7/2008 | |
| WO | WO-2008086541 | A2 | 7/2008 | |
| WO | WO-2008115409 | A1 | 9/2008 | |
| WO | WO-2008124597 | A1 | 10/2008 | |
| WO | WO-2009010396 | A1 | 1/2009 | |
| WO | WO-2009035773 | A1 | 3/2009 | |
| WO | WO-2010022387 | A1 | 2/2010 | |
| WO | WO-2010078263 | A2 | 7/2010 | |
| WO | WO-2010091005 | A1 | 8/2010 | |
| WO | WO-2010091028 | A1 | 8/2010 | |
| WO | WO-2010091105 | A2 | 8/2010 | |
| WO | WO-2010099507 | A1 | 9/2010 | |
| WO | WO-2011025549 | A1 | 3/2011 | |
| WO | WO-2011077893 | A1 | 6/2011 | |
| WO | WO-2012103429 | A2 | 8/2012 | |
| WO | WO-2012131827 | A1 | 10/2012 | |
| WO | WO-2012142502 | A2 | 10/2012 | |
| WO | WO-2012143370 | A2 | 10/2012 | |
| WO | WO-2013035455 | A1 | 3/2013 | |
| WO | WO-2013136968 | A1 | 9/2013 | |
| WO | WO-2014045448 | A1 | 3/2014 | |
| WO | WO-2015131432 | A1 | 9/2015 | |
| WO | WO-2016120920 | A1 | 8/2016 | |
| WO | WO-2017040849 | A1 | 3/2017 | |
| WO | WO-2017098277 | A1 | 6/2017 | |
| WO | WO-2017170212 | A1 | 10/2017 | |
| WO | WO-2017172781 | A1 | 10/2017 | |

(56)                References Cited

FOREIGN PATENT DOCUMENTS

WO    WO-2017205899 A1    12/2017
WO    WO-2018156953 A1     8/2018
WO    WO-2019083939 A1     5/2019

OTHER PUBLICATIONS

US 8,027,708 B1, 09/2011, Shults et al. (withdrawn)
JP-WO2012131827-A1-translation (Year: 2012).*
JP-2004506468-A-translation (Year: 2004).*
JP-2004524869-A-translation (Year: 2004).*
JP-7612782-B2-translation (Year: 2024).*
Aalders, et al., "Development of a Wearable Glucose Sensor; Studies in Healthy Volunteers and in Diabetic Patients," The International Journal Of Artificial Organs, 1991, vol. 14, No. 2, pp. 102-108.
Abe, et al., "Characterization of Glucose Microsensors for Intracellular Measurements," Analytical Chemistry, 1992, vol. 64, No. 18, pp. 2160-2163.
Abel, et al., "Biosensors For in Vivo Glucose Measurements: Can We Cross the Experimental Stage," Biosensors & Bioelectronics, 2002, vol. 17, pp. 1059-1070.
Abel, et al., "Experience With An Implantable Glucose Sensor as a Prerequisite of an Artificial Beta Cell," Biomed. Biochim. Actan, 1984, vol. 43, No. 5, pp. 577-584.
Adhesives Research®, "Product Information Sheet ARclad® 9032-70," retrieved from https://www.adhesivesresearch.com/wp-content/uploads/2021/03/ARclad%C2%AE-9032-70-Product-Information-Sheet.pdf, 2021, 2 pages.
Adilman, et al., "Videogames: Knowing The Score, Creative Computing," Dec. 1983, Dialog: File 148; IAC Trade & Industry Database, vol. 9, p. 224(5) (9 pages).
Alcock S.J., et al., "Continuous Analyte Monitoring To Aid Clinical Practice," IEEE Engineering in Medicine & Biology, 1994, vol. 13, pp. 319-325.
Amer M.M.B., "An Accurate Amperometric Glucose Sensor Based Glucometer with Eliminated Cross-Sensitivity," Journal of Medical Engineering & Technology, vol. 26 (5), Sep./Oct. 2002, pp. 208-213.
American Diabetes Association., "Position Statement: Diagnosis and Classification of Diabetes Mellitus," Diabetes Care, vol. 30, Supplement 01, Jan. 2007, pp. S42-S47.
American Diabetes Association., "Position Statement: Standards of Medical Care in Diabetes," Diabetes Care, vol. 30, Supplement 01, Jan. 2007, pp. S4-S41.
American Diabetes Association., "Summary of Revisions for the 2007 Clinical Practice Recommendations," Diabetes Care, vol. 30, Supplement 01, Jan. 2007, pp. S3.
Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.
Armour J.C., et al., "Application of Chronic Intravascular Blood Glucose Sensor in Dogs," Diabetes, Dec. 1990, vol. 39, pp. 1519-1526.
Arnold M.A., et al., "Selectivity Assessment of Noninvasive Glucose Measurements Based on Analysis of Multivariate Calibration Vectors," Journal of Diabetes Science and Technology, vol. 1 (4), Jul. 2007, pp. 454-462.
Asberg P., et al., "Hydrogels of a Conducting Conjugated Polymer as 3-D Enzyme Electrode," Biosensors Bioelectronics, 2003, vol. 19, pp. 199-207.
Assolant-Vinet C.H., et al., "New Immobilized Enzyme Membranes for Tailor-Made Biosensors," Analytical Letters, 1986, vol. 19(7 &8), pp. 875-885.
Atanasov P., et al., "Biosensor for Continuous Glucose Monitoring," Biotechnology and Bioengineering, John Wiley & sons Inc, 1994, vol. 43, pp. 262-266.

Atanasov P., et al., "Implantation of a Refillable Glucose Monitoring-Telemetry Device," Biosensors and Bioelectronics, vol. 12 (7), 1997, pp. 669-680.
Aussedat B., et al., "A User-Friendly Method For Calibrating a Subcutaneous Glucose Sensor-Based Hypoglycaemic Alarm," Elsevier Science Limited, Biosensors & Bioelectronic, 1997, vol. 12, No. 11, pp. 1061-1071.
Aussedat B., et al., "Interstitial Glucose Concentration and Glycemia: Implications for Continuous Subcutaneous Glucose Monitoring," American Journal of Physiology—Endocrinology and Metabolism, vol. 278 (4), Apr. 1, 2000, pp. E716-E728.
Bailey T.S., et al., "Reduction in Hemoglobin A1C with Real-Time Continuous Glucose Monitoring: Results from a 12-Week Observational Study," Diabetes Technology & Therapeutics, vol. 9 (3), 2007, pp. 203-210.
Baker D.A., et al., "Dynamic Concentration Challenges for Biosensor Characterization," Biosensors & Bioelectronics, vol. 8, 1993, pp. 433-441.
Baker D.A., et al., "Dynamic Delay and Maximal Dynamic Error in Continuous Biosensors," Analytical Chemistry, vol. 68 (8), Apr. 15, 1996, pp. 1292-1297.
Bard A.J., et al., "Electrochemical Methods," Fundamentals and Applications, John Wiley & Sons, New York, 1980, pp. 173-175.
Bardeletti G., et al., "A Reliable L-Lactate Electrode with a New Membrane for Enzyme Immobilization for Amperometric Assay of Lactate," Analytica Chemica Acta, vol. 187, 1986, pp. 47-54.
Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.
Bellucci F., et al., "Electrochemical Behaviour of Graphite-Epoxy Composite Materials (GECM) in Aqueous Salt Solutions," Journal of Applied Electrochemistry, vol. 16 (1), Jan. 1986, pp. 15-22.
Bennion N., et al., "Alternate Site Glucose Testing: a Crossover Design," Diabetes Technology & Therapeutics, vol. 4 (1), 2002, pp. 25-33.
Berger M., et al., "Computer Programs to Assist the Physician in the Analysis of Self-Monitored Blood Glucose Data," Proceedings of the Annual Symposium on Computer Applications in Medical Care, 1988, pp. 52-57.
Bertrand C., et al., "Multipurpose Electrode with Different Enzyme Systems Bound to Collagen Films," Analytica Chemica Acta, 1981, vol. 126, pp. 23-34.
Bessman S.P., et al., "Progress toward a Glucose Sensor for the Artificial Pancreas," Proceedings of a Workshop on Ion-Selective Microelectrodes, Jun. 4-5, 1973, Boston University, 1973, pp. 189-197.
Biermann E., et al., "How Would Patients Behave if they were Continually Informed of their Blood Glucose Levels? A Simulation Study Using a "Virtual" Patient," Diabetes Technology & Therapeutics, vol. 10 (3), 2008, pp. 178-187.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Bindra D.S., et al., "Pulsed Amperometric Detection of Glucose in Biological Fluids at a Surface-Modified Gold Electrode," Analytical Chemistry, vol. 61 (22), Nov. 15, 1989, pp. 2566-2570.
Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.
Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.
Bland J.M., et al., "Statistical Methods for Assessing Agreement Between Two Methods of Clinical Measurement," The Lancet, Feb. 8, 1986, pp. 307-310.
Blank T.B., et al., "Clinical Results From a Non-Invasive Blood Glucose Monitor," Optical Diagnostics and Sensing of Biological Fluids and Glucose and Cholesterol Monitoring II, Proceedings of SPIE, vol. 4624, 2002, pp. 1-10.

(56)                 References Cited

OTHER PUBLICATIONS

Bobbioni-Harsch E., et al., "Lifespan of Subcutaneous Glucose Sensors and their Performances during Dynamic Glycaemia Changes in Rats," J. Biomed. Eng., vol. 15, 1993, pp. 457-463.

Bode B.W., "Clinical Utility of the Continuous Glucose Monitoring System," Diabetes Technology & Therapeutics, vol. 2, Supplement 1, 2000, pp. S35-S41.

Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.

Bode B.W., et al., "Using the Continuous Glucose Monitoring System to Improve the Management of Type 1 Diabetes," Diabetes Technology & Therapeutics, vol. 2, Supplement 1, 2000, pp. S43-S48.

Boedeker Plastics Inc, "Polyethylene Specifications," Polyethylene Data Sheet, Retrieved from http://www.boedeker.com/polye.sub.--p.htm on Aug. 19, 2009, 4 pages.

Boland E., et al., "Limitations of Conventional Methods of Self-Monitoring of Blood Glucose," Diabetes Care, vol. 24 (11), Nov. 2001, pp. 1858-1862.

Bolinder J., et al., "Self-Monitoring of Blood Glucose in Type I Diabetic Patients: Comparison with Continuous Microdialysis Measurements of Glucose in Subcutaneous Adipose Tissue during Ordinary Life Conditions," Diabetes Care, vol. 20 (1), Jan. 1997, pp. 64-70.

Bolinder J., et al., "Microdialysis Measurement of the Absolute Glucose Concentration in Subcutaneous Adipose Tissue Allowing Glucose Monitoring in Diabetic Patients," Rapid Communication, Diabetologia, vol. 35, 1992, pp. 1177-1180.

Bott A.W., "A Comparison of Cyclic Voltammetry and Cyclic Staircase Voltammetry," Current Separations, vol. 16 (1), 1997, pp. 23-26.

Bott A.W., "Electrochemical Methods for the Determination of Glucose," Current Separations, vol. 17 (1), 1998, pp. 25-31.

Bowman L., et al., "The Packaging of Implantable Integrated Sensors," IEEE Transactions in Biomedical Engineering, vol. BME-33 (2), Feb. 1986, pp. 248-255.

Boyne M.S., et al., "Timing of Changes in Interstitial and Venous Blood Glucose Measured With a Continuous Subcutaneous Glucose Sensor," Diabetes, vol. 52, Nov. 2003, pp. 2790-2794.

Brauker, et al., "Sustained Expression of High Levels of Human Factor IX from Human Cells Implanted within an Immunoisolation Device into Athymic Rodents," Human Gene Therapy, Apr. 10, 1998, vol. 9, pp. 879-888.

Brauker J., et al., "Local Inflammatory Response Around Diffusion Chambers Containing Xenografts," Transplantation, vol. 61 (12), Jun. 27, 1996, pp. 1671-1677.

Brauker J H., et al., "Neovascularization of Synthetic Membranes Directed by Membrane Microarchitecture," Journal of Biomedical Material Research, 1995, vol. 29, pp. 1517-1524.

Brauker J., "Unraveling Mysteries at the Biointerface: Molecular Mediator of Inhibition of Blood Vessel Formation in the Foreign Body Capsule Revealed," SurFACTS in Biomaterials, vol. 6 (3), 2001, pp. 1,5.

Braunwald E., "Biomarkers in Heart Failure," Medical Progress, The New England Journal of Medicine, vol. 358, May 15, 2008, pp. 2148-2159.

Bremer T., et al., "Is Blood Glucose Predictable from Previous Values? A Solicitation for Data," Perspectives in Diabetes, vol. 48, Mar. 1999, pp. 445-451.

Bremer T.M., et al., "Benchmark Data from the Literature for Evaluation of New Glucose Sensing Technologies," Diabetes Technology & Therapeutics, vol. 3 (3), 2001, pp. 409-418.

Brooks S.L., et al., "Development of an On-line Glucose Sensor for Fermentation Monitoring," Biosensors, vol. 3, 1987/1988, pp. 45-56.

Bruckel J., et al., "In Vivo Measurement of Subcutaneous Glucose Concentrations with an Enzymatic Glucose Sensor and a Wick Method," Klin Wochenschr, vol. 67, 1989, pp. 491-495.

Brunner G.A., et al., "Validation of Home Blood Glucose Meters with Respect to Clinical and Analytical Approaches," Diabetes Care, vol. 21, No. 4, Apr. 1998, pp. 585-590.

Brunstein E., et al., "Preparation and Validation of Implantable Electrodes for the Measurement of Oxygen and Glucose," Biomed Biochim. Acta, vol. 48 (11/12), 1989, pp. 911-917.

Cai Q., et al., "A Wireless, Remote Query Glucose Biosensor Based on a pH-Sensitive Polymer," Analytical Chemistry, vol. 76 (14), Jul. 15, 2004, pp. 4038-4043.

Cameron T., et al., "Micromodular Implants to Provide Electrical Stimulation of Paralyzed Muscles and Limbs," IEEE Transactions on Biomedical Engineering, vol. 44 (9), Sep. 1997, pp. 781-790.

Campanella L., et al., "Biosensor for Direct Determination of Glucose and Lactate in Undiluted Biological Fluids," Biosensors & Bioelectronics, vol. 8, 1993, pp. 307-314.

Candas B., et al., "An Adaptive Plasma Glucose Controller Based on a Nonlinear Insulin/Glucose Model," IEEE Transactions on Biomedical Engineering, vol. 41 (2), Feb. 1994, pp. 116-124.

Cass A.E.G., et al., "Ferrocene-Mediated Enzyme Electrodes for Amperometric Determination of Glucose," Analytical Chemistry, vol. 56 (4), Apr. 1984, pp. 667-671.

Cassidy J.F., et al., "Novel Electrochemical Device for the Detection of Cholesterol or Glucose," Analyst, vol. 118, Apr. 1993, pp. 415-418.

Chase H.P., et al., "Continuous Subcutaneous Glucose Monitoring in Children with Type 1 Diabetes," Pediatrics, vol. 107 (2), Feb. 2001, pp. 222-226.

Chase J.G., et al., "Targeted Glycemic Reduction in Critical Care Using Closed-Loop Control," Diabetes Technology & Therapeutics, vol. 7 (2), 2005, pp. 274-282.

Chen X., et al., "Glucose Microbiosensor Based on Alumina Sol-gel Matrix/Electropolymerized Composite Membrane," Biosensors and Bioelectronics, vol. 17, 2002, 9 pages.

Chen C., et al., "A Noninterference Polypyrrole Glucose Biosensor," Biosensors and Bioelectronics, vol. 22, 2006, pp. 639-643.

Chen T., et al., "In Situ Assembled Mass-Transport Controlling Micromembranes and Their Application in Implanted Amperometric Glucose Sensors," Analytical Chemistry, Aug. 15, 2000, vol. 72, No. 16, pp. 3757-3763.

Chen T., et al., "Defining the Period of Recovery of the Glucose Concentration after its Local Perturbation by the Implantation of a Miniature Sensor," Clinical Chemistry and Laboratory Medicine, vol. 40 (8), 2002, pp. 786-789.

Cheyne E.H., et al., "Performance of a Continuous Glucose Monitoring System During Controlled Hypoglycaemia in Healthy Volunteers," Diabetes Technology & Therapeutics, vol. 4 (5), 2002, pp. 607-613.

Chia C.W., et al., "Glucose Sensors: Toward Closed Loop Insulin Delivery," Endocrinology and Metabolism Clinics of North America, vol. 33, 2004, pp. 175-195.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Choleau C., et al., "Calibration of a Subcutaneous Amperometric Glucose Sensor Part 1. Effect of Measurement Uncertainties on the Determination of Sensor Sensitivity and Background Current," Biosensors and Bioelectronics, vol. 17, 2002, pp. 641-646.

Chung T.D., "In vitro Evaluation of the Continuous Monitoring Glucose Sensors with Perfluorinated Tetrafluoroethylene Coatings," Bulletin of the Korean Chemical Society, 2003, vol. 24, No. 4, pp. 514-516.

CIBA Specialty Chemicals, "Ciba® IRGACURE® 2959," Coating Effects Segment, Photoinitiator Product Description, Basel Switzerland, Apr. 2, 1998, 3 pages.

Claremont D.J., et al., "Potentially-Implantable, Ferrocene-Mediated Glucose Sensor," Journal of Biomedical Engineering, vol. 8, Jul. 1986, pp. 272-274.

Claremont D.J., et al., "Subcutaneous Implantation of a Ferrocene-Mediated Glucose Sensor in Pigs," Diabetologia, vol. 29, 1986, pp. 817-821.

Clark L.C., et al., "Configurational Cyclic Voltammetry: Increasing the Specificity and Reliability of Implanted Electrodes," IEEE/

(56) References Cited

OTHER PUBLICATIONS

Ninth Annual Conference of the Engineering in Medicine and Biology Society, 1987, pp. 0782-0783.

Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.

Clark L.C., et al., "One-Minute Electrochemical Enzymic Assay for Cholesterol in Biological Materials," Clinical Chemistry, vol. 27 (12), 1981, pp. 1978-1982.

Clarke W.L., et al., "Evaluating Clinical Accuracy of Systems for Self Monitoring of Blood Glucose," Technical Articles, Diabetes Care, vol. 10 (5), Sep.-Oct. 1987, pp. 622-628.

Colangelo V.J., et al., "Corrosion Rate Measurements in Vivo," Journal of Biomedical Materials Research, vol. 1, 1967, pp. 405-414.

Colowick S.P., et al., "Methods in Enzymology," vol. XLIV, Immobilized Enzymes, Edited by Mosbach K, New York Academic Press, 1976, 11 pages.

Coulet P.R., et al., "Enzymes Immobilized on Collagen Membranes: A Tool for Fundamental Research and Enzyme Engineering," Journal of Chromatography, vol. 215, 1981, pp. 65-72.

Coulet P.R., "Polymeric Membranes and Coupled Enzymes in the Design of Biosensors," Journal of Membrane Science, 1992, vol. 68, pp. 217-228.

Cox D.J., et al., "Accuracy of Perceiving Blood Glucose in IDDM," Diabetes Care, vol. 8 (6), Nov.-Dec. 1985, pp. 529-536.

Csoregi E., et al., "Amperometric Microbiosensors for Detection of Hydrogen Peroxide and Glucose Based on Peroxidase-Modified Carbon Fibers," Electroanalysis, vol. 6, 1994, pp. 925-933.

Csoregi E., et al., "Design and Optimization of a Selective Subcutaneously Implantable Glucose Electrode Based on 'Wired' Glucose Oxidase," Analytical Chemistry, vol. 67 (7), Apr. 1, 1995, pp. 1240-1244.

Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.

Cunningham D.D., et al., "In Vivo Glucose Sensing," Chemical Analysis, 2010, vol. 174, 466 pages.

Currie J.F., et al., "Novel Non-Intrusive Trans-Dermal Remote Wireless Micro-Fluidic Monitoring System Applied to Continuous Glucose and Lactate Assays for Casualty Care and Combat Readiness Assessment," RTO HFM Symposium, RTO-MP-HFM-109, Aug. 16-18, 2004, pp. '24-1' - '24-18'.

Dai W.S., et al., "Hydrogel Membranes with Mesh Size Asymmetry based on the Gradient Crosslinking of Poly(Vinyl Alcohol)," Journal of Membrane Science, 1999, vol. 156, pp. 67-79.

Danielsson B., et al., "Enzyme Thermistors," Methods in Enzymology, vol. 137, 1988, pp. 181-197.

D'Arrigo G., et al., "Porous-Si Based Bio Reactors for Glucose Monitoring and Drugs Production," Proceedings of SPIE, 2003, vol. 4982, pp. 178-184.

Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.

Davies M.L., et al., "Polymer Membranes in Clinical Sensor Applications," An overview of membrane function, Biomaterials, vol. 13 (14), 1992, pp. 971-978.

Davis G., et al., "Bioelectrochemical Fuel Cell and Sensor Based on a Quinoprotein, Alcohol Dehydrogenase," Enzyme and Microbial Technology, vol. 5 (5), Sep. 1983, pp. 383-388.

De Vos P., et al., "Considerations for Successful Transplantation of Encapsulated Pancreatic Islets," Diabetologia, vol. 45, 2002, pp. 159-173.

Deutsch T., et al., "Time Series Analysis and Control of Blood Glucose Levels in Diabetic Patients," Computer Methods and Programs in Biomedicine, Elsevier Scientific Publishers, vol. 41, 1994, pp. 167-182.

Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.

DuPont, "Dimension® AR Clinical Chemistry System," The Chemistry Analyzer that Makes the most of your Time, Money and Effort, Dade International, Chemistry Systems, Newark, 1998, 18 pages.

Durliat H., et al., "Spectrophotometric and Electrochemical Determinations of L( +)-Lactate in Blood by Use of Lactate Dehydrogenase from Yeast," Clinical Chemistry, vol. 22 (11), 1976, pp. 1802-1805.

Edwards Lifesciences, "Accuracy for You and Your Patients," Marketing materials, 2002, 4 pages.

El Degheidy M.M., et al., "Optimization of an Implantable Coated Wire Glucose Sensor," Journal of Biomedical Engineering, vol. 8, Apr. 1986, pp. 121-129.

ELCO Diagnostics Company, "Direct 30/30® Blood Glucose Sensor," Markwell Medical Catalog, 1990, 1 page.

El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.

El-Sa'ad L., et al., "Moisture Absorption by Epoxy Resins: The Reverse Thermal Effect," Journal of Materials Science, vol. 25, 1990, pp. 3577-3582.

Eren-Oruklu M., et al., "Estimation of Future Glucose Concentrations with Subject-Specific Recursive Linear Models," Diabetes Technology & Therapeutics, vol. 11 (4), 2009, pp. 243-253.

Ernst H., et al., "Reliable Glucose Monitoring Through the Use of Microsystem Technology," Analytical Bioanalytical Chemistry, vol. 373, 2002, pp. 758-761.

Fabietti P.G., et al., "Clinical Validation of a New Control-Oriented Model of Insulin and Glucose Dynamics in Subjects with Type 1 Diabetes," Diabetes Technology & Therapeutics, vol. 9 (4), 2007, pp. 327-338.

Fahy B.G., et al., "An Analysis: Hyperglycemic Intensive Care Patients Need Continuous Glucose Monitoring-Easier Said Than Done," Journal of Diabetes Science and Technology, Diabetes Technology Society, vol. 2 (2), Mar. 2008, pp. 201-204.

Fare T.L., et al., "Functional Characterization of a Conducting Polymer-Based Immunoassay System," Biosensors & Bioelectronics, vol. 13 (3-4), 1998, pp. 459-470.

Feldman B., et al., "A Continuous Glucose Sensor Based on Wired Enzyme TM Technology—Results from a 3-Day Trial in Patients with Type 1 Diabetes," Diabetes Technology & Therapeutics, vol. 5 (5), 2003, pp. 769-779.

Feldman B., et al., "Correlation of Glucose Concentrations in Interstitial Fluid and Venous Blood During Periods of Rapid Glucose Change," Abbott Diabetes Care, Inc. Freestyle Navigator Continuous Glucose Monitor Pamphlet, 2004, 1 page.

Fischer U., et al., "Assessment of Subcutaneous Glucose Concentration: Validation of the Wick Technique as a Reference for Implanted Electrochemical Sensors in Normal and Diabetic Dogs," Diabetologia, vol. 30, 1987, pp. 940-945.

Fischer U., et al., "Hypoglycaemia-Warning by Means of Subcutaneous Electrochemical Glucose Sensors: An Animal Study," Horm. Metab. Res, vol. 27, 1995, p. 53. (Abstract Only).

Fischer U., et al., "Oxygen Tension at the Subcutaneous Implantation Site of Glucose Sensors," Biomed. Biochim. Acta, vol. 48 (11/12), 1989, pp. 965-971.

Freedman D., et al., "Statistics," Second Edition, W.W. Norton & Company, New York & London, 1991, p. 74 (3 pages).

Freiberger P., "Video Game Takes on Diabetes Superhero 'Captain Novolin' Offers Treatment Tips," Fourth Edition, Jun. 26, 1992, Business Section, 2 pages.

Frohnauer M.K., et al., "Graphical Human Insulin Time-Activity Profiles Using Standardized Definitions," Diabetes Technology & Therapeutics, vol. 3 (3), 2001, pp. 419-429.

Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.

(56) References Cited

OTHER PUBLICATIONS

Gabby R.A., et al., "Optical Coherence Tomography-Based Continuous Noninvasive Glucose Monitoring in Patients with Diabetes," Diabetes Technology & Therapeutics, vol. 10, Nov. 3, 2008, pp. 188-193.

Gamry Instruments, "Basics of Electrochemical Impedance Spectroscopy," 2007, 30 pages.

Ganesan N., et al., "Gold Layer-Based Dual Crosslinking Procedure of Glucose Oxidase with Ferrocene Monocarboxylic Acid Provides a Stable Biosensor," Analytical Biochemistry, Notes & Tips, vol. 343, 2005, pp. 188-191.

Ganesh A., et al., "Evaluation of the VIA® Blood Chemistry Monitor for Glucose in Healthy and Diabetic Volunteers," Journal of Diabetes Science and Technology, vol. 2 (2), Mar. 2008, pp. 182-193.

Garg S.K., et al., "Correlation of Fingerstick Blood Glucose Measurements With GlucoWatch Biographer Glucose Results in Young Subjects With Type 1 Diabetes," Emerging Treatments and Technologies, Diabetes Care, vol. 22 (10), Oct. 1999, pp. 1708-1714.

Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.

Garg S.K., "New Insulin Analogues," Diabetes Technology & Therapeutics, vol. 7 (5), 2005, pp. 813-817.

Geller R.I., et al., "Use of an Immunoisolation Device for Cell Transplantation and Tumor Immunotherapy," Annals of the New York Academy of Science, 1997, vol. 831, pp. 438-451.

Georgescu B., et al., "Real-Time Multi-Model Tracking of Myocardium in Echocardiography Using Robust Information Fusion," Medical Image Computing and Computer-Assisted Intervention, Springer-Verlag Berlin Heidelberg, 2004, pp. 777-785.

Gerritsen M., et al., "Influence of Inflammatory Cells and Serum on the Performance of Implantable Glucose Sensors," Journal of Biomedical Material Research, 2001, vol. 54, pp. 69-75.

Gerritsen M., et al., "Performance of Subcutaneously Implanted Glucose Sensors for Continuous Monitoring," The Netherlands Journal of Medicine, vol. 54, 1999, pp. 167-179.

Gerritsen M., et al., "Problems Associated with Subcutaneously Implanted Glucose Sensors," Diabetes Care, vol. 23 (2), Feb. 2000, pp. 143-145.

Gilligan B.J., et al., "Evaluation of a Subcutaneous Glucose Sensor Out to 3 Months in a Dog Model" Diabetes Care, vol. 17 (8), Aug. 1994, pp. 882-887.

Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.

Godsland I.F., et al., "Maximizing the Success Rate of Minimal Model Insulin Sensitivity Measurement in Humans: The Importance of Basal Glucose Levels," The Biochemical Society and the Medical Research Society, Clinical Science, vol. 101, 2001, pp. 1-9.

Goldman J.M., et al., "Masimo Signal Extraction Pulse Oximetry," Journal of Clinical Monitoring and Computing, vol. 16 (7), 2000, pp. 475-483.

Gouda M.D., et al., "Thermal Inactivation of Glucose Oxidase," The Journal of Biological Chemistry, vol. 278 (27), Issue of Jul. 4, 2003, pp. 24324-24333.

Gough D.A., et al., "Frequency Characterization of Blood Glucose Dynamics," Annals of Biomedical Engineering, vol. 31, 2003, pp. 91-97.

Gough D.A., et al., "Immobilized Glucose Oxidase in Implantable Glucose Sensor Technology," Diabetes Technology & Therapeutics, vol. 2 (3), 2000, pp. 377-380.

Gough D.A., "The implantable Glucose Sensor: An Example of Bioengineering Design," Introduction to Bioengineering, 2001, Chapter 3, pp. 57-66.

Gregg B A., et al., "Cross-Linked Redox Gels Containing Glucose Oxidase for Amperometric Biosensor Applications," Anal Chem, 1990, vol. 62, pp. 258-263.

Gross, et al., "Diabetes Technology & Therapeutics," Letters to the Editor, Diabetes Technology & Therapeutics, vol. 3 (1), 2001, pp. 129-131.

Gross T.M., et al., "Efficacy and Reliability of the Continuous Glucose Monitoring System," Diabetes Technology & Therapeutics, vol. 2, Supplement 1, 2000, pp. S19-S26.

Gross T.M., et al., "Performance Evaluation Of The Minimed® Continuous Glucose Monitoring System During Patient Home Use," Diabetes Technology & Therapeutics, vol. 2(1), 2000, pp. 49-56.

Guerci B., et al., "Clinical Performance of CGMS in Type 1 Diabetic Patients Treated by Continuous Subcutaneous Insulin Infusion Using Insulin Analogs," Diabetes Care, vol. 26, 2003, pp. 582-589.

Hagvik J., "Glucose Measurement: Time for a Gold Standard," Journal of Diabetes Science and Technology, vol. 1 (2), Mar. 2007, pp. 169-172.

Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.

Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.

Hall S.B., et al., "Electrochemical Oxidation of Hydrogen Peroxide at Platinum Electrodes. Part III: Effect of Temperature," Electrochimica Acta, vol. 44, 1999, pp. 2455-2462.

Hall S.B., et al., "Electrochemical Oxidation of Hydrogen Peroxide at Platinum Electrodes. Part IV: Phosphate Buffer Dependence," Electrochimica Acta, vol. 44, 1999, pp. 4573-4582.

Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.

Hamilton, "Complete Guide to Selecting the Right Hamilton Gastight, Microliter, and Specialty Syringe for your Application," Syringe Selection, www.hamiltoncompany.com 2006, 20 pages.

Harrison, et al., "Characterization of Perfluorosulfonic Acid Polymer Coated Enzyme Electrodes and a Miniaturized Integrated Potentiostat for Glucose Analysis in Whole Blood," Analytical Chemistry, 1988, vol. 60, pp. 2002-2007.

Hashiguchi Y., et al., "Development of a Miniaturized Glucose Monitoring System by Combining a Needle-Type Glucose Sensor with Microdialysis Sampling Method: Long-term subcutaneous tissue glucose monitoring in ambulatory diabetic patients," Diabetes Care, vol. 17, No. 5, May 1994, pp. 387-396.

Heinemann L., et al., "Review: Measurement of Insulin Absorption and Insulin Action," Diabetes Technology & Therapeutics, vol. 6 (5), 2004, pp. 698-718.

Heinemann L., "Measurement Quality of Blood Glucose Meters: Is There a Need for an Institution with an Unbiased View?," Journal of Diabetes Science and Technology, vol. 1 (2), Mar. 2007, pp. 178-180.

Heinemann L., "Review: Variability of Insulin Absorption and Insulin Action," Diabetes Technology & Therapeutics, vol. 4 (5), 2002, pp. 673-682.

Heise T., et al., "Hypoglycemia warning signal and glucose sensors: Requirements and concepts," Diabetes Technology & Therapeutics, vol. 5, No. 4, 2003, pp. 563-571.

Heller A., "Electrical Connection of Enzyme Redox Centers to Electrodes," J. Phys. Chem., vol. 96, 1992, pp. 3579-3587.

Heller A., "Electrical Wiring of Redox Enzymes," Ace. Chem. Res., vol. 23, 1990, pp. 128-134.

Heller A., et al., "Electrochemical Glucose Sensors and Their Applications in Diabetes Management," Chemical Reviews, May 9, 2008, vol. 108, No. 6 pp. 2482-2505.

Heller A., "Implanted Electrochemical Glucose Sensors for the Management of Diabetes," Annu. Rev., Biomed Eng., vol. 1, 1999, pp. 153-175.

Heller A., "Plugging Metal Connectors into Enzymes," Nature Biotechnology, vol. 21, No. 6, Jun. 2003, pp. 631-632.

Hicks J.M., "In Situ Monitoring," Clinical Chemistry, vol. 31 (12), 1985, pp. 1931-1935.

(56) References Cited

OTHER PUBLICATIONS

Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.

Hoel P.G., "Elementary Statistics," Fourth Edition, John Wiley & Sons, Inc., 1976, pp. 113-114.

Hoss U., et al., "Continuous Glucose Monitoring in Subcutaneous Tissue Using Factory-Calibrated Sensors: A Pilot Study," Diabetes Technology & Therapeutics, 2010, vol. 12 (8), pp. 591-597.

Houghton Mifflin Company, "American Heritage Dictionary," 4th Edition, 2000, pp. 82.

Houghton Mifflin Company, "Xenogenic, the American Heritage Stedman's Medical Dictionary," 2002, Answers.Com, retrieved from http://www.answers.com/topic/xenogenic , on Nov. 7, 2006, 2 Pages.

Hovorka R., et al., "Closing the Loop: The Adicol Experience," Diabetes Technology & Therapeutics, vol. 6 (3), 2004, pp. 307-318.

Hovorka R., et al., "Nonlinear Model Predictive Control of Glucose Concentration in Subjects with Type 1 Diabetes," Physiological Measurement, vol. 25, Jul. 2004, pp. 905-920.

Hrapovic S., et al., "Picoamperometric Detection of Glucose at Ultrasmall Platinum-Based Biosensors Preparation and Characterization," Anal. Chem, vol. 75, 2003, pp. 3308-3315.

Hu Y., et al., "A Needle-Type Enzyme-Based Lactate Sensor for In Vivo Monitoring," Analytica Chimica Acta, vol. 281, 1993, pp. 503-511.

Huang C., et al., "Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode," U.S. Department of Commence/NTIS, 1975, 126 pages.

Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.

Hunsley B., et al., "Whole Blood Glucose Standard Is Key to Accurate Insulin Dosages," Journal of Diabetes Science and Technology, vol. 1 (2), Mar. 2007, pp. 173-177.

Hunter I., et al., "Minimally Invasive Glucose Sensor and Insulin Delivery System," MIT Home Automation and Healthcare Consortium, Mar. 31, 2000, Progress Report No. 25, 17 pages.

International Preliminary Report on Patentability for Application No. PCT/US2005/006301, mailed Aug. 30, 2006, 4 pages.

International Preliminary Report on Patentability for Application No. PCT/US2007/080848 mailed Apr. 13, 2010, 6 pages.

International Preliminary Report on Patentability for Application No. PCT/US2008/058158, mailed Sep. 29, 2009, 9 pages.

International Preliminary Report on Patentability for Application No. PCT/US2008/065978 mailed Jun. 19, 2008, 14 pages.

International Preliminary Report on Patentability for Application No. PCT/US2016/068102 mailed on Jul. 12, 2018, 08 pages.

International Preliminary Report on Patentability for Application No. PCT/US2018/039122 mailed Jan. 2, 2020, 99 pages.

International Preliminary Report on Patentability for Application No. PCT/US2018/057011 mailed May 7, 2020, 8 pages.

International Search Report and Written Opinion for Application No. PCT/US2005/006301, mailed Jun. 22, 2005, 4 pages.

International Search Report and Written Opinion for Application No. PCT/US2007/080848 mailed Aug. 28, 2008, 6 pages.

International Search Report and Written Opinion for Application No. PCT/US2008/058158, mailed Aug. 8, 2008, 10 pages.

International Search Report and Written opinion for Application No. PCT/US2008/065978 mailed Oct. 2, 2008, 14 pages.

International Search Report and Written Opinion for Application No. PCT/US2016/068102 mailed on May 18, 2017, 10 pages.

International Search Report and Written opinion for Application No. PCT/US2018/039122 mailed Dec. 7, 2018, 106 pages.

International Search Report and Written opinion for Application No. PCT/US2018/057011 mailed Feb. 6, 2019, 9 pages.

Isermann R., et al., "Trends in the Application of Model-Based Fault Detection and Diagnosis of Technical Processes", Control Engineering Practice, vol. 5 (5), 1997, pp. 709-719.

Isermann R., "Supervision, Fault-Detection and Fault-Diagnosis Methods—An Introduction," Control Engineering Practice, vol. 5 (5), 1997, pp. 639-652.

Ishikawa M., et al., "Initial Evaluation of A 290-Mm Diameter Subcutaneous Glucose Sensor: Glucose Monitoring With A Biocompatible, Flexible-Wire, Enzyme-Based Amperometric Microsensor in Diabetic and Nondiabetic Humans," Journal of Diabetes and Its Complications, vol. 12, 1998, pp. 295-301.

Jablecki M., et al., "Simulations of the Frequency Response of Implantable Glucose Sensors," Analytical Chemistry, vol. 72, 2000, 1853-1859.

Jaffari S.A., et al., "Recent Advances in Amperometric Glucose Biosensors for In Vivo Monitoring," Physiological Measurement, 1995, vol. 16, pp. 1-15.

Jaremko J., et al., "Advances Toward the Implantable Artificial Pancreas for Treatment of Diabetes," Diabetes Care, vol. 21 (3), Mar. 1998, pp. 444-450.

Jensen M.B., et al., "Fast Wave Forms for Pulsed Electrochemical Detection of Glucose by Incorporation of Reductive Desorption of Oxidation Products,"Analytical Chemistry, vol. 69 (9), May 1997, pp. 1776-1781.

Jeong R.A., et al., "In Vivo Calibration of the Subcutaneous Amperometric Glucose Sensors Using a Non-Enzyme Electrode," Biosensors and Bioelectronics, Elsevier, vol. 19, 2003, pp. 313-319.

Jeutter D.C., "A Transcutaneous Implanted Battery Recharging and Biotelemeter Power Switching System," IEEE Transactions on Biomedical Engineering, vol. BME-29 (5), May 1982, pp. 314-321.

Jeutter D.C., et al., "Design of a Radio-Linked Implantable Cochlear Prosthesis Using Surface Acoustic Wave Devices," IEEE Transactions on Ultrasonics, Ferroelectrics and Frequency Control, vol. 40 (5), Sep. 1993, pp. 469-477.

Jimenez C., et al., "Glucose Sensor Based on an Amperometric Microelectrode with Photopolymerizable Enzyme Membrane," Sensors and Actuators B, vol. 26-27, 1995, pp. 421-424.

Jobst G., et al., "Thin-Film Microbiosensors for Glucose-Lactate Monitoring," Anal Chem, Sep. 15, 1996, vol. 68(18), pp. 3173-3179.

Johnson K.W., et al., "In Vivo Evaluation of an Electroenzymatic Glucose Sensor Implanted in Subcutaneous Tissue," Biosensors and Bioelectronics, 1992, vol. 7, pp. 709-714.

Johnson K.W., "Reproducible Electrodeposition of Biomolecules for the Fabrication of Miniature Electroenzymatic Biosensors," Sensors and Actuators B, vol. 5, 1991, pp. 85-89.

Johnson P.C., "Peripheral Circulation," John Wiley & Sons, 1978, p. 198 (5 pages).

Jones S.M., et al., "Optimal Insulin Pump Dosing and Postprandial Glycemia Following a Pizza Meal Using the Continuous Glucose Monitoring System," Diabetes Technology & Therapeutics, vol. 7 (2), Apr. 2005, pp. 233-240.

Joung G.B., et al., "An Energy Transmission System for an Artificial Heart Using Leakage Inductance Compensation of Transcutaneous Transformer," IEEE Transactions on Power Electronics, vol. 13 (6), Nov. 1998, pp. 1013-1022.

Jovanovic L.M.D., "The Role of Continuous Glucose Monitoring in Gestational Diabetes Mellitus," Diabetes Technology and Therapeutics, vol. 2 (1), 2000, pp. S67-S71.

Jungheim K., et al., "How Rapid Does Glucose Concentration Change in Daily Life of Patients with Type 1 Diabetes?," Diabetologia, 2002, vol. 45, pp. A250-A276.

Jungheim K., et al., "Risky Delay of Hypoglycemia Detection by Glucose Monitoring at the Arm," Diabetes Care, vol. 24 (7), Jul. 2001, pp. 1303-1304.

Kacaniklic V., et al., "Amperometric Biosensors for Detection of L- and D-Amino Acids Based on Coimmoblized Peroxidase and L- and D-Amino Acid Oxidases in Carbon Paste Electrodes," Electroanalysis, vol. 6, May-Jun. 1994, pp. 381-390.

Kamath A., et al., "Calibration of a Continuous Glucose Monitor: Effect of Glucose Rate of Change," Eighth Annual Diabetes Technology Meeting, Nov. 13-15, 2008, pp. A88 (2 pages).

(56)     References Cited

OTHER PUBLICATIONS

Kang S.K., et al., "In Vitro and Short-Term in Vivo Characteristics of a Kel-F Thin Film Modified Glucose Sensor," Analytical Sciences, vol. 19, Nov. 2003, pp. 1481-1486.

Kaplan S.M., "Wiley Electrical and Electronics Engineering Dictionary," IEEE Press, John Wiley & Sons, Inc., 2004, pp. 141, 142, 548 & 549.

Kargol M., et al., "Studies on the Structural Properties of Porous Membranes: Measurement of Linear Dimensions of Solutes," Biophysical Chemistry, 2001, vol. 91, pp. 263-271.

Karube I., et al., "Microbiosensors for Acetylcholine and Glucose," Biosensors & Bioelectronics, 1993, vol. 8, pp. 219-228.

Kaufman F.R., et al., "A Pilot Study of the Continuous Glucose Monitoring System," Diabetes Care, vol. 24 (12), Dec. 2001, pp. 2030-2034.

Kaufman F.R., "Role of the Continuous Glucose Monitoring System in Pediatric Patients," Diabetes Technology and Therapeutics, vol. 2 (1), 2000, S49-S52.

Kawagoe J.L., et al., "Enzyme-Modified Organic Conducting Salt Microelectrode," Analytical Chemistry, vol. 63, 1991, pp. 2961-2965.

Keedy F.H., et al., "Determination of Urate in Undiluted Whole Blood by Enzyme Electrode," Biosensors and Bioelectronics, vol. 6, 1991, pp. 491-499.

Kerner, et al., "A Potentially Implantable Enzyme Electrode for Amperometric Measurement of Glucose," Hormone and Metabolic Research Supplement, vol. 20, 1988, pp. 8-13.

Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.

Kerner W., "Implantable Glucose Sensors: Present Status and Future Developments," Experimental and Clinical Endocrinol Diabetes, vol. 109 (2), 2001, pp. S341-S346.

Kiechle F.L., "The Impact of Continuous Glucose Monitoring on Hospital Point-of-Care Testing Programs," Diabetes Technology and Therapeutics, vol. 3 (4), 2001, pp. 647-649.

Kizilel S., et al., "Review: The Bioartificial Pancreas: Progress and Challenges," Diabetes Technology & Therapeutics, vol. 7 (6), 2005, pp. 968-985.

Klonoff D., et al., "Performance Metrics for Continuous Interstitial Glucose Monitoring; Approved Guideline," Clinical and Laboratory Standards Institute, POCT05-A, vol. 28 (33), 2008, 72 pages.

Klonoff D.C., "Editorial: Current, Emerging, and Future Trends in Metabolic Monitoring," Diabetes Technology & Therapeutics, vol. 4 (5), 2002, pp. 583-588.

Klueh U., et al., "Inflammation and Glucose Sensors: Use of Dexamethasone to Extend Glucose Sensor Function and Life Span in Vivo," Journal of Diabetes Science and Technology, vol. 1 (4), Jul. 2007, pp. 496-504.

Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.

Kondo T., et al., "A Miniature Glucose Sensor, Implantable in the Blood Stream," Diabetes Care, vol. 5 (3), May-Jun. 1982, 218-221.

Koschinsky T., et al., "Sensors For Glucose Monitoring: Technical And Clinical Aspects," Diabetes Metabolism Research and Reviews, vol. 17, No. 2, Jan. 1, 2001, pp. 113-123.

Koschinsky T., et al., "New Approach to Technical and Clinical Evaluation of Devices for Self-Monitoring of Blood Glucose," Diabetes Care, vol. 11 (8), Sep. 1988, pp. 619-629.

Koschinsky T., et al., "Review: Glucose Sensors and the Alternate Site Testing-like Phenomenon: Relationship Between Rapid Blood Glucose Changes and Glucose Sensor Signals," Diabetes Technology & Therapeutics, vol. 5 (5), 2003, pp. 829-842.

Kost J., et al., "Glucose-Sensitive Membranes Containing Glucose Oxidase: Activity, Swelling, And Permeability Studies," Journal of Biomedical Materials Research, vol. 19, 1985, pp. 1117-1133.

Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.

Koudelka M., et al., "In-Vivo Behaviour of Hypodermically Implanted Microfabricated Glucose Sensors," Biosensors and Bioelectronics, vol. 6, 1991, pp. 31-36.

Kovatchev B.P., et al., "Evaluating the Accuracy of Continuous Glucose-Monitoring Sensors: Continuous Glucose-Error Grid Analysis Illustrated by TheraSense Freestyle Navigator Data," Diabetes Care, vol. 27 (8), Aug. 2004, pp. 1922-1928.

Kovatchev B.P., et al., "Graphical and Numerical Evaluation of Continuous Glucose Sensing Time Lag," Diabetes Technology & Therapeutics, vol. 11 (3), 2009, pp. 139-143.

Kraver., et al., "A Mixed-Signal Sensor Interface Microinstrument," Sensors and Actuators A, Physical 2001, vol. 91, pp. 266-277.

Krouwer J.S., "Setting Performance Goals and Evaluating Total Analytical Error for Diagnostic Assays," Clinical Chemistry, vol. 48 (6), 2002, pp. 919-927.

Kruger D., et al., "Psychological Motivation and Patient Education: A Role for Continuous Glucose Monitoring," Diabetes Technology and Therapeutics, vol. 2 (1), 2000, pp. S93-S97.

Kulys J., et al., "Carbon-Paste Biosensors Array for Long-Term Glucose Measurement," Biosensors & Bioelectronics, vol. 9, 1994, pp. 491-500.

Kunjan K., et al., "Automated Blood Sampling and Glucose Sensing in Critical Care Settings," Journal of Diabetes Science and Technology, vol. 2 (2), Mar. 2008, pp. 194-200.

Kunzler J., et al.," Hydrogels based on Hydrophilic Side Chain Siloxanes," Poly Mat Sci and Eng, 1993, vol. 69, pp. 226-227.

Kunzler J F., et al., "Contact Lens Materials," Chemistry & Industry, Aug. 21, 1995, pp. 651-655.

Kurnik R.T., et al., "Application of the Mixtures of Experts Algorithm for Signal Processing in a Noninvasive Glucose Monitoring System," Sensors and Actuators B, vol. 60, 1999, pp. 19-26.

Kurtz T.W., et al., "Recommendations for Blood Pressure Measurement in Humans and Experimental Animals, Part 2: Blood Pressure Measurement In Experimental Animals: A Statement for Professionals From the Subcommittee of Professional and Public Education of the American Heart Association Council on High Blood Pressure Research," Hypertension, Feb. 2005, vol. 45, pp. 299-310.

Kuure-Kinsey M., et al., "A Dual-Rate Kalman Filter for Continuous Glucose Monitoring," Conf Proc IEEE Eng Med Biol Soc., 2006, vol. 1, pp. 63-66.

Lacourse W.R., et al., "Optimization of Waveforms for Pulsed Amperometric Detection of Carbohydrates Based on Pulsed Voltammetry," Analytical Chemistry, vol. 65, 1993, pp. 50-52.

Ladd M.F.C., et al., "Structure Determination By X-Ray Crystallography," 3rd Edition, Plenum Press, 1994, Ch. 1, pp. xxi-xxiv and 1-58.

Lee E., et al., "Effects of Pore Size, Void vol. and Pore Connectivity on Tissue Responses to Porous Silicone Implants," Society for Biomaterials, 25th Annual Meeting, 1999, p. 171.

Lee S.W., et al., "Combined Insulin Pump Therapy with Real-Time Continuous Glucose Monitoring Significantly Improves Glycemic Control Compared to Multiple Daily Injection Therapy in Pump Naïve Patients with Type 1 Diabetes; Single Center Pilot Study Experience," Journal of Diabetes Science and Technology, vol. 1 (3), May 2007, pp. 400-404.

Lehmann E.D., et al., Retrospective Validation of a Physiological Model of Glucose-Insulin Interaction in Type 1 Diabetes Mellitus. Medical Engineering & Physics, vol. 16, May 1994, pp. 193-202.

Lerner., et al., "An Implantable Electrochemical Glucose Sensor," Ann. N. Y. Acad. Sci., vol. 428, May 1984, pp. 263-278.

Lewandowski J.J., et al., "Evaluation of a Miniature Blood Glucose Sensor," Transaction—American Society for Artificial Internal Organs, vol. 34, 1988, pp. 255-258.

Leypoldt J.K., et al., "Model of a Two-Substrate Enzyme Electrode for Glucose," Analytical Chemistry, vol. 56, 1984, pp. 2896-2904.

Linke B., et al., "Amperometric Biosensor for In Vivo Glucose Sensing Based on Glucose Oxidase Immobilized In A Redox Hydrogel," Biosensors and Bioelectronics, vol. 9, 1994, pp. 151-158.

(56)                    References Cited

OTHER PUBLICATIONS

Lodwig V., et al., "Continuous Glucose Monitoring with Glucose Sensors: Calibration and Assessment Criteria," Diabetes Technology & Therapeutics, vol. 5 (4), 2003, pp. 572-587.

Loffler P., et al., "Separation and Determination of Traces of Ammonia in Air by Means of Chromatomembrane Cells," Fresenius Journal of Analytical Chemistry, 1995, vol. 352, pp. 613-614.

Lohn A., et al., "A Knowledge-Based System for Real-Time Validation of Calibrations and Measurements," Chemometrics and Intelligent Laboratory Systems, vol. 46, 1999, pp. 57-66.

Lortz J., et al., "What is Bluetooth? We Explain the Newest Short-Range Connectivity Technology," In Smart Computing Learning Series, Wireless Computing, vol. 8 (5), 2002, pp. 72-74.

Lowe C.R., "Biosensors," Trends in Biotechnology, vol. 2 (3), 1984, pp. 59-65.

Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.

Lyandres O., et al. "Progress toward an In Vivo Surface-Enhanced Raman Spectroscopy Glucose Sensor," Diabetes Technology and Therapeutics, vol. 10 (4), 2008, pp. 257-265.

Lyman D J., "Polyurethanes. I. The Solution Polymerization of Diisocyanates with Ethylene Glycol," Journal of Polymer Science, 1960, vol. XLV, pp. 49-59.

Lynch S.M., et al., "Estimation-Based Model Predictive Control of Blood Glucose in Type I Diabetics: A Simulation Study," Proceedings of the IEEE 27th Annual Northeast Bioengineering Conference, 2001, pp. 79-80.

Lynn P.A., "Recursive Digital Filters for Biological Signals," Med. & Biol. Engineering, vol. 9, 1971, pp. 37-43.

Madaras M B., et al., "Microfabricated Amperometric Creatine and Creatinine Biosensors," Analytica Chimica Acta, 1996, vol. 319, pp. 335-345.

Maher R.C., "A Method for Extrapolation of Missing Digital Audio Data," Preprints of Papers Presented at the AES Convention, New York, 1993, pp. 1-19.

Maher R.C., "Audio Enhancement Using Nonlinear Time-Frequency Filtering," AES 26th International Conference, Jul. 7-9, 2005, pp. 1-9.

Maidan R., et al., "Elimination of Electrooxidizable Interferent-Produced Currents in Amperometric Biosensors," Analytical Chemistry, vol. 64, 1992, pp. 2889-2896.

Makale M.T., et al., "Tissue Window Chamber System for Validation of Implanted Oxygen Sensors," American Journal of Physiology-Heart and Circulatory Physiology, vol. 284, Feb. 21, 2003, pp. 1-27.

Malin S.F., et al., "Noninvasive Prediction of Glucose by Near-Infrared Diffuse Reflectance Spectroscopy," Clinical Chemistry, vol. 45 (9), 1999, pp. 1651-1658.

Mancy K.H., et al., "A Galvanic Cell Oxygen Analyzer," Journal of Electroanalytical Chemistry, vol. 4, 1962, pp. 65-92.

Maran A., et al., "Continuous Subcutaneous Glucose Monitoring in Diabetic Patients," A Multicenter Analysis, Diabetes Care, vol. 25 (2), Feb. 2002, pp. 347-352.

March W.F., "Dealing with the Delay," Diabetes Technology & Therapeutics, vol. 4 (1), 2002, pp. 49-50.

Marena S., et al., "The Artificial Endocrine Pancreas in Clinical Practice and Research," Panminerva Medica, vol. 35 (2), 1993, pp. 67-74.

Martin R.F., "General Deming Regression for Estimating Systematic Bias and its Confidence Interval in Method-Comparison Studies," Clinical Chemistry, vol. 46 (1), 2000, pp. 100-104.

Mascini M., et al., "Glucose Electrochemical Probe with Extended Linearity for Whole Blood," Journal Pharmaceutical and Biomedical Analysis, vol. 7 (12), 1989, pp. 1507-1512.

Mastrototaro J.J., et al., "An Electroenzymatic Glucose Sensor Fabricated on a Flexible Substrate," Sensors and Actuators B, vol. 5, 1991, pp. 139-144.

Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.

Mastrototaro J.J., "The MiniMed Continuous Glucose Monitoring System," Diabetes Technology & Therapeutics, vol. 2, Supplement 1, 2000, pp. S13-S18.

Matsuki H., "Energy Transfer System Utilizing Amorphous Wires For Implantable Medical Devices," IEEE Transactions on Magnetics, vol. 31 (2), 1994, pp. 1276-1282.

Matsumoto T., et al., "A long-Term Lifetime Amperometric Glucose Sensor with a Perfluorocarbon Polymer Coating," Biosensors & Bioelectronics, vol. 16, 2001, pp. 271-276.

Matsumoto T., et al., "A Micro-Planar Amperometric Glucose Sensor Unsusceptible to Interference Species," Sensors and Actuators B, 49, 1998, pp. 68-72.

Matthews D.R., et al., "An Amperometric Needle-Type Glucose Sensor Testing in Rats and Man," Diabetic Medicine, vol. 5, 1988, pp. 248-252.

Mazze R.S., et al., "Characterizing Glucose Exposure for Individuals with Normal Glucose Tolerance Using Continuous Glucose Monitoring and Ambulatory Glucose Profile Analysis," Diabetes Technology & Therapeutics, vol. 10 (3), 2008, pp. 149-159.

Mazzola F., et al., "Video Diabetes: A Teaching Tool for Children with Insulin-Dependent Diabetes," IEEE, Proceedings 7th Annual Symposium on Computer Applications in Medical Care, Oct. 1983, 1 page Abstract.

McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.

McGarraugh G., et al., "Glucose Measurements Using Blood Extracted From The Forearm And The Finger," TheraSense, Inc., 2001, pp. 1-8.

McGarraugh G., et al., "Physiological Influences on Off-Finger Glucose Testing", Diabetes Technology & Therapeutics, vol. 3 (3), 2001, pp. 367-376.

McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.

McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.

Memoli A., et al., "A Comparison between Different Immobilised Glucoseoxidase-Based Electrodes," Journal of Pharmaceutical and Biomedical Analysis, vol. 29, 2002, pp. 1045-1052.

Merriam Webster Online Dictionary, Definition for "Aberrant," retrieved from https://www.merriam-webster.com/dictionary/aberrant Aug. 19, 2008, 1 page.

Merriam-Webster Online Dictionary, Definition of "Acceleration" retrieved from http://www.merriam-webster.com/dictionary/Acceleration Jan. 11, 2010, 1 page.

Merriam-Webster Online Dictionary, Definition of "Nominal" retrieved from http://www.merriam-webster.com/dictionary/nominal Apr. 23, 2007, 1 page.

Merriam-Webster Online Dictionary, Definition of "System". http://www.merriamwebster.com/dictionary/System Jan. 11, 2010, 2 pages.

Metzger M., et al., "Reproducibility of Glucose Measurements using the Glucose Sensor," Diabetes Care, vol. 25 (6), Jul. 2002, pp. 1185-1191.

Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.

Miller J.A., et al., "Development of an Autotuned Transcutaneous Energy Transfer System," ASAIO Journal, vol. 39, 1993, pp. M706-M710.

Miller K.M., et al., "Generation of IL-1 like Activity in Response to Biomedical Polymer Implants: a Comparison of in Vitro and in Vivo Models," Journal of Biomedical Materials Research, vol. 23(9), 1989, pp. 1007-1026.

(56)        References Cited

OTHER PUBLICATIONS

Miller K.M., et al., "Human monocyte/macrophage activation and interleukin 1 generation by biomedical polymers," Journal of Biomedical Materials Research, vol. 22 (8), 1988, pp. 713-731.

Miller K.M., et al., "In Vitro Stimulation of Fibroblast Activity by Factors Generated from Human Monocytes Activated by Biomedical Polymers," Journal of Biomedical Materials Research, vol. 23(8), 1989, pp. 911-930.

Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.

Moatti-Sirat D., et al., "Reduction of Acetaminophen Interference in Glucose Sensors by a Composite Nafion Membrane: Demonstration in Rats and Man," Diabetologia, vol. 37 (6), Jun. 1994, pp. 610-616.

Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.

Monsod T.P., et al., "Do Sensor Glucose Levels Accurately Predict Plasma Glucose Concentrations During Hypoglycemia And Hyperinsulinemia? ,"Diabetes Care, vol. 25 (5), 2002, pp. 889-893.

Morbiducci U., et al., "Improved Usability of the Minimal Model of Insulin Sensitivity Based on Automated Approach and Genetic Algorithms for Parameter Estimation," Clinical Science, vol. 112 (4), 2006, 24 pages.

Morff R.J., et al., "Microfabrication of Reproducible, Economical, Electroenzymatic Glucose Sensors," Annual International Conference of the IEEE Engineering in Medicine and Biology Society, vol. 12 (2), 1990, pp. 0483-0484.

Mosbach K., et al., "Determination of Heat Changes in the Proximity of Immobilized Enzymes with an Enzyme Thermistor and its Use for the Assay of Metabolites," Biochimica Biophysica Acta, vol. 403, 1975, pp. 256-265.

Motonaka J., et al., "Determination of Cholesterol and Cholesterol Ester with Novel enzyme Microsensors," Anal. Chem., vol. 65, 1993, pp. 3258-3261.

Mougiakakou S.G., et al., "A Real Time Simulation Model of Glucose-Insulin Metabolism for Type 1 Diabetes Patients," Conf Proc IEEE Eng Med Biol Soc. 2005, vol. 1, pp. 298-301.

Moussy F., et al., "A Miniaturized Nafion-Based Glucose Sensor: In Vitro and In Vivo Evaluation in Dogs," International Journals of Artificial Organs, vol. 17 (2), 1994, pp. 88-94.

Moussy F., et al., "Biomaterials community examines biosensor biocompatibility," Diabetes Technology & Therapeutics, vol. 2(3), 2000, pp. 473-477.

Moussy F., et al., "Performance of Subcutaneously Implanted Needle-Type Glucose Sensors Employing a Novel Trilayer Coating," Analytical Chemistry, vol. 65, Aug. 1, 1993, pp. 2072-2077.

Moussy F., "Implantable Glucose Sensor: Progress and Problems," IEEE, Nov. 2002, pp. 270-273.

Mowery K.A., et al., "Preparation and Characterization by Hydrophobic Polymeric Films that are Thromboresistant via Nitric Oxide Release," Biomaterials, vol. 21, 2000, pp. 9-21.

Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.

Muslu, "Trickling Filter Performance," Applied Biochemistry and Biotechnology, vol. 37, 1992, pp. 211-224.

Myler S., et al., "Ultra-Thin-Polysiloxane-Film-Composite Membranes for the Optimisation of Amperometric Oxidase Enzyme Electrodes," Biosensors & Bioelectronics, vol. 17, 2002, pp. 35-43.

Nakayama Y., et al., "Surface Fixation of Hydrogels: Heparin and Glucose Oxidase Hydrogelated Surfaces" ASAIO Journal, 1992, pp. M421-M424.

Nam Y.S., et al., "A Novel Fabrication Method of Macroporous Biodegradable Polymer Scaffolds Using Gas Foaming Salt as a Porogen Additive," J Biomed Mater Res, 2000, vol. 53, pp. 1-7.

Neuburger G.G., et al., "Pulsed Amperometric Detection of Carbohydrates at Gold Electrodes with a Two-Step Potential Waveform," Anal. Chem., vol. 59, 1987, pp. 150-154.

Newsrx, "Glucose Monitoring: FDA OKs New Device to Manage Diabetes," Medical Letter on the CDC & FDA via NewsRx.com, Aug. 3, 2003, 1 page.

Nintendo Healthcare, Wired, Dec. 1993, 1 page.

Noujaim S.E., et al., "Accuracy Requirements for a Hypoglycemia Detector: An Analytical Model to Evaluate the Effects of Bias, Precision and Rate of Glucose Change," Journal of Diabetes Science & Technology, vol. 1 (5), Sep. 2007, pp. 652-668.

Novo Nordisk Pharmaceuticals Inc., "Diabetes Educational Video Game Recognized by Software Publishers Association," Press Release, Mar. 14, 1994, 4 pages.

O'Donoghue M., et al., "Electrochemical Impedance Spectroscopy: Testing Coatings for Rapid Immersion Service," Materials Performance, Sep. 2003, pp. 36-41.

Ohara T.J., et al., "Glucose Electrodes Based On Cross-Linked [Os(bpy)2Cl](+/2+) Complexed Poly(1-Vinylimidazole) Films," Analytical Chemistry, vol. 65, Dec. 1993, pp. 3512-3517.

Ohara T.J., et al., ""Wired" Enzyme Electrodes for Amperometric Determination of Glucose or Lactate in the Presence of Interfering Substances," Anal Chem, vol. 66, 1994, pp. 2451-2457.

Okuda, et al., "Mutarotase Effect on Micro Determinations of D-Glucose and its Anomers with β D-Glucose Oxidase," Anal Biochem, vol. 43 (1), 1971, pp. 312-315.

Oxford English Dictionary Online, Definition of "Impending," http://www.askoxford.com/results/?view=devdict&field-12668446_Impending&branch Jan. 11, 2010, 1 page.

Palmisano F., et al., "Simultaneous Monitoring of Glucose and Lactate by an Interference and Cross- Talk Free Dual Electrode Amperometric Biosensor Based on Electropolymerized Thin Films," Biosensors & Bioelectronics, vol. 15, 2000, pp. 531-539.

Panetti T.S., "Differential Effects of Sphingosine 1-Phosphate and Lysophosphatidic Acid on Endothelial Cells," Biochimica et Biophysica Acta, vol. 1582, 2002, pp. 190-196.

Panteleon A.E., et al., "The Role of the Independent Variable to Glucose Sensor Calibration," Diabetes Technology & Therapeutics, vol. 5 (3), 2003, pp. 401-410.

Park, et al., "Novel Instrumentation in Electrochemical Impedance Spectroscopy and a Full Description of an Electrochemical System," Pure Appl. Chem., 2006, vol. 78 (5), pp. 1069-1080.

Parker R.S., et al., "A Model-Based Algorithm for Blood Glucose Control In Type I Diabetic Patients," IEEE Trans Biomed Engg (BME), vol. 46(2), 1999, pp. 148-157.

Parker R.S., et al., "Robust H∞ Glucose Control in Diabetes Using a Physiological Model," AIChE Journal, vol. 46 (12), Dec. 2000, pp. 2537-2549.

Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.

Peacock W.F., et al., "Cardiac Troponin and Outcome in Acute Heart Failure," N. Engl. J. Med., vol. 358, 2008, pp. 2117-2126.

Peguin S., et al., "Pyruvate Oxidase and Oxaloacetate Decarboxylase Enzyme Electrodes—Simultaneous Determination of Transaminases with a Two-electrode-based Analyzer," Analytica Chimica Acta, vol. 222, 1989, pp. 83-93.

Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.

Pfeiffer E.F., "The Glucose Sensor: The Missing Link in Diabetes Therapy," Horm Metab Res Suppl., vol. 24, 1990, pp. 154-164.

Phillips R.E., et al., "Biomedical Applications of Polyurethanes: Implications of Failure Mechanisms," Journal of Biomedical application, vol. 3, Oct. 1988, pp. 206-227.

Phillips R.P., "A High Capacity Transcutaneous Energy Transmission System," ASIAO Journal, vol. 41, 1995, pp. M259-M262.

Pichert J.W., et al., "Issues for the Coming Age of Continuous Glucose Monitoring," Diabetes Educator, vol. 26 (6), Nov.-Dec. 2000, pp. 969-980.

(56)        References Cited

OTHER PUBLICATIONS

Pickup J.C., et al., "Developing Glucose Sensors for In Vivo Use," Elsevier Science Publishers Ltd (UK), TIBTECH, vol. 11, 1993, pp. 285-291.

Pickup J.C., et al., "Implantable Glucose Sensors: Choosing the Appropriate Sensor Strategy," Biosensors, vol. 3, (1987/1988), pp. 335-346.

Pickup J.C., et al., "In Vivo Molecular Sensing in Diabetes Mellitus: An Implantable Glucose Sensor with Direct Electron Transfer," Diabetologia, vol. 32, 1989, pp. 213-217.

Pickup J.C., et al., "Potentially-Implantable, Amperometric Glucose Sensors with Mediated Electron Transfer: Improving the Operating Stability," Biosensors, vol. 4, 1989, pp. 109-119.

Pickup J.C., et al., "Progress Towards in Vivo Glucose Sensing with a Ferrocene-Mediated Amperometric Enzyme Electrode," Horm Metab Res Suppl, vol. 20, 1988, pp. 34-36.

Pickup J.C., et al., "Responses and Calibration of Amperometric Glucose Sensors Implanted in the Subcutaneous Tissue of Man," ACTA Diabetol, vol. 30, 1993, pp. 143-148.

Pineda L.M., et al., "Bone Regeneration with Resorbable Polymeric Membranes. III. Effect of Poly(L-lactide) Membrane Pore Size on the Bone Healing Process in Large Defects," Journal of Biomedical Materials Research, vol. 31, 1996, pp. 385-394.

Pinner S.H., et al., "Cross-Linking of Cellulose Acetate by Ionizing Radiation," Nature, vol. 184, Oct. 24, 1959, pp. 1303-1304.

Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.

Pitzer K.R., et al., "Detection of Hypoglycemia with the Glucowatch Biographer," Diabetes Care, vol. 24 (5), 2001, pp. 881-885.

Poirier J.Y., et al., "Clinical and Statistical Evaluation of Self-Monitoring Blood Glucose Meters," Diabetes Care, vol. 21 (11), Nov. 1998, pp. 1919-1924.

Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.

Poitout V., et al., "Development of a Glucose Sensor for Glucose Monitoring in Man: The Disposable Implant Concept," Clinical Materials, vol. 15, 1994, pp. 241-246.

Poitout V., et al., "In Vitro and In Vivo Evaluation in Dogs of a Miniaturized Glucose Sensor," ASAIO Transactions, vol. 37, 1991, pp. M298-M300.

Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.

Prabhu V.G., et al., "Electrochemical Studies of Hydrogen Peroxide at a Platinum Disc Electrode," Electrochimica Acta, vol. 26 (6), 1981, pp. 725-729.

Quinn C.A.P., et al., "Biocompatible, Glucose-Permeable Hydrogel for In situ Coating of Implantable Biosensors," Biomaterials, vol. 18 (24), 1997, pp. 1665-1670.

Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.

Rabah M.A., et al., "Electrochemical Wear of Graphite Anodes During Electrolysis of Brine," Carbon, vol. 29 (2), 1991, pp. 165-171.

Rafael E., "Cell Transplantation and Immunoisolation: Studies on a Macroencapsulation Device," Departments of Transplantation Surgery and Pathology, Karolinska Institutet, Huddinge Hospital, Stockholm, Sweden, 1999, pp. 1-83.

Ratner B.D., "Reducing Capsular Thickness and Enhancing Angiogenesis around Implant Drug Release Systems," Journal of Controlled Release, vol. 78, 2002, pp. 211-218.

RAYA Systems Pioneers, "Raya Systems Pioneers Healthy Video Games," PlayRight, Nov. 1993, pp. 14-15.

Reach G., "A Method for Evaluating in vivo the Functional Characteristics of Glucose Sensors," Biosensors, vol. 2, 1986, pp. 211-220.

Reach G., et al., "Can Continuous Glucose Monitoring Be Used for the Treatment of Diabetes?," Analytical Chemistry, vol. 64 (6), Mar. 15, 1992, pp. 381A-386A.

Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.

Rebrin K., et al., "Automated Feedback Control of Subcutaneous Glucose Concentration in Diabetic Dogs," Diabetologia, vol. 32, 1989, pp. 573-576.

Rebrin K., et al., "Subcutaneous Glucose Monitoring by Means of Electrochemical Sensors: Fiction or Reality?," Journal of Biomedical Engineering, vol. 14, Jan. 1992, pp. 33-40.

Rebrin K., et al., "Subcutaneous Glucose Predicts Plasma Glucose Independent of Insulin: Implications for Continuous Monitoring," The American Physiological Society, vol. 277, 1999, pp. E561-E571.

Renard E., "Implantable Closed-Loop Glucose Sensing and Insulin Delivery: The Future for Insulin Pump Therapy," Current Opinion in Pharmacology, vol. 2 (6), 2002, pp. 708-716.

Reush, "Organometallic Compounds," Chemical Reactivity, Virtual Textbook of Organic Chemistry, Retrieved from http://www.cem.msu.edu/-reuschlVirtualText/orgmetal.htm 2004, pp. 1-16.

Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.

Rigla M., et al., "Real-Time Continuous Glucose Monitoring Together with Telemedical Assistance Improves Glycemic Control and Glucose Stability in Pump-Treated Patients," Diabetes Technology & Therapeutics, vol. 10 (3), 2008, pp. 194-199.

Rinken T., et al., "Calibration of Glucose Biosensors By Using Pre-Steady State Kinetic Data," Biosensors & Bioelectronics, vol. 13, 1998, pp. 801-807.

Ristic S., et al., "Review: Effects of Rapid-Acting Insulin Analogs on Overall Glycemic Control in Type 1 and Type 2 Diabetes Mellitus," Diabetes Technology & Therapeutics, vol. 5 (1), 2003, pp. 57-66.

Rivers E.P., et al., "Central Venous Oxygen Saturation Monitoring in the Critically Ill Patient," Current Opinion in Critical Care, 2001, vol. 7, pp. 204-211.

Roe J.N., et al., "Bloodless Glucose Measurements," Critical Reviews™ in Therapeutic Drug Carrier Systems, vol. 15 (3), 1998, pp. 199-241.

Sachlos E., et al., "Making Tissue Engineering Scaffolds Work Review on the Application of Solid Freeform Fabrication Technology to the Production of Tissue Engineering Scaffolds," European Cells and Materials, vol. 5, 2003, pp. 29-40.

Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.

Sakakida M., et al., "Ferrocene-Mediated Needle Type Glucose Sensor Covered with Newly Designed Biocompatible Membrane," Sensors and Actuators B, vol. 13-14, 1993, pp. 319-322.

Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.

Salehi C., et al., "A Telemetry-Instrumentation System for Long-Term Implantable Glucose and Oxygen Sensors," Analytical Letters, vol. 29 (13), 1996, pp. 2289-2308.

Samuels M.P., "The Effects of Flight and Altitude," Arch Dis Child, vol. 89, 2004, pp. 448-455.

San Diego Plastics Inc, "Polyethylene," Datasheet, Retrieved from http://www.sdplastics.com/polyeth.html on Aug. 19, 2009, 7 pages.

Sanders E., et al., "Fibrous Encapsulation of Single Polymer Microfibers Depends on their Vertical Dimension in Subcutaneous Tissue Polymer Microfibers," Journal of Biomedical Material Research, vol. 67A, 2003, pp. 1181-1187.

(56) References Cited

OTHER PUBLICATIONS

Sansen W., et al., "A Smart Sensor for the Voltammetric Measurement of Oxygen or Glucose Concentrations," Sensors and Actuators B1, 1990, pp. 298-302.

Sansen W., et al., "Glucose Sensor with Telemetry System," In Implantable Sensors for Closed Loop Prosthetic Systems edited by KO W.H, Chapter 12, 1985, pp. 167-175.

Schaffar B.P.H., "Thick Film Biosensors for Metabolites in Undiluted Whole Blood and Plasma Samples," Analytical Bioanalytical Chemistry, Dec. 2001, vol. 372, pp. 254-260.

Schmidt F.J., et al., "Calibration of a Wearable Glucose Sensor," The International Journal of Artificial Organs, Wichtig Publishing, IT, vol. 15 (1), Jan. 1, 1992, pp. 55-61.

Schmidt F.J., et al., "Glucose Concentration in Subcutaneous Extracellular Space," Diabetes Care, vol. 16 (5), May 1993, pp. 695-700.

Schmidtke D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Analytical Chemistry, vol. 70 (10), May 15, 1998, pp. 2149-2155.

Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.

Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.

Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.

Schuler, et al., "Modified Gas-Permeable Silicone Rubber Membranes for Covalent Immobilisation of Enzymes and their Use in Biosensor Development," Analyst, 1999, vol. 124, pp. 1181-1184.

Selam J.L., "Management of Diabetes with Glucose Sensors and Implantable Insulin Pumps," From the Dream of the 60s to the Realities of the 90s, ASAIO Journal 1997, vol. 43, pp. 137-142.

Service F.J., et al., "Mean Amplitude of Glycemic Excursions, A Measure of Diabetic Instability," Diabetes, vol. 19 (9), Sep. 1970, pp. 644-655.

Service F.J., et al., "Measurements of Glucose Control," Diabetes Care, vol. 10 (2), Mar.-Apr. 1987, pp. 225-237.

Service R.F., "Can Sensors Make a Home in the Body?," Science, Materials Science: Soft Surface, vol. 297, Aug. 9, 2002, pp. 962-963.

Sharkawy A.A., et al., "Engineering the Tissue Which Encapsulates Subcutaneous Implants. I. Diffusion Properties," Journal of Biomedical Materials Research, vol. 37, 1996, pp. 401-412.

Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.

Shichiri, et al., "In Vivo Characteristics of Needle-Type Glucose Sensor-Measurements of Subcutaneous Glucose Concentrations in Human Volunteers," Implantable Glucose Sensors—The State of the Art, Hormone and Metabolic Research Supplement Series, 1988, vol. 20, pp. 17-20.

Shichiri M., et al., "Glycaemic Control in Pancreatectomized Dogs with a Wearable Artificial Endocrine Pancreas," Diabetologia, vol. 24, 1983, pp. 179-184.

Shichiri M., et al., "Membrane Design for Extending the Long-Life of an Implantable Glucose Sensor," Diabetes Nutrition & Metabolism, vol. 2 (4), 1989, pp. 309-313.

Shichiri M., et al., "Needle Type Glucose Sensor for Wearable Artificial Endocrine Pancreas," In Implantable Sensors for Closed-Loop Prosthetic Systems edited by KO W.H, Chapter 15, 1985, pp. 197-210.

Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.

Shichiri M., et al., "Wearable Artificial Endocrine Pancreas with Needle-Type Glucose Sensor," Preliminary Communication, Lancet, vol. 2, Nov. 20, 1982, pp. 1129-1131.

Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.

Sieminski, et al., "Biomaterial-Microvasculature Interactions," Biomaterials, 2000, vol. 21, pp. 2233-2241.

Sigma-Aldrich Corp., "Cellulose Acetate," Product Description, Product No. 419028, St. Louis, MO, 2005, 1 page.

Sigma-Aldrich Corp. "Nafion® 117 Solution Product Description, Product No. 70160," retrieved from https//: www.sigmaaldrich.com/cgi-bin/hsrun/Suite7/Suite/HAHTpage/Suite.HsExternalProd on Apr. 7, 2005, 1 page.

Skyler U.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.

Slater-Maclean L., et al., "Accuracy of Glycemic Measurements in the Critically Ill," Diabetes Technology and Therapeutics, vol. 10 (3), 2008, pp. 169-177.

Smith B., et al., "An Externally Powered, Multichannel, Implantable Stimulator-Telemeter for Control of Paralyzed Muscle," IEEE Transactions on Biomedical Engineering, vol. 45 (4), Apr. 1998, pp. 463-475.

Smith, et al.," A Comparison of Islet Transplantation and Subcutaneous Insulin Injections for the Treatment of Diabetes Mellitus," Computers in Biology and Medicine, 1991, vol. 21 (6), pp. 417-427.

Sokol L., et al., "Immobilized-Enzyme Rate-Determination Method for Glucose Analysis," Clinical Chemistry, vol. 26 (1), 1980, pp. 89-92.

Sokolov S., et al., "Metrological Opportunities of the Dynamic Mode of Operating an Enzyme Amperometric Biosensor," Medical Engineering & Physics, vol. 17 (6), 1995, pp. 471-476.

Sparacino G., et al., "Continuous Glucose Monitoring Time Series and Hypo-Hyperglycemia Prevention: Requirements, Methods, Open Problems," Current Diabetes Reviews, vol. 4 (3), 2008, pp. 181-192.

Sproule B.A., et al., "Fuzzy Pharmacology: Theory and Applications," Trends in Pharmacological Sciences, vol. 23 (9), Sep. 2002, pp. 412-417.

Sriyudthsak M., et al., "Enzyme-Epoxy Membrane Based Glucose Analyzing System and Medical Applications," Biosensors & Bioelectronics, vol. 11 (8), 1996, pp. 735-742.

Steil G.M., et al., "Closed-Loop Insulin Delivery—the Path of Physiological Glucose Control," Advanced Drug Delivery Reviews, vol. 56, 2004, pp. 125-144.

Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.

Stern M., et al., "Electrochemical Polarization: I. A Theoretical Analysis of the Shape of Polarization Curves," Journal of the Electrochemical Society, vol. 104 (1), Jan. 1957, pp. 56-63.

Sternberg, et al., "Covalent Enzyme Coupling on Cellulose Acetate Membranes for Glucose Sensor Development," Anal Chem, Dec. 1988, vol. 60(24), pp. 2781-2786.

Sternberg F., et al., "Does Fall in Tissue Glucose Precede Fall in Blood Glucose?," Diabetologia, vol. 39, 1996, pp. 609-612.

Sternberg R., et al., "Study and Development of Multilayer Needle-type Enzyme Based Glucose Microsensors," Biosensors, Mar. 20, 1988, vol. 4 (1), pp. 27-40.

Stokes, "Polyether Polyurethanes: Biostable or Not," Journal of Biomaterials Applications, Oct. 1988, vol. 3, pp. 228-259.

Street, et al., "Islet Graft Assessment in the Edmonton Protocol: Implications for Predicting Long-Term Clinical Outcome," Diabetes, 2004, vol. 53, pp. 3107-3114.

Street J.O., et al., "A Note on Computing Robust Regression Estimates Via Iteratively Reweighted Least Squares," The American Statistician, vol. 42 (2), May 1988, pp. 152-154.

Suh, et al., "Behavior of Fibroblasts on a Porous Hyaluronic Acid Incorporated Collagen Matrix," Yonsei Medical Journal, 2002, vol. 43 (2), pp. 193-202.

(56) References Cited

OTHER PUBLICATIONS

Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.

Takatsu I., et al., "Solid State Biosensors Using Thin-Film Electrodes," Sensors and Actuators, 1987, vol. 11, pp. 309-317.

Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.

Tamura T., et al., "Preliminary Study of Continuous Glucose Monitoring with a Microdialysis Technique and a Null Method-A Numerical Analysis," Frontiers of Medical & Biological Engineering, vol. 10 (2), 2000, pp. 147-156.

Tanenberg R.J., et al., "Continuous Glucose Monitoring System: A New Approach to the Diagnosis of Diabetic Gastroparesis," Diabetes Technology & Therapeutics, vol. 2, Supplement 1, 2000, pp. S73-S80.

Tang, et al., "Fibrin(ogen) Mediates Acute Inflammatory Responses to Biomaterials," J.Exp.Med, 1993, vol. 178, pp. 2147-2156.

Tang, et al., "Inflammatory Responses to Biomaterials," Am J Clin Pathol, 1995, vol. 103, pp. 466-471.

Tang, et al., "Mast Cells Mediate Acute Inflammatory Responses to Implanted Biomaterials," Proceedings of the National Academy of Sciences of the USA, 1998, vol. 95, pp. 8841-8846.

Tang, et al., "Molecular Determinants of Acute Inflammatory Responses to Biomaterials," J Clin Invest, 1996, vol. 97, pp. 1329-1334.

Tatsuma T., et al., "Oxidase/Peroxidase Bilayer-Modified Electrodes as Sensors for Lactate, Pyruvate, Cholesterol and Uric Acid," Analytica Chimica Acta, vol. 242, 1991, pp. 85-89.

The Diabetes Control and Complications Trial Research Group, "The Effect of Intensive Treatment of Diabetes on the Development and Progression of Long-Term Complications in Insulin-Dependent Diabetes Mellitus," The New England, Journal of Medicine, vol. 329 (14), Sep. 30, 1993, pp. 977-986.

Thennadil S.N., et al., "Comparison of Glucose Concentration in Interstitial Fluid, and Capillary and Venous Blood During Rapid Changes in Blood Glucose Levels," Diabetes Technology & Therapeutics, vol. 3 (3), 2001, pp. 357-365.

Thijssen, et al., "A Kalman Filter for Calibration, Evaluation of Unknown Samples and Quality Control in Drifting Systems," Part 1, Theory and Simulations, Analytica chimica Acta, 1984, vol. 156, pp. 87-101.

Thijssen, et al., "A Kalman Filter for Calibration, Evaluation of Unknown Samples and Quality Control in Drifting Systems," Part 3,Variance Reduction ,Analytica chimica Acta, 1985, vol. 173, pp. 265-272.

Thijssen, et al., "A Kalman Filter for Calibration, Evaluation of Unknown Samples and Quality Control in Drifting Systems," Part 4,Flow Injection Analysis, Analytica chimica Acta, 1985, vol. 174, pp. 27-40.

Thijssen P.C., "A Kalman Filter for Calibration, Evaluation of Unknown Samples and Quality Control in Drifting Systems," Part 2,Optimal Designs, Analytica chimica Acta, vol. 162, 1984, pp. 253-262.

Thome V., et al., "(Abstract) Can the Decrease in Subcutaneous Glucose Concentration Precede the Decrease in Blood Glucose Level? Proposition for a Push-Pull Kinetics Hypothesis," Horm. metab. Res., vol. 27, 1995, p. 53.

Thome-Duret V., et al., "Continuous Glucose Monitoring in the Free-Moving Rat," Metabolism, vol. 47 (7), Jul. 1998, pp. 799-803.

Thome-Duret V., et al., "Modification of the Sensitivity of Glucose Sensor Implanted into Subcutaneous Tissue," Diabetes & Metabolism, vol. 22, 1996, pp. 174-178.

Thome-Duret V., et al., "Use of a Subcutaneous Glucose Sensor to Detect Decreases in Glucose Concentration Prior to Observation in Blood," Analytical Chemistry, vol. 68 (21), Nov. 1, 1996, pp. 3822-3826.

Thompson M., et al., "In Vivo Probes: Problems and Perspectives," Clinical Biochemistry, vol. 19 (5), Oct. 1986, pp. 255-261.

Tibell, et al., "Survival of Macroencapsulated Allogeneic Parathyroid Tissue One Year after Transplantation in Nonimmunosuppressed Humans," Cell Transplantation, 2001, vol. 10, pp. 591-599.

Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.

Tierney M.J., et al., "The Gluco Watch® Biographer: A Frequent, Automatic and Noninvasive Glucose Monitor," Annals of Medicine, vol. 32, 2000, pp. 632-641.

Tilbury J.B., et al., "Receiver Operating Characteristic Analysis for Intelligent Medical Systems—A New Approach for Finding Confidence Intervals," IEEE Transactions on Biomedical Engineering, vol. 47 (7), Jul. 2000, pp. 952-963.

Torjman M.C., et al., "Glucose Monitoring in Acute Care: Technologies on the Horizon," Journal of Diabetes Science and Technology, vol. 2 (2), Mar. 2008, pp. 178-181.

Trajanoski Z., et al., "Neural Predictive Controller For Insulin Delivery Using The Subcutaneous Route," IEEE Transactions on Biomedical Engineering, vol. 45(9), 1998, pp. 1122-1134.

Trecroci D., "A Glimpse into the Future-Continuous Monitoring of Glucose with a Microfiber," Diabetes Interview, Jul. 2002, pp. 42-43.

TSE P.S.H., et al., "Time-Dependent Inactivation of Immobilized Glucose Oxidase and Catalase," Biotechnology & Bioengineering, vol. 29, 1987, pp. 705-713.

Turner A.P.F., "Amperometric Biosensor based on Mediator-Modified Electrodes," Methods in Enzymology, 1988, vol. 137, pp. 90-103.

Turner A.P.F., et al., "Carbon Monoxide: Acceptor Oxidoreductase from Pseudomonas Thermocarboxydovorans Strain C2 and its Use in a Carbon Monoxide Sensor," Analytica Chimica Acta, vol. 163, 1984, pp. 161-174.

Turner A.P.F., et al., "Diabetes Mellitus: Biosensors for Research and Management," Biosensors, vol. 1, 1985, pp. 85-115.

Unger J., et al., "Glucose Control in the Hospitalized Patient," Emergency Medicine, vol. 36 (9), 2004, pp. 12-18.

Updike S.J., et al., "A Subcutaneous Glucose Sensor with Improved Longevity, Dynamic Range, and Stability of Calibration," Diabetes Care, vol. 23 (2), Feb. 2000, pp. 208-214.

Updike S.J., et al., "Continuous Glucose Monitor Based on an Immobilized Enzyme Electrode Detector," Journal of Laboratory and Clinical Medicine, vol. 93(4), 1979, pp. 518-527.

Updike S.J., et al., "Enzymatic Glucose Sensor: Improved Long-Term Performance in Vitro and In Vivo," ASAIO Journal, vol. 40 (2), Apr.-Jun. 1994, pp. 157-163.

Updike S.J., et al., "Implanting the Glucose Enzyme Electrode: Problems, Progress, and Alternative Solutions," Diabetes Care, vol. 5 (3), May-Jun. 1982, pp. 207-212.

Updike S.J., et al., "Laboratory Evaluation of New Reusable Blood Glucose Sensor," Diabetes Care, vol. 11 (10), Nov.-Dec. 1988, pp. 801-807.

Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.

Updike S.J., et al., "The Enzyme Electrode," Nature, vol. 214, Jun. 3, 1967, pp. 986-988.

Utah Medical Products Inc., "Deltran—Disposable Blood Pressure Transducers," Product Specifications, 2003-2006, 6 pages.

Vadgama P., "Diffusion Limited Enzyme Electrodes," NATO ASI Series: Series C, Math and Phys. Sci, vol. 226, 1988, pp. 359-377.

Vadgama P., "Enzyme Electrodes as Practical Biosensors," Journal of Medical Engineering & Technology, vol. 5 (6), Nov. 1981, pp. 293-298.

Valdes T.I., et al., "In Vitro and In Vivo Degradation of Glucose Oxidase Enzyme used for an Implantable Glucose Biosensor," Diabetes Technology & Therapeutics, vol. 2 (3), 2000, pp. 367-376.

(56)                References Cited

OTHER PUBLICATIONS

Van Den Berghe, "Tight Blood Glucose Control with Insulin in "Real-Life" Intensive Care," Mayo Clinic Proceedings, vol. 79 (8), Aug. 2004, pp. 977-978.

Velho G., et al., "In Vitro and In Vivo Stability of Electrode Potentials in Needle-Type Glucose Sensors," Influence of Needle Material, Diabetes, vol. 38, Feb. 1989, pp. 164-171.

Velho G., et al., "Strategies for Calibrating a Subcutaneous Glucose Sensor," Biomed Biochim Acta, vol. 48 (11/12), 1989, pp. 957-964.

Vesper H.W., et al., "Assessment of Trueness of a Glucose Monitor Using Interstitial Fluid and Whole Blood as Specimen Matrix," Diabetes Technology & Therapeutics, vol. 8 (1), 2006, pp. 76-80.

Von Woedtke T., et al., "In Situ Calibration of Implanted Electrochemical Glucose Sensors," Biomed. Biochim. Acta 48 Vol.11/12, 1989, pp. 943-952.

Wade L.G., "Reactions of Aromatic Compounds," Organic Chemistry, Chapter 17, 5th edition, 2003, pp. 762-763.

Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.

Wang J., et al., "Highly Selective Membrane-Free Mediator-Free Glucose Biosensor," Analytical Chemistry, vol. 66 (21), Nov. 1, 1994, pp. 3600-3603.

Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.

Ward W.K., et al., "A New Amperometric Glucose Microsensor: In Vitro and Short-Term In Vivo Evaluation," Biosensors & Bioelectronics, vol. 17, 2002, pp. 181-189.

Ward W.K., et al., "Assessment of Chronically Subcutaneous Glucose Sensors in Dogs: The Effect of Surrounding Fluid Masses," ASAIO Journal, 1999, vol. 45 (6), pp. 555-561.

Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.

Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.

Wentholt I.M.E., et al., "Relationship between Interstitial and Blood Glucose in Type 1 Diabetes Patients: Delay and the Push-pull Phenomenon Revisited," Diabetes Technology & Therapeutics, vol. 9 (2), 2007, pp. 169-175.

Whipple G., "Low Residual Noise Speech Enhancement Utilizing Time-Frequency Filtering," Proceedings of the International Conference on Acoustics, Speech, and Signal Processing, 1994, pp. I5-I8.

Wientjes K.J.C., "Development of a Glucose Sensor for Diabetic Patients," (Ph.D. Thesis), 2000, 212 pages.

Wikipedia., "Intravenous Therapy," http://en.wikipedia.org/wiki/Intravenous_therapy, Aug. 15, 2006, 6 pages.

Wilkins E., et al., "Glucose Monitoring: State of the Art and Future Possibilities," Med. Eng. Phys., vol. 18 (4), 1996, pp. 273-288.

Wilkins E., et al., "Integrated Implantable Device for Long-Term Glucose Monitoring," Biosensors & Bioelectronics, vol. 10, 1995, pp. 485-494.

Wilkins E.S., et al., "The Coated Wire Electrode Glucose Sensor," Horm Metab Res Suppl., vol. 20, 1988, pp. 50-55.

Wilson G.S., et al., "Enzyme-Based Biosensors for In Vivo Measurements," Chem. Rev., vol. 100, 2000, pp. 2693-2704.

Wilson G.S., et al., "Progress Toward the Development of an Implantable Sensor for Glucose," Clinical Chemistry, vol. 38 (9), 1992, pp. 1613-1617.

Wolfe P.J., et al., "Interpolation of Missing Data Values for Audio Signal Restoration Using a Gabor Regression Model," 2005 IEEE International Conference on Acoustics, Speech, and Signal Processing, vol. 5, 2005, pp. 517-520.

Wolpert H., "Establishing a Continuous Glucose Monitoring Program," Journal of Diabetes Science and Technology, Mar. 2008, vol. 2 (2), pp. 307-310.

Wolpert H.A., "Commentary: A Clinician's Perspective on Some of the Challenges in Closed Loop," Diabetes Technology & Therapeutics, vol. 5 (5), 2003, pp. 843-846.

Wood W D., et al., "Hermetic Sealing with Epoxy," Pave Technology—Mechanical Engineering, Mar. 1990, 3 pages.

Woodward S.C., "How Fibroblasts and Giant Cells Encapsulate Implants: Considerations in Design of Glucose Sensors," Diabetes Care, vol. 5 (3) May-Jun. 1982, pp. 278-281.

Worsley G.J et al., "Measurement of Glucose in Blood with a Phenylboronic Acid Optical Sensor," Journal of Diabetes Science and Technology, vol. 2 (2), Mar. 2008, pp. 213-220.

Wright M., et al., "Bioelectrochemical Dehalogenations Via Direct Electrochemistry of Poly(ethylene oxide)-Modified Myoglobin," Electrochemistry Communications, vol. 1, 1999, pp. 609-613.

Wu H., et al., "In Situ Electrochemical Oxygen Generation with an Immunoisolation Device," Annals New York Academy of Sciences, vol. 875, 1999, pp. 105-125.

Yamasaki Y., et al., "Direct Measurement of Whole Blood Glucose by a Needle-Type Sensor," Clinica Chimica Acta. 93, 1989, pp. 93-98.

Yamasaki Y., "The Development of a Needle-Type Glucose Sensor for Wearable Artificial Endocrine Pancreas," Medical Journal of Osaka University, vol. 35 (1-2), Sep. 1984, pp. 25-34.

Yang S., et al., "Glucose Biosensors Based on Oxygen Electrode with Sandwich-Type Membranes," Annals of Biomedical Engineering, 1995, vol. 23, pp. 833-839.

Yang C., et al., "A Comparison of Physical Properties and Fuel Cell Performance of Nafion and Zirconium Phosphate/Nation Composite Membranes," Journal of Membrane Science, vol. 237, 2004, pp. 145-161.

Yang Q., et al., "Development of Needle-Type Glucose Sensor with High Selectivity," Science and Actuators B, vol. 46, 1998, pp. 249-256.

Yang S., et al., "A Glucose Biosensor Based On an Oxygen Electrode: In-Vitro Performances in a Model Buffer Solution and in Blood Plasma," Biomedical Instrumentation & Technology, vol. 30 (1), 1996, pp. 55-61.

Yang S., et al., "Glucose Biosensors with Enzyme Entrapped in Polymer Coating," Biomedical Instrument and Technology, Mar./Apr. 1995, vol. 29 (2), pp. 125-133.

Ye L., et al., "High Current Density Wired' Quinoprotein Glucose Dehydrogenase Electrode," Analytical Chemistry, vol. 65, 1993, pp. 238-241.

Yoo, et al., "An Electrochemical Impedance Measurement Technique Employing Fourier Transform," Anal. Chem. 2000, vol. 72, pp. 2035-2041.

Zamzow K.L., et al., "Development and Evaluation of a Wearable Blood Glucose Monitor," ASAIO Transactions, vol. 36 (3), 1990, pp. M588-M591.

Zavalkoff S.R., et al., "Evaluation Of Conventional Blood Glucose Monitoring as An Indicator of Integrated Glucose Values Using a Continuous Subcutaneous Sensor," Diabetes Care, vol. 25(9), 2002, pp. 1603-1606.

Zethelius B., et al., "Use Of Multiple Biomarkers to Improve the Prediction of Death From Cardiovascular Causes," N. Engl. J. Med., vol. 358, May 2008, pp. 2107-2116.

Zhang, et al., "Elimination of the Acetaminophen Interference in an Implantable Glucose Sensor," Analytical Chemistry, 1994, vol. 66 (7), pp. 1183-1188.

Zhang Y., et al., "Electrochemical Oxidation Of H2O2 On Pt and Pt + Ir Electrodes in Physiological Buffer and its Applicability to H2O2-Based Biosensors," J. Electro Analytical Chemistry, vol. 345, 1993, pp. 253-271.

Zhang Y., et al., "In Vitro and In Vivo Evaluation of Oxygen Effects on a Glucose Oxidase Based Implantable Glucose Sensor," Analytica Chimica Acta, vol. 281, 1993, pp. 513-520.

Zhu, et al., "Fabrication and Characterization of Glucose Sensors Based on a Microarray H2O2 Electrode," Biosensors & Bioelectronics, 1994, vol. 9, pp. 295-300.

(56) References Cited

OTHER PUBLICATIONS

Zhu, et al., "Planar Amperometric Glucose Sensor Based on Glucose Oxidase Immobilized by Chitosan Film on Prussian blue Layer," Sensors, 2002, vol. 2, pp. 127-136.

Ziaie, et al., "A Single-Channel Implantable Microstimulator for Functional Neuromuscular Stimulation," IEEE Transactions on Biomedical Engineering, 1997, vol. 44(10), pp. 909-920.

* cited by examiner

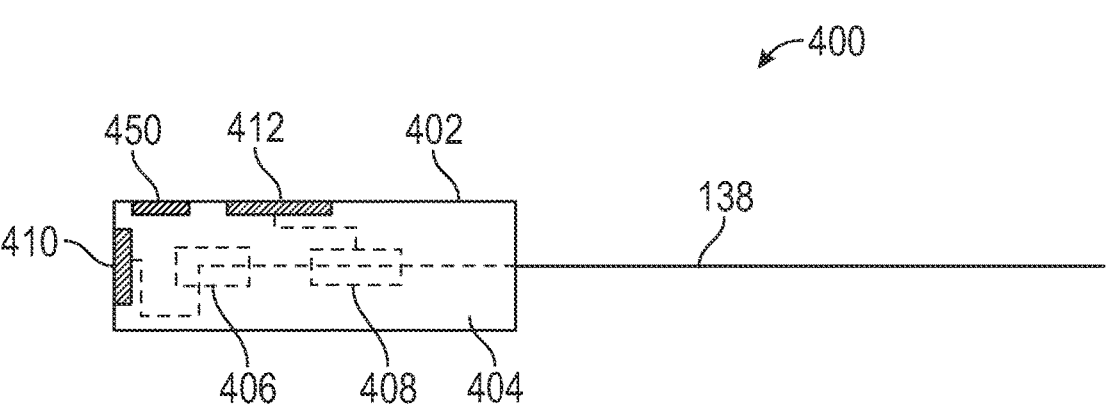
FIG. 4A
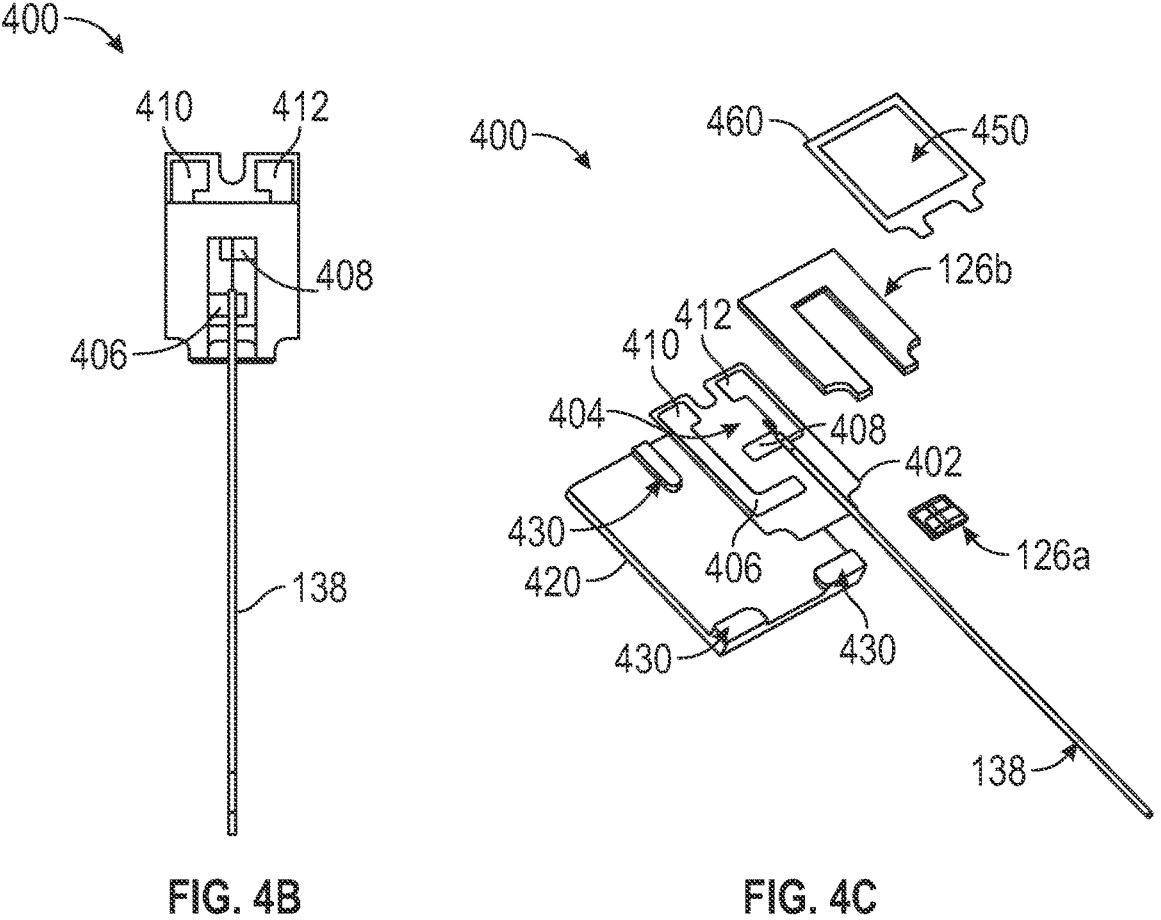
FIG. 4B                    FIG. 4C

Manufacturing Station

Testing Station

Calibration Station

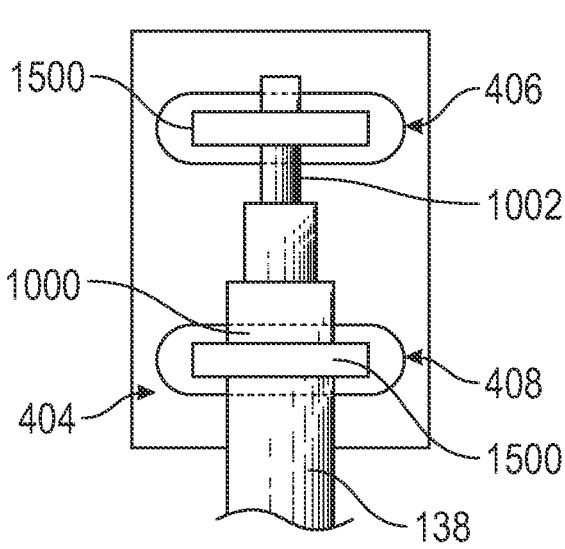
FIG. 16
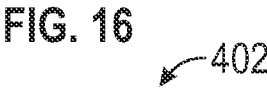
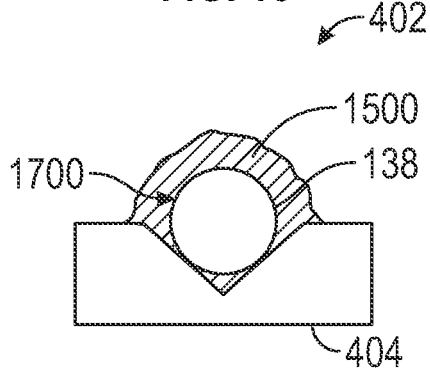
FIG. 18
FIG. 17
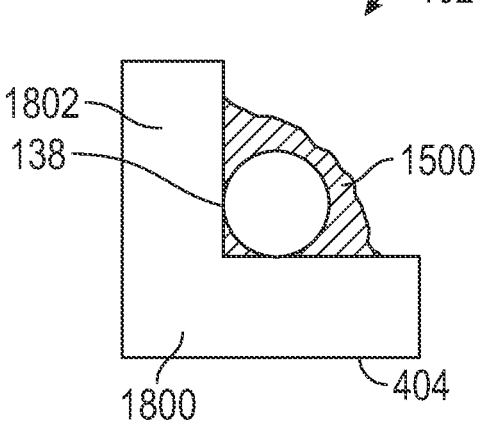
FIG. 19
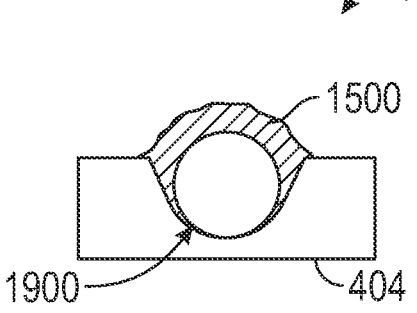
FIG. 20

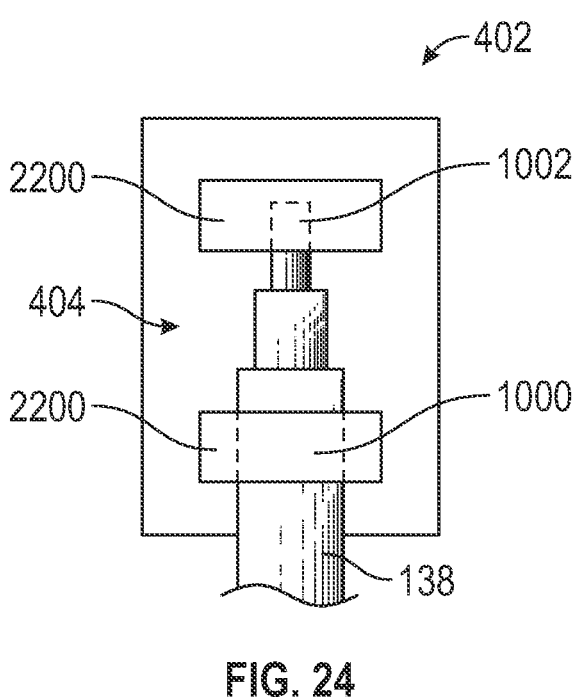
FIG. 24
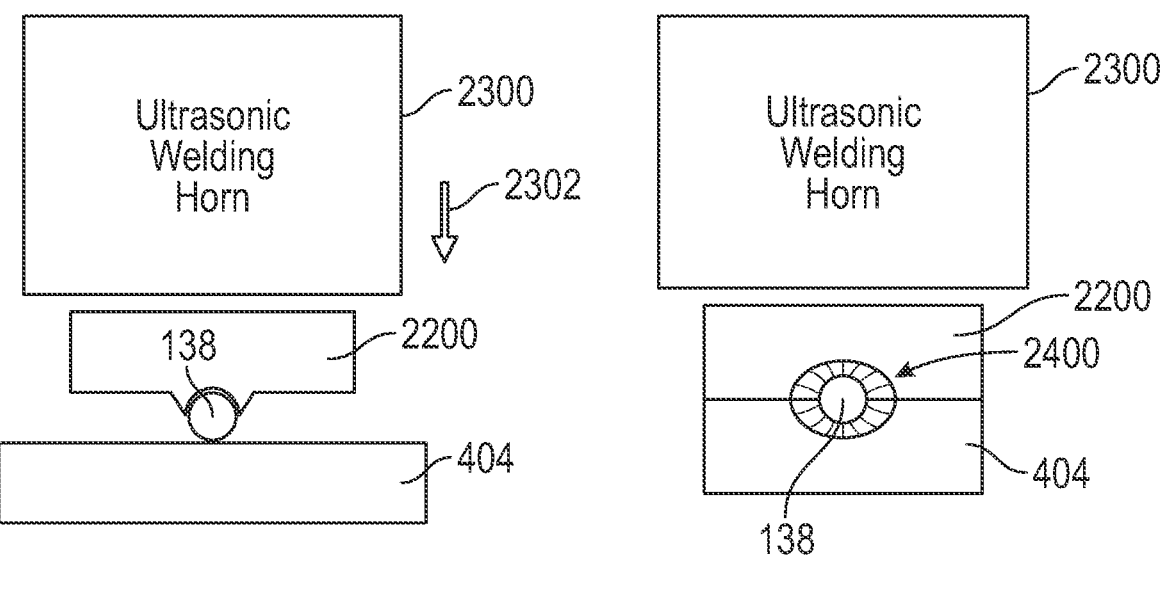
FIG. 25                    FIG. 26

138

1000F

512

1002F

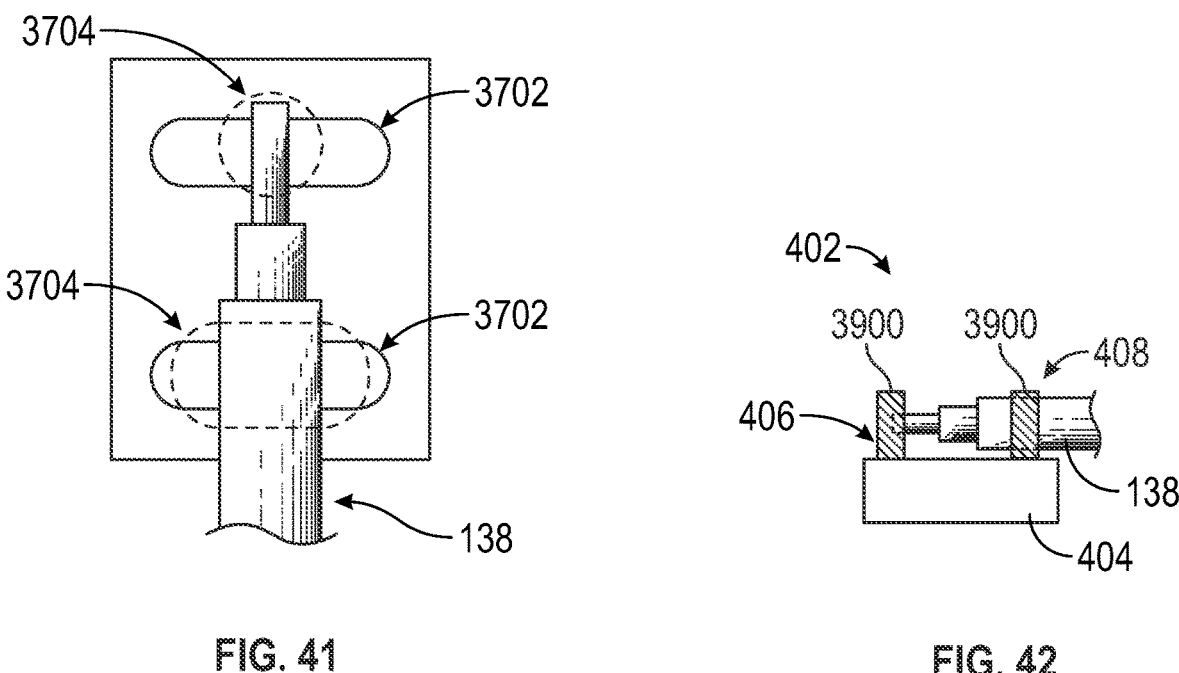
FIG. 41
FIG. 42
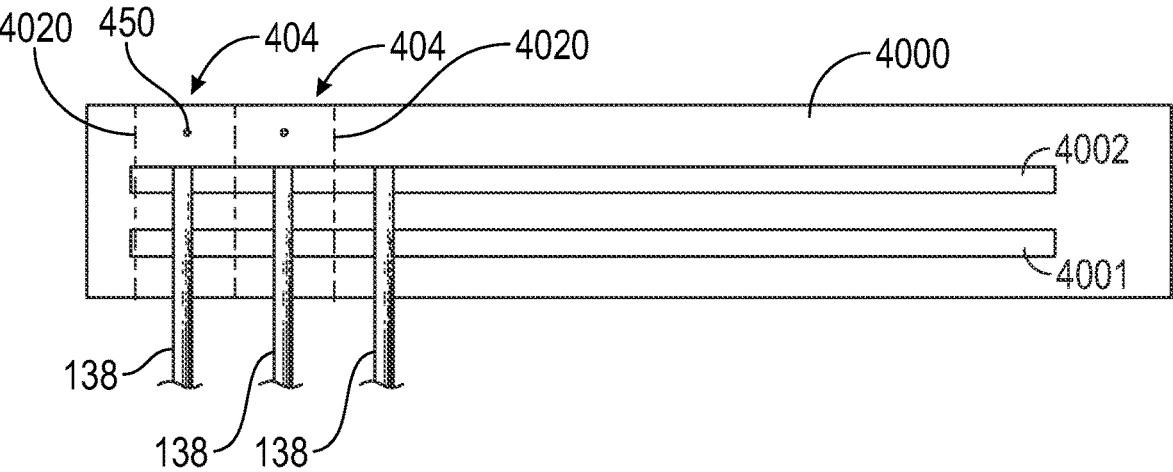
FIG. 43

400

138

406

408

4804

4802

402

410                    412

4850

402

4802

4804

138

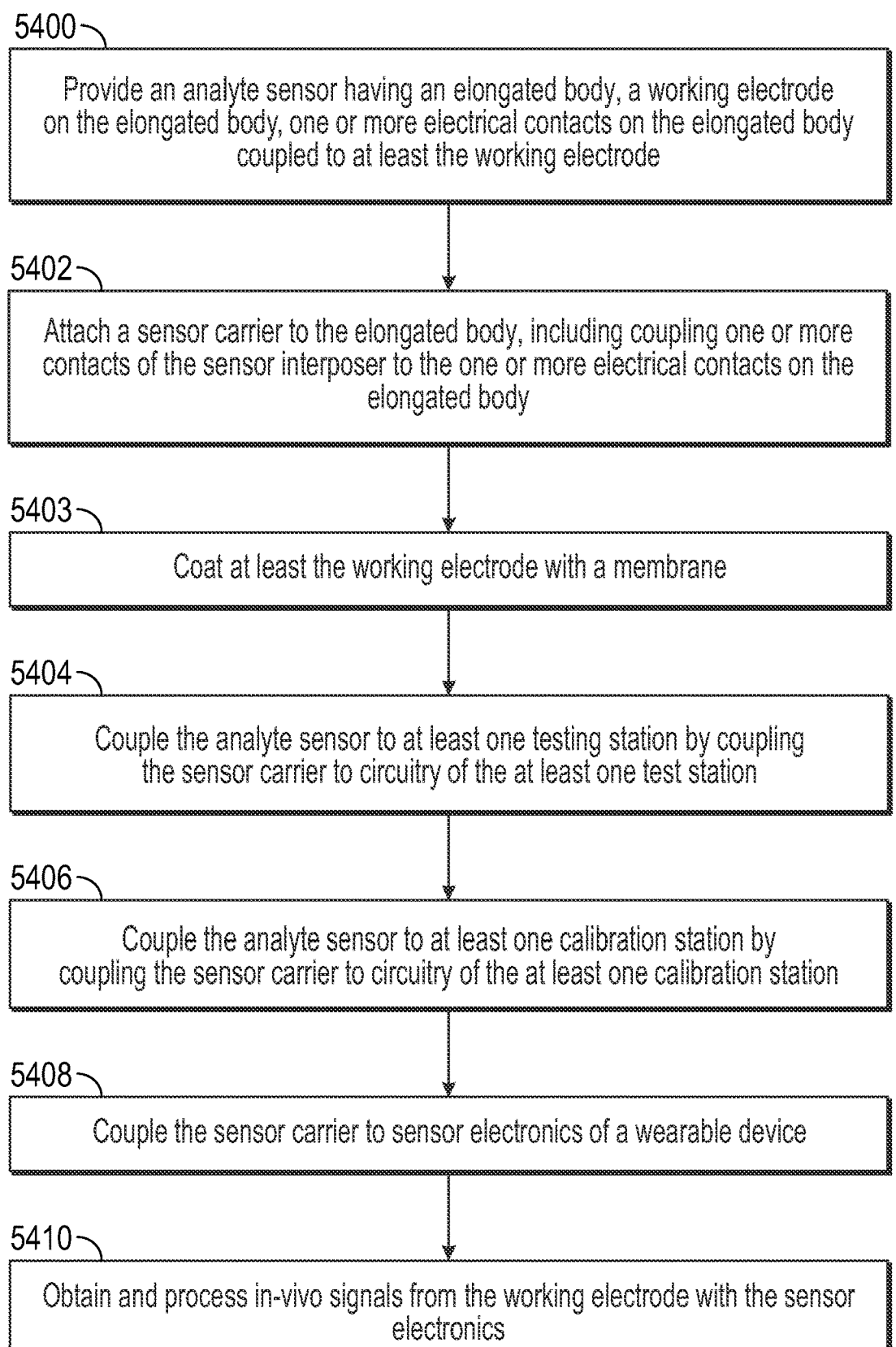

5400 —

Provide an analyte sensor having an elongated body, a working electrode on the elongated body, one or more electrical contacts on the elongated body coupled to at least the working electrode

5402 —

Attach a sensor carrier to the elongated body, including coupling one or more contacts of the sensor interposer to the one or more electrical contacts on the elongated body

5403 —

Coat at least the working electrode with a membrane

5404 —

Couple the analyte sensor to at least one testing station by coupling the sensor carrier to circuitry of the at least one test station

5406 —

Couple the analyte sensor to at least one calibration station by coupling the sensor carrier to circuitry of the at least one calibration station

5408 —

Couple the sensor carrier to sensor electronics of a wearable device

5410 —

Obtain and process in-vivo signals from the working electrode with the sensor electronics

FIG. 57

PRE-CONNECTED ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 17/719,181, filed Apr. 12, 2022, now U.S. Pat. No. 11,706,876, which is a continuation of U.S. application Ser. No. 17/464,547, filed on Sep. 1, 2021, now U.S. Pat. No. 11,350,862, which is a continuation of U.S. application Ser. No. 17/369,535, filed on Jul. 7, 2021, now U.S. Pat. No. 11,160,926, which is a continuation of U.S. patent application Ser. No. 16/167,976, filed on Oct. 23, 2018, now U.S. Pat. No. 11,382,540, which claims the benefit of U.S. Provisional Application No. 62/576,560, filed on Oct. 24, 2017. The aforementioned applications are incorporated by reference herein in their entireties, and each is hereby expressly made a part of this specification.

TECHNICAL FIELD

The present disclosure generally relates to sensors and, more particularly, to analyte sensors such as continuous analyte sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

There are various steps in the manufacturing process of an analyte sensor such as a continuous analyte sensor for which temporary mechanical and electrical connections between the sensor and manufacturing equipment such as testing and/or calibration equipment are used. These connections are facilitated by accurate placement and alignment of the sensor to mechanical and electrical interfaces of the testing and/or calibration equipment. A device such as an "interconnect", "interposer" or "sensor carrier" can be attached to an elongated body of the sensor, as described hereinafter, to assist with handling, and both temporary and permanent, electrical and mechanical connections. A sensor carrier (also referred to as a "sensor interposer") may also include features for tracking, data storage, and sealing sensor electrodes, from each other and from the environment. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In accordance with a first aspect, a method of manufacturing a sensor is provided. The method includes providing an analyte sensor having an elongated body, a first electrode, a second electrode coaxially located within the first electrode, and at least two electrical contacts longitudinally aligned and spaced along a longitudinal axis of the sensor. The method includes attaching a sensor carrier to the analyte sensor, the sensor carrier including an intermediate body, a first conductive portion disposed on the intermediate body, the first conductive portion in electrical communication with the first electrode, a second conductive portion disposed on the intermediate body, the second conductive portion in electrical communication with the second electrode. The first and second conductive portions form a connection portion configured to establish electrical connection between the sensor and a separate device.

In a generally applicable embodiment (i.e. independently combinable with any of the aspects or embodiments identified herein) of the first aspect, the method further includes coupling an outer layer to the intermediate body. The outer layer includes an identifier. The outer layer, the sensor, and the intermediate body can form a laminated configuration. The identifier can be a QR code sheet. The identifier can include any of an optical identifier, a radio-frequency identifier, or a memory-encoded identifier. The identifier can identify the analyte sensor, calibration data for the analyte sensor, or a history of the analyte sensor.

In a generally applicable embodiment (i.e. independently combinable with any of the aspects or embodiments identified herein) of the first aspect, the method further includes coating the sensor with a membrane after attaching the sensor to the sensor carrier.

In a generally applicable embodiment (i.e. independently combinable with any of the aspects or embodiments identified herein) of the first aspect, the first conductive portion and the second conductive portion are traces. The traces can extend from a distal position of the sensor carrier and terminate at a proximal end of the sensor carrier. The traces can form exposed contact surfaces in the connection portion. The first and second conductive portions can be embedded into the intermediate body.

In a generally applicable embodiment (i.e. independently combinable with any of the aspects or embodiments identified herein) of the first aspect, the first conductive portion and the second conductive portion are solder welds. The solder welds can attach the sensor to the sensor carrier.

In a generally applicable embodiment (i.e. independently combinable with any of the aspects or embodiments identified herein) of the first aspect, the first conductive portion and the second conductive portion are conductive tapes. The conductive tapes can attach the sensor to the sensor carrier.

In a generally applicable embodiment (i.e. independently combinable with any of the aspects or embodiments identified herein) of the first aspect, the connection portion is configured to mechanically mate with the separate device.

In a generally applicable embodiment (i.e. independently combinable with any of the aspects or embodiments identified herein) of the first aspect, the separate device is an electronics unit configured to measure analyte data.

In a generally applicable embodiment (i.e. independently combinable with any of the aspects or embodiments identified herein) of the first aspect, the separate device is a component of a manufacturing station. The method can further include performing at least one of a potentiostat measurement, a dipping process, a curing process, a calibration process, or a sensitivity measurement while the electrical connection is established between the sensor and the manufacturing station. The method can further include de-establishing electrical connection between the sensor and the calibration station. The method can further include establishing electrical connection between the sensor and at least one testing station via the connection portion of the sensor carrier.

In a generally applicable embodiment (i.e. independently combinable with any of the aspects or embodiments identified herein) of the first aspect, the intermediate body further includes a datum structure that controls a position and spatial orientation of the analyte sensor relative to a substrate of the intermediate body. The datum structure can include a flexible portion of the substrate that is folded over at least a portion of the analyte sensor.

In a generally applicable embodiment (i.e. independently combinable with any of the aspects or embodiments identified herein) of the first aspect, the first conductive portion and/or the second conductive portion comprise at least one of a coil spring, a leaf spring, or a conductive elastomer.

In accordance with a second aspect, an apparatus is provided that includes an analyte sensor having an elongated body, a first electrode in electrical communication with a first conductive contact, a second electrode in electrical communication with a second conductive contact. The sensor carrier can be attached to the analyte sensor. The sensor carrier can include an intermediate body, a first conductive portion disposed on the intermediate body, the first conductive portion in electrical communication with the first conductive contact, and a second conductive portion disposed on the intermediate body, the second conductive portion in electrical communication with the second conductive contact. The first and second conductive portions can form a connection portion configured to establish electrical communication between the first and second conductive contacts and a separate device.

In a generally applicable embodiment (i.e. independently combinable with any of the aspects or embodiments identified herein) of the second aspect, the apparatus further includes an identifier coupled to the intermediate body. The identifier, the sensor, and the intermediate body can form a laminated configuration. The identifier can be a QR code sheet. The identifier can be any of an optical identifier, a radio-frequency identifier, or a memory-encoded identifier. The identifier can be configured to identify any of the analyte sensor, calibration data for the analyte sensor, and a history of the analyte sensor.

In a generally applicable embodiment (i.e. independently combinable with any of the aspects or embodiments identified herein) of the second aspect, the first conductive portion and the second conductive portion are traces. The traces can form exposed contact surfaces in the connection portion. The first and second conductive portions can be at least partially embedded into the intermediate body.

In a generally applicable embodiment (i.e. independently combinable with any of the aspects or embodiments identified herein) of the second aspect, the first conductive portion and the second conductive portion include at least one of a solder weld, a conductive tape, a coil spring, a leaf spring, or a conductive elastomer.

In a generally applicable embodiment (i.e. independently combinable with any of the aspects or embodiments identified herein) of the second aspect, the connection portion is configured to mechanically mate with the separate device.

In a generally applicable embodiment (i.e. independently combinable with any of the aspects or embodiments identified herein) of the second aspect, the separate device is an electronics unit configured to measure analyte data.

In a generally applicable embodiment (i.e. independently combinable with any of the aspects or embodiments identified herein) of the second aspect, the separate device is a component of a manufacturing station. At least one of a potentiostat measurement, a dipping process, a curing process, a calibration process, or a sensitivity measurement can be configured to be performed while the electrical connection is established between the sensor and the manufacturing station. The manufacturing station can comprise a calibration station configured to de-establish electrical connection between the sensor and the calibration station and establish electrical connection between the sensor and at least one testing station via the connection portion of the sensor carrier.

In a generally applicable embodiment (i.e. independently combinable with any of the aspects or embodiments identified herein) of the second aspect, the intermediate body further comprises a datum structure configured to control a position and spatial orientation of the analyte sensor relative to a substrate of the intermediate body.

In a generally applicable embodiment (i.e. independently combinable with any of the aspects or embodiments identified herein) of the second aspect, the first electrode may be positioned coaxially within the second electrode, and the first electrical contact and the second electrical contact may be longitudinally aligned and spaced along a longitudinal axis of the sensor.

In a generally applicable embodiment (i.e. independently combinable with any of the aspects or embodiments identified herein) of the second aspect, the first electrode and the second electrode may be affixed to a flexible planar substrate. In addition, the first electrical contact and the second electrical contact may be affixed to the flexible planar substrate.

In a generally applicable embodiment (i.e. independently combinable with any of the aspects or embodiments identified herein) of the second aspect, the first conductive contact and the second conductive contact are affixed to the intermediate body with conductive adhesive.

In a generally applicable embodiment (i.e. independently combinable with any of the aspects or embodiments identified herein) of the second aspect, the first conductive contact and the second conductive contact are affixed to the intermediate body with anisotropic conductive film.

In accordance with a third aspect, an array of pre-connected analyte sensors is provided. The array includes a substrate, a first plurality of electrical contacts disposed on the substrate, a second plurality of electrical contacts disposed on the substrate, and a plurality of analyte sensors disposed on the substrate. Each of the plurality of analyte sensors includes a first sensor electrical contact coupled to a corresponding one of the first plurality of electrical contacts on the substrate, and a second sensor electrical contact coupled to a corresponding one of the second plurality of electrical contacts on the substrate. The array may comprise one or more strips.

In a generally applicable embodiment (i.e. independently combinable with any of the aspects or embodiments identified herein) of the third aspect, the first plurality of electrical contacts are aligned along the substrate. The first plurality of electrical contacts can be formed from an exposed contact surface.

In a generally applicable embodiment (i.e. independently combinable with any of the aspects or embodiments identified herein) of the third aspect, the second plurality of electrical contacts are aligned along the substrate. The second plurality of electrical contacts can be formed from an exposed contact surface.

In a generally applicable embodiment (i.e. independently combinable with any of the aspects or embodiments identified herein) of the third aspect, the first and second plurality of electrical contacts are configured to connect with a separate device. The separate device can be a component of a manufacturing station.

In a generally applicable embodiment (i.e. independently combinable with any of the aspects or embodiments identified herein) of the third aspect, the substrate includes at least one singulation feature configured to facilitate singulation of the substrate into a plurality of sensor carriers, wherein each of the plurality of sensor carriers is attached to a corresponding one of the analyte sensors.

In a generally applicable embodiment (i.e. independently combinable with any of the aspects or embodiments identified herein) of the third aspect, the strip further includes a plurality of identifiers disposed on the substrate.

In a generally applicable embodiment (i.e. independently combinable with any of the aspects or embodiments identified herein) of the third aspect, the substrate includes an elongated dimension, wherein the plurality of analyte sensors extend beyond an edge of the substrate in a direction orthogonal to the elongated dimension. The strip can further include a feed-guide strip that runs along an opposing edge of the substrate in the elongated dimension. The substrate can further include a flexible substrate configured to be rolled onto a reel. The feed-guide strip can be removable from the substrate.

In a generally applicable embodiment (i.e. independently combinable with any of the aspects or embodiments identified herein) of the third aspect, the substrate comprises a molded thermoplastic having a plurality of datum features that control a position and orientation of the plurality of analyte sensors, and wherein the a first plurality of electrical contacts and the second plurality of electrical contacts each comprise embedded conductive traces in the molded thermoplastic.

In a generally applicable embodiment (i.e. independently combinable with any of the aspects or embodiments identified herein) of the third aspect, the strip further includes a first datum structure coupled to the strip, the first datum structure configured to position the plurality of analyte sensors. The first datum structure includes at least one singulation feature configured to facilitate singulation of the first datum structure into a plurality of second datum structures, wherein each of the plurality of second datum structures is coupled to a corresponding one of a plurality of sensor carriers formed by the substrate.

In a generally applicable embodiment (i.e. independently combinable with any of the aspects or embodiments identified herein) of the third aspect, the strip further includes a carrier having processing circuitry configured to perform at least potentiostat measurements for the plurality of analyte sensors. The strip can further include communications circuitry operable by the processing circuitry to send and receive data associated with each of the analyte sensors together with an identifier for that analyte sensor.

In accordance with a fourth aspect, a method is provided. The method includes providing a pre-connected analyte sensor, the pre-connected analyte sensor comprising an intermediate body, an analyte sensor permanently attached to the intermediate body, and an identifier coupled to the intermediate body. The method includes communicatively coupling the analyte sensor to a processing circuitry of a manufacturing station by coupling the intermediate body to a corresponding feature of the manufacturing station. The method includes operating the processing circuitry of the manufacturing station to communicate with the pre-connected analyte sensor.

In a generally applicable embodiment (i.e. independently combinable with any of the aspects or embodiments identified herein) of the fourth aspect, operating the processing circuitry includes obtaining a signal from the analyte sensor via the connection portion. Operating the processing circuitry can include operating an optical, infrared, or radio-frequency reader of the manufacturing station to obtain the identifier.

In a generally applicable embodiment (i.e. independently combinable with any of the aspects or embodiments identified herein) of the fourth aspect, the method further includes storing, with the processing circuitry of the manufacturing station and in connection with the identifier, sensor data corresponding to the signal. The identifier can identify any of the analyte sensor, calibration data for the analyte sensor, and a history of the analyte sensor.

In a generally applicable embodiment (i.e. independently combinable with any of the aspects or embodiments identified herein) of the fourth aspect, the signal includes a glucose sensitivity signal.

In a generally applicable embodiment (i.e. independently combinable with any of the aspects or embodiments identified herein) of the fourth aspect, the method further includes removing the pre-connected analyte sensor from the manufacturing station and communicatively coupling the analyte sensor to processing circuitry of a wearable device by mechanically coupling an anchoring feature of the intermediate body to a corresponding feature of a wearable device. The method can further include obtaining in vivo measurement data from the analyte sensor with the processing circuitry of the wearable device.

In a generally applicable embodiment (i.e. independently combinable with any of the aspects or embodiments identified herein) of the fourth aspect, the analyte sensor is permanently attached to the intermediate body with conductive adhesive.

In a generally applicable embodiment (i.e. independently combinable with any of the aspects or embodiments identified herein) of the fourth aspect, the analyte sensor is permanently attached to the intermediate body with anisotropic conductive film.

In accordance with a fifth aspect, a wearable device is provided. The wearable device comprises a housing and electronic circuitry configured to process analyte sensor signals. The electronic circuitry is enclosed within the housing. An analyte sensor has a distal portion positioned outside the housing. An intermediate body has an electrical connection to both a proximal portion of the analyte sensor and the electronics, wherein the electrical connection between the intermediate body and the proximal portion of the analyte sensor is external to the housing.

In generally applicable embodiments (i.e. independently combinable with any of the aspects or embodiments identified herein) of the fifth aspect the intermediate body may be positioned adjacent to an exterior surface of the housing. The device may include electrical contacts coupled to both the electronics and the intermediate body. The intermediate body may be electrically connected to the electrical contacts with conductive epoxy. The intermediate body is electrically connected to the electrical contacts with anisotropic conductive film. The intermediate body may be sealed. The electrical contacts may extend through the housing. The intermediate body may be positioned in a recess on the exterior surface of the housing. The electrical contacts may extend through the housing in the recess to electrically couple the intermediate body to the electronic circuitry enclosed within the housing. The intermediate body may be covered with a polymer in the recess.

In generally applicable embodiments (i.e. independently combinable with any of the aspects or embodiments identified herein) of the fifth aspect the analyte sensor is formed as an elongated body with a distal portion configured for percutaneous implantation in a subject and a proximal portion configured for electrically connecting to the intermediate body. The distal portion of the analyte sensor may extend away from an opening through the housing. The electronic circuitry may comprise a potentiostat and/or a wireless transmitter.

In accordance with a sixth aspect, a method of making a pre-connected analyte sensor is provided. The method comprises mechanically and electrically connecting a proximal portion of an elongated conductor to a conductive portion of an intermediate body, and after the connecting, coating a distal portion of the elongated conductor with a polymer membrane to form an analyte sensor having a working electrode region configured to support electrochemical reactions for analyte detection in the distal portion of the elongated conductor.

In generally applicable embodiments (i.e. independently combinable with any of the aspects or embodiments identified herein) of the sixth aspect, the method additionally comprises testing the analyte sensor, wherein the testing comprises electrically coupling the intermediate body to a testing station. The method may additionally comprise calibrating the analyte sensor, wherein the calibrating comprises electrically coupling the intermediate body to a testing station. The coating may comprise dip coating.

In generally applicable embodiments (i.e. independently combinable with any of the aspects or embodiments identified herein) of the sixth aspect, the intermediate body may be part of an array formed by a plurality of coupled intermediate bodies, wherein the method further comprises mechanically and electrically connecting a proximal portion of each of a plurality of elongated electrodes to a conductive portion of each intermediate body of the array. The coating may be performed in parallel on each distal portion of each of the plurality of elongated electrodes connected to the intermediate bodies of the array. The method may comprise singulating one or more of the intermediate bodies of the array after the coating.

In generally applicable embodiments (i.e. independently combinable with any of the aspects or embodiments identified herein) of the sixth aspect, mechanically and electrically connecting comprises applying conductive paste to the elongated conductor and the conductive portion of the intermediate body. In some embodiments, mechanically and electrically connecting comprises compressing anisotropic conductive film between the proximal portion of the elongated conductor and the conductive portion of the intermediate body. The connecting may be performed at a location remote from the coating. In some embodiments, the coating, testing, and calibrating are all performed at a location remote from the connecting.

In accordance with a seventh aspect, a method of making an on-skin wearable percutaneous analyte sensor comprises assembling electronic circuitry into an internal volume of a housing, wherein the electronic circuitry is configured for (1) detecting signals generated from an electrochemical reaction under the skin of a subject at a working electrode of an analyte sensor, and (2) wirelessly transmitting data derived from the detected signals outside of the housing for processing and/or display by a separate device. After assembling the electronic circuitry into the internal volume of the housing, attaching a proximal portion of the analyte sensor to an external electrical interface coupled to the electronic circuitry such that the electronic circuitry becomes connected to the analyte sensor to receive signals therefrom without opening the housing.

In generally applicable embodiments (i.e. independently combinable with any of the aspects or embodiments identified herein) of the seventh aspect, the method comprises sealing the interface after attaching the proximal portion of the analyte sensor. The method may comprise testing the electronic circuitry for functionality prior to the attaching. The method may comprise testing the analyte sensor for functionality prior to the attaching. The assembling may be performed at a location remote from the attaching.

In generally applicable embodiments (i.e. independently combinable with any of the aspects or embodiments identified herein) of the seventh aspect, the method may comprise coupling an intermediate body to the proximal portion of the analyte sensor, and the attaching may comprise attaching the intermediate body to the external electrical interface. The method may then comprise performing at least one manufacturing or testing procedure on the working electrode using the intermediate body prior to the attaching. The performing may comprise coating the working electrode of the analyte sensor. The coupling may be performed at a first location, the assembling may be performed at a second location, and the performing may be performed at a third location, wherein the first, second, and third locations are remote from one another. The attaching and/or the coupling may be performed with anisotropic conductive film The method may further comprise attaching an inserter to the housing for implanting the working electrode into a subject.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

US 12,666,543 B2

9

BRIEF DESCRIPTION OF THE DRAWINGS

The present embodiments now will be discussed in detail with an emphasis on highlighting the advantageous features. These embodiments are for illustrative purposes only and are not to scale, instead emphasizing the principles of the disclosure. These drawings include the following figures, in which like numerals indicate like parts:

FIG. 4A illustrates a schematic of a pre-connected analyte sensor, according to some embodiments.

FIG. 4B illustrates another schematic of a pre-connected analyte sensor, according to some embodiments.

FIG. 4C illustrates a layered view of a pre-connected analyte sensor, according to some embodiments.

10

FIG. 16 illustrates a top view of a sensor carrier attached to an analyte sensor with conductive adhesive, according to some embodiments.

FIG. 17 illustrates an end view of a sensor carrier attached to an analyte sensor with conductive adhesive, according to some embodiments.

FIG. 18 illustrates an end view of a sensor carrier attached to an analyte sensor with conductive adhesive in a recess of a sensor carrier substrate, according to some embodiments.

FIG. 19 illustrates an end view of a sensor carrier attached to an analyte sensor with conductive adhesive in a corner of a sensor carrier substrate, according to some embodiments.

FIG. 20 illustrates an end view of a sensor carrier attached to an analyte sensor with conductive adhesive in a rounded recess of a sensor carrier substrate, according to some embodiments.

Figure 21A:
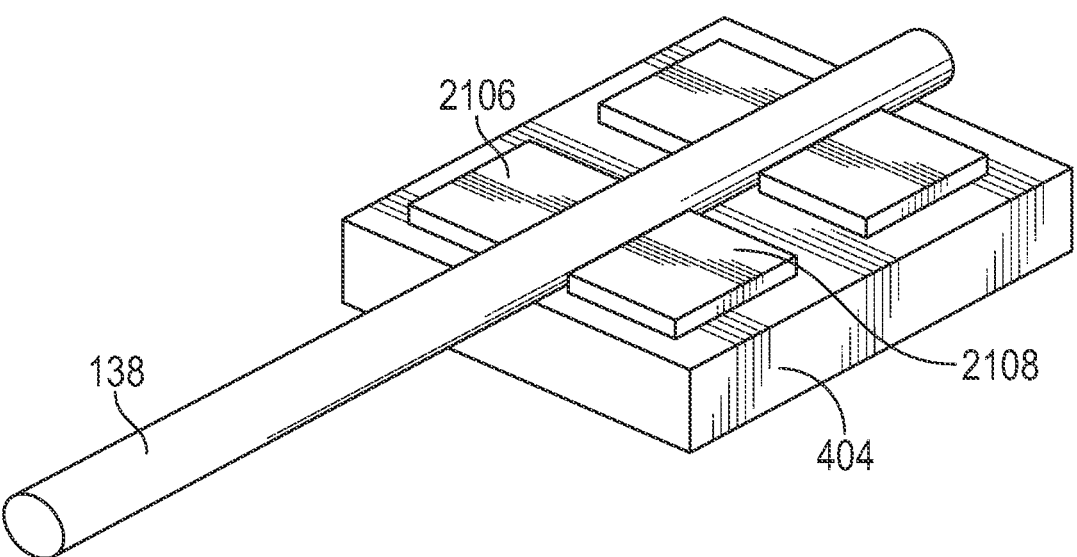
Figure 21B:
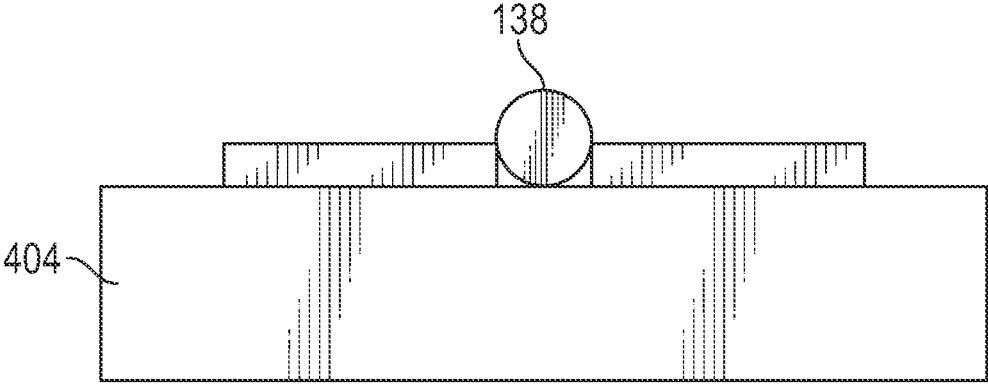

FIGS. 21A and 21B illustrate a perspective view and an end view respectively of an analyte sensor attached to a sensor carrier in guide structures.

Figure 22:
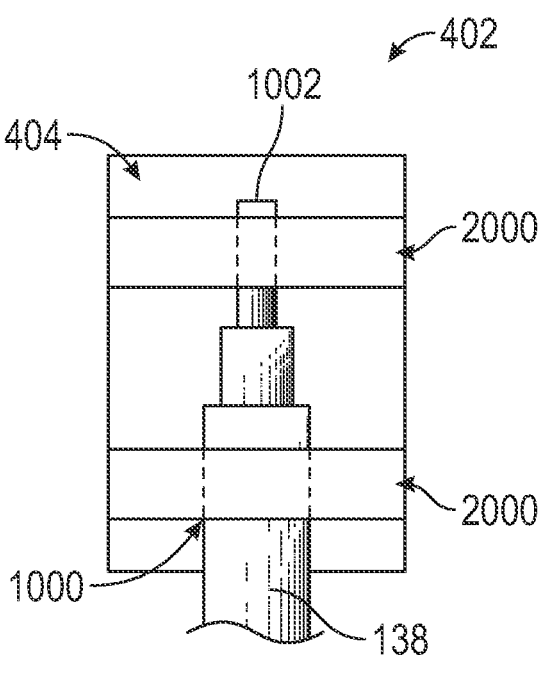

FIG. 22 illustrates a top view of a sensor carrier attached to an analyte sensor with conductive tape, according to some embodiments.

Figure 23:
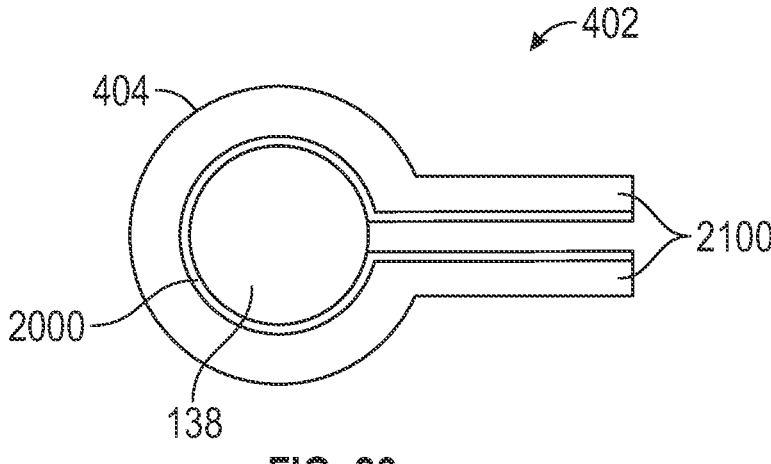

FIG. 23 illustrates a top view of a sensor carrier having a substrate attached to and wrapped around an analyte sensor, according to some embodiments.

FIG. 24 illustrates a top view of a sensor carrier attached to an analyte sensor with welded conductive plastic, according to some embodiments.

FIGS. 25 and 26 illustrate manufacturing equipment for attaching a sensor carrier to an analyte sensor with conductive plastic, according to some embodiments.

Figure 27:
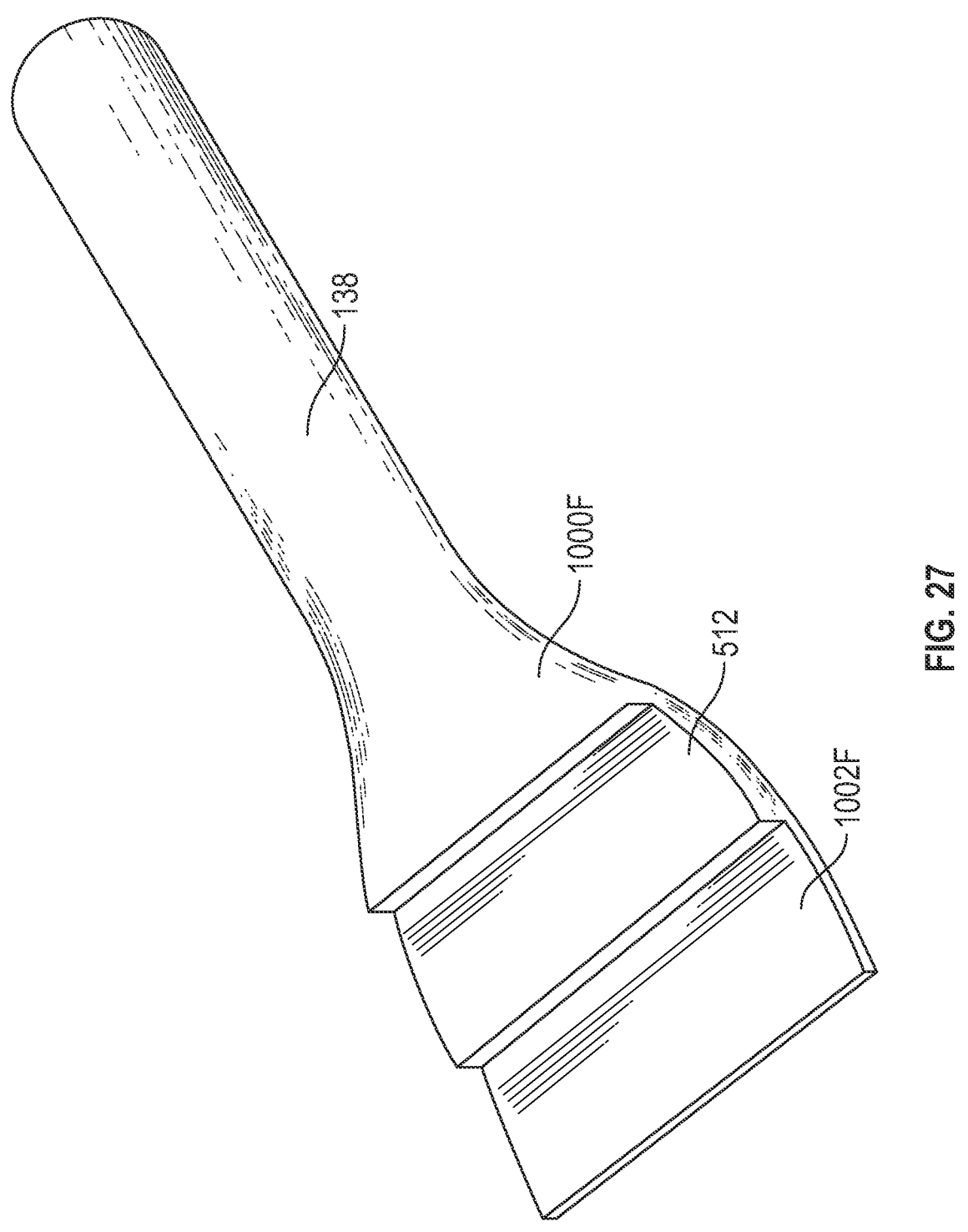

FIG. 27 is a perspective-view schematic illustrating a proximal portion of an analyte sensor having flattened electrical connector portions, according to some embodiments.

Figure 28:
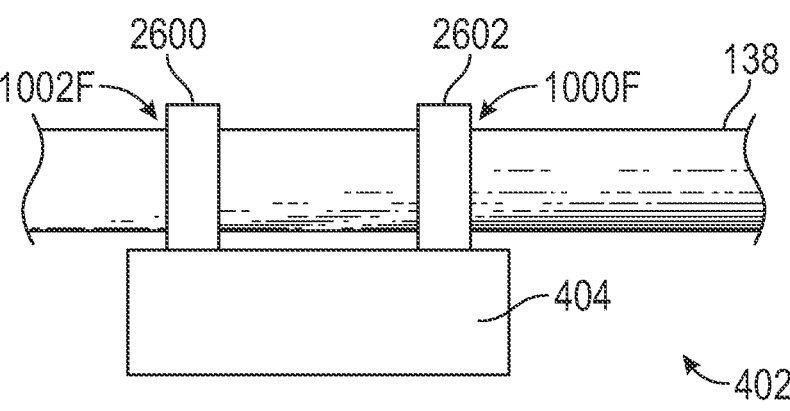

FIG. 28 illustrates a side view of the analyte sensor of FIG. 24 attached to a sensor carrier, according to some embodiments.

Figure 29:
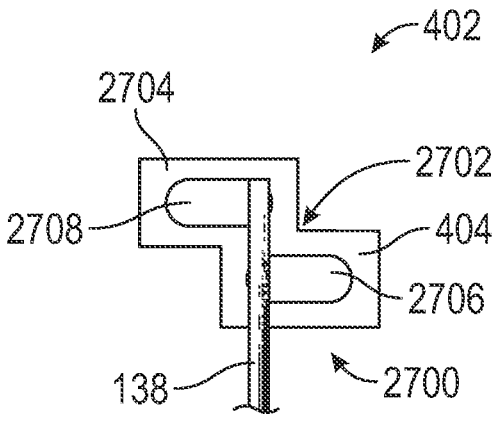

FIG. 29 illustrates a top view of a sensor carrier having a flexible substrate configured to wrap around an analyte sensor, according to some embodiments.

Figure 30:
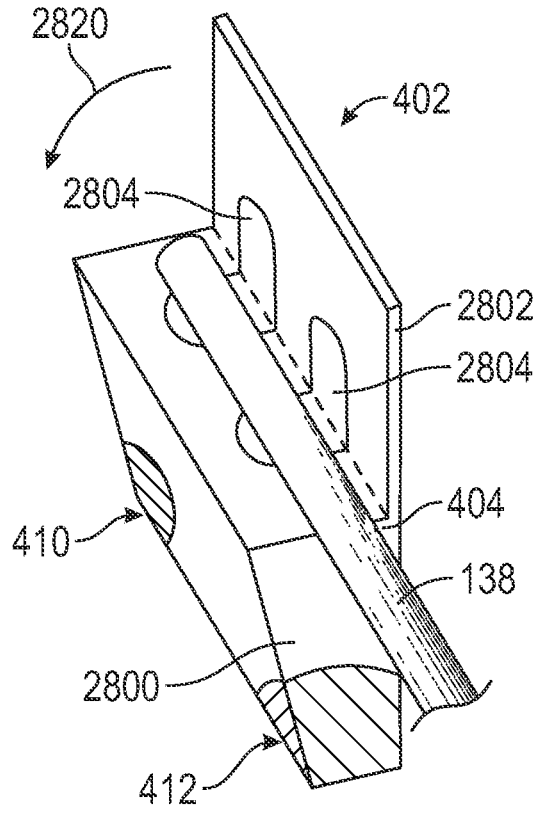

FIG. 30 illustrates a perspective view of a sensor carrier having substrate with a flexible portion configured to wrap around an analyte sensor, according to some embodiments.

Figure 31A:
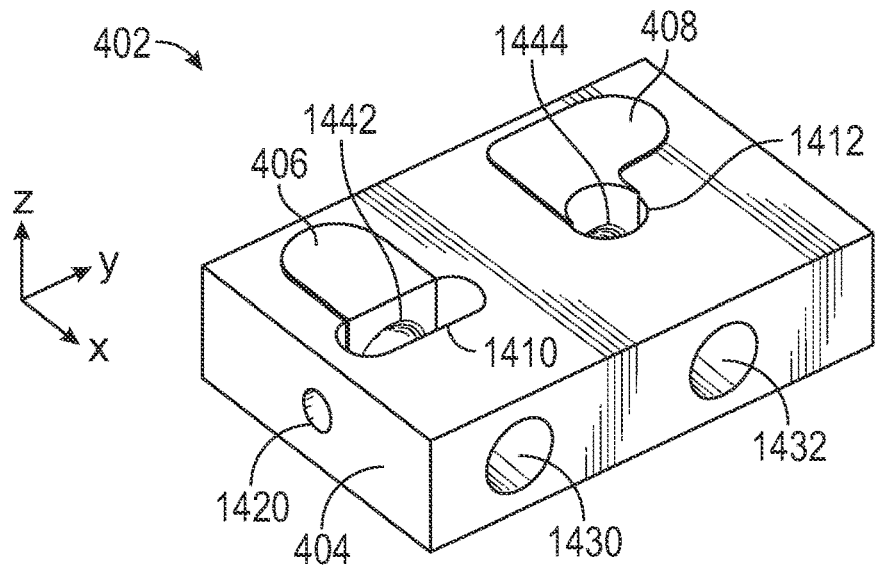
Figure 31B:
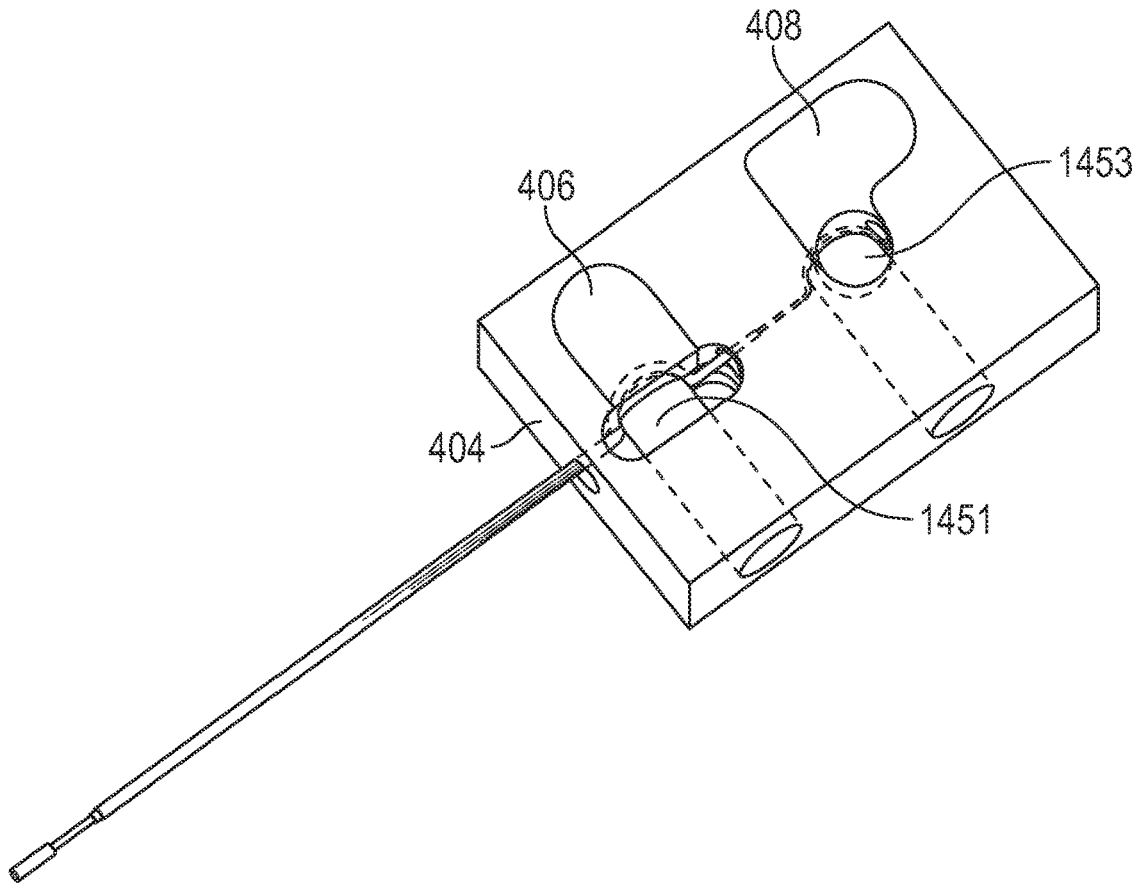

FIGS. 31A and 31B illustrate another embodiment of a sensor carrier attached to an analyte sensor.

Figures 32, 33, 34:
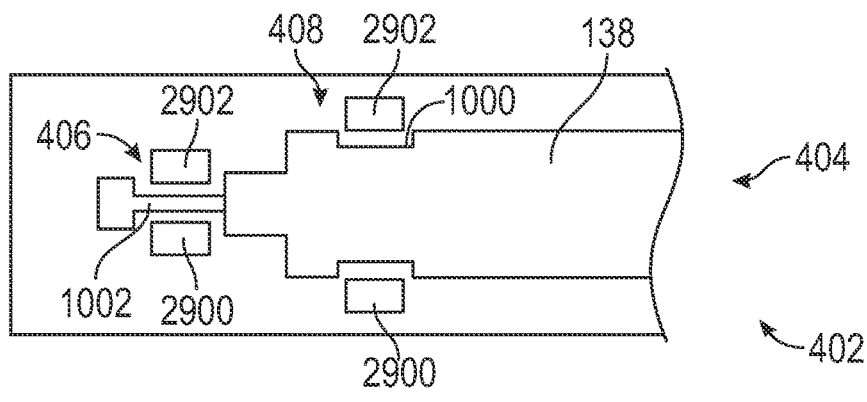

FIG. 32 illustrates a top view of a sensor carrier having a movable fastener for attaching an analyte sensor, according to some embodiments.

FIG. 33 illustrates a perspective view of the movable fastener of FIG. 29, according to some embodiments.

FIG. 34 illustrates a perspective view of a sensor carrier implemented as a barrel fastener, according to some embodiments.

Figure 35A:
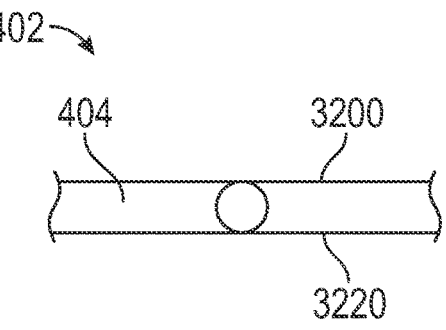

FIG. 35A illustrates a face-on view of a sensor carrier having a flexible substrate wrapped around an analyte sensor, according to some embodiments.

Figure 35B:
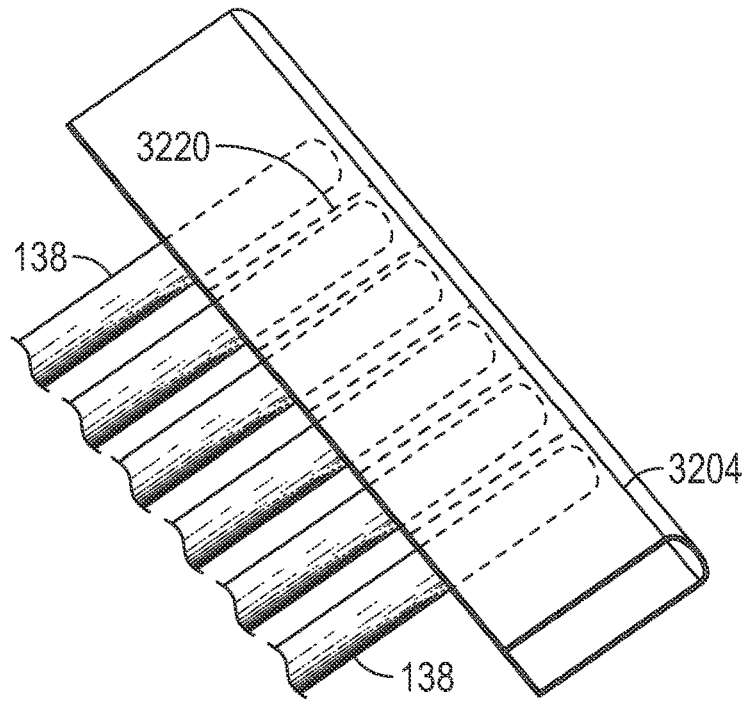

FIG. 35B illustrates a perspective view of a sensor carrier having a flexible substrate wrapped around multiple analyte sensors, according to some embodiments.

Figure 36:
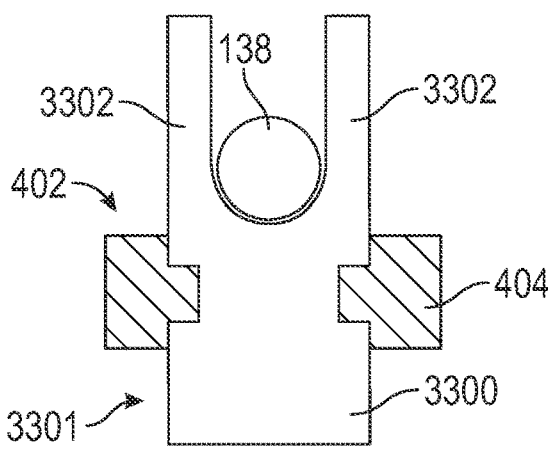

FIG. 36 illustrates an end view of a sensor carrier having a crimp connector, according to some embodiments.

Figure 37:
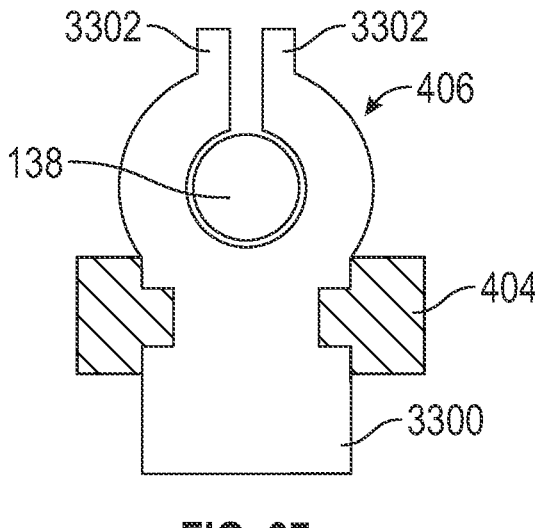

FIG. 37 illustrates an end view of a sensor carrier attached to an analyte sensor by a crimp connector, according to some embodiments.

Figure 38:
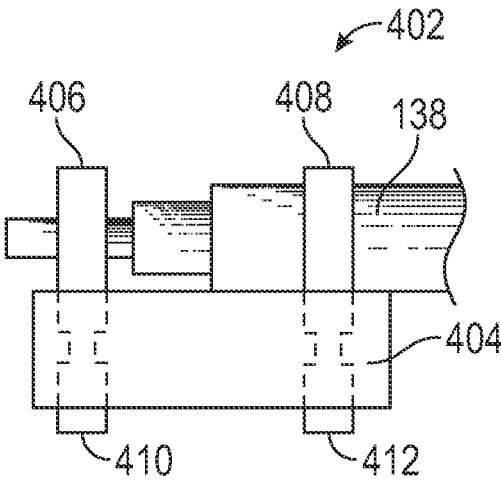

FIG. 38 illustrates a side view of a sensor carrier having crimp connectors, according to some embodiments.

Figure 39:
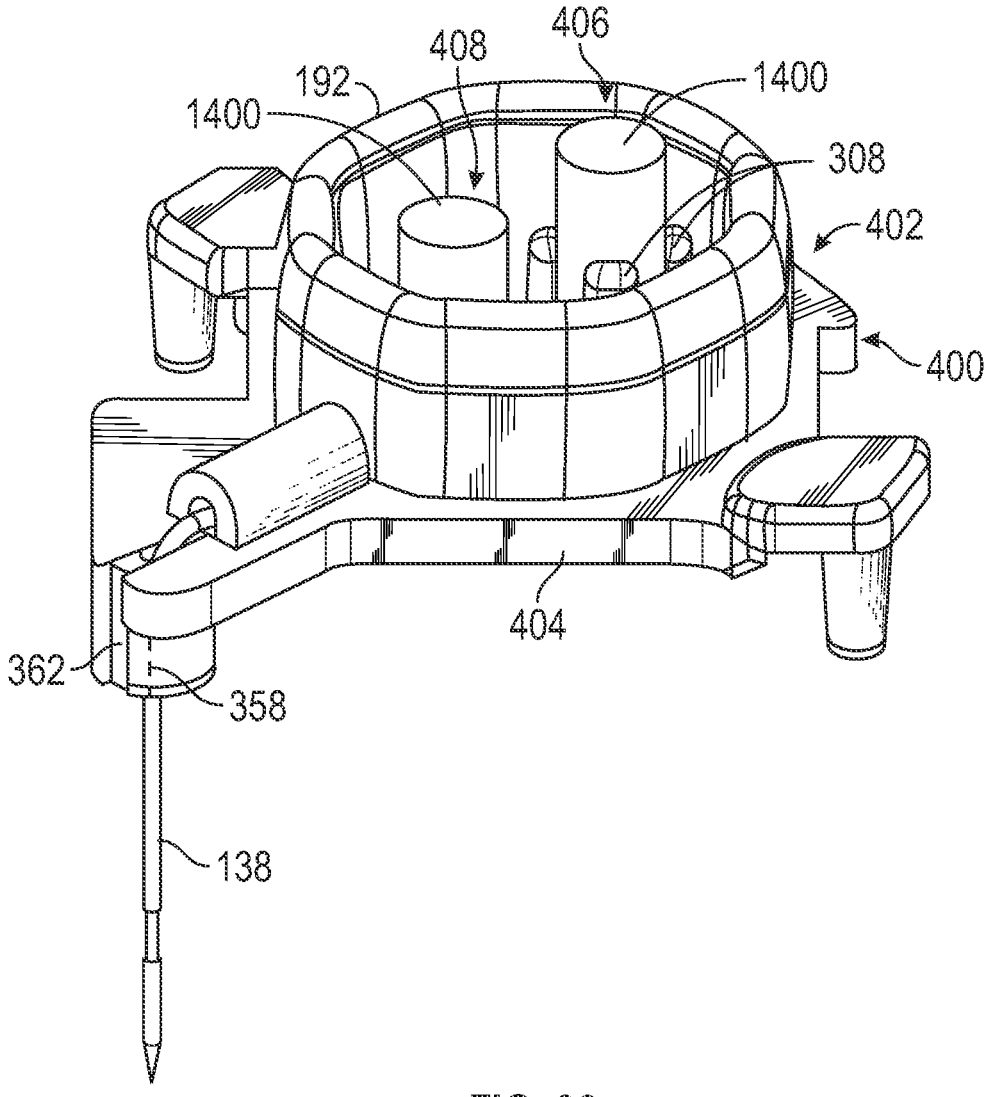

FIG. 39 illustrates a perspective view of a sensor carrier, according to some embodiments.

Figure 40:
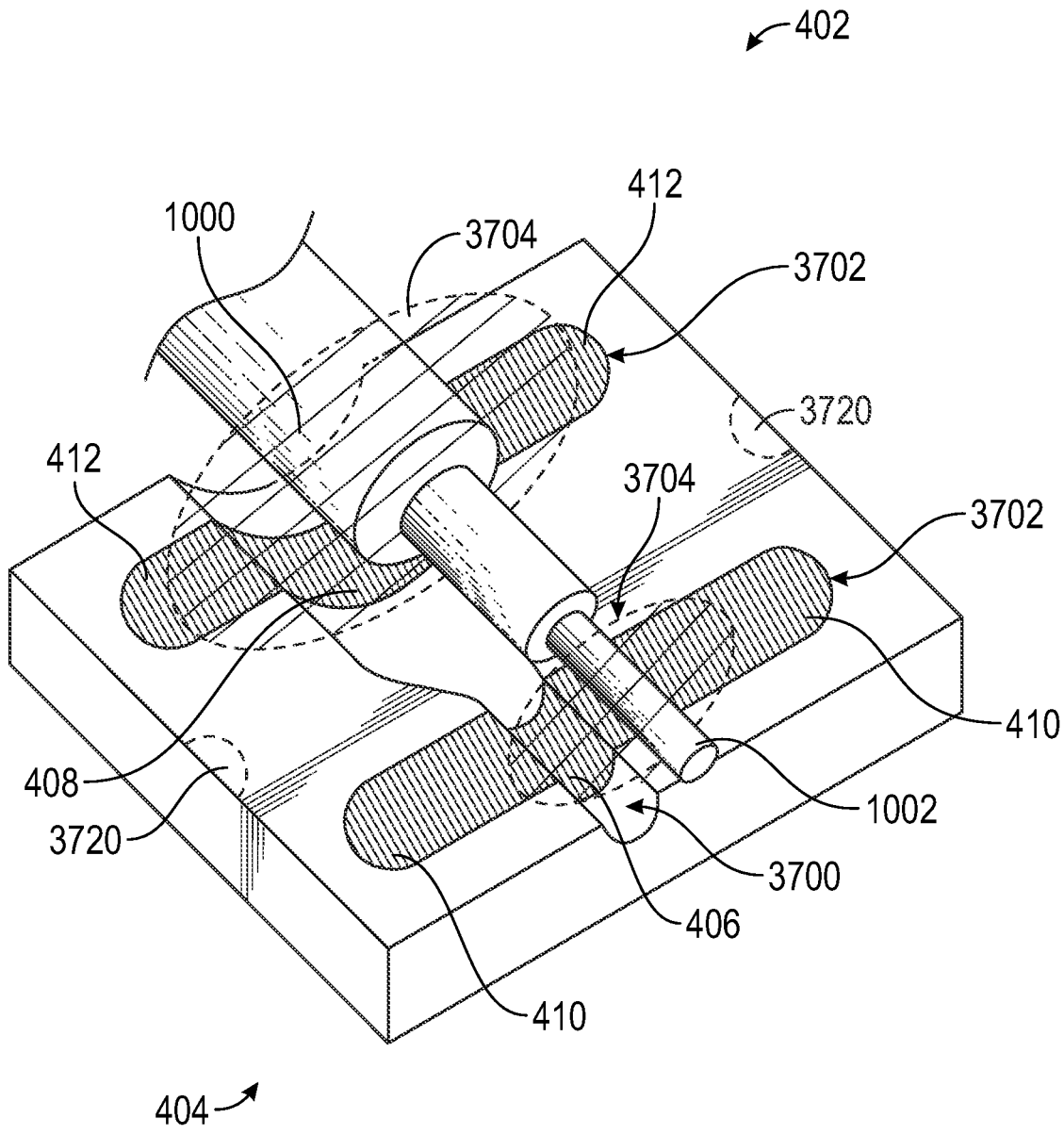

FIG. 40 illustrates a perspective view of a sensor carrier formed from a molded interconnect device, according to some embodiments.

FIG. 41 illustrates a top view of a sensor carrier formed from a molded interconnect device, according to some embodiments.

FIG. 42 illustrates a side view of a sensor carrier attached to an analyte sensor by a conductive coupler, according to some embodiments.

FIG. 43 illustrates a side view of a sensor carrier having an elongated dimension for attachment to multiple analyte sensors, according to some embodiments.

Figures 44, 45, 46:
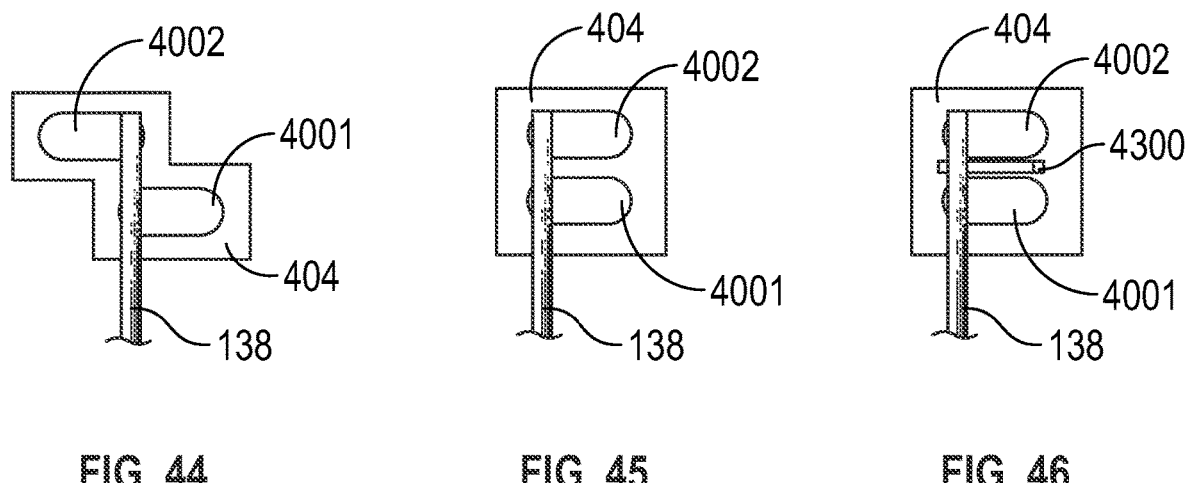

FIG. 44 illustrates a top view of a sensor carrier having a flexible substrate for wrapping around an analyte sensor, according to some embodiments.

FIG. 45 illustrates a top view of another sensor carrier having a flexible substrate for wrapping around an analyte sensor, according to some embodiments.

FIG. 46 illustrates a top view of another sensor carrier having a flexible substrate for wrapping around an analyte sensor, according to some embodiments.

Figure 47A:
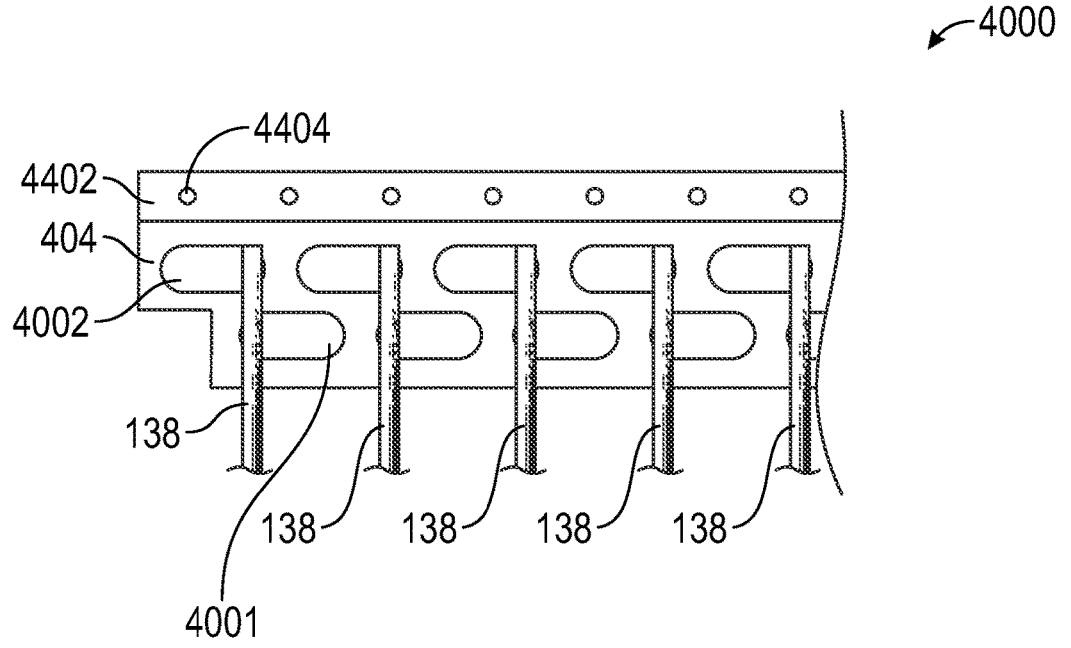

FIG. 47A illustrates a side view of a sensor carrier having a feed-guide strip on an elongated dimension for attachment to multiple analyte sensors, according to some embodiments.

Figure 47B:
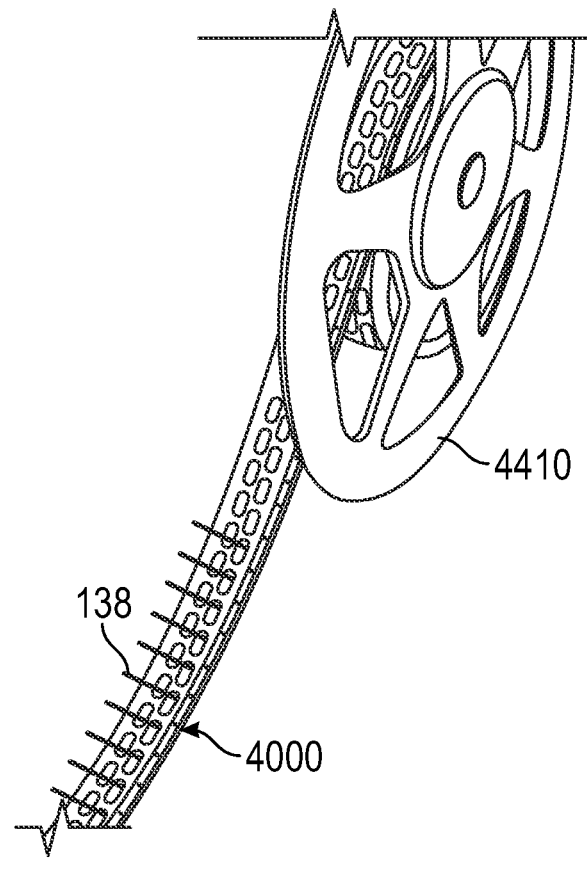

FIG. 47B illustrates a perspective view of the sensor carrier of FIG. 47A wrapped on a reel, according to some embodiments.

Figure 48:
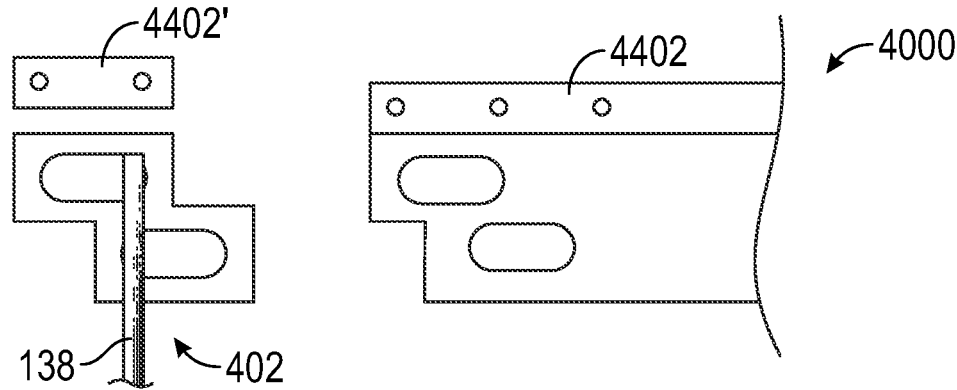

FIG. 48 illustrates a top view of the sensor carrier of FIG. 47A with a sensor carrier singulated from the sensor carrier, according to some embodiments.

Figure 49:
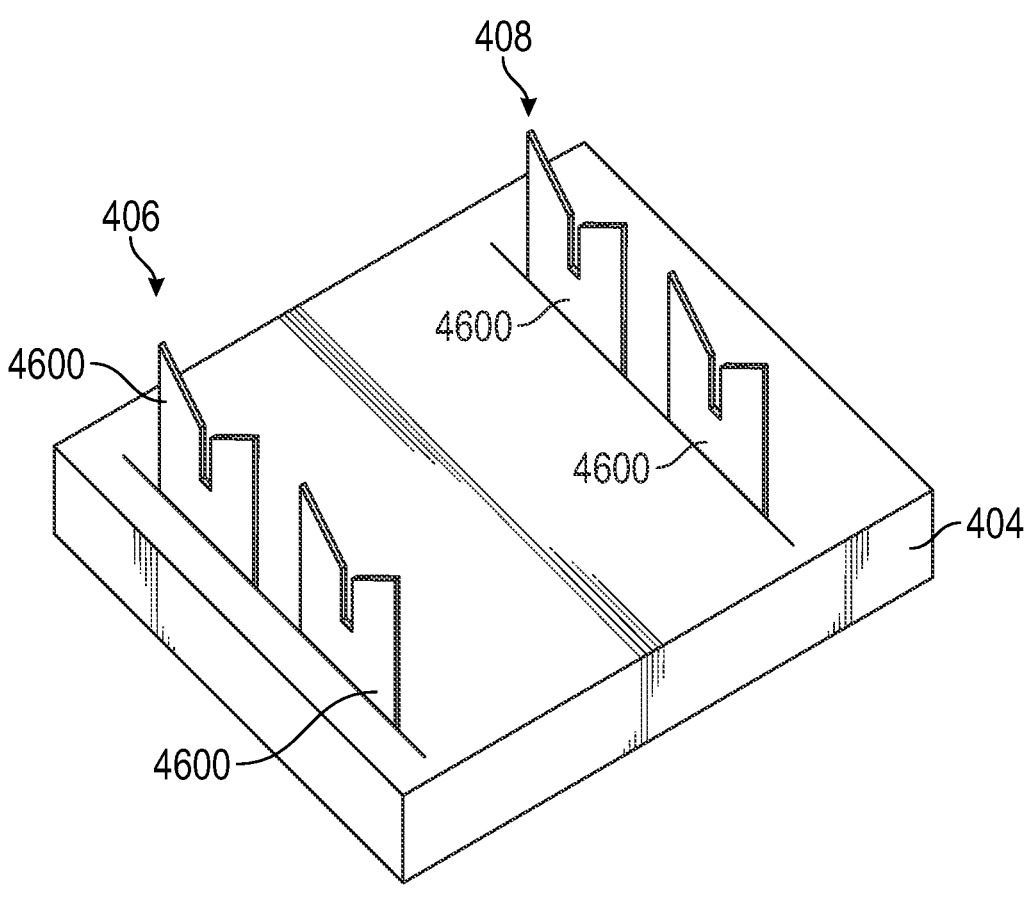

FIG. 49 illustrates a perspective view of a sensor carrier having spring-loaded receptacles for attachment of multiple analyte sensors, according to some embodiments.

Figure 50:
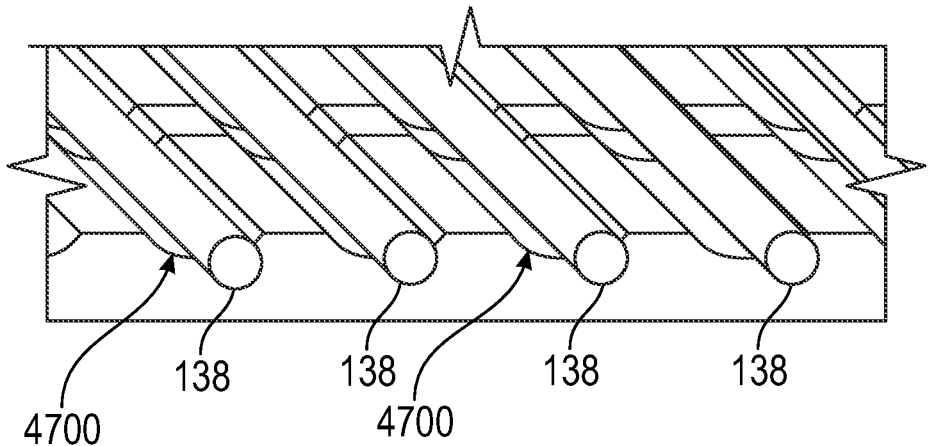

FIG. 50 illustrates a perspective view of a sensor carrier having magnetic datum features for positioning and orientation of multiple analyte sensors, according to some embodiments.

Figure 51A:
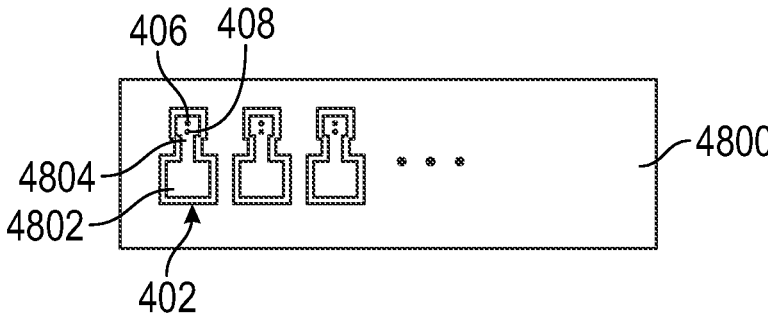

FIG. 51A illustrates a top view of a sensor carrier having a rigid flex panel for attachment to multiple analyte sensors, according to some embodiments.

Figure 51B:
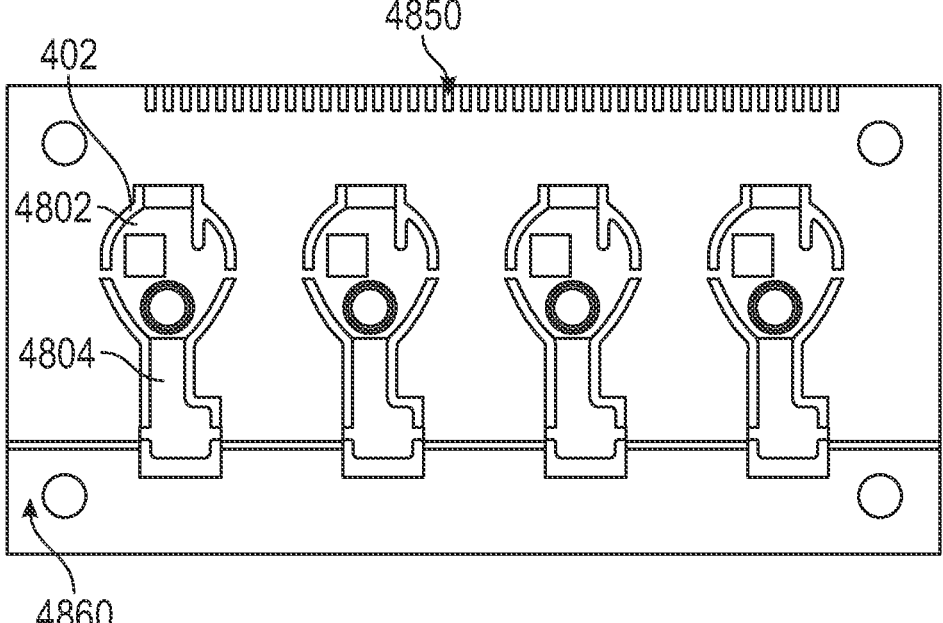

FIG. 51B illustrates a top view of a sensor carrier having a rigid flex panel for attachment to multiple analyte sensors having an edge card connector pad for electronic connection, according to some embodiments.

Figures 52A, 52B:
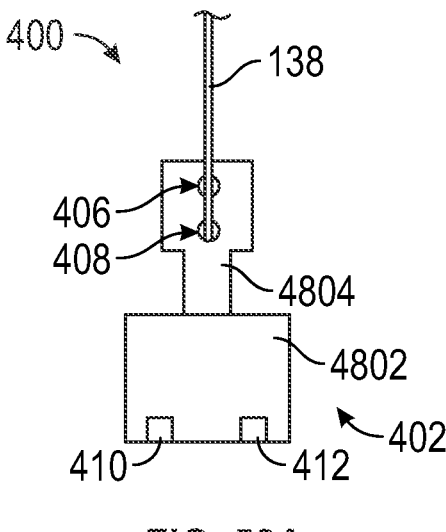

FIG. 52A illustrates a top view of a sensor carrier singulated from the sensor carrier of FIG. 48 and attached to an analyte sensor to form a pre-connected sensor, according to some embodiments.

FIG. 52B illustrates a sensor carrier having a rigid flex panel for attachment to multiple analyte sensors of FIG. 48B without the V-score portion, according to some embodiments.

Figure 53A:
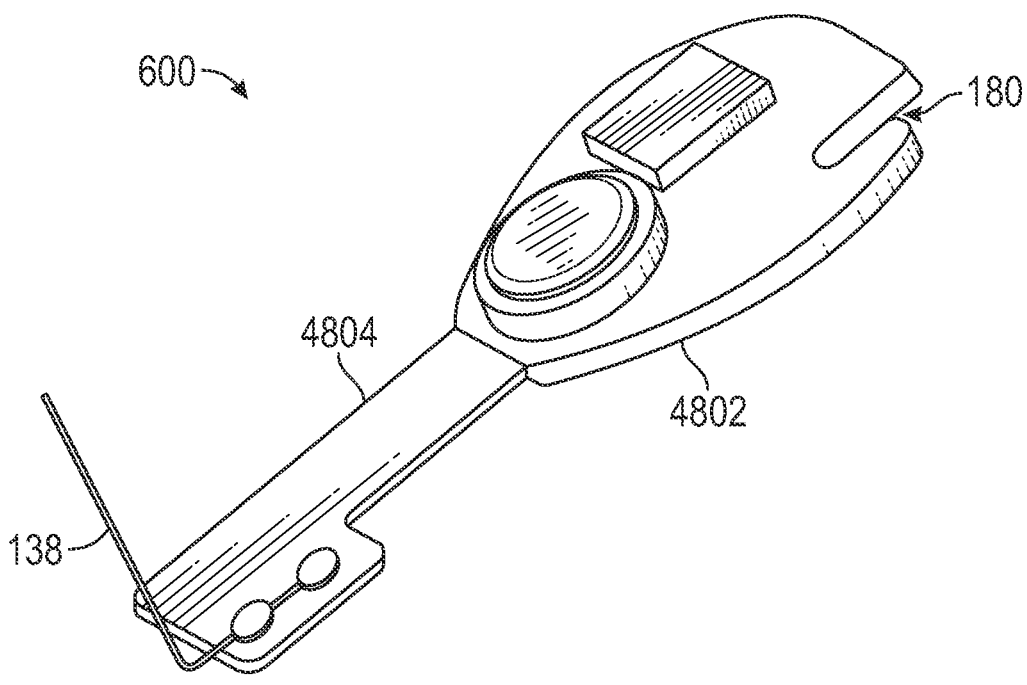

FIG. 53A illustrates the pre-connected sensor to be installed in a wearable device, according to some embodiments.

Figure 53B:
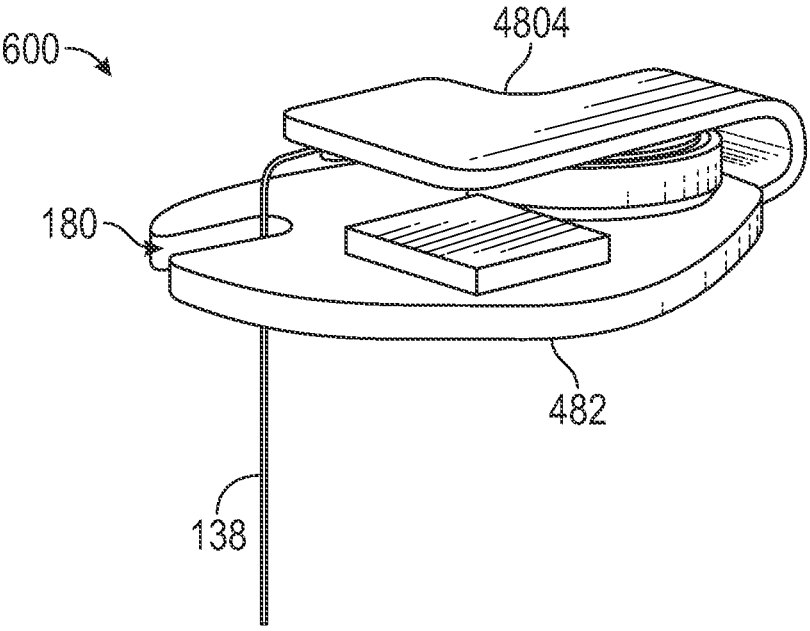

FIG. 53B illustrates the pre-connected sensor in a folded position to be installed in a wearable device, according to some embodiments.

Figure 54:
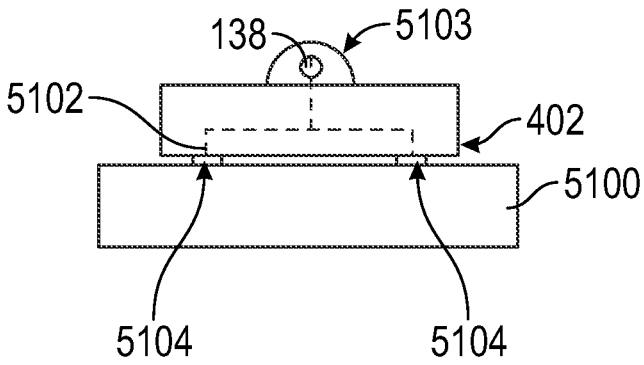

FIG. 54 illustrates a sensor carrier implemented as a daughter board for connection to an analyte sensor, according to some embodiments.

Figure 55:
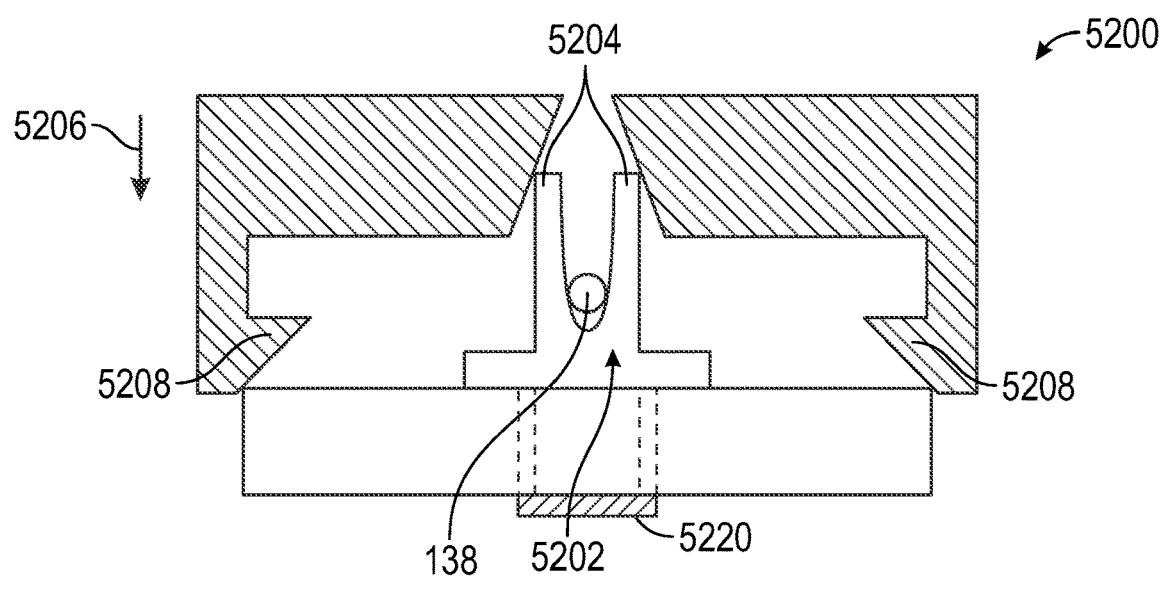

FIG. 55 illustrates a sensor carrier implemented with a pinch clip, according to some embodiments.

Figure 56:
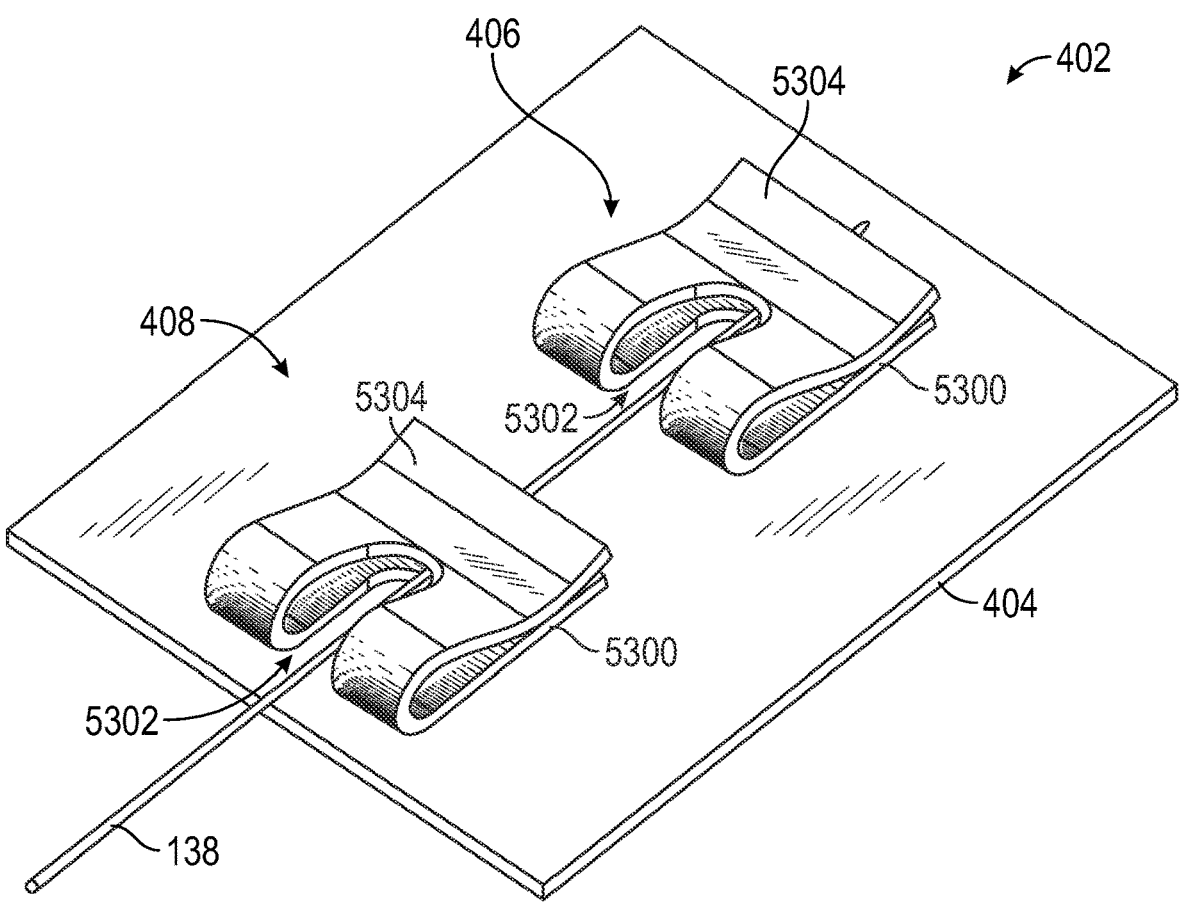

FIG. 56 illustrates a sensor carrier having clips for connection to an analyte sensor, according to some embodiments.

FIG. 57 is a flow chart of illustrative operations that may be performed for manufacturing and using a pre-connected sensor, according to some embodiments.

Figures 58, 59, 60:
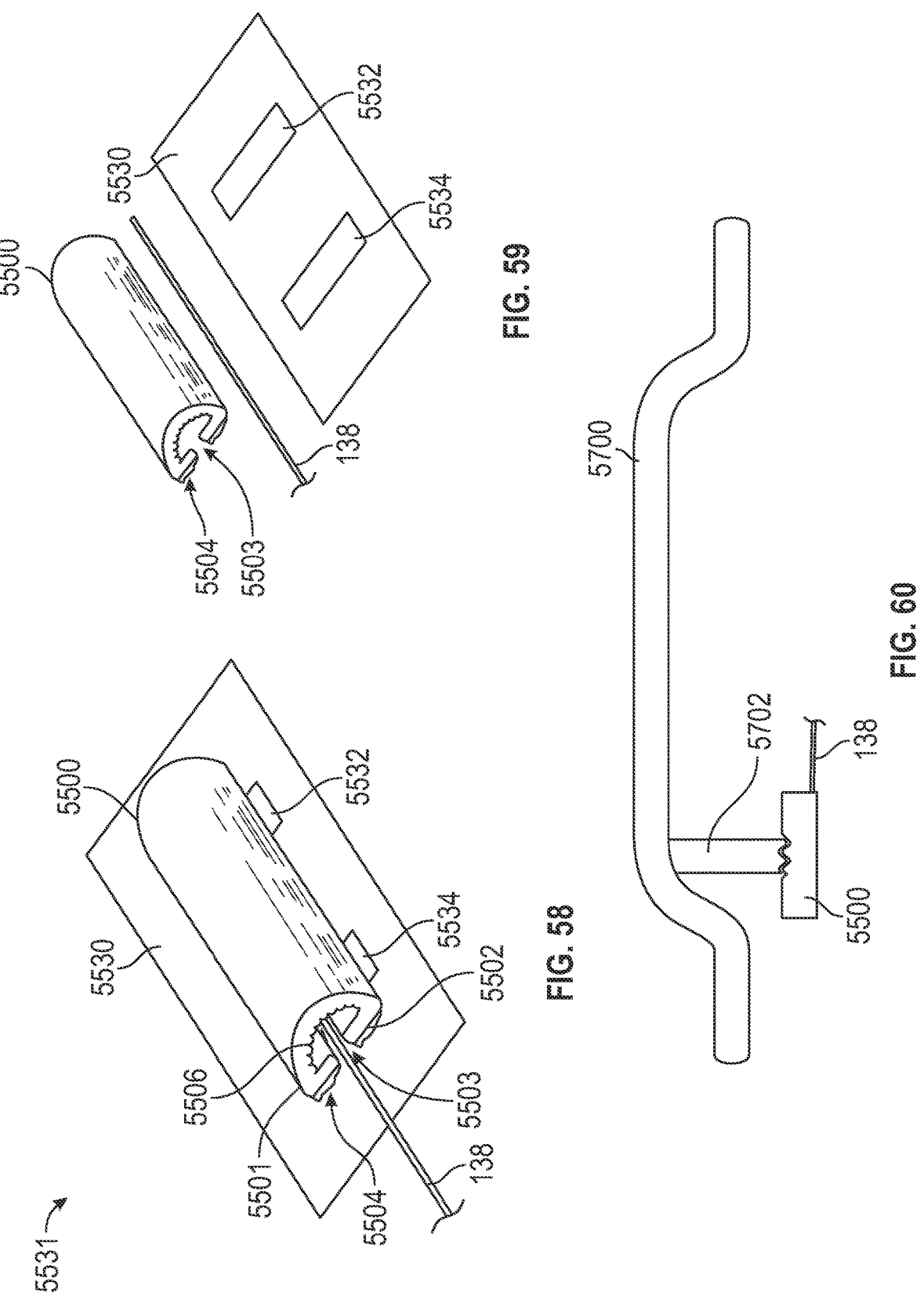

FIG. 58 illustrates a perspective view of a sensor-holding apparatus having a fluted flexible tube, according to some embodiments FIG. 59 illustrates an exploded perspective view of the apparatus of FIG. 58, according to some embodiments.

FIG. 60 illustrates a device that includes a sensor mounted in the apparatus of FIG. 55, according to some embodiments.

Figure 61:
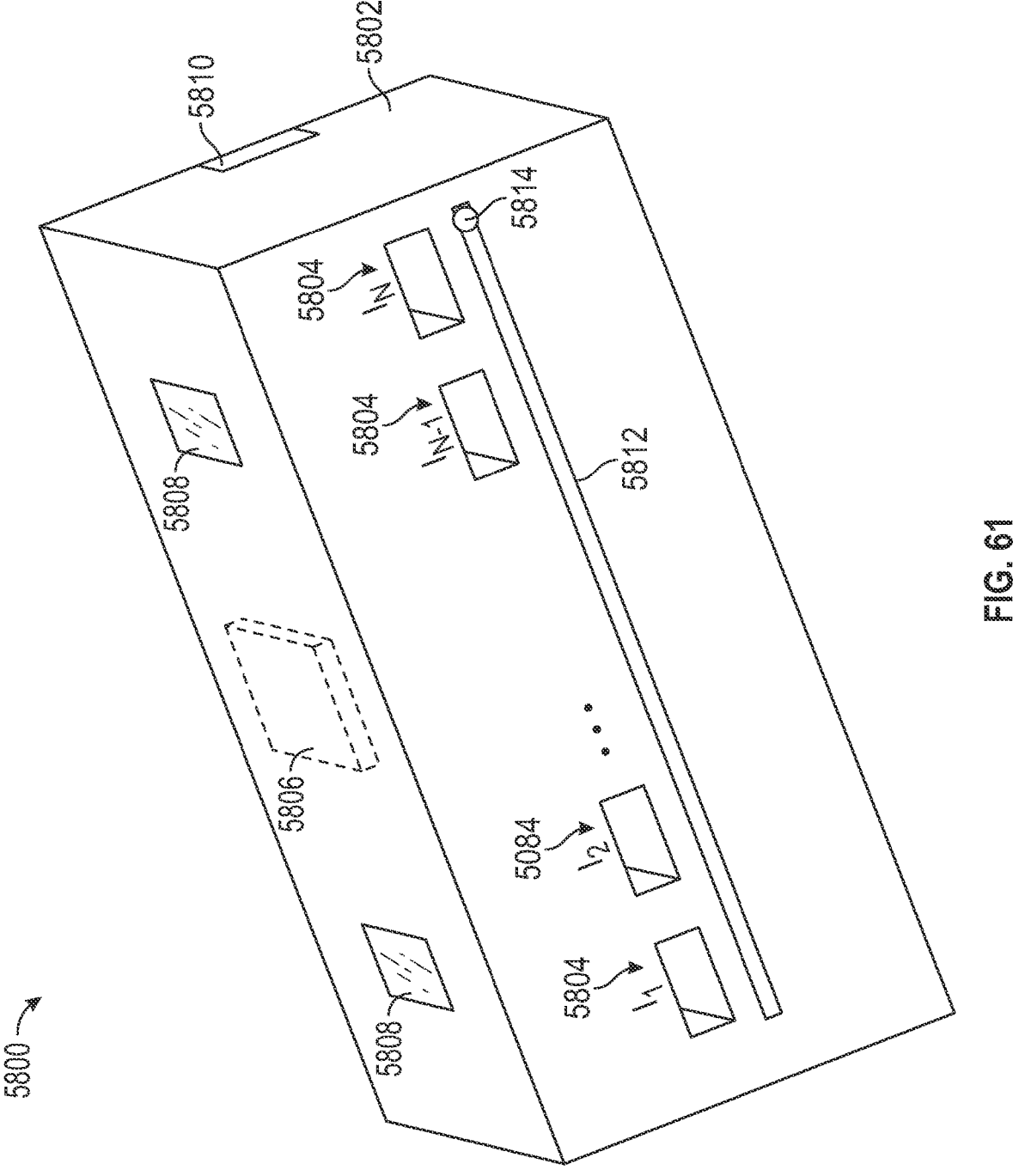

FIG. 61 illustrates a diagram of a carrier for pre-connected sensors, according to some embodiments.

Like reference numerals refer to like elements throughout. Elements are not to scale unless otherwise noted.

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Definitions

In order to facilitate an understanding of the various embodiments described herein, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), hi stidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; D-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine;

dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, including by use of a sensitivity, to provide a meaningful value to a user.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified. A "lot" of sensors generally refers to a group of sensors that are manufactured on or around the same day and using the same processes and tools/materials. Additionally, sensors that measure temperature, pressure etc. may be referred to as a "sensor".

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like. Determining may also include ascertaining that a parameter matches a predetermined criterion, including that a threshold has been met, passed, exceeded, and so on.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signals directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data. As described in further detail hereinafter (see, e.g., FIG. 2) "sensor electronics" may be arranged and configured to measure, convert, store, transmit, communicate, and/or retrieve sensor data associated with an analyte sensor.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., H2O2) associated with the measured analyte (e.g., glucose). For example, in one embodiment, a sensor has a sensitivity from about 1 to about 300 picoAmps of current for every 1 mg/dL of glucose analyte.

The term "sample," as used herein, is a broad term, and is to be given its ordinary and customary meaning to a person of ordinary skill in the art (and it is not to be limited to a special or customized meaning), and refers without limitation to a sample of a host body, for example, body fluids, including, blood, serum, plasma, interstitial fluid, cerebral spinal fluid, lymph fluid, ocular fluid, saliva, oral fluid, urine, excretions, or exudates.

The term "distal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "proximal to," as used herein, is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The terms "electrical connection" and "electrical contact," as used herein, are broad terms, and are to be given their ordinary and customary meaning to a person of ordinary skill in the art (and are not to be limited to a special or customized meaning), and refer without limitation to any connection between two electrical conductors known to those in the art. In one embodiment, electrodes are in electrical connection with (e.g., electrically connected to) the electronic circuitry of a device. In another embodiment, two materials, such as but not limited to two metals, can be in electrical contact with each other, such that an electrical current can pass from one of the two materials to the other material and/or an electrical potential can be applied.

The term "elongated conductive body," as used herein, is a broad term, and is to be given its ordinary and customary meaning to a person of ordinary skill in the art (and is not to be limited to a special or customized meaning), and refers without limitation to an elongated body formed at least in part of a conductive material and includes any number of coatings that may be formed thereon. By way of example, an "elongated conductive body" may mean a bare elongated conductive core (e.g., a metal wire), an elongated conductive core coated with one, two, three, four, five, or more layers of material, each of which may or may not be conductive, or an elongated non-conductive core with conductive coatings, traces, and/or electrodes thereon and coated with one, two, three, four, five, or more layers of material, each of which may or may not be conductive.

The term "ex vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted to remain and/or exist outside of a living body of a host.

The term "in vivo portion," as used herein, is a broad term, and is to be given its ordinary and customary meaning to a person of ordinary skill in the art (and is not to be limited to a special or customized meaning), and refers without limitation to a portion of a device (for example, a sensor) adapted for insertion into and/or existence within a living body of a host.

The term "potentiostat," as used herein, is a broad term, and is to be given its ordinary and customary meaning to a person of ordinary skill in the art (and is not to be limited to a special or customized meaning), and refers without limitation to an electronic instrument that controls the electrical potential between the working and reference electrodes at one or more preset values.

The term "processor module," as used herein, is a broad term, and is to be given its ordinary and customary meaning to a person of ordinary skill in the art (and are not to be limited to a special or customized meaning), and refers without limitation to a computer system, state machine, processor, components thereof, and the like designed to perform arithmetic or logic operations using logic circuitry that responds to and processes the basic instructions that drive a computer.

The term "sensor session," as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of (e.g., disconnection from) system electronics).

The terms "substantial" and "substantially," as used herein, are broad terms, and are to be given their ordinary and customary meaning to a person of ordinary skill in the art (and are not to be limited to a special or customized meaning), and refer without limitation to a sufficient amount that provides a desired function.

"Coaxial two conductor wire based sensor": A round wire sensor consisting of a conductive center core, an insulating middle layer and a conductive outer layer with the conductive layers exposed at one end for electrical contact.

"Pre-connected sensor": A sensor that has a "sensor interconnect/interposer/sensor carrier" attached to it. Therefore this "Pre-connected sensor" consists of two parts that are joined: the sensor itself, and the interconnect/interposer/sensor carrier. The term "pre-connected sensor" unit refers to the unit that is formed by the permanent union of these two distinct parts.

Other definitions will be provided within the description below, and in some cases from the context of the term's usage.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade) ° F. (degrees Fahrenheit), Pa (Pascals), kPa (kiloPascals), MPa (megaPascals), GPa (gigaPascals), Psi (pounds per square inch), kPsi (kilopounds per square inch).

Overview/General Description of System

In vivo analyte sensing technology may rely on in vivo sensors. In vivo sensors may include an elongated conductive body having one or more electrodes such as a working electrode and a reference electrode.

For example, a platinum metal-clad, tantalum wire is sometimes used as a core bare sensing element with one or more reference or counter electrodes for an analyte sensor. This sensing element is coated in membranes to yield the final sensor.

Described herein are pre-connected sensors that include an analyte sensor attached to a sensor carrier (also referred to herein as a "sensor interposer"). The analyte sensor may include a working electrode and a reference electrode at a distal end of an elongated conductive body. The sensor carrier may include a substrate, one or more electrical contacts coupled to one or more electrical contacts of the sensor, and circuitry such as one or more additional or external electrical contacts for coupling the one or more electrical contacts that are coupled to the sensor contact(s) to external equipment such as a membrane dip coating station, a testing station, a calibration station, or sensor electronics of a wearable device. In some embodiments, the substrate can be referred to as an intermediate body.

The following description and examples described the present embodiments with reference to the drawings. In the drawings, reference numbers label elements of the present embodiments. These reference numbers are reproduced below in connection with the discussion of the corresponding drawing features.

Sensor System

Figure 1:
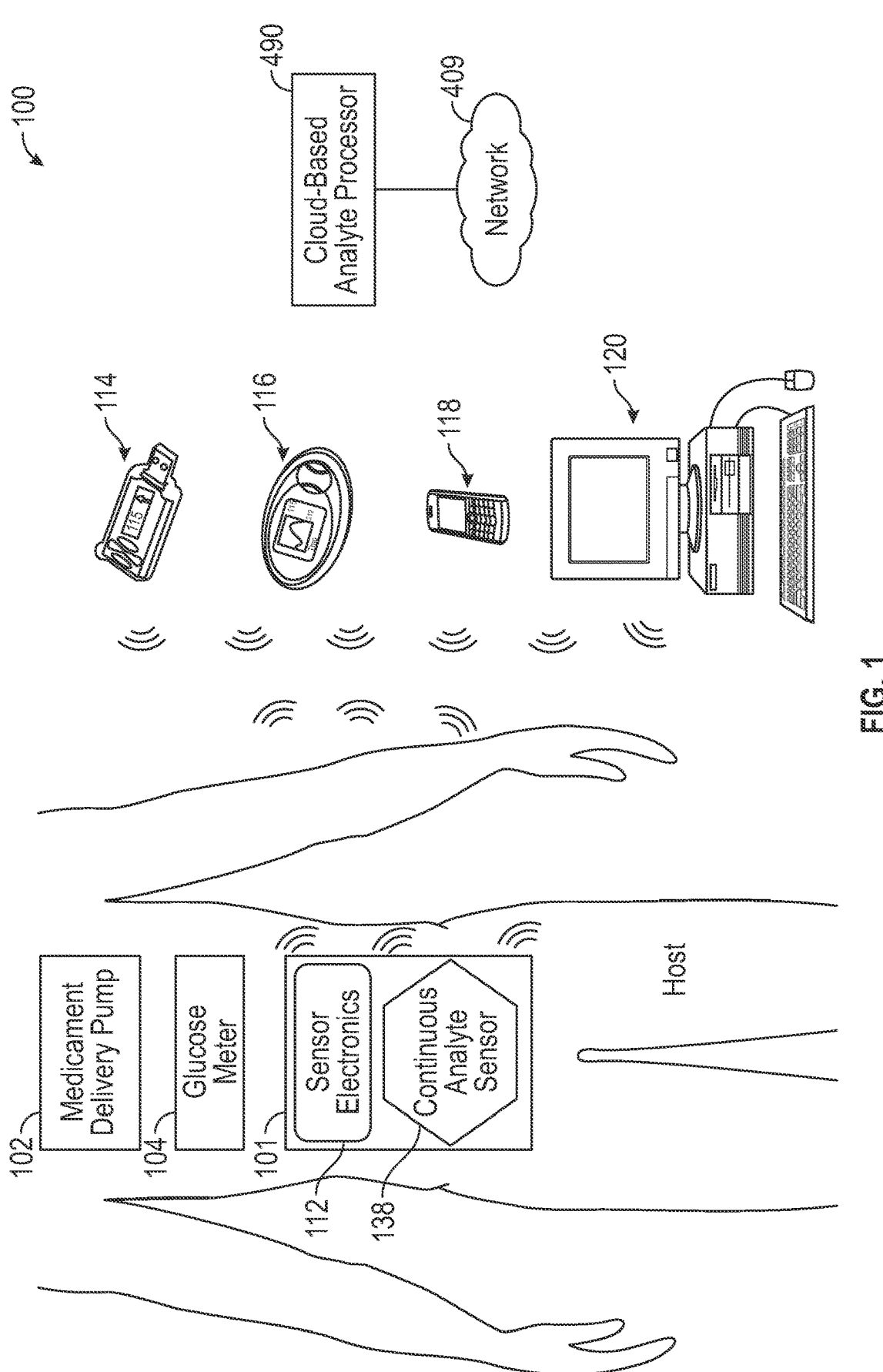
FIG. 1 is a schematic view of an analyte sensor system attached to a host and communicating with a plurality of example devices, according to some embodiments.

FIG. 1 depicts an example system 100, in accordance with some example implementations. The system 100 includes an analyte sensor system 101 including sensor electronics 112 and an analyte sensor 138. The system 100 may include other devices and/or sensors, such as medicament delivery pump 102 and glucose meter 104. The analyte sensor 138 may be physically connected to sensor electronics 112 and may be integral with (e.g., non-releasably attached to) or releasably attachable to the sensor electronics. For example, continuous analyte sensor 138 may be connected to sensor electronics 112 via a sensor carrier that mechanically and electrically interfaces the analyte sensor 138 with the sensor electronics. The sensor electronics 112, medicament delivery pump 102, and/or glucose meter 104 may couple with one or more devices, such as display devices 114, 116, 118, and/or 120.

In some example implementations, the system 100 may include a cloud-based analyte processor 490 configured to analyze analyte data (and/or other patient-related data) provided via network 409 (e.g., via wired, wireless, or a combination thereof) from sensor system 101 and other devices, such as display devices 114, 116, 118, and/or 120 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, entitled "Cloud-Based Processing of Analyte Data" and filed on Mar. 7, 2013, published as U.S. Patent Application Publication 2013/0325352, herein incorporated by reference in its entirety. In some implementations, one or more steps of the factory calibration algorithm can be performed in the cloud.

In some example implementations, the sensor electronics 112 may include electronic circuitry associated with measuring and processing data generated by the analyte sensor 138. This generated analyte sensor data may also include algorithms, which can be used to process and calibrate the analyte sensor data, although these algorithms may be provided in other ways as well. The sensor electronics 112 may include hardware, firmware, software, or a combination thereof, to provide measurement of levels of the analyte via an analyte sensor, such as a glucose sensor. An example implementation of the sensor electronics 112 is described further below with respect to FIG. 2.

In one implementation, the factory calibration algorithms described herein may be performed by the sensor electronics.

The sensor electronics 112 may, as noted, couple (e.g., wirelessly and the like) with one or more devices, such as display devices 114, 116, 118, and/or 120. The display devices 114, 116, 118, and/or 120 may be configured for presenting information (and/or alarming), such as sensor information transmitted by the sensor electronics 112 for display at the display devices 114, 116,118, and/or 120.

In one implementation, the factory calibration algorithms described herein may be performed at least in part by the display devices.

In some example implementations, the relatively small, key fob-like display device 114 may comprise a wrist watch, a belt, a necklace, a pendent, a piece of jewelry, an adhesive patch, a pager, a key fob, a plastic card (e.g., credit card), an identification (ID) card, and/or the like. This small display device 114 may include a relatively small display (e.g., smaller than the large display device 116) and may be configured to display certain types of displayable sensor information, such as a numerical value, and an arrow, or a color code.

In some example implementations, the relatively large, hand-held display device 116 may comprise a hand-held receiver device, a palm-top computer, and/or the like. This large display device may include a relatively larger display (e.g., larger than the small display device 114) and may be configured to display information, such as a graphical representation of the sensor data including current and historic sensor data output by sensor system 100.

In some example implementations, the analyte sensor 138 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the analyte sensor 138 includes a glucose sensor, the glucose sensor may comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the analyte sensor 138 may be implanted as at least one of the following types of analyte sensors: an implantable glucose sensor, a transcutaneous glucose sensor, implanted in a host vessel or extra-corporeally, a subcutaneous sensor, a refillable subcutaneous sensor, an intravascular sensor.

Although the disclosure herein refers to some implementations that include an analyte sensor 138 comprising a glucose sensor, the analyte sensor 138 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

In some manufacturing systems, sensors 138 are manually sorted, placed and held in fixtures. These fixtures are manually moved from station to station during manufacturing for various process steps including interfacing electrical measurement equipment for testing and calibration operations. However, manual handling of sensors can be inefficient, can cause delays due to non-ideal mechanical and electrical connections, and can risk damage to the sensor and/or testing and calibration equipment and can induce sensor variability that can lead to inaccurate verification data being collected in manufacturing. In addition, the process of packaging sensor 138 with the sensor electronics 112 into a wearable device involves further manual manipulation of the sensor that can damage the sensor 138.

Various systems, devices, and methods described herein help to reduce or eliminate manual interaction with a sensor. For example, a pre-connected sensor may be provided that includes a sensor interconnect or sensor carrier electrically coupled to sensor electrodes and having mechanical and electrical features configured to accurately interface with wearable electronics, automation equipment and/or robustly connect to measurement equipment.

Identification and other data associated with each sensor may be stored on the sensor carrier for logging and tracking of each sensor during manufacturing, testing, calibration, and in vivo operations. Following testing and calibration operations, the sensor carrier may be used to connect the sensor to sensor electronics of a wearable device, such as an on-skin sensor assembly, in an arrangement that is sealed and electrically robust.

Figure 2:
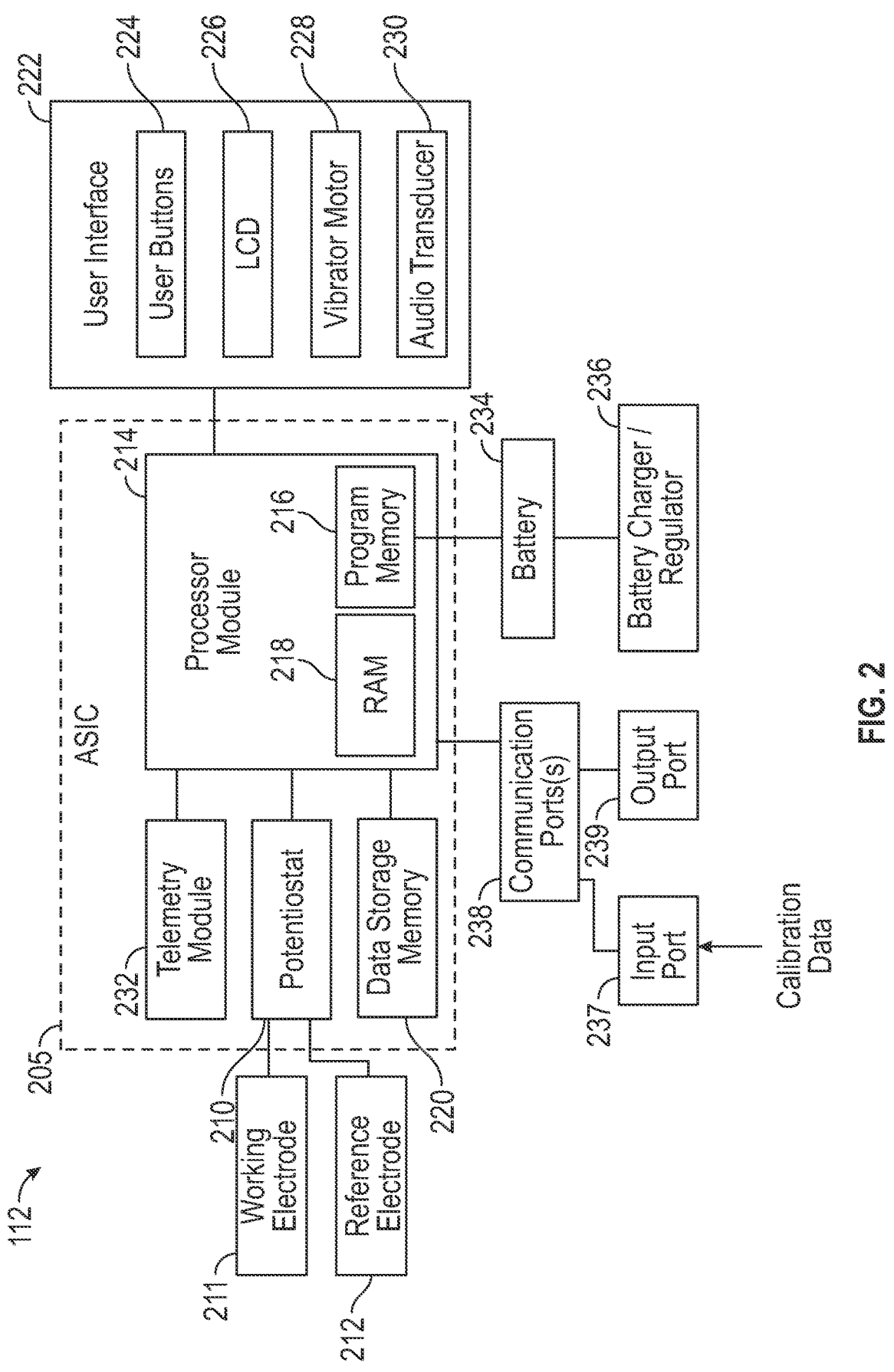
FIG. 2 is a block diagram that illustrates electronics associated with the sensor system of FIG. 1, according to some embodiments.

FIG. 2 depicts an example of electronics 112 that may be used in sensor electronics 112 or may be implemented in a manufacturing station such as a testing station, a calibration station, a smart carrier, or other equipment used during manufacturing of device 101, in accordance with some example implementations. The sensor electronics 112 may include electronics components that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information such as may be determined by factory calibration algorithms as disclosed herein, smoothing and/or filtering algorithms of sensor data, and/or the like.

In some embodiments, a processor module 214 is configured to achieve a substantial portion, if not all, of the data processing, including data processing pertaining to factory calibration. Processor module 214 may be integral to sensor electronics 112 and/or may be located remotely, such as in one or more of devices 114, 116, 118, and/or 120 and/or cloud 490. For example, in some embodiments, processor module 214 may be located at least partially within a cloud-based analyte processor 490 or elsewhere in network 409.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 114, 116, 118, and/or 120, to enable calibration of the sensor data from sensor 138. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms. The processor module 214 may further be configured to store and use calibration information determined from a factory calibration, as described below.

In some example implementations, the sensor electronics 112 may comprise an application-specific integrated circuit (ASIC) 205 coupled to a user interface 222. The ASIC 205 may further include a potentiostat 210, a telemetry module 232 for transmitting data from the sensor electronics 112 to one or more devices, such as devices 114, 116, 118, and/or 120, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 2, through a first input port 211 for sensor data the potentiostat 210 is coupled to an analyte sensor 138, such as a glucose sensor to generate sensor data from the analyte. The potentiostat 210 may be coupled to a working electrode 211 and reference electrode 212 that form a part of the sensor 138. The potentiostat may provide a voltage to one of the electrodes 211, 212 of the analyte sensor 138 to bias the sensor for measurement of a value (e.g., a current) indicative of the analyte concentration in a host (also referred to as the analog portion of the sensor). The potentiostat 210 may have one or more connections to the sensor 138 depending on the number of electrodes incorporated into the analyte sensor 138 (such as a counter electrode as a third electrode).

In some example implementations, the potentiostat 210 may include a resistor that translates a current value from the sensor 138 into a voltage value, while in some example implementations, a current-to-frequency converter (not shown) may also be configured to integrate continuously a measured current value from the sensor 138 using, for example, a charge-counting device. In some example implementations, an analog-to-digital converter (not shown) may digitize the analog signal from the sensor 138 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 112 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although Bluetooth technology may also be implemented in a combination of the telemetry module 232 and the processor module 214.

The processor module 214 may control the processing performed by the sensor electronics 112. For example, the processor module 214 may be configured to process data (e.g., counts), from the sensor, filter the data, calibrate the data, perform fail-safe checking, and/or the like.

Potentiostat 210 may measure the analyte (e.g., glucose and/or the like) at discrete time intervals or continuously, for example, using a current-to-voltage or current-to-frequency converter.

The processor module 214 may further include a data generator (not shown) configured to generate data packages for transmission to devices, such as the display devices 114, 116, 118, and/or 120. Furthermore, the processor module 214 may generate data packets for transmission to these outside sources via telemetry module 232. In some example implementations, the data packages may include an identifier code for the sensor and/or sensor electronics 112, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 112 and/or charge the battery 234.

The program memory 216 may be implemented as a semi-static memory for storing data, such as an identifier for a coupled sensor 138 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods described below, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, electrically erasable programmable read only memory (EE-PROM), rewritable ROMs, flash memory, and the like.

The data storage memory 220 may be coupled to the processor module 214 and may be configured to store a variety of sensor information. In some example implementations, the data storage memory 220 stores one or more days of analyte sensor data. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information such as from factory calibration), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host).

The battery 234 may be operatively connected to the processor module 214 (and possibly other components of the sensor electronics 12) and provide the necessary power for the sensor electronics 112. In other implementations, the receiver can be transcutaneously powered via an inductive coupling, for example.

A battery charger and/or regulator 236 may be configured to receive energy from an internal and/or external charger. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 112. The communication port, for example, may comprise a serial (e.g., universal serial bus or "USB") communication port, and allow for communicating with another computer system (e.g., PC, personal digital assistant or "PDA," server, or the like). In some example implementations, factory information may be sent to the algorithm from the sensor or from a cloud data source.

The one or more communication ports 238 may further include an input port 237 in which calibration data may be received, and an output port 239 which may be employed to transmit calibrated data, or data to be calibrated, to a receiver or mobile device. FIG. 2 illustrates these aspects schematically. It will be understood that the ports may be separated physically, but in alternative implementations a single communication port may provide the functions of both the second input port and the output port.

In some analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 112 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Figure 3A:
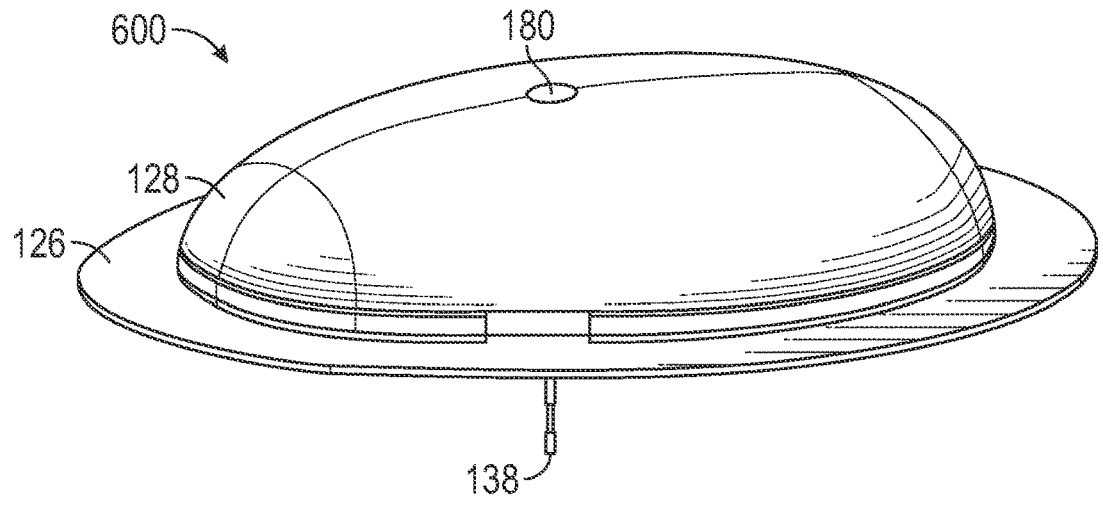
FIGS. 3A-3C illustrate a wearable device having an analyte sensor, according to some embodiments.
Figure 3B:
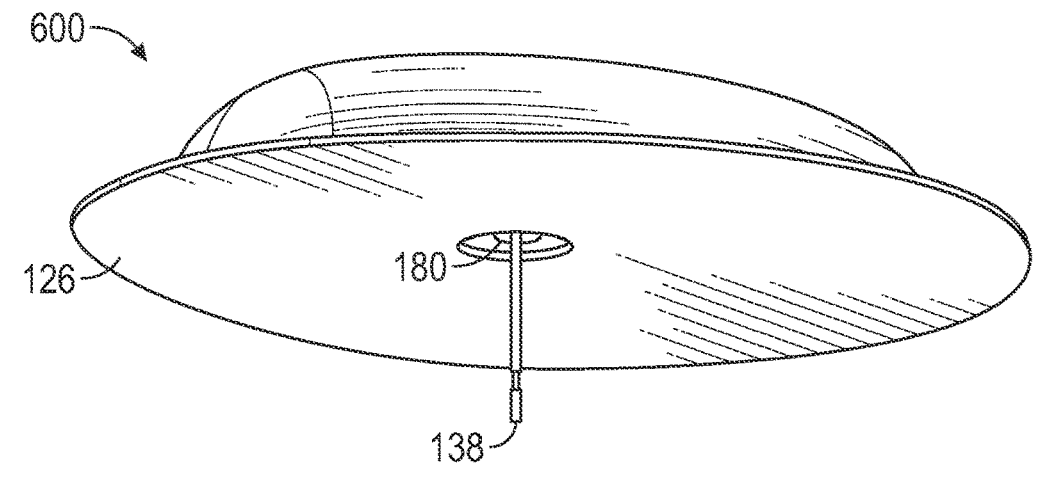
Figure 3C:
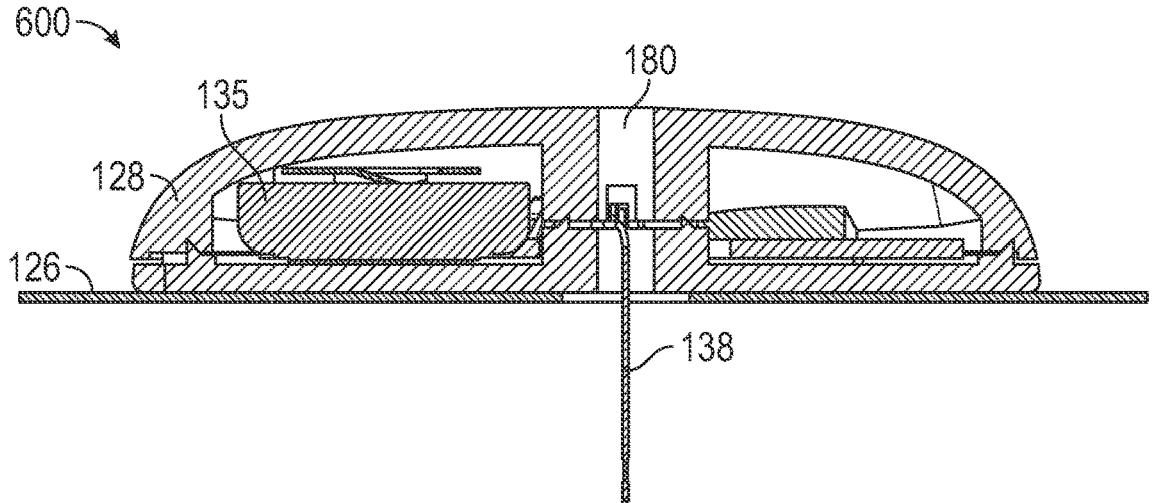

FIGS. 3A, 3B, and 3C illustrate an exemplary implementation of analyte sensor system 101 implemented as a wearable device such as an on-skin sensor assembly 600. As shown in FIG. 3, on-skin sensor assembly comprises a housing 128. An adhesive patch 126 can couple the housing 128 to the skin of the host. The adhesive 126 can be a pressure sensitive adhesive (e.g. acrylic, rubber based, or other suitable type) bonded to a carrier substrate (e.g., spun lace polyester, polyurethane film, or other suitable type) for skin attachment. The housing 128 may include a through-hole 180 that cooperates with a sensor inserter device (not shown) that is used for implanting the sensor 138 under the skin of a subject.

The wearable sensor assembly 600 can include sensor electronics 112 operable to measure and/or analyze glucose indicators sensed by glucose sensor 138. Sensor electronics 112 within sensor assembly 600 can transmit information (e.g., measurements, analyte data, and glucose data) to a remotely located device (e.g., 114, 116, 118, 120 shown in FIG. 1). As shown in FIG. 3C, in this implementation the sensor 138 extends from its distal end up into the through-hole 180 and is routed to an electronics module 135 inside the enclosure 128. The working electrode 211 and reference electrode 212 are connected to circuitry in the electronics module 135 which includes the potentiostat.

Figure 3D:
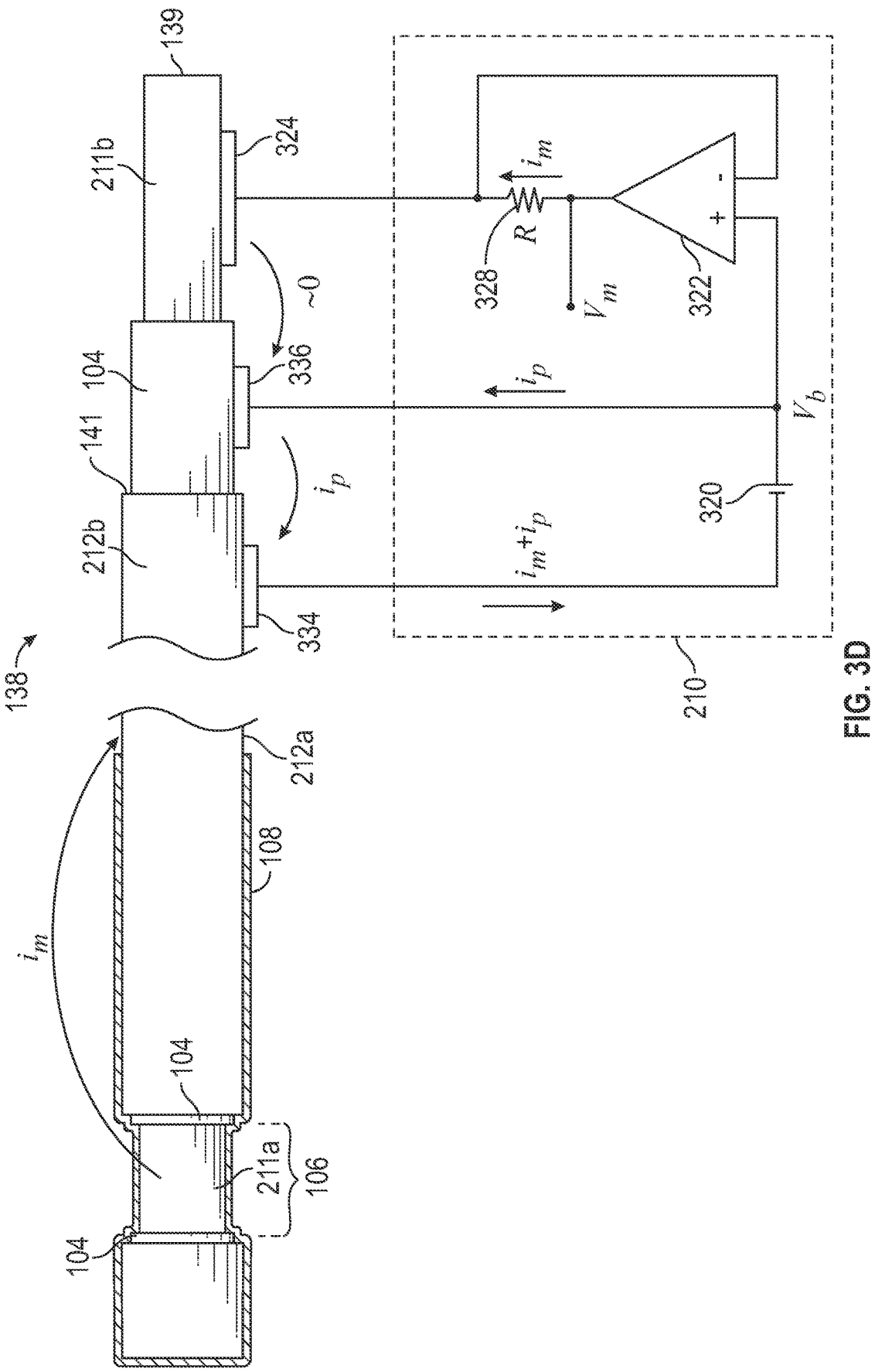
FIG. 3D illustrates one implementation of an elongated sensor connected to a potentiostat.

FIG. 3D illustrates one exemplary embodiment of an analyte sensor 138 which includes an elongated body portion. The elongated body portion may be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated herein as having a circular cross-section, in other embodiments the cross-section of the elongated conductive body can be ovoid, rectangular, triangular, or polyhedral, star-shaped, C-shaped, T-shaped, X-shaped, Y-shaped, irregular, or the like.

In the implementation of FIG. 3D, the analyte sensor 138 comprises a wire core 139. At a distal, in vivo portion of the sensor 138, the wire core 139 forms an electrode 211a. At a proximal, ex vivo portion of the sensor 138, the wire core 139 forms a contact 211b. The electrode 211a and the contact 211b are in electrical communication over the length of the wire core 139 as it extends along the elongated body portion of the sensor 138. The wire core can be made from a single material such as platinum or tantalum, or may be formed as multiple layers, such as a conducting or non-conducting material with an outer coating of a different conducting material.

A layer 104 surrounds a least a portion of the wire core 139. The layer 104 may be formed of an insulating material, such as polyimide, polyurethane, parylene, or any other known insulating materials. For example, in one embodiment the layer 104 is disposed on the wire core 139 and configured such that the electrode 211a is exposed via window 106.

In some embodiments, the sensor 138 further comprises a layer 141 surrounding the insulating layer 104 like a sleeve that comprises a conductive material. At a distal, in vivo portion of the sensor 138, the sleeve layer 141 forms an electrode 212a. At a proximal, ex vivo portion of the sensor 138, the sleeve layer 141 forms a contact 212b. The electrode 212a and the contact 212b are in electrical communication over the length of the sleeve layer 141 as it extends along the elongated body portion of the sensor 138. This sleeve layer 141 may be formed of a silver-containing material that is applied onto the insulating layer 104. The silver-containing material may include any of a variety of materials and be in various forms, such as, Ag/AgCl-polymer pastes, paints, polymer-based conducting mixture, and/or inks that are commercially available, for example. This layer 141 can be processed using a pasting/dipping/coating step, for example, using a die-metered dip coating process. In one exemplary embodiment, an Ag/AgCl polymer paste is applied to an elongated body by dip-coating the body (e.g., using a meniscus coating technique) and then drawing the body through a die to meter the coating to a precise thickness. In some embodiments, multiple coating steps are used to build up the coating to a predetermined thickness.

The sensor 138 shown in FIG. 3D also includes a membrane 108 covering at least a portion of the distal in vivo portion of the sensor 138. This membrane is typically formed of multiple layers, which may include one or more of an interference domain, an enzyme domain, a diffusion resistance domain, and a bioprotective domain. This membrane is important to support the electrochemical processes that allow analyte detection and it is generally manufactured with great care by dip-coating, spraying, or other manufacturing steps. It is preferable for the distal in vivo portion of the sensor 138 to be subject to as little handling as possible from the time the membrane 108 is formed to the time the distal in vivo portion of the sensor 138 is implanted into a subject. In some embodiments, electrode 211a forms a working electrode of an electrochemical measuring system, and electrode 212a forms a reference electrode for that system. In use, both electrodes may be implanted into a host for analyte monitoring.

Although the above description is applicable specifically to a coaxial wire type structure, the embodiments herein are also applicable to other physical configurations of electrodes. For example, the two electrodes 211a and 212a could be affixed to a distal in vivo portion of an elongated flexible strip of a planar substrate such as a thin, flat, polymer flex circuit. The two contacts 211b and 212b could be affixed to the proximal ex vivo portion of this flexible planar substrate. Electrodes 211a, 212a could be electrically connected to their respective contacts 211b, 212b a circuit traces on the planar substrate. In this case, the electrodes 211a and 212a and the contacts 211b and 212b may be adjacent to one another on a flat surface rather than being coaxial as shown in FIG. 3D.

Also shown in FIG. 3D is an illustration of the contact 211b and the contact 212b electrically coupled to a simple current-to-voltage converter based potentiostat 210. The potentiostat includes a battery 320 that has an output coupled to an input of an operational amplifier 322. The output of the operational amplifier 322 is coupled to a contact 324 that is electrically coupled to the working electrode contact 211b through a resistor 328. The amplifier 322 will bias the contact 324 to the battery voltage $V_b$, and will drive the current $i_m$ required to maintain that bias. This current will flow from the working electrode 211a through the interstitial fluid surrounding the sensor 138 and to the reference electrode 212a. The reference electrode contact 212b is electrically coupled to another contact 334 which is connected to the other side of the battery 320. For this circuit, the current $i_m$ is equal to $(V_b - V_m)/R$, where $V_m$ is the voltage measured at the output of the amplifier 322. The magnitude of this current for a given bias on the working electrode 211a is a measure of analyte concentration in the vicinity of the window 106.

The contacts 324 and 334 are typically conductive pads/traces on a circuit board. There is always some level of parasitic leakage current $i_p$ over the surface of this board during the test. If possible, this leakage current should not form part of the measurement of current due to analyte. To reduce the effect this leakage current has on the measured current, an optional additional pad/trace 336 may be provided between the biased contact 324 and the return contact 334 that is connected directly to the battery output. This optional additional pad/trace may be referred to as a "guard trace." Because they are held at the same potential, there will be essentially no leakage current from the biased contact 324 and the guard trace 336. Furthermore, leakage current from the guard trace 336 to the return contact 334 does not pass through the amplifier output resistor 328, and therefore is not included in the measurement. Additional aspects and implementations of a guard trace may be found in paragraphs [0128] and [0129] of U.S. Patent Publication 2017/0281092, which are incorporated herein by reference.

During manufacturing, various coating, testing, calibration, and assembly operations are performed on the sensor 138. However, it can be difficult to transport individual sensors and electrically interface the sensors with multiple testing and calibration equipment installations. These processes also subject the sensors to damage from handling. To help address these issues, the sensor 138 may be provided as a part of a pre-connected sensor that includes a sensor carrier as described in greater detail below.

FIG. 4A shows a schematic illustration of a pre-connected sensor 400. As shown in FIG. 4A, pre-connected sensor 400 includes sensor carrier 402 permanently attached to sensor 138. In the example of FIG. 4A, sensor carrier 402 includes an intermediate body such as substrate 404, and also includes one or more contacts such as first internal contact 406, and second internal contact 408. First internal contact 406 is electrically coupled to a first contact on a proximal end of sensor 138 and contact internal contact 408 is electrically coupled to a second contact on the proximal end of sensor 138. The distal end of sensor 138 is a free end configured for insertion into the skin of the host. Contacts 406 and 408 may, for example, correspond to contacts 324 and 334 of FIG. 3D in some implementations.

As shown in FIG. 4A, first internal contact 406 may be electrically coupled to a first external contact 410 and second internal contact 408 may be electrically coupled to a second external contact 412. As described in further detail hereinafter, external contacts 410 and 412 may be configured to electrically interface with sensor electronics 112 in wearable device 600. Furthermore, external contacts 410 and 412 may be configured to electrically interface with processing circuitry of manufacturing equipment such one or more testing stations and/or one or more calibration stations. Although various examples are described herein in which two external contacts 410 and 412 on the sensor carrier are coupled to two corresponding contacts on sensor 138, this is merely illustrative. In other implementations, sensor carrier 402 and sensor 138 may each be provided with a single contact or may each be provided with more than two contacts, for example, any N number of external contacts (e.g., more than two external contacts 410 and 412) of the sensor carrier and any M number of contacts (e.g., more than two contacts 406 and 408) of sensor 138 that can be coupled. In some implementations, sensor carrier 402 and sensor 138 may have the same number of contacts (i.e., N=M). In some implementations, sensor carrier 402 and sensor 138 may have a different number of contacts (i.e., N M). For example, in some implementations, sensor carrier 402 may have additional contacts for coupling to or between various components of a manufacturing station.

As described in further detail hereinafter, substrate 404 may be configured to couple with sensor electronics 112 in wearable device 600. In some embodiments, substrate 404 may be sized and shaped to mechanically interface with housing 128 and electrically interface with sensor electronics 112 inside housing 128. Further, substrate 404 may be sized and shaped to mechanically interface with manufacturing equipment, assembly equipment, testing stations and/or one or more calibration stations. As described in further detail hereinafter, sensor carrier 402 may be attached and/or electrically coupled to sensor 138. Sensor 138 may be permanently coupled to a component of sensor carrier 402 (e.g. substrate 404) by using, for example, adhesive (e.g. UV cure, moisture cure, multi part activated, heat cure, hot melt, etc.), including conductive adhesive (e.g. carbon filled, carbon nanotube filled, silver filled, conductive additive, etc.), conductive ink, spring contacts, clips, wrapped flexible circuitry, a conductive polymer (e.g. conductive elastomer, conductive plastic, carbon filled PLA, conductive graphene PLA), conductive foam, conductive fabric, a barrel connector, a molded interconnect device structure, sewing, wire wrapping, wire bonding, wire threading, spot welding, swaging, crimping, stapling, clipping, soldering or brazing, plastic welding, or overmolding. In some embodiments, sensor 138 may be permanently coupled to substrate 404 by rivets, magnets, anisotropic conductive films, metallic foils, or other suitable structures or materials for mechanically and electrically attaching sensor carrier 402 to sensor 138 before or during assembly, manufacturing, testing and/or calibration operations. In some embodiments, sensor carrier 402 may be 3-D printed around sensor 138 to form pre-connected sensor 400. Additionally, sensor carrier 402 may include datum features 430 (sometimes referred to as datum structures) such as a recess, an opening, a surface or a protrusion for aligning, positioning, and orienting sensor 138 relative to sensor carrier 402. Sensor carrier 402 may also include, or may itself form, one or more anchoring features for securing and aligning the analyte sensor during manufacturing (e.g., relative to a manufacturing station). Additionally, sensor carrier 402 may include an identifier 450 configured to identify the sensor. In some embodiments, identifier 450 is formed on substrate 404. Identifier 450 will be explained further below.

FIG. 4B illustrates another schematic of a pre-connected analyte sensor 400. The pre-connected analyte sensor 400 shown in FIG. 4B may include similar components of pre-connected analyte sensor 400 shown in FIG. 4A. FIG. 4B is shown without optional cover 460 for clarity. FIG. 4C illustrated an exploded view of pre-connected analyte sensor 400 shown in FIG. 4B.

In the example of FIG. 4B, sensor carrier 402 includes an intermediate body such as a substrate 404, and also includes one or more traces such as first trace 414 and second trace 416. First trace 414 may include a first internal contact 406 and a first external contact 410. Second trace 416 may include a second internal contact 408 and a second external contact 412. In some embodiments, first internal contact 406 is electrically coupled to a first contact on a proximal end of sensor 138 and second internal contact 408 is electrically coupled to a second contact on the proximal end of sensor 138. The distal end of sensor 138 is a free end configured for insertion into the skin of the host. The electrical coupling is described in connection with various embodiments herein, such as clips, conductive adhesive, conductive polymer, conductive ink, metallic foil, conductive foam, conductive fabric, wire wrapping, wire threading or any other suitable methods. In some embodiments, a non-conductive adhesive 426 (e.g. epoxy, cyanoacrylate, acrylic, rubber, urethane, hot melt, etc.) can be used to attach the sensor 138 to substrate 404. Non-conductive adhesive 426 may be configured to affix, seal, insulate, or provide a strain relief to the sensor 138. Sensor 138 may be attached to substrate 404 by other methods, such as those described in FIG. 4A above.

As shown in FIG. 4C, a pressure sensitive adhesive 428 may be configured to isolate an exposed end of traces 414 and 416. For instance, pressure sensitive adhesive 428 may laminate sensor 138 between substrate 404 and cover 460. In such instances, sensor 138, substrate 404, pressure sensitive adhesive 428, and cover 460 may form a laminated configuration. In the laminated configuration, sensor 138 and its connection to one or more contacts (e.g. first internal contact 406 and second internal contact 408) are isolated from one or more exposed contacts (e.g. first external contact 410 and second external contact 412). Furthermore, the laminated configuration may create a moisture sealed region surrounding the sensor 138. The moisture seal may be created as embodied by a combination of a pressure sensitive adhesive 428 and a non-conductive adhesive 426. In other embodiments, the laminated structure can be created by one or a combination of the following materials and methods: A non-conductive adhesive, a pressure sensitive adhesive tape, an elastomer, heat bonding, hot plate welding, laser welding, ultrasonic welding, RF welding, or any suitable type of lamination method. The cover 460 may consist of a polymer sheet, structure, or film that at least partially covers the substrate 404. The cover 460 may optionally contain an identifier 450, which can identify the sensor 138. In some embodiments, identifier 450 may incorporate various identification protocols or techniques such as, but not limited to, NFC, RFID, QR Code, Bar code, Wi-Fi, Trimmed resistor, Capacitive value, Impedance values, ROM, Memory, IC, Flash memory, etc.

Guide fixture 420, which is an optional component, is an exemplary embodiment of an interface with a work station, such as a testing station, a calibration station, an assembly station, a coating station, manufacturing stations, or as part of the wearable assembly. The guide fixture 420 includes datum features (or datum structures) 430, such as a recess, an opening, a surface or a protrusion for aligning, positioning, and orienting sensor 138 relative to sensor carrier 402. Datum features 430 may be used in manufacturing and for assembly into a wearable electronic component. In some embodiments, datum features 430 are raised protrusions configured to align with corresponding datum features 432 of substrate 404. Corresponding datum features 432 of substrate 404 may feature cutouts, slots, holes, or recesses. The corresponding datum features 432 in the sensor carrier may be placement features that can interface with datum features 430 in a work station, such as a testing station, a calibration station, an assembly station, a coating station, or other manufacturing stations. Guide fixture 420 may be configured to ensure proper placement of the sensor carrier 402 to align the exposed external contacts 410 and 412 for connecting to a work station, such as a testing station, a calibration station, an assembly station, a coating station, or other manufacturing stations. In other embodiments, datum features 430 may consist of female features to engage with male corresponding datum features 432.

Figure 4D:
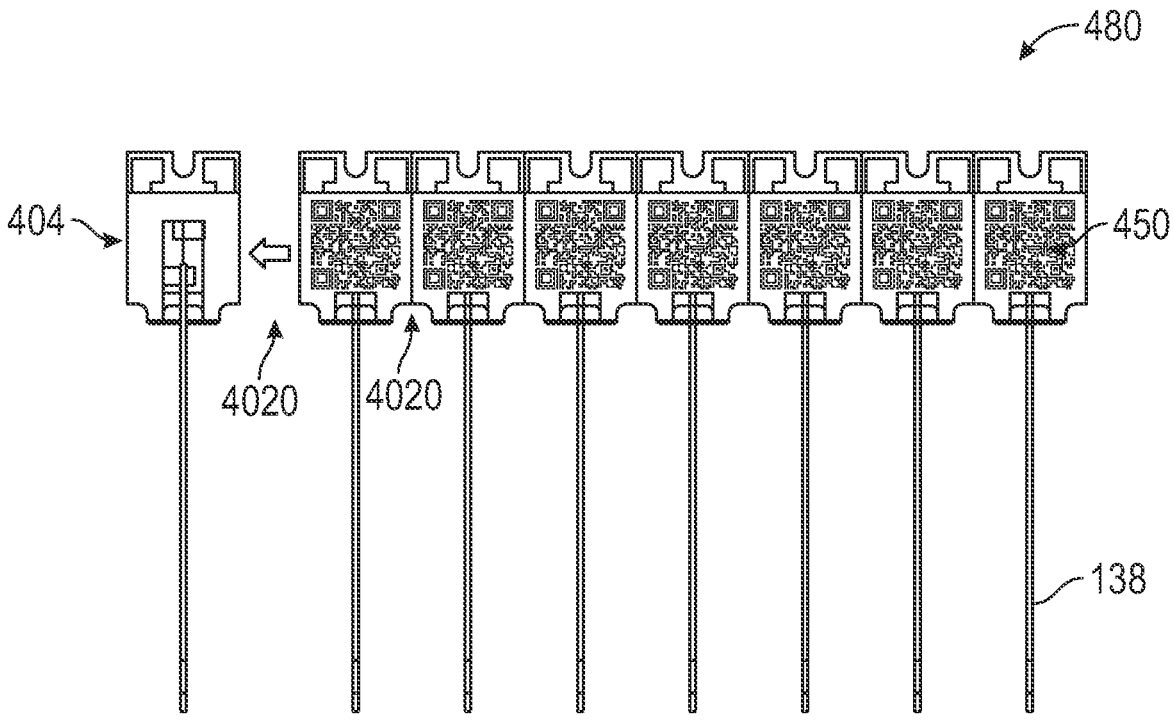
FIG. 4D illustrates a schematic view of an array of pre-connected analyte sensors, according to some embodiments.
Figures 5A, 5B, 5C, 5D, 5E:
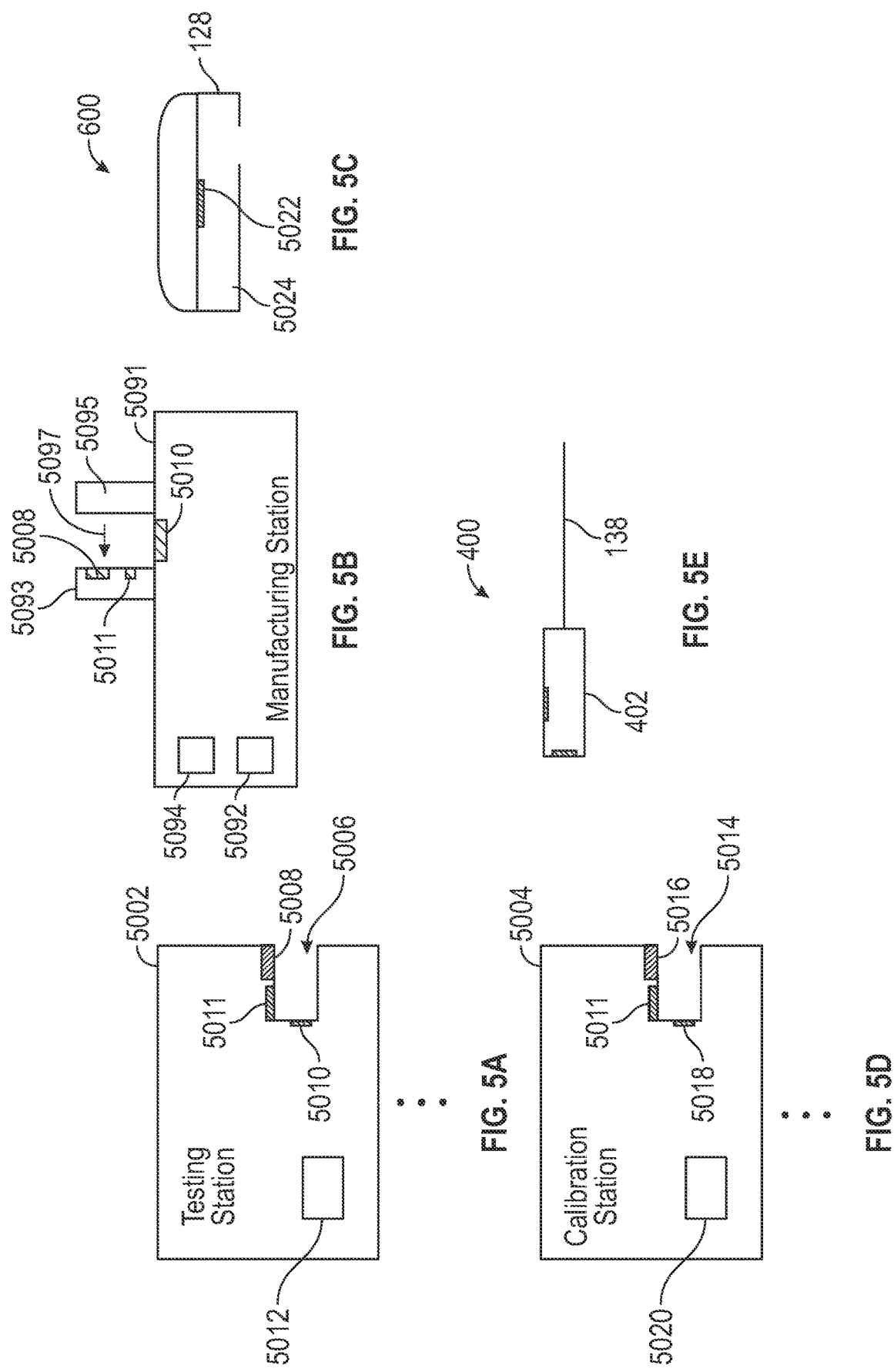
FIGS. 5A-5E illustrate block diagrams of a system having a manufacturing system and a wearable device for an analyte sensor, according to some embodiments.

FIG. 4D illustrates a schematic view of an array 480 of pre-connected analyte sensors 400 having a plurality of pre-connected sensors 400 with optional identifiers 450. In FIG. 4D, an array formed as a one-dimensional strip of pre-connected analyte sensors 400 is shown, but a two-dimensional array could also be implanted. In some embodiments, the array 480 of pre-connected analyte sensors may be disposed in a cartridge. Each of the plurality of pre-connected sensors 400 can be singulated. In some embodiments, scoring 4020 may be provided to facilitate singulation into individual pre-connected sensors 400. In some embodiments, the array 480 can be used in facilitating manufacturing, testing and/or calibrating multiple sensors 138 individually in sequential or random manners. In some embodiments, the array 480 can be used in facilitating manufacturing, testing and/or calibrating multiple sensors 138 concurrently.

FIGS. 5A-5E show block diagrams of various machines and assemblies the pre-connected analyte sensor 400 may be associated with during its pre-implant lifetime. Such machines and assemblies may include manufacturing equipment such as one or more manufacturing stations 5091, one or more testing stations 5002 and/or one more calibration stations 5004, and an on-skin wearable assembly 600. At least some of these are configured to receive sensor carrier 402 and to communicatively couple the machines and assemblies to sensor 138 via sensor carrier 402.

It is one aspect of some embodiments that the sensor 138 is coupled to the sensor carrier 402 before the membrane 108 described above is applied. With the sensor 138 attached to the sensor carrier, and potentially with multiple carrier mounted sensors attached together as shown in FIG. 4D, subsequent device production steps such as membrane coating, testing, calibration, and assembly into a wearable unit can be performed with easier mounting and dismounting from manufacturing and testing equipment, less sensor handling, less chance of damaging the membrane, producing a significant overall improvement in production efficiency.

Another benefit of the pre-connected sensor construction is that it is easier to separate different kinds of manufacturing and testing among different facilities that are better equipped to handle them. For example, fabricating the electrodes may require various kinds of metal forming/extrusion machines, whereas membrane application, testing, and calibration requires a wet chemistry lab and sensitive electronic test equipment. Accordingly, the sensor electrodes may be formed and mounted on the carrier in one facility in one location, and then shipped to a different remote facility that is equipped for membrane application, testing, and calibration. Remote in this context means not in the same production facility in the same building. It can even be advantageous for different commercial entities to perform the different tasks that specialize in the appropriate manufacturing and testing technologies.

Manufacturing station 5091 may comprise a testing station as described herein, a calibration station as described herein, or another manufacturing station. Manufacturing station 5091 may include processing circuitry 5092 and/or mechanical components 5094 operable to perform testing operations, calibration operations, and/or other manufacturing operations such as sensor straightening operations, membrane application operations, curing operations, calibration-check operations, glucose sensitivity operations (e.g., sensitivity slope, baseline, and/or noise calibration operations), and/or visual inspection operations.

The pre-connected analyte sensor 400 may be connected to one or more testing stations 5002 having processing circuitry 5012 configured to perform testing operations with sensor 138 to verify the operational integrity of sensor 138. Testing operations may include verifying electrical properties of a sensor 138, verifying communication between a working electrode and contact 408, verifying communication between a reference electrode or additional electrodes and contact 406, and/or other electronic verification operations for sensor 138. Processing circuitry 5012 may be communicatively coupled with sensor 138 for testing operations by inserting substrate 404 into a receptacle 5006 (e.g., a recess in a housing of testing station 5002) until contact 410 is coupled to contact 5010 of testing station 5002 and contact 412 is coupled to contact 5008 of testing station 5002.

System 5000 may include one or more calibration stations 5004 having processing circuitry 5020 configured to perform calibration operations with sensor 138 to obtain calibration data for in vivo operation of sensor 138. Calibration data obtained by calibration equipment 5004 may be provided to on-skin sensor assembly 600 to be used during operation of sensor 138 in vivo. Processing circuitry 5020 may be communicatively coupled with sensor 138 for calibration operations by inserting substrate 404 into a receptacle 5014 (e.g., a recess in a housing of calibration station 5004) until contact 410 is coupled to contact 5018 of testing station 5002 and contact 412 is coupled to contact 5016 of testing station 5002.

In the examples of FIGS. 5A-5E, testing station 5002 and calibration station 5004 include receptacles 5006 and 5014. However, this is merely illustrative and sensor carrier 402 may be mounted to testing station 5002 and calibration station 5004 and/or manufacturing station 5091 using other mounting features such as grasping, clipping, or clamping figures. For example, manufacturing station 5091 includes grasping structures 5093 and 5095, at least one of which is movable to grasp sensor carrier 402 (or a carrier having multiple sensor carriers and sensors). Structure 5093 may be a stationary feature having one or more electrical contacts such as contact 5008. Structure 5095 may be a movable feature that moves (e.g., slides in a direction 5097) to grasp and secure sensor carrier 402 in an electrically coupled position for manufacturing station 5091. In other implementations, both features 5093 and 5095 are movable.

Sensor carrier 402 may also include an identifier 450 (see, e.g., FIGS. 4A-4D). Identifier 450 may be formed on or embedded within substrate 404. Identifier 450 may be implemented as a visual or optical identifier (e.g., a barcode or QR code pre-printed or printed on-the-fly on substrate 404 or etched in to substrate 404), a radio frequency (RF) identifier, or an electrical identifier (e.g., a laser-trimmed resistor, a capacitive identifier, an inductive identifier, or a micro storage circuit (e.g., an integrated circuit or other circuitry in which the identifier is encoded in memory of the identifier) programmable with an identifier and/or other data before, during, or after testing and calibration). Identifier 450 may be used for tracking each sensor through the manufacturing process for that sensor (e.g., by storing a history of testing and/or calibration data for each sensor). In other words, the identifier 450 identifies any of the analyte sensor, calibration data for the analyte sensor, and a history of the analyte sensor. For example, identifier 450 may be used for binning of testing and calibration performance data. Identifier 450 may be a discrete raw value or may encode information in addition to an identification number. Identifier 450 may be used for digitally storing data in non-volatile memory on substrate 404 or as a reference number for storing data external to sensor carrier 402.

Testing station 5002 may include a reader 5011 (e.g., an optical sensor, an RF sensor, or an electrical interface such as an integrated circuit interface) that reads identifier 450 to obtain a unique identifier of sensor 138. Testing data obtained by testing station 5002 may be stored and/or transmitted along with the identifier of sensor 138.

Calibration station 5004 may include a reader 5011 (e.g., an optical sensor, an RF sensor, or an electrical interface) that reads identifier 450 to obtain a unique identifier of sensor 138. Calibration data obtained by calibration station 5004 may be stored and/or transmitted along with the identifier of sensor 138. In some implementations, calibration data obtained by calibration station 5004 may be added to identifier 450 by calibration station 5004 (e.g., by programming the calibration data into the identifier). In some implementations, calibration data obtained by calibration station 5004 may be transmitted to a remote system or device along with identifier 450 by calibration station.

As shown in FIGS. 5A-5E and described in further detail hereinafter, on-skin sensor assembly 600 may include one or more contacts such as contact 5022 configured to couple internal electronic circuitry to contacts 410 and 412 of sensor carrier 402 and thus to sensor 138. Sensor carrier 402 may be sized and shaped to be secured within a cavity 5024 in or on the housing 128 such that sensor 138 is coupled to electronics in the housing 128 via sensor carrier 402, and sensor 138 may be positionally secured to extend from the housing 128 for insertion for in vivo operations.

Although one calibration station and one testing station are shown in FIGS. 5A-5E, it should be appreciated that more than one testing station and/or more than one calibration station may be utilized in the manufacturing and testing phase of production. Although calibration station 5004 and testing station 5002 are shown as separate stations in FIGS.

5A-5E, it should be appreciated that, in some implementations calibration stations and testing stations may be combined into one or more calibration/testing stations (e.g., stations in which processing circuitry for performing testing and calibration operations is provided within a common housing and coupled to a single interface 5006).

Wearable assembly 600 may also include a reader (e.g., an optical sensor, an RF sensor, or an electrical interface) positioned near the contacts 5022 that reads identifier 450 to obtain a unique identifier of sensor 138. Sensor electronics may obtain calibration data for in vivo operation of sensor 138 based on the read identifier 450. The calibration data may be stored in, and obtained, from identifier 450 itself, or identifier 450 may be used to obtain the calibration data for the installed sensor 138 from a remote system such as a cloud-based system.

Figure 6:
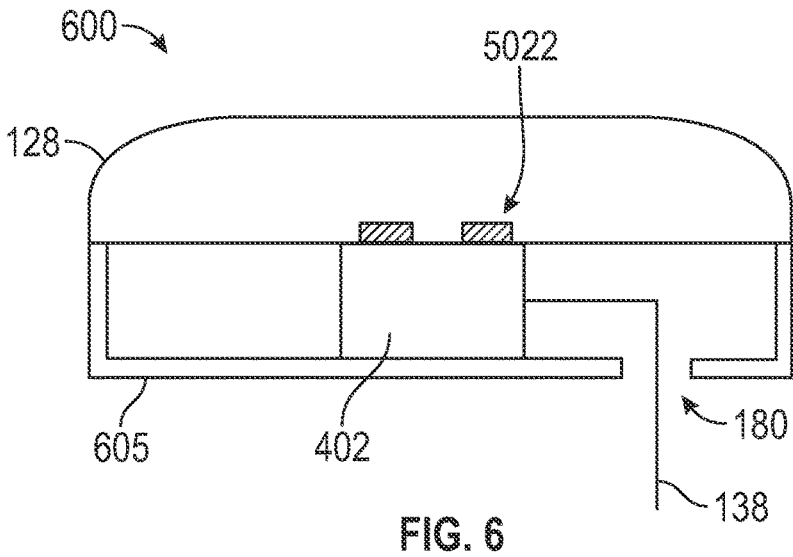
FIG. 6 illustrates a cross-sectional schematic view of a wearable device with a pre-connected analyte sensor, according to some embodiments.
Figure 7:
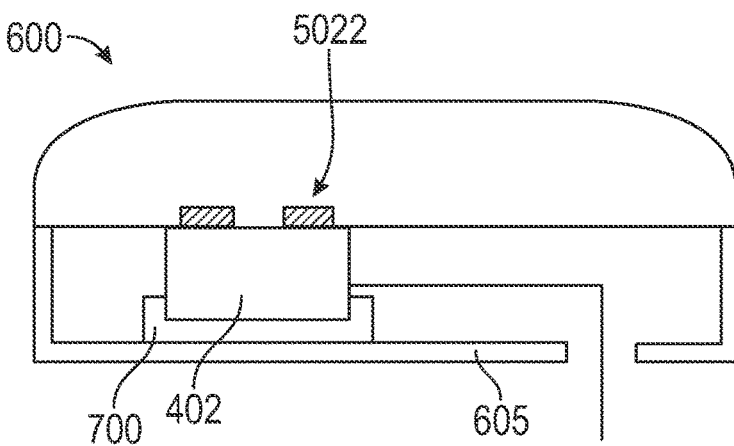
FIG. 7 illustrates a cross-sectional schematic view of a wearable device with a pre-connected analyte sensor, according to some embodiments.
Figure 8:
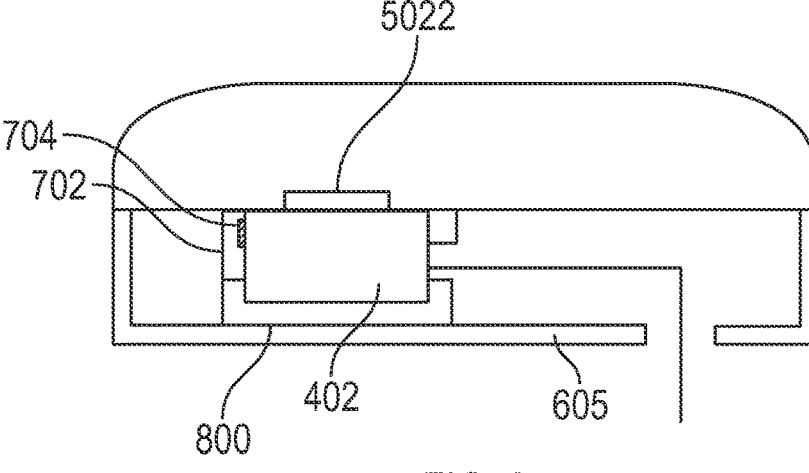
FIG. 8 illustrates a cross-sectional schematic view of a wearable device with a pre-connected analyte sensor, according to some embodiments.

FIGS. 6-8 are schematic illustrations of various implementations of securement of a pre-connected sensor 400 within wearable assembly 600. In the example of FIG. 6, sensor carrier 402 is in direct contact with a base wall 605 and housing 128, and contact 5022 includes multiple contacts on the housing 128 for contacting both contacts 410 and 412 of sensor carrier 402 (e.g., both located on a top surface of sensor carrier 402). In the example of FIG. 7, a mechanical receiver 700 is provided on base wall 605 for mechanically securing sensor carrier 402. In the example of FIG. 8, mechanical receiver 800 is provided on base wall 605 for mechanically securing sensor carrier 402 in cooperation with receiver 702. In the example of FIG. 8, receiver 702 includes an additional contact 704 for contacting contact 410 of sensor carrier 402 located on a rear surface of the sensor carrier.

Figure 9:
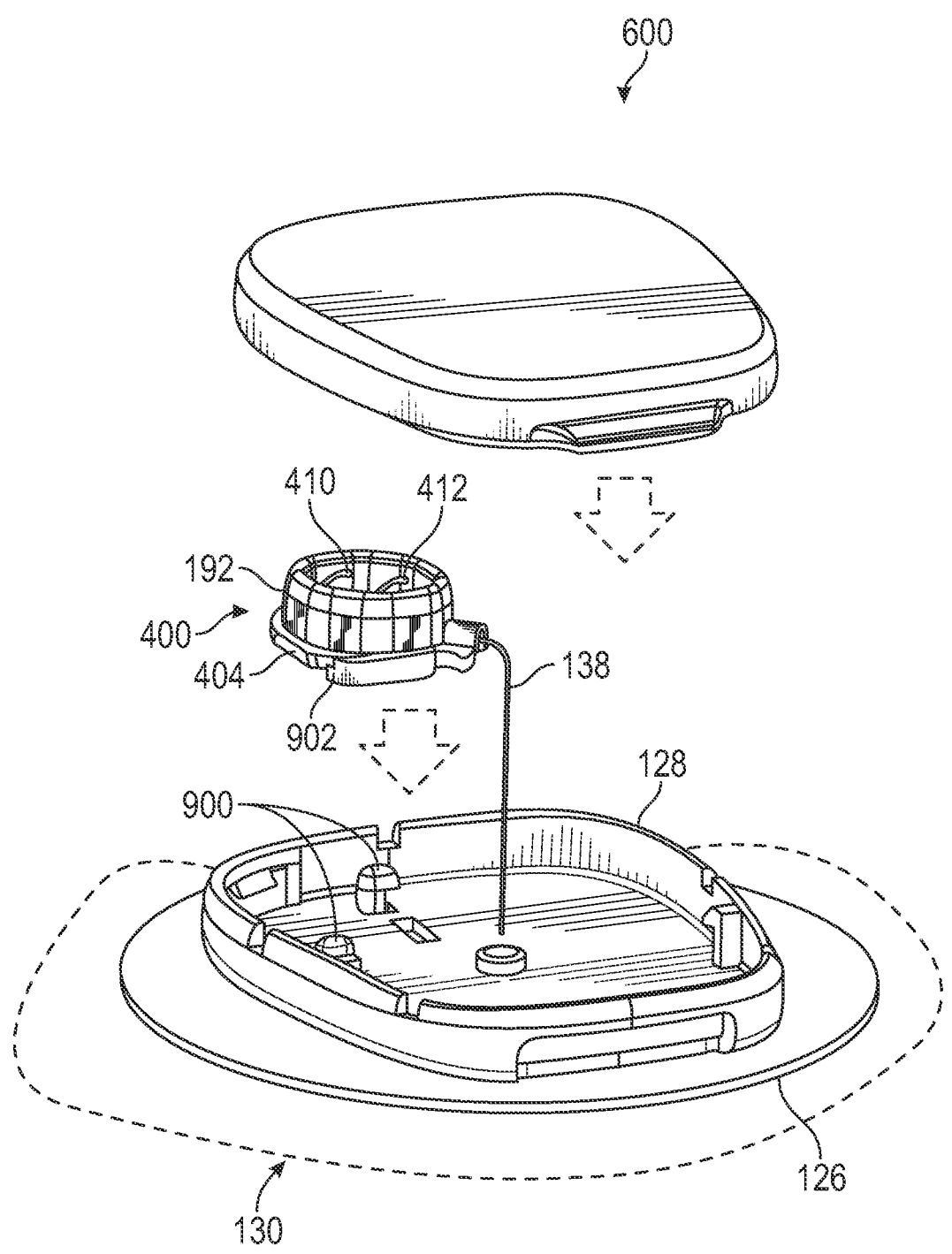
FIG. 9 illustrates a perspective view of an on-skin sensor assembly, according to some embodiments.

FIG. 9 shows a detailed example of a sensor module 300 including a pre-connected sensor 400 and a sealing structure 192. As shown, sealing structure 192 may be disposed on a substrate 404, in which sealing structure 192 may be configured to prevent moisture ingress toward contacts 410 and 412. Furthermore, contacts 410 and 412 may be implemented as leaf spring contact for coupling to sensor electronics. In some embodiments, pre-connected sensor 400 includes at least one contact. In some embodiments, pre-connected sensor 400 includes at least two contacts. In some embodiments, pre-connected sensor 400 includes at least three contacts. In some embodiments, pre-connected sensor 400 includes at least four contacts. An adhesive 126 can couple the housing 128 to the skin 130 of the host. The adhesive 126 can be a pressure sensitive adhesive (e.g. acrylic, rubber based, or other suitable type) bonded to a carrier substrate (e.g., spun lace polyester, polyurethane film, or other suitable type) for skin attachment. As shown in FIG. 9, substrate 404 may include at least one arm 202 or other mechanical features for interfacing with corresponding mating features on base 128 (e.g., mechanical interlocks such as snap fits, clips, and/or interference features) to mechanically secure substrate 404 to housing 128. Coupling features such as arm 902 and/or other features of substrate 404 may be sized and shaped for releasably mechanically attaching substrate 404 to a connector associated with manufacturing equipment such as one or more of connectors 5006, 5014, and/or 5093/5095 of FIGS. 5A-5E for testing and/or calibration operations during manufacturing and prior to attachment to features 900 of housing 128.

Figure 10:
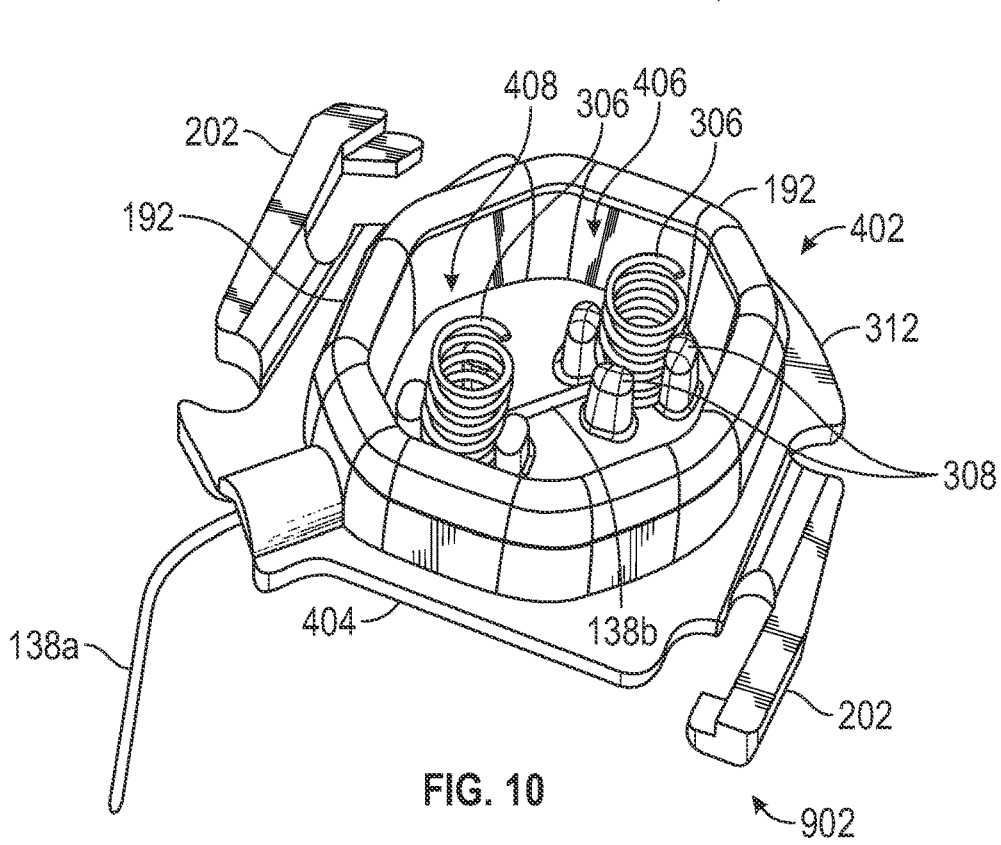
FIGS. 10 and 11 illustrate perspective views of sensor carriers that have springs, according to some embodiments.

FIG. 10 illustrates a perspective view of the sensor module 400 in an implementation in which contacts 406 and 408 are implemented using coil springs 306. In the example of FIG. 10, protrusions 308 on substrate 404 can align sensor 138 and secure springs 306 to substrate 404. (Not all the protrusions 308 are labeled in order to increase the clarity of FIG. 10.) Protrusions 308 can protrude distally.

At least three, at least four, and/or less than ten protrusions 308 can be configured to contact a perimeter of a spring 306. Protrusions 308 can be separated by gaps. The gaps enable protrusions 308 to flex outward as spring 306 is inserted between protrusions 308. A downward force for coupling electronics unit 500 to base 128 can push spring 306 against sensor 138 to electrically couple spring 306 to the sensor 138. Sensor 138 can run between at least two of protrusions 308. Testing station 5002 and/or calibration station 5004 may also have a mating connector structure that, when substrate 404 is inserted into recess 5006 or 5014, compresses springs 306 to couple springs 306 electrically between sensor 138 and processing circuitry 5012 or 5020.

Sensor 138 may include a distal portion 138a configured for subcutaneous sensing and a proximal portion 138b mechanically coupled to sensor carrier 402 having an electrical interconnect (e.g., springs 306) mechanically coupled to the substrate 404 and electrically coupled to proximal portion 138b. Springs 306 can be conical springs, helical springs, or any other type of spring mentioned herein or suitable for electrical connections.

Substrate 404 may have a base portion 312 that includes at least two proximal protrusions 308 located around a perimeter of spring 306. Proximal protrusions 308 are configured to help orient spring 306. A segment of glucose sensor 138 is located between the proximal protrusions 308 (distally to the spring 306).

Base portion 312 may be configured to be mechanically coupled to the housing 128, to manufacturing equipment 5091, testing equipment 5002, and/or calibration equipment 5004. For example, base portion 312 includes anchoring features such as arms 202. Anchoring features may include arms 202 and/or may include features such as one or more notches, recesses, protrusions, or other features in base 312, arms 202, and/or substrate 404 that mechanically interface with corresponding features of, for example, a receptacle such as one of receptacles 5006 of 5014 of FIGS. 5A-5E or a clamping connector formed by clamping connector features such as features 5093 and 5095 of FIGS. 5A-5E to secure and align sensor 138. In one suitable example, a slidable (or otherwise actuable or rotatable) feature such as feature 5095 of FIGS. 5A-5E may be arranged to slide over, around, or otherwise engage with one or more of arms 202, base 312, and/or sensor carrier 402 altogether to secure sensor carrier 402 to the manufacturing equipment. For example, in other implementations of sensor carrier 402 in which arms 202 are not provided, a receptacle connector such as one of receptacles 5006 of 5014 of FIGS. 5A-5E or a clamping connector formed by clamping connector features such as features 5093 and 5095 of FIGS. 5A-5E may include a clamshell component, a sliding component, or other movable component that bears against or covers sensor carrier 402 to latch sensor carrier 402 to the manufacturing, testing, and/or calibration equipment.

Figure 11:
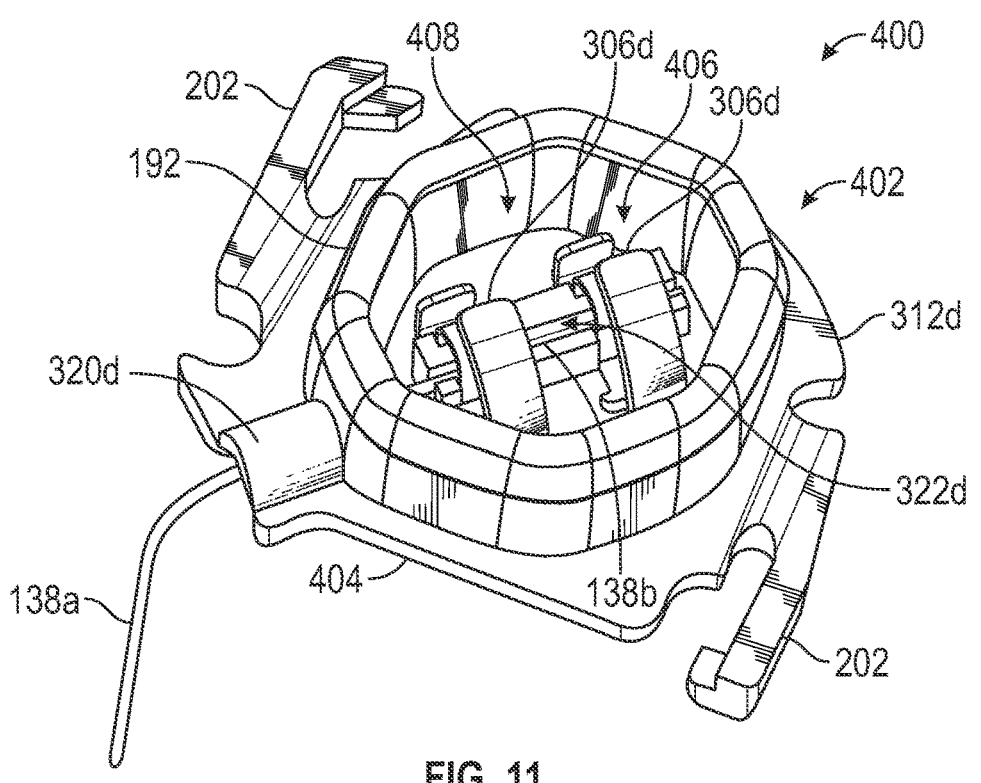
Figure 12:
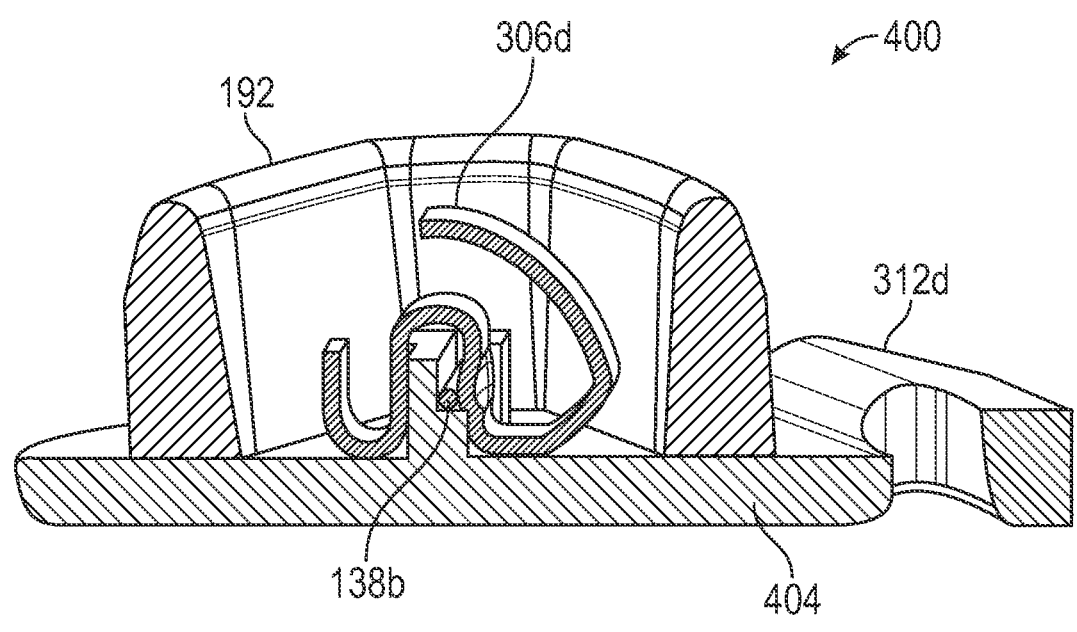
FIG. 12 illustrates a cross-sectional perspective view of a portion of a sensor carrier, according to some embodiments.

Referring now to FIGS. 11 and 12, another implementation of sensor module 400 is shown that includes a base portion 312d; a glucose sensor 138 having a distal portion 138a configured for subcutaneous sensing and a proximal portion 138b mechanically coupled to base portion 312d; and an electrical interconnect (e.g., leaf springs 306d) mechanically coupled to substrate 404 and electrically coupled to the proximal portion 138b. Leaf springs 306d can be configured to bend in response to pressure from testing station contacts, calibration station contacts, and/or electronics unit 500 coupling with base 128 while pre-connected sensor 400 is disposed between electronics unit 500 coupling with base 128.

As used herein, cantilever springs are a type of leaf spring. As used herein, a leaf spring can be made of a number of strips of curved metal that are held together one above the other. As used herein in many embodiments, leaf springs only include one strip (e.g., one layer) of curved metal (rather than multiple layers of curved metal). For example, leaf spring 306d in FIG. 11 can be made of one layer of metal or multiple layers of metal. In some embodiments, leaf springs include one layer of flat metal secured at one end (such that the leaf spring is a cantilever spring).

As shown in FIGS. 11 and 12, base portion 312d includes a proximal protrusion 320d having a channel 322d in which at least a portion of proximal portion 138b is located. The channel 322d positions a first area of proximal portion 138b such that the area is electrically coupled to leaf spring 306d.

As shown in the cross-sectional, perspective view of FIG. 12, leaf spring 306d arcs away from the first area and protrudes proximally to electrically couple with testing station 5002, calibration station 5004, and/or wearable assembly 600. At least a portion of leaf spring 306d forms a "W" shape. At least a portion of leaf spring 306d forms a "C" shape. Leaf spring 306d bends around the proximal protrusion 320d. Leaf spring 306d protrudes proximally to electrically couple testing station 5002, calibration station 5004, and/or electronics unit 500. Seal 192 is configured to impede fluid ingress to leaf spring 306d.

Leaf spring 306d is oriented such that coupling sensor carrier 402 to testing station 5002, calibration station 5004, and/or electronics unit 500 presses leaf spring 306d against a first electrical contact of the testing station 5002, calibration station 5004, and/or electronics unit 500 and a second electrical contact of the glucose sensor 138 to electrically couple the glucose sensor 138 to the testing station 5002, calibration station 5004, and/or electronics unit 500. The proximal height of seal 192 may be greater than a proximal height of leaf spring 306d such that the testing station 5002, calibration station 5004, and/or electronics unit 500 contacts the seal 192 prior to contacting the leaf spring 306d. Springs 306 and/or leaf springs 306d may cooperate with underlying features on substrate 404 (e.g., features 308) and/or channel 322d, as shown, to form datum features that secure and align sensor 138 with respect to sensor carrier 402 (e.g., for manufacturing, calibration, testing, and/or in vivo operations).

Figure 13A:
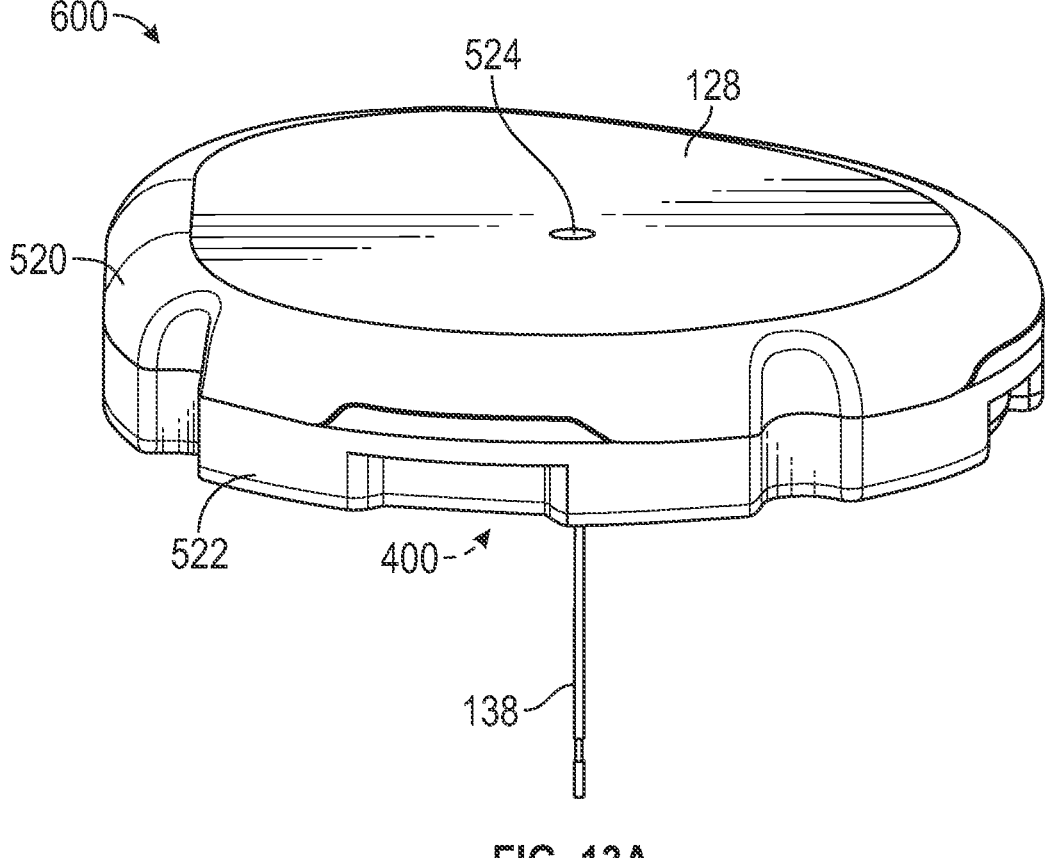
FIGS. 13A-13B illustrate perspective views of a wearable sensor assembly, according to some embodiments.
Figure 13B:
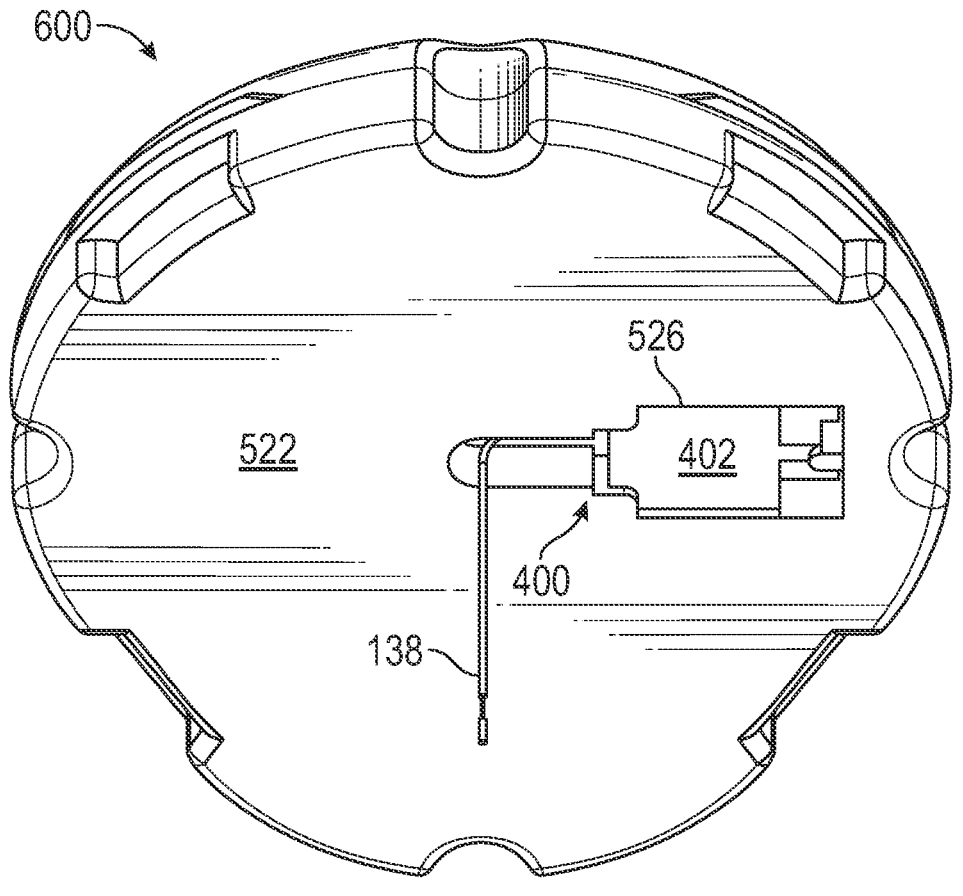

FIGS. 13A and 13B show perspective views of an embodiment of a wearable assembly 600 including a pre-connected sensor 400. Wearable assembly 600 may include sensor electronics and an adhesive patch (not shown). Pre-connected sensor 400 may include a sensor carrier such as sensor carrier 402 described in FIGS. 4A-4D. The sensor carrier 402 may be placed in or on housing 128. Housing 128 may be composed of two housing components, top housing 520 and bottom housing 522. Top housing 520 and bottom housing 522 can be assembled together to form housing 128. Top housing 520 and bottom housing 522 can be sealed to prevent moisture ingress to an internal cavity of housing 128. The sealed housing may include an encapsulating material (e.g. epoxy, silicone, urethane, or other suitable material). In other embodiments, housing 128 is formed as a single component encapsulant (e.g. epoxy) configured to contain sensor carrier 402 and sensor electronics. FIG. 13A illustrates an aperture 524 within top housing 520 configured to allow for an insertion component (e.g. hypodermic needle, C-needle, V-needle, open sided needle, etc.) to pass through the wearable assembly 600 for insertion and/or retraction. Aperture 524 may be aligned with a corresponding aperture in bottom housing 522. In other embodiments, aperture 524 may extend through an off-center location of housing 128. In other embodiments, aperture 524 may extend through an edge of the housing 128, forming a C-shaped channel. In some embodiments the aperture 524 includes a sealing material such as a gel, adhesive, elastomer, or other suitable material located within aperture 524.

FIG. 13B shows a perspective view of the bottom of wearable assembly 600. As illustrated, pre-connected sensor 400 may be disposed within the housing 128. Pre-connected sensor 400 may be installed within an aperture 526 of bottom housing 522. As shown in the figure, sensor 138 may extend out from aperture 526. Aperture 526 may be sized and shaped to retain pre-connected sensor 400. Furthermore, aperture 526 may be sized and shaped to retain pre-connected sensor 400 in which sensor 138 extends approximately parallel to the skin surface and forms a 90 degree bend for insertion into the skin. It should be understood that the bottom surface of bottom housing 522 can contain an attachment member (e.g. an adhesive patch) for adhering the wearable assembly to the skin surface of a user.

Figure 13C:
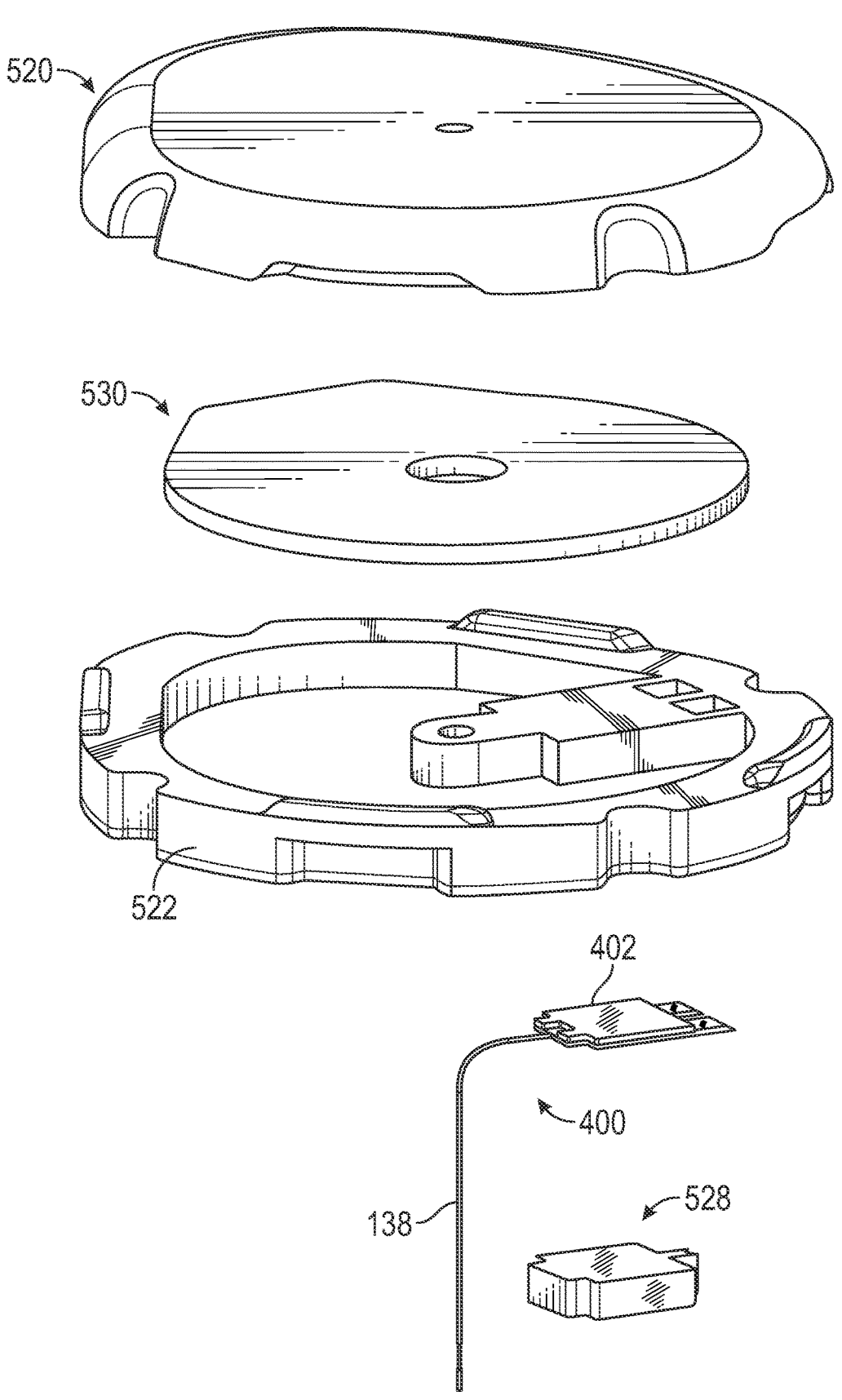
FIG. 13C illustrates an exploded view of components of a wearable sensor assembly, according to some embodiments.

FIG. 13C shows an exploded view of the wearable assembly 600. Various electronic components such as the potentiostat 210 and other components illustrated in FIG. 2 may be mounted on or to an electronics assembly substrate 530, typically some form of printed circuit board. It is contemplated that sensor carrier 402 has an electrical coupling with electronics assembly substrate 530. Various methods may be used to establish electrical connection (e.g. pins, solder, conductive elastomer, conductive adhesive, etc.) between one or more contacts of pre-connected sensor 400, such as external contacts 410 and 412 and electronics assembly substrate 530. Sensor carrier 402 may be configured to interface with electronics assembly substrate 530 through the bottom housing 522. In other implementations, the sensor carrier 402 may be configured to interface with the electronics assembly substrate 530 through top housing 520. In some other implementations, the sensor carrier 402 is configured to interface with the electronics assembly substrate 530 through the side of wearable assembly 600. Also shown in the figure, an optional sealing member 528 may be configured to insulate at least a portion of sensor carrier 402 from potential moisture ingress. In some instances, the sealing member 528 may be liquid dispensed (e.g., adhesive, gel) or a solid material (e.g., elastomer, polymer). The sealing member 528 may be an assembled component that is welded (e.g., laser or ultrasonic, hot plate), or otherwise permanently attached (e.g., anisotropic adhesive film, pressure sensitive adhesive, cyanoacrylate, epoxy, or other suitable adhesive) to create a sealed region. The sealing member 528 may be used to physically couple and/or provide a sealed region for the sensor carrier 402 to the wearable assembly 600.

Figure 14A:
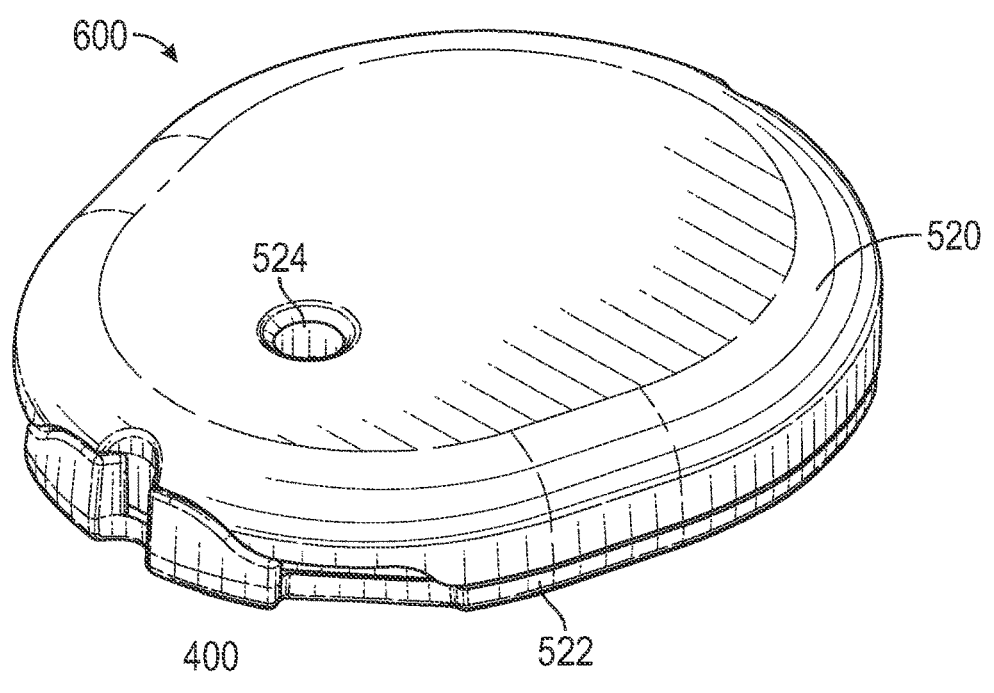
FIGS. 14A-14B illustrate perspective views of another wearable sensor assembly, according to some embodiments.
Figure 14B:
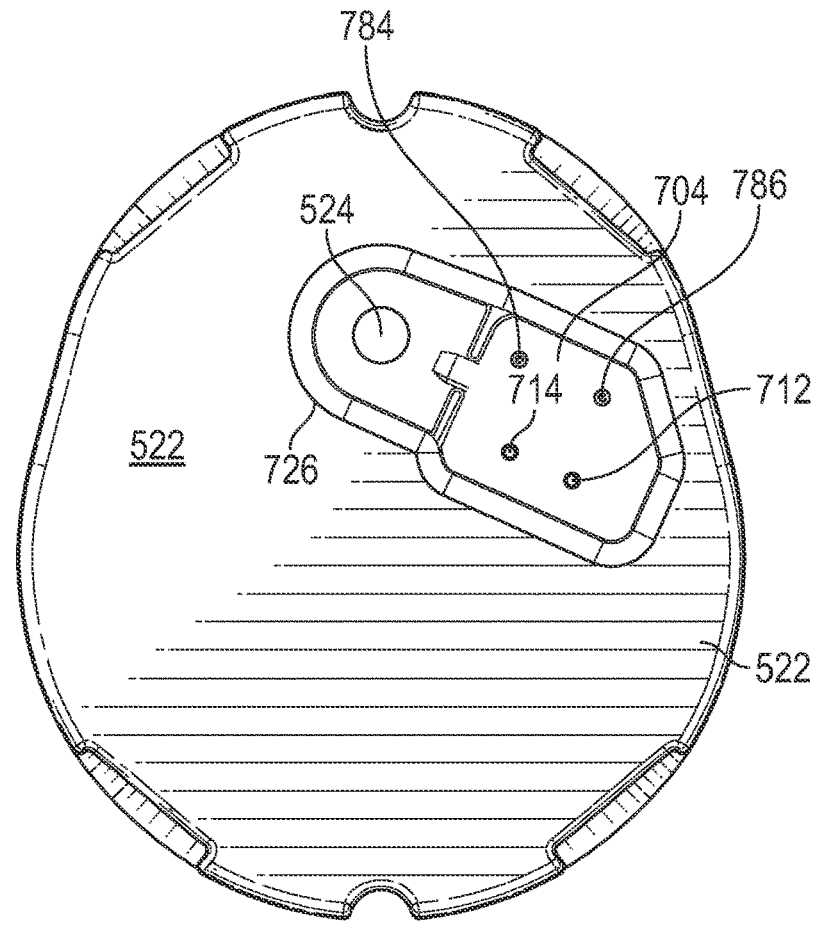
Figures 14C, 14D:
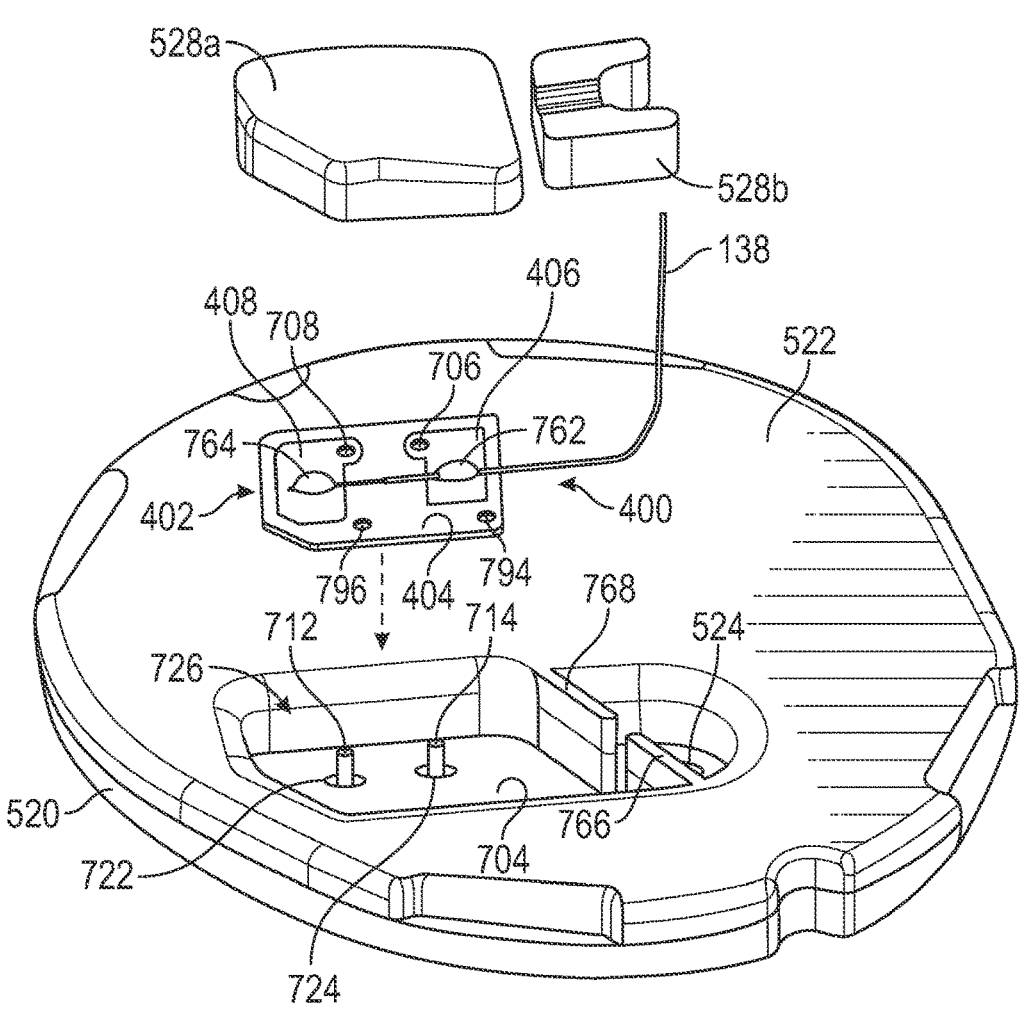
FIG. 14C illustrates an exploded view of components of another wearable sensor assembly, according to some embodiments, including an external electrical interface embodiment.
FIG. 14D illustrates a top plan view of the external electrical interface of FIG. 14C with a pre-connected sensor assembly installed.
Figure 14E:
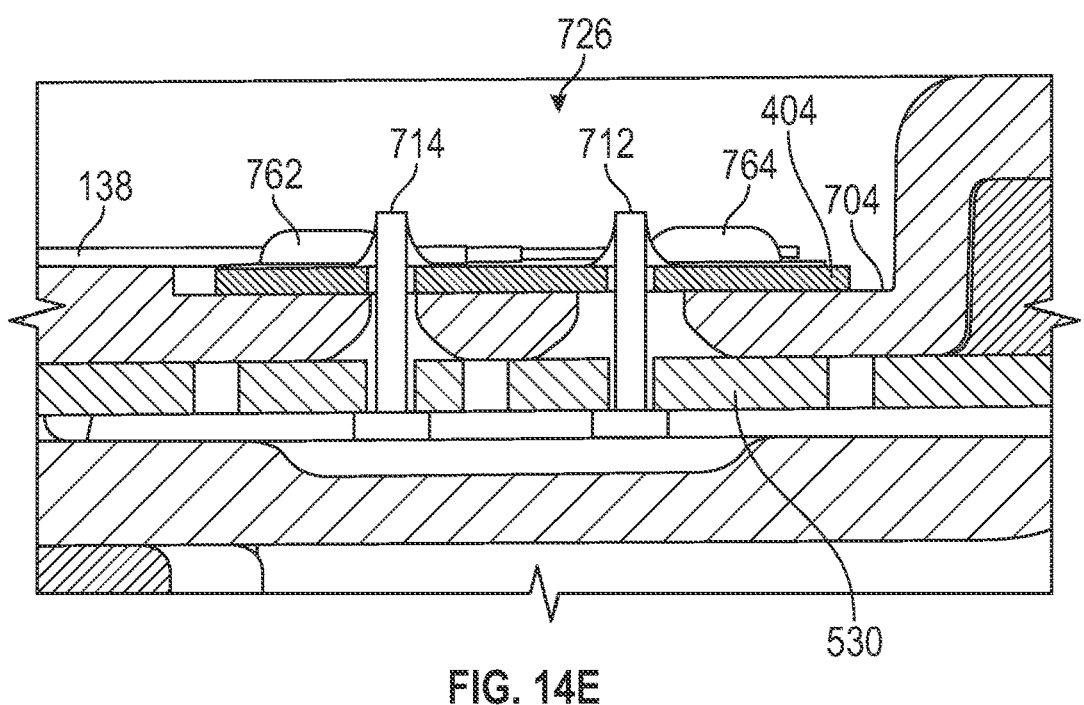
FIG. 14E is a cross section along lines E-E in FIG. 14D.

FIGS. 14A-14E illustrate another implementation of a wearable assembly 600. The implementation of FIGS. 14A-14E share some similarities to the implementation shown in FIGS. 13A-13C. As illustrated in FIG. 14A, the wearable assembly 600 includes a housing formed as a top housing 520 and a bottom housing 522. The wearable assembly also includes a through hole 524 for use during interstitial insertion of the sensor 138 into a subject. Referring especially to FIGS. 14B, C, and D, the bottom housing 522 includes a recess 726 with a floor 704. The floor 704 may include locating pins 784 and 786 that extend upward from the floor 704 and two apertures 722 and 724. The locating pins may be formed as an integral part of the floor 704, during for example molding of the housing, or they may be separate parts that are coupled to the floor with friction fit, adhesive, or any other means. In some embodiments, there is at least one locating pin. In some embodiments, there are at least two locating pins. In some embodiments, there are at least three locating pins. On the opposite side of the floor 704 is a printed circuit board 530 (visible in FIG. 14E) with some or all of the sensor electronic circuitry (e.g. the potentiostat 210 or at least traces that connect to the potentiostat) mounted thereon. The printed circuit board 530 may also have conductive pins 712 and 714 mounted thereon which extend through apertures 722 and 724 in the floor 704, forming an external electrical interface that is accessible without opening the housing. The pre-connected sensor 400 drops into this recess 726. Holes 794 and 796 drop over locating pins 784 and 786 and conductive pins 712 and 714 extend through holes 706 and 708 in the sensor carrier substrate 404. These holes 706 and 708 extend through plated metal (e.g. copper) contacts 406 and 408 on the substrate 404, similar to those shown in a different embodiment in FIGS. 4A to 4C. Generally, the number of holes 706, 708 in the substrate 404 correspond to the number of electrodes present in the sensor 138, which may in turn correspond to the number of pins 712, 714. For example, a three-electrode system with a working, reference, and counter electrode may have three holes in the substrate corresponding to three pins extending up through floor 704. The pins 712 and 714 may be electrically connected to the contacts 408 and 406 in a variety of ways such as solder, swaging, or conductive glue, paste, adhesive, or film. After this connection is made, the electronic circuitry for detecting and/or processing analyte sensor signals that is placed inside the housing becomes connected to the analyte sensor to receive signals therefrom. The connection material bonding the sensor 138 to the sensor carrier 402 is designated 762 and 764 in FIGS. 14D and 14E. These connections may be established by any of the methods described above with reference to FIG. 4A.

Once the substrate 404 is placed over the pins 712, 714, the proximal portion of the sensor 138 can be secured to the floor 704 with a pressure sensitive adhesive 772 to retain the proximal portion of the sensor on or near the housing prior to extending downward at the inserter opening 524. This allows for accurate sensor insertion position and controls the bias force into the insertion needle. A variety of methods and/or structural features may be used to perform this retention function such as a protrusion or shelf in the floor 704, an overmolded part, a snap-fit additional plastic piece installed over the sensor, or any sort of glue or adhesive placed before or after the pre-connected sensor is placed in the recess 726. As is also shown in FIGS. 13C, optional sealing members 528a and 528b may be configured to seal and insulate at least a portion of sensor carrier 402 from potential moisture ingress. In some instances, the sealing member 528 may be liquid dispensed (e.g., adhesive, gel) or a solid material (e.g., elastomer, polymer). The sealing member 528 may be an assembled component that is welded (e.g., laser or ultrasonic, hot plate), or otherwise permanently attached (e.g., pressure sensitive adhesive, cyanoacrylate, epoxy, or other suitable adhesive) to create a sealed region. The sealing member 528 may be used to physically couple and/or provide a sealed region for the sensor carrier 402 to the wearable assembly 600. The two sealing members 528a and 528b are partially separated by walls 766 and 768. These walls allow two different sealing methods to be used in the two different portions of the recess 726 that are separated by the walls. For example, 528b may be a solid polymer that is press fit into the recess portion with opening 524 on one side of the walls. The other portion of the recess 726 may then be filled with a liquid UV cured epoxy which hardens to form sealing member 528a. The depth of the two recess portions on either side of the walls may be the same or different.

Figure 15A:
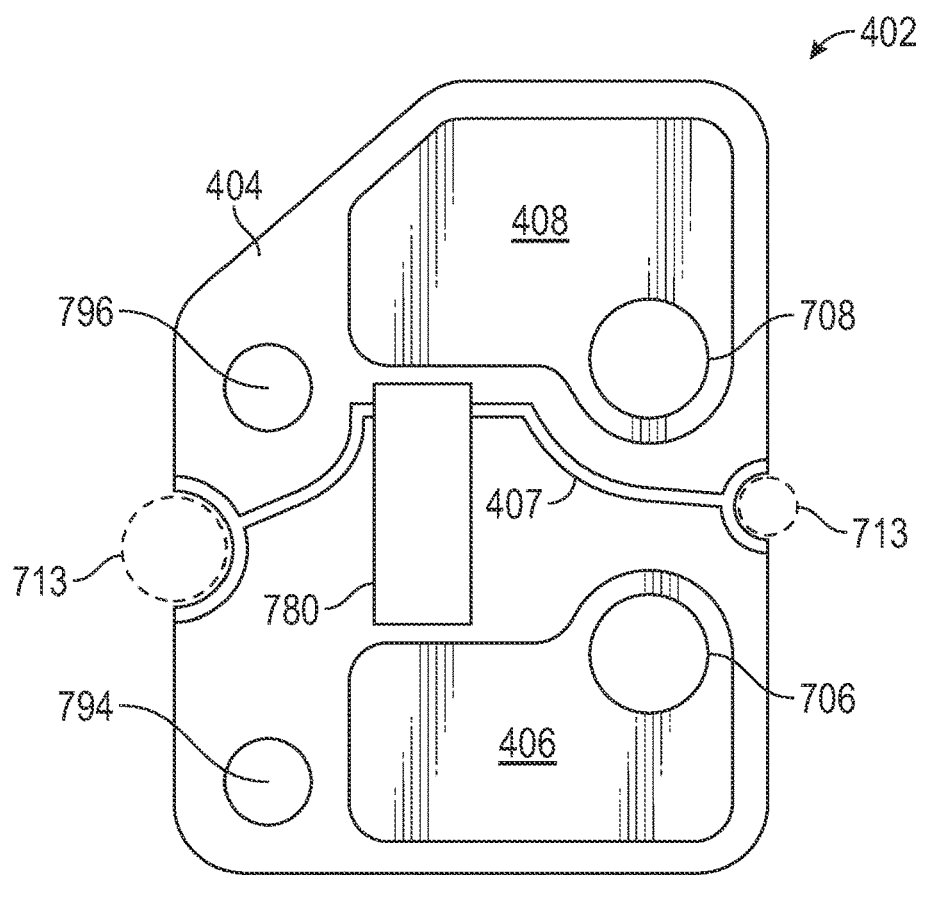
FIG. 15A illustrates another embodiment of a printed circuit board substrate for a sensor carrier.

FIG. 15A shows an alternative embodiment of a sensor carrier 402, also potentially taking the form of a printed circuit board. In this implementation, a guard trace 407 such as described above with reference to item 336 in FIG. 3D is provided on the substrate 404 of the sensor carrier 402. As explained above, this guard trace 407 is positioned between contacts 406 and 408 and is connected to the bias voltage by the sensor electronics. The guard trace 407 can be coupled to the sensor electronics with or more conductive pins 713 (not shown in FIGS. 14A to 14E) that extend through the floor 704 similar to pins 712 and 714. In FIG. 15A, the pins are shown connected to castellated contacts on the side of the substrate 404. An insulating layer 780 such as solder mask may be positioned over the guard trace 407 to eliminate the risk of the analyte sensor electrodes shorting to it.

Figures 15B, 15C:
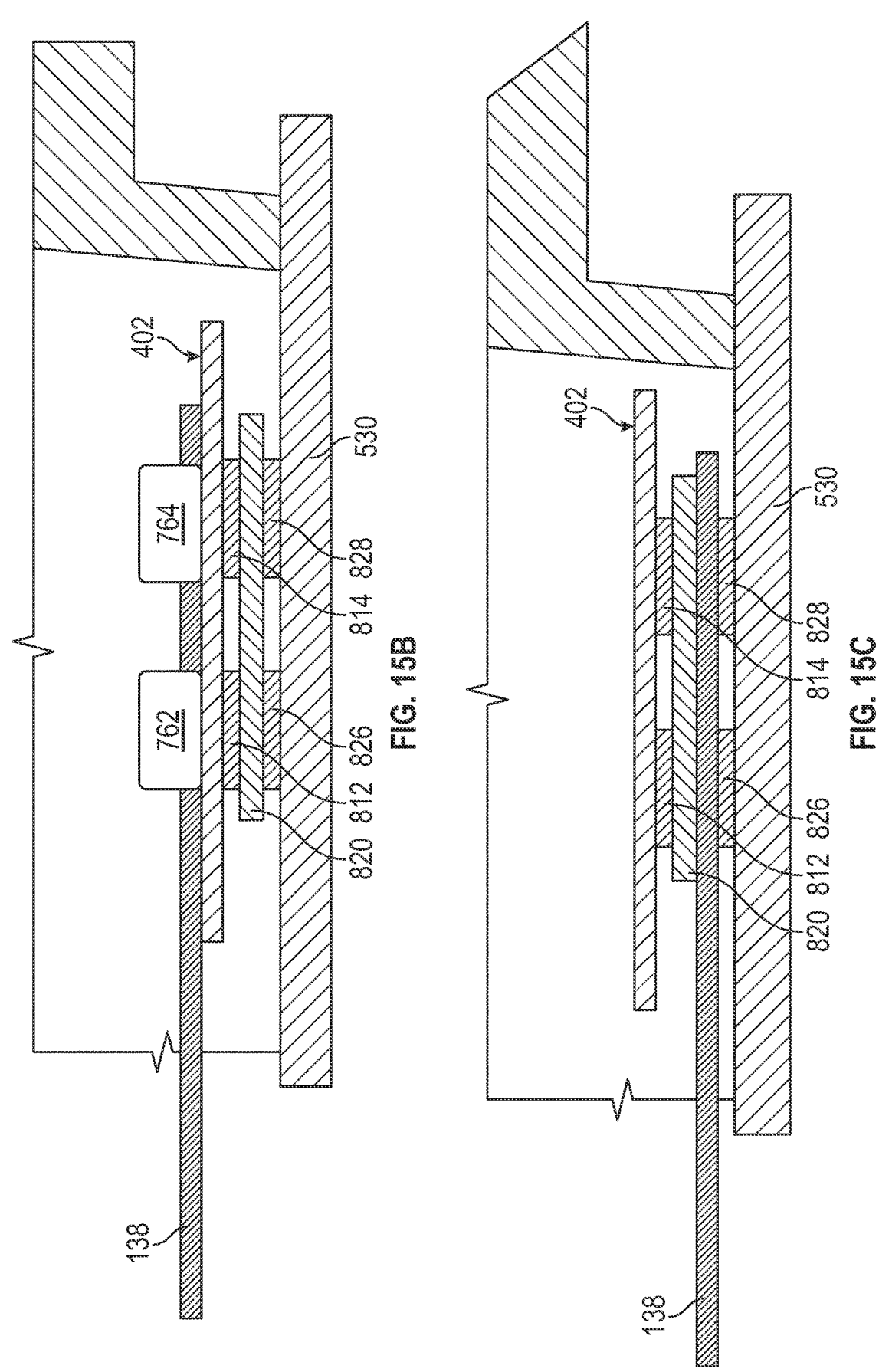
FIGS. 15B and 15C illustrate alternative embodiments for coupling a sensor and sensor carrier to an electrical interface of a wearable sensor assembly.

FIGS. 15B and 15C illustrated other implementations of connecting a sensor carrier 402 having an analyte sensor 138 mounted thereon to electronic circuitry internal to a wearable sensor. In FIG. 15B, the sensor 138 is coupled to the sensor carrier 402 with conductive adhesive 762 and 764 as shown above with reference to FIGS. 14C and 14D. On the other side of the sensor carrier substrate are conductive contact pads 812 and 814. The circuit board 530 also has contact pads 826 and 828 bonded thereto and which are accessible through the floor 704 of the recess 726. An anisotropic film 820 is used to electrically and mechanically bond the sensor carrier contact 812 to circuit board contact 826 and also sensor carrier contact 814 to circuit board contact 828. The anisotropic film 820 is compressed with heat between the contacts, which makes conductive particles in the film 820 bridge the gap vertically between the contact pairs 812/826 and 814/828. The conductive particles in the film 820 are spaced apart horizontally, so no shorting between the contact pairs occurs. This electrical and mechanical bonding technique has found widespread use in display applications for small electronics such as smart phones and lends itself to easy and consistent connections in production environments.

In FIG. 15C, the proximal region of sensor 138 is coupled to the sensor carrier 402 contacts 812 and 814 with anisotropic film 820. A different area of the same anisotropic film 820 may be used to connect the sensor carrier contacts 812 and 814 to circuit board contacts 826 and 828 respectively. In this implementation, the area of the film 820 that connects the sensor 138 to the contacts 812 and 814 may be horizontally adjacent to or otherwise separated from the area of the film 820 that connects the circuit board contacts 826 and 828 to the sensor carrier contacts 812 and 814.

In the examples of FIGS. 10-15, pre-connected sensor 400 can be installed as a standalone interface between sensor 138 and the sensor electronics. However, it should be appreciated that, in some implementations described herein, pre-connected sensor 400 may include a sensor carrier that couples to an additional interface between the sensor 138 and the sensor electronics inside the wearable assembly 600. For example, channel 322d and leaf spring 306d can be formed on separate substrate that, following calibration and testing operations, mechanically attaches to base portion 312d within seal 192 for installation into wearable assembly 600.

It is one benefit of the analyte sensor connection techniques described above that the fabrication of the pre-connected sensor 400 may be separated from the fabrication of the electronics enclosed within the housing. As described above with reference to the pre-connected sensor structure and the subsequent coating, testing and calibrating processes, the housing with the internally contained electronics can be manufactured in a separate facility from the one that attaches the pre-connected sensor 400 to the sensor electrical interface. This is made possible by providing an analyte sensor electronics interface that is accessible from outside the housing. The housing need not be opened to attach the sensor.

In some advantageous methods, the electrodes for the pre-connected sensor are fabricated and mounted on the substrate in a first location and are shipped to a second location for coating testing and calibrating. The housing with internal electronics is manufactured in a third location. The housing with the electronics is shipped from the third location to the second location, where the completed analyte sensor is attached to the external electrical interface. The three locations can all be remote from each other. This minimizes handling of the sensitive membrane coated sensor, but still allows separate manufacturing of the other components of the complete device.

FIG. 16 shows a top view of an implementation of sensor carrier 402 in which substrate 404 is a substantially planar substrate and sensor 138 is attached to substrate 404 with a conductive adhesive 1500. As shown in FIG. 16, conductive adhesive 1500 may be applied to contacts 1000 and 1002 of sensor 138 to mechanically attach sensor 138 to substrate 404. Once applied the conductive adhesive 1500 on contacts 1000 and 1002, may itself form contacts 408 and 406 for coupling to testing station 5002, calibration station 5004, and/or electronics unit 500. FIG. 17 shows an end view of sensor carrier 402 of FIG. 16 in which conductive adhesive 1500 can be seen covering a portion of sensor 138 at the proximal end. In other embodiments, sensor 138 may be attached to substrate 404 with a conductive adhesive 1500, or via any other suitable methods via the use of, for example, clips, conductive polymer, metallic foil, conductive foam, conductive fabric, wire wrapping, wire threading or via any other suitable methods.

FIGS. 18, 19, and 20 show examples of substrate 404 of FIG. 16, with additional datum features for controlling the position and spatial orientation of sensor 138 on substrate 404. In the example of FIG. 18, substrate 404 includes a v-shaped recess 1700. Sensor 138 is disposed partially within recess 1700 to orient sensor 138 in a direction along the recess, and conductive adhesive 1500 substantially covers sensor 138 and fills in portions of recess 1700 not filled by sensor 138 to secure sensor 138 within the recess. In the example of FIG. 19, substrate 404 includes a first planar portion 1800 and a second planar portion 1802 extending at a non-parallel (e.g., perpendicular) angle with respect to the first planar portion, and sensor 138 is attached at the interface of the first and second planar portions by conductive adhesive 1500. In the example of FIG. 20, substrate 404 includes a rounded recess 1900 in which sensor 138 is attached by conductive adhesive 1500 that substantially covers sensor 138 and fills in portions of recess 1700 not filled by sensor 138 to secure sensor 138 within the recess.

FIGS. 21A and 21B show an example sensor carrier 402 with at least one pair of guide structures 2106 and 2108 formed on the substrate 404, such as on one or both contacts 406 and 408. These guide structures can assist placement of the sensor body 138 on the appropriate location when applying conductive adhesive to bond the two together. This can eliminate the need for external guide fixtures when assembling the sensor to the sensor carrier during manufacturing. The structures 2106, 2108 can be made of solder or other conductive adhesive. Although not shown in FIGS. 21A and 21B, an additional adhesive bonding material can be provided between the guide structures to fix the sensor to the guide structures during manufacturing.

Conductive adhesive 1500 may be, for example, a conductive liquid dispensed glue. The conductive liquid dispensed glue may be a one or two-part adhesive that cures (e.g., at room temperate or an elevated curing temperate). The conductive liquid dispensed glue may be a snap-cure adhesive. A two-part conductive liquid dispensed glue may include a base adhesive (e.g., epoxy, polyurethane, etc.) and a conductive filler (e.g., silver, carbon, nickel, etc.). Conductive adhesive 1500 may include, for example, an adhesive resin with one or more embedded conductive materials such as silver, copper or graphite. Conductive adhesive 1500 may be a heat curable conductive adhesive.

FIG. 22 shows a top view of an implementation of sensor carrier 402 in which substrate 404 is a substantially planar substrate and sensor 138 is attached to substrate 404 with a conductive tape 2000. As shown in FIG. 22, conductive tape 2000 may be applied to one or more contacts (e.g. connection areas 1000 and 1002) of sensor 138 to mechanically attach sensor 138 to substrate 404. Once applied the conductive tape 2000 on contacts 1000 and 1002, may itself form contacts 408 and 406 for coupling to testing station 5002, calibration station 5004, and/or electronics unit 500. Tape 200 may be applied over sensor 138 as shown in FIG. 22, or may be interposed between substrate 404 and sensor 138. In implementations in which tape 2000 is disposed between substrate 404 and sensor 138, substrate 404 may be a flexible substrate that can be rolled or folded around sensor 138 as shown in the end view of FIG. 23. The rolled substrate of FIG. 23 includes extending portions 2100 that can form one or more contacts (e.g. 406 or 408).

Conductive tape 2000 may be configured for use as a multi-zoned tape with one or more conductive tapes 2000 and non-conductive tape sections. The combination of conductive and non-conductive regions can be used to electrically isolate connection regions. Using a multi-zoned tape may simplify the assembly of multiple connection regions in a single assembly step. The pitch of the conductive regions on the tape may be matched to the targeted connection area of the sensor wire 138. In other embodiments the pitch of the conductive region of the tape is significantly less than the spacing of the targeted connection area of the sensor wire 138. A shorter pitch may allow for more variability in tape placement while ensuring isolated connection between the sensor 138 and the substrate 404. Conductive tape 2000 may be formed from a polymer substrate with a conductive adhesive (e.g. carbon-impregnated adhesive, metal-impregnated adhesive). As another example, conductive tape 2000 may be a metallic substrate with conductive and non-conductive adhesive. Some examples of non-conductive substrates are polyimide, composite, polymers, etc. Some examples of conductive substrates are metals (e.g. Foils, plating, cladding, etc), conductive polymers, and conductive elastomers. Examples of non-conductive adhesive are epoxy, cyanoacrylate, acrylic, rubber, urethane, hot melt, etc. Examples of conductive adhesives are carbon filled adhesive, nano particle filled adhesive, metal filled adhesive (e.g. silver), conductive inks, etc.

FIG. 24 shows a top view of an implementation of sensor carrier 402 in which substrate 404 is a substantially planar substrate and sensor 138 is attached to substrate 404 with a conducive plastic 2200 welded or bonded to a non-conductive (e.g., plastic) substrate 404. As shown in FIG. 24, conductive plastic 2200 may be applied to contacts 1000 and 1002 of sensor 138 to mechanically attach sensor 138 to substrate 404. Once applied the conductive plastic 2200 on contacts 1000 and 1002, may itself form contacts 408 and 406 for coupling to testing station 5002, calibration station 5004, and/or electronics unit 500.

FIGS. 25 and 26 show an exemplary ultrasonic welding system for welding conductive plastic 2200 to substrate 404. As shown in FIG. 25, substrate 404 may be provided with a recess within which a protrusion on a conductive plastic member 2200 can be received. Sensor 138 may be disposed within a recess in the protrusion on conductive plastic member 2200 and conductive plastic member 2200 can be pressed in direction 2302 and vibrated by ultrasonic welding horn 2300 to form a melt region 2400 that, when horn 2300 is removed, solidifies to secure sensor 138 between substrate 404 and conductive plastic 2200 to form a conductive contact to sensor 138.

In some implementations, in order to provide a sensor 138 with additional surface area for clipping or soldering of contacts to substrate 404, the proximal end of sensor 138 may be rolled or otherwise flattened as shown in FIG. 27. As shown in FIG. 27, contacts 1000F and 1002F may be flat contacts that converge into a cylindrical wire sensor 138. As shown in the side view of sensor carrier 402 in FIG. 28, flattened contacts 1000F and 1002F may be attached to substrate 404 with conductive attachment members 2600 and 2602 such as clips, solder welds, an anisotropic conductive film, a conductive tape, a plastic member with embedded conductors, conductive springs, or elastomeric conductive members (as examples).

In one example, connectors such as contacts 1000F and 1002F (and/or other forms of contacts 1000 and 1002 described herein) may be laser soldered to corresponding contacts on substrate 404. In implementations in which sensor 138 is laser soldered to substrate 404, a trace surface of substrate 404 may be preheated by laser illumination at a soldering location. The surface heat emission may reflow a pre-deposited solder material on either side of sensor 139. A guide such as a borosilicate glass "angle" may be placed over the sensor and per-deposited solder to retain the solder, driving molten solder towards the sensor. A resulting "cradle" bond may then securely anchor the sensor to the trace on substrate 404 which may help increase or maximize a trace-to-solder-sensor contact wire bonding area. Use of a guide such as a borosilicate glass angle may also protect printed circuit board assembly electronics that may be included on and/or in the substrate from solder debris during the hot portion of the soldering process.

In another example, connectors such as contacts 1000F and 1002F (and/or other forms of contacts 1000 and 1002 described herein) may be soldered to corresponding contacts on substrate 404 without a laser. In these example, solder wire may be pre-fed onto a tip of a soldering iron to build up a blob of molten solder on the tip. The iron may then be moved down so the blob touches the sensor and conductive trace on the substrate. A coating on the sensor such as the Ag/AgCl coating described herein may be provided with a low thermal mass such that the sensor coating heats up quickly without freezing the solder. Once the coating is heated, the solder wets to the coating. The trace would also have minimal thermal mass so it will heat up quickly without freezing the solder. A solder mask may be provided around the trace that prevents the solder flowing off the edge of the trace.

In some implementations, substrate 404 may be formed, at least in part, by a flexible circuit (e.g., a polyimide substrate having conductive traces or other suitable flex circuit) that folds over and/or around at least a portion of sensor 138 to conductive traces of the flex circuit. FIG. 29 shows a top view of a flex circuit implementation of substrate 404 in which substrate 404 is a flexible circuit having a central, non-conductive, elongated portion 2702 along which sensor 138 is oriented and having upper and lower extensions 2700 and 2704 that extend from central portion in a directed perpendicular to the elongated dimension of central portion 2702. Extensions 2700 and 2704 respectively include conductive contacts 2706 and 2708 that form contacts 408 and 406. Conductive contacts 2706 and 2708 may be coupled, via traces and/or conductive vias on or within substrate 404 to external contacts that form contacts 412 and 410. In some instances, extensions 2700 and 2704 may allow for testing, calibration, sensor electronics or other equipment to connect to sensor carrier/sensor assembly in area that is not occupied by the sensor. This may allow for additional connection types and/or improve electrical coupling of connection.

FIG. 30 shows an implementation of sensor carrier 402 in which substrate 404 includes a wedge-shaped base portion 2800 and a foldable flexible portion 2802. Conductive contacts 2804 may extend from base portion 2800 to foldable portion 2802 so that, when sensor 138 is placed on base portion 2800 and optionally foldable portion 2802 is be folded over sensor 138 (e.g., in direction 2820) to wrap over and around sensor 138, contacts 410 and 412 electrically couple to sensor 138. Base portion 2800 may be rigid and may taper in a direction away from sensor 138. Base portion 2800 may include conductive contacts 410 and 412 at a narrow end. Base portion 2800 may, for example, be removably inserted into recesses 5006 and 5014 of testing station 5002 and calibration station 5004 for testing and calibration operations. In the examples of FIGS. 27 and 28, the flexible substrate may be folded over the sensor and secured (e.g., to the sensor and/or to itself to secure the sensor by a welding soldering, a mechanical crimp, spring contacts, rivets, adhesive such as epoxies, or the like.

FIGS. 31A and 31B illustrate another embodiment of a sensor carrier 402. In this embodiment, the sensor carrier 402 comprises a block 404 made of non-conducting material such as a polymer or ceramic. The block 404 includes a through-hole 1420 extending therethrough along the y-axis through which the proximal ex vivo portion of the analyte sensor 138 extends. Slots or blind holes 1410 and 1412 intersect the through-hole 1420 on an orthogonal z-axis to the through hole y-axis. Conductive contact material 406 and 408 is plated on the top surface and extends into the slots 1410 and 1412. Additional holes 1430 and 1432 extending along the x-axis intersect both the through-hole 1420 and the slots 1410 and 1412. Each hole 1430 and 1432 extends across its respective slot and partway into the block on the other side of each slot forming a blind hole or depression 1442, 1444 on the other side. Plugs 1451 and 1453, which may be conductive or non-conductive are inserted into the holes 1430 and 1432 and push the contacts 212b and 211b of the wire analyte sensor into the depressions 1442, 1444, causing the contacts 212b and 211b to come into electrical contact with the sensor carrier contacts 406 and 408.

FIG. 32 shows a top view of a sensor carrier having a substrate 404, a datum feature 2900, and a movable connector 2902 for each of contacts 406 and 408. Sensor 138 may be aligned against datum features 2900 and movable connectors 2902 may be moved to secure each of contacts 1000 and 1002 between the corresponding datum feature and movable connector. Movable connectors 2902 and/or datum features 2900 conductively couple to contacts 1000 and 1002. Movable connectors 2902 and/or datum features 2900 may be conductively coupled to other contacts (not shown) on substrate 404 that form contacts 410 and 412. FIG. 33 is a perspective view of one of datum features 2900 and an associate movable contact 2902, movable in a direction 2904 toward datum feature 2900 to secure sensor 138. Contacts 1000 and 1002 may be flattened to enhance contact with datum feature 2900 and contact 2902. Additional conductive material 2906 may be formed on substrate 404 between datum feature 2900 and contact 2902 to enhance electrical contact with sensor 138 if desired. The additional conductive material may be an exposed surface of a portion of an embedded conductive layer (e.g., a copper or other conductive metal layer) within substrate 404 or may be solder or a conductive adhesive (as examples).

FIG. 34 shows a perspective view of a pre-connected sensor formed from a sensor carrier implemented as a barrel connector that substantially surrounds sensor 138. In the example of FIG. 34, substrate 404 may be an insulating layer formed around sensor 138 with conductive bands that extend from an internal contact with contacts 1000 and 1002 to an external surface that forms contacts 410 and 412. As shown in FIG. 34, annular contacts 410 and 412 may be removable received by a press fit into conductive brackets 3102 and 3104 of a device 3100 (e.g., testing station 5002, calibration station 5004, and/or electronics unit 500). Conductive brackets 3102 and 3104 may establish electrical communication between sensor 138 and device 3100 (e.g., testing station 5002, calibration station 5004, and/or electronics unit 500).

FIG. 35A shows an implementation of sensor carrier 402 in which a flexible circuit is wrapped over an end of sensor 138 such that a top portion 3200 and a bottom portion 3202 of the flexible substrate are formed on opposing sides of sensor 138. As shown in FIG. 35B, top portion 3200 and bottom portion 3202 may be wrapped over the ends of multiple sensors 138 such that a flex circuit strip 3404 forms a common sensor carrier for multiple sensors. Flex circuit strip 3204 may include pairs of internal contacts for coupling to contacts 1000 and 1002 of each sensor 138 and pairs of external contacts, each pair of external contacts coupled to a corresponding pair of internal contacts and forming contacts for coupling to testing station 5002 and/or calibration station 5004. In this way, multiple sensors can be transported and coupled to testing and calibration equipment as a group. Strip sensor carrier 3204 may include identifiers for each sensor 138 so that testing and/or calibration data for each sensor can be logged and stored. Individual pre-connected sensors may be formed by singulating strip sensor carrier 3204 into individual sensor carriers for each sensor that can be installed in an electronics unit, such as the wearable sensor units of FIGS. 13 and 14. Strip 3204 may include singulation features 3220 (e.g., markings and/or scoring that facilitate singulation into individual pre-connected sensors.

Although FIGS. 35A and 35B show a flexible circuit strip that is wrapped around the ends of sensor 138, this is merely illustrative. It should be appreciated that a flex strip carrier for more one or more sensors 138 may be attached to the sensor(s) in other ways. For example, the ends or other portions of sensors 138 may extend into a substrate of flexible circuit strip 3204 to couple to internal conductive contacts in the strip or the ends or other portions of sensors 138 may be attached to a surface of flexible circuit strip 3204 (e.g., using an anisotropic conductive film (ACF) or other conductive adhesive, a laser solder or other solder, a clip or other attachment mechanisms and/or datum features that position and align the sensor).

FIG. 36 shows an implementation of sensor carrier 302 in which a crimp connector 3301 extends through a portion of substrate 404. As shown in FIG. 36, crimp connector 3301 may have a base portion 3300 that extends from a first side of substrate 404 (e.g., to form one of contacts 410 and 412). Crimp connector 3301 also includes arms 3302 extend from an opposing second side of substrate 404. As shown in FIG. 37, arms 3302 can be pressed together or crimped to mechanically secure and conductively couple to sensor 138, thereby forming, for example, contact 406. FIG. 38 shows a side view of the sensor carrier of FIGS. 36 and 37 and shows how two crimp connectors may be provided that extend through substrate 404 and form contacts 406 and 408 on a first side and contacts 410 and 412 on a second side. Although contacts 410 and 412 are formed on the second side of substrate 404 in FIG. 38, it should be appreciated that contacts 410 and 412 can be formed on the first side, or on a sidewall or edge of substrate 404 (e.g., by including one or more bends or other conductive couplings within substrate 404).

FIG. 39 shows an implementation of pre-connected sensor in which sensor carrier 402 includes a distally oriented channel 358 that directs sensor 138 distally such that sensor 138 includes a bend that is at least 45 degrees and/or less than 135 degrees. A channel cover 362 secures the glucose sensor 138 in the distally oriented channel 358. In the example of FIG. 39, one or more contacts (e.g. 408 and 406) are implemented using conductive elastomeric members 1400. In other embodiments contacts may be any suitable type (e.g. coil springs 306, leaf spring 306*d*). Contacts (e.g. conductive elastomeric members 1400) form a conductive coupling between sensor 138 and external equipment (e.g., testing station 5002, calibration station 5004, and/or on-skin sensor assembly 600). Contacts may cooperate with underlying features on substrate 404 (e.g., protrusions 308) and/or channel 322*d*, as shown, to form datum features that secure and align sensor 138 with respect to sensor carrier 402 (e.g., for manufacturing, calibration, testing, and/or in vivo operations). In some implementations, the sensor 138 maybe bent, glued, or bonded so as to be affixed within sensor carrier 402.

FIG. 40 shows an implementation of sensor carrier 402 in which substrate 404 is a molded interconnect device. In the example of FIG. 40, substrate 404 is formed from molded thermoplastic or thermoset (e.g., acrylonitrile butadiene styrene, a liquid crystal polymer, a polyimide/polyphthalamide plastic, or other thermoplastic or thermoset polymer materials) that includes conductive traces 3702. Conductive traces 3702 may be formed on a surface of substrate 404 and/or may pass into and/or through portions of substrate 404 to form suitable connections. Conductive traces may be formed on the molded substrate using a variety of techniques (e.g. selective plating via laser etching, combining platable and non platable substrate polymers, or other suitable methods). In other embodiments, a conductive material (e.g. conductive polymer, metal stamping, plated polymer, metallic structure) may be overmolded with a non-conductive material.

To create suitable electrical connections as shown in FIG. 40, conductive traces 3702 are electrically coupled between contacts (e.g. contact region 1000 and 1002 on sensor 138)

and external contacts (e.g. contacts 410 and 412). Although contacts (e.g. 410 and 412) are formed on the same surface of substrate 404 to which sensor 138 is attached in the example of FIG. 37, this is merely illustrative. It should be appreciated that contacts (e.g. contacts 410 and 412) may be formed on an opposing surface or on an edge or sidewall of substrate 404 and coupled to contacts (e.g. contacts 408 and 406) by conductive materials (e.g. conductive layers, structures, adhesive, clips, solder, or interconnects) within or on substrate 404. For example, contacts (e.g. contacts 410 and 412) may form a designated area to interface electrical coupling on a different surface or region of substrate 404 on which sensor 138 is attached. The designated area may form a channel, groove, recess, slot, or similar alignment feature for orienting the sensor.

Molded thermoplastic substrate 404 may be an injection-molded substrate having features that facilitate various aspects of testing, calibration, and wearable device installation for sensor 138. For example, molded thermoplastic substrate 404 may include datum features or other locating features or positioning features such as a recess 3700 having a shape that is complementary to the shape of the proximal end of sensor 138. For example, recess 3700 may include three or more stepped regions that correspond to the steps between the different layers of the coaxial analyte sensor such as shown in FIG. 3D. In other configurations, molded thermoplastic substrate 404 may include a flat-walled recess as in the example of FIG. 18, a wall that forms a corner as in the example of FIG. 19, or a rounded recess as in the example of FIG. 20. In yet other configurations, molded thermoplastic substrate 404 may include raised features or protrusions on the surface that position and align sensor 138. For example, a raised channel having a shape corresponding to the shape of sensor 138 may be provided on the surface of molded thermoplastic substrate 404. As another example one more posts may extend from the surface of molded thermoplastic substrate 404. For example, one or more lines of protrusions can be formed on the surface of molded thermoplastic substrate 404 against which and/or between which sensor 138 can be positioned and aligned. In this way, various configurations can be provided for a molded thermoplastic substrate 404 including datum features that orient sensor 138 in a preferred direction at a preferred position.

Molded thermoplastic substrate 404 may also include other shaped features such as finger holds 3720 on opposing sides the substrate that facilitate grasping, holding, and transporting of sensor 138. Molded thermoplastic substrate 404 may also include other shaped features such as anchoring features corresponding to the shape of connectors for manufacturing equipment 5091, testing equipment 5004, and calibration equipment 5004 such as grasping connector features 5093/5095 of manufacturing equipment 5091 and/or recess connectors 5006 and 5014 of testing equipment 5002 and calibration equipment 5004. Anchoring features formed on molded thermoplastic substrate 404 and/or by molded thermoplastic substrate 404 itself may include one or more protrusions such as posts, snap-fit features, arms such as arms 202 (see, e.g., FIGS. 11-14), recesses, notches, hooks, and/or tapered portions similar to the tapered portions shown in FIG. 28 (as examples). In some examples, a portion of molded thermoplastic substrate 404 or the entire molded thermoplastic substrate 404 may have a shape that corresponds to the shape of a mounting receptacle on or within one or more of manufacturing equipment 5091, testing equipment 5002, calibration equipment 5004, carriers, and/or a wearable device.

Although substrate 404 is shown in FIG. 40 as being substantially rectilinear, a molded thermoplastic substrate 404 can be provided with features 3720 and/or an overall shape such as a handle shape for inserting, pulling, or otherwise manipulating sensor 138 during manufacturing and assembly operations. For example, molded thermoplastic substrate 404 may include a main portion configured to mechanically and electrically interface with manufacturing equipment 5091, testing equipment 5002, calibration equipment 5004, and/or a wearable device, and a gripping portion that extends from the main portion. The gripping portion may extend from the manufacturing equipment 5091, testing equipment 5002, or calibration equipment 5004 during manufacturing operations to facilitate removal of sensor carrier 402 and sensor 138 from the equipment after or between the manufacturing operations. The gripping portion may be integrally formed with the main portion or may be a separate component that extends from the surface of, or from within, molded thermoplastic substrate 404. The gripping component may be a post, a stock, a shaft, or an arched handle shaped for gripping by a gripping tool or by hand (e.g., by a technician).

As shown in FIG. 40, sensor 138 may be placed in recess 3700 and secured to substrate 404 using adhesive 3704 (e.g., a conductive adhesive as described herein). Adhesive 3704 may be applied to couple contact 1000 of sensor 138 to a first conductive trace 3702 on substrate 404 to form contact 408 between sensor 138 and sensor carrier 402. Adhesive 3704 may be also applied to couple contact 1002 of sensor 138 to a second conductive trace 3702 on substrate 404 to form contact 406 between sensor 138 and sensor carrier 402. In this way, molded thermoplastic substrate 404 can provide a handle and/or a strain relief member for moving and/or otherwise handling sensor 138.

FIG. 41 shows a top view of sensor carrier 402 of FIG. 40. As shown in FIGS. 40 and 41, the first conductive trace 3702 may extend from a contact portion with contact 1000 within recess 3700 to form one or more exposed portions on the surface of substrate 404 that form external contact 412 for coupling to testing station 5002, calibration station 5004, and/or electronics unit 500. The second conductive trace 3702 may extend from a contact portion with contact 1002 within recess 3700 to form one or more exposed portions on the surface of substrate 404 that form external contact 410 for coupling to testing station 5002, calibration station 5004, and/or electronics unit 500.

FIG. 42 shows a specific implementation of sensor carrier 402 as illustrated in FIGS. 40 and 41. In this implementation of sensor carrier 402, sensor 138 is attached to substrate 404 with a conductive coupler 3900, such as, for example, clips, conductive adhesive, conductive polymer, metallic foil, conductive foam, conductive fabric, wire wrapping, wire threading or via any suitable methods. As shown in FIG. 43, a substrate 4000 may have an elongated dimension along which parallel conductive strips 4001 and 4002 are formed. Multiple sensor 138 may be attached to substrate 4000 and extend beyond an edge of the substrate in a direction perpendicular to the elongated dimension of the substrate. Singulation features such as scoring 4020 may be provided that facilitate singulation of substrate 4000 into individual sensor carrier substrates 404 for each sensor and/or that electrically isolate portions of conductive strips 4001 and 4002 for each sensor. Each sensor may be attached to substrate 4000 using, for example clips 3900 or any other methods including, via the use of conductive adhesive, conductive polymer, metallic foil, conductive foam, conductive fabric, wire wrapping, wire threading or any other suitable methods. An identifier 450 for each sensor may be provided on a corresponding portion of substrate 4000.

Sensors 138 may each have a pair of sensor electrical contacts (e.g., contacts 1000 and 1002) coupled to a corresponding pair of electrical contacts formed from strips 4001 and 4002 on the substrate. Openings in substrate 4000 and/or vias that extend through substrate 4000 may provide exposed portions of strips 4001 and 4002 that form a plurality of pairs of electrical contacts for coupling each sensor 138 to testing station 5002, calibration station 5004, and/or electronics unit 500 (e.g., an electronics unit of a wearable device). Each of the plurality of pairs of electrical contacts is coupled to an associated pair of portions of strips 4001 and 4002 via the substrate.

FIGS. 44-46 show various contact configurations on sensor carriers that can be singulated from a sensor carrier strip of the type shown in FIG. 43. In the example of FIG. 44, a z-shaped contact configuration on substrate 4000 has been singulated to form a pre-connected sensor on a smaller portion of the substrate, referred to as substrate 404. In this instance, the z-shaped contact configuration may allow for greater distance between connectors (e.g., larger pitch connection) on testing, manufacturing, or calibration equipment, though a z-shaped substrate is not necessary to generate the greater distance and other substrate shapes can be used. In the example of FIG. 45, a square portion of substrate 4000 has been singulated to form a pre-connected sensor on the substrate 404. In the example of FIG. 46 a square portion of substrate 4000 has been singulated to form a pre-connected sensor and an opening 4300 (e.g., an air gap) is provided in the singulated substrate 404 to improve electrical isolation between singulated contact strip portions 4001 and 4002.

As shown in FIG. 47A, in some implementations, an elongate substrate 4000 that forms a sensor carrier for multiple sensor 138 can be provided with a feed-guide strip 4402 that runs along an elongated edge of the elongate substrate. Feed-guide strip 4402 may include locating features 4404 that can be accessed and manipulated to move and register a strip of pre-connected sensors through one or more manufacturing stations.

In the implementation of FIG. 47A, sensors 138 can be attached to substrate 4000 in bulk and singulated on substrate 404 after manufacturing or testing operations. As shown in FIG. 47B, a strip of pre-connected sensors as shown in FIG. 47A can be provided on a reel 4410 for bulk storage and/or transportation and optionally automatically pulled from the reel using feed-guide strip 4402 to be moved through one or more testing stations and/or one or more calibration stations. FIG. 48 shows a pre-connected sensor having a sensor carrier that has been singulated from substrate 4000 and separated from a singulated portion 4402 of feed-guide strip 4402. Alternatively, feed-guide strip 4402 can be separated as a strip prior to singulation of individual pre-connected sensors. In other embodiments, the feed guide is integrated into the final product configuration and not removed from the sensor carrier during or after singulation.

FIG. 49 shows an implementation of sensor carrier 402 in which a plurality of sets of contacts 406 and 408 are formed from receptacles 4600 having a slot for receiving a corresponding plurality of sensors 138. In some implementations, the receptacles 4600 may be an elongated member comprising a resilient or flexible material. The receptacles 4600 may have slots that optionally pierce through an insulation layer or deform a portion of the outer layer so as to make contact with the sensors 138.

FIG. 50 shows an implementation of a sensor carrier for multiple sensors 138 having recesses 4700 that form datum features to hold each sensor in an accurate alignment and position. Complementary magnetic features may be provided on sensor 138 and substrate 404 to hold each sensor in an accurate alignment and position and thereby facilitate accurate sensor processing.

FIG. 51A shows an implementation of an elongate substrate 4800 formed using printed circuit board technology from either a rigid, flexible, or a combination rigid/flexible substrate, from which multiple sensor carriers 402 can be singulated. Flexible portion of the substrate may be manufactured from a material such as polyimide, PEEK, polyester or any suitable type. Rigid portion of the substrate may be manufactured from a material such as FR4, FR5, FR6, insulated metal substrate (IMS), PTFE, or any suitable type. As shown in FIG. 51A, each sensor carrier may include a sensor connection portion 4804 and an interface or processing portion 4802. In some implementations, each sensor carrier may include a sensor connection portion 4804 that extends from a rigid or flexible portion and an interface or processing portion 4802 that extends from a rigid or flexible portion. In these implementations, one or more contacts, such as contacts 406 and 408 can be formed on the sensor connection portion 4804 of each sensor carrier 402. Sensor connection portions 4804 of substrate 4800 may contain anchoring or datum features of sensor carriers 402.

FIG. 51B shows another implementation of an elongate substrate 4800 as shown in FIG. 51A with an optional electrical connection interface 4850 for connecting to a work station, such as a testing station, a calibration station, an assembly station, a coating station, or other manufacturing stations. The optional electrical connection interface 4850 may be coupled to one or more sensor carriers 402 through electrical traces configured on one or more layers of the circuit board. As shown in FIG. 51B, a plurality of sensor carriers 402 are assembled in a panel, and each of the sensor carrier 402 may include a sensor connection portion 4804 that extends from a flexible or rigid portion and an interface or processing portion 4802 that extends from a flexible or rigid portion. In these implementations, one or more contacts, such as contacts 406 and 408 can be formed on the sensor connection portion 4804 of each sensor carrier 402. Sensor connection portions 4804 of substrate 4800 may contain anchoring or datum features of sensor carriers 402. In some implementations, the elongate substrate 4800 shown in FIG. 51B may be configured to allow the sensor 138 to extend beyond the edge of the substrate. This may be accomplished by removing a portion of the elongated substrate 4860 for further processing. In some embodiments a perforation (e.g. V-score, mouse bites, or other suitable type) is included in elongated substrate 4800 for enabling the removal of the bottom portion of the panel 4860 for dipping or calibration. In this implementation, the elongated substrate 4800 can be configured for dipping or calibration, as described in FIG. 52B.

Now referring to FIG. 52A, an implementation of a sensor carrier 402 is shown with one or more sensor contacts (e.g. contacts 406 and 408) on sensor connection portion 4804 and one or more one or more interface contacts (e.g. contacts 410 and 412) on an interface or processing portion 4802. One or more interface contacts (e.g., 410 and 412) may be formed on sensor carrier 402 for coupling to testing station 5002, calibration station 5004, and/or electronics unit 500. In this configuration, testing and/or calibration operations can be performed by coupling portion 4802 to the testing and/or calibration equipment.

FIG. 52B shows an example panel implementation of a plurality of sensor carriers 402 with electrical connection interface 4850 for interfacing with electronics of a work station, such as a testing station, a calibration station, an assembly station, a coating station, or other manufacturing stations. The illustration of FIG. 52B shows the elongate substrate 4800 of FIG. 48B after the bottom panel portion 4860 has been removed (from the illustration of FIG. 51B) and with sensor 138 attached via one or more sensor contacts (e.g. contacts 406 and 408). In some implementations, the sensors can be permanently connected (e.g. conductive adhesive, conductive polymer, conductive ink, solder, welding, brazing, or other suitable methods) to the sensor carriers 402 and both components can be calibrated together or separately. In other implementations, the sensors can be releasably attached (e.g. via clips, metallic foil, conductive foam, conductive fabric, wire wrapping, wire threading or any other suitable methods).

Following testing and/or calibration operations, flexible portion 4802 may be folded around, folded over, wrapped around, wrapped over, or manipulated to envelope portion 4804 for installation into on-skin sensor assembly 600. In the example of FIG. 53A, portion 4802 may form a stand-alone processing circuit for sensor 138 (e.g., an implementation of sensor electronics 112. In other implementations, portion 4802 may be coupled directly to signal processing circuit for assembly 600, to a system in package (SIP) implementation of the sensor electronics or a main printed circuit board for the sensor electronics. In the example of FIG. 53B, the flexible portion 4804 is folded to envelope portion 4802 for installation into on-skin sensor assembly 600 so as to have sensor 138 positionally secured to extend (e.g. through opening 4808) for insertion for in vivo operations.

FIG. 54 shows an implementation in which sensor carrier 402 is manufactured using printed circuit board technology as a daughter board for a main printed circuit board 5100 for the sensor electronics. As shown in FIG. 54, one or more contacts such as contacts 5104 (e.g., solder contacts) may be formed between sensor carrier 402 and main PCB 5100 to form sensor electronics unit for sensor 138 in on-skin sensor assembly 600. Conductive traces 5102 may couple contacts 5104 to sensor 138 via a conductive attachment mechanism 5103 (e.g., solder, conductive adhesive, a conductive tape, or other conductive attachment as discussed herein).

FIG. 55 shows an implementation of sensor carrier 402 in which a pinch clip 5200 is provided to close the arms 5204 of a crimp connector 5202 to secure sensor 138 to substrate 404. Connector 5204 may be formed form a conductive material that forms one of contacts 410 and 412. As shown in FIG. 55, pinch clip 5200 includes clasping arms 5208 with ramped surfaces that push the arms outward as pinch clip 5200 is move toward substrate 404 in direction 5206 and snap back to secure pinch clip 5200 to substrate 404. In other implementations, pinch clip 5200 may be provided without clasping arms 5208 so that pinch clip 5200 is removable after arms 5204 are pinched closed so that pinch clip 5200 does not form a part of the sensor carrier. As shown in FIG. 55, one or more electrode breakouts 5220 may be provided to form, for example, one or more of contacts 410 and 412 on substrate 404. Although breakout 5220 is formed on a surface of substrate 404 that is opposed to the surface to which sensor 138 is attached in the example of FIG. 55, this is merely illustrative. It should be appreciated that breakouts for contacts such as contacts 410 and 412 may be formed on the opposing surface, on the same surface as sensor 138, or on an edge or sidewall of substrate 404 and coupled to contacts 408 and 406 by conductive vias or other conductive layers, structures, or interconnects within or on substrate 404. In some implementations, a pinch clip 5200 may be used to apply bias force against sensor 138 in combination with crimp connector 5202 or directly against substrate without crimp connector 5202. Pinch clip 5202 may apply force radially, axially, or in a suitable direction to provide a biasing force on sensor 138 and conductive pathway.

FIG. 56 shows an implementation of sensor carrier 402 in which contacts 406 and 408 are formed from foldable conductive clips 5300. Sensor 138 may be inserted through openings 5302 in each clip 5300 and mechanically secured to substrate 404 and conductively coupled to clips 5300 by a folding a portion 5304 of each of clips 5300 over onto sensor 138.

Portions 5304 of clips 5300 may also form contacts 410 and 412 for coupling to external equipment such as a manufacturing station (e.g., a testing station, a calibration station, an assembly station, a coating station, or other manufacturing stations). However, this is merely illustrative. In other implementations, one or more electrode breakouts that are conductively coupled to clips 5300 may be provided to form, for example, one or more of contacts 410 and 412 on substrate 404. Such breakouts may be formed on a surface of substrate 404 that is opposed to the surface to which sensor 138 is attached, on the same surface as sensor 138, or on an edge or sidewall of substrate 404 and coupled to clips 5300 by conductive vias or other conductive layers, structures, or interconnects within or on substrate 404.

Clips 5300 also form datum features for positioning and aligning sensor 138 relative to substrate 404. Substrate 404 may be sized and shaped (or may include structural features) that form anchoring features for substrate 404 relative to manufacturing stations and/or a housing of a wearable device. In this way, sensor carrier 402 may be used to easily position and align sensor 138 for both manufacturing and assembly operations (e.g., using the datum features to align the sensor relative to substrate 404 and the anchoring features to align the substrate relative to the manufacturing or wearable equipment).

The conductive components of the sensor carrier 402 in the various embodiments described herein are electrically isolated from each other and the environment when installed in on-skin sensor assembly 600. For example, contacts 406, 408, 410, and 412 may be electrically isolated from each other and the environment, using a non-conductive adhesive such as a one or two-part epoxy, using a polyurethane, using a low pressure overmolding such as a moldable polyamide or a moldable polyolefin, using an injection overmolded thermoplastic or thermoset, using a non-elastomer such as welded clamshell plastic, adhesively bonded clamshell, single or 2-sided cavity potted with sealant, e.g., epoxy, urethane, silicone, etc., or using a factory pre-compressed elastomer such as a constrained two-part cavity that holds an elastomer in a compressed state. The two-part cavity may hold the elastomer in the compressed state by a snap fit, a bonding such as an ultrasonic weld, a laser weld, a solvent bond, or a heat stake, or a mechanical fastener such as a screw, rivet, clip, or other fastener.

Illustrative operations that may be performed for manufacturing and using a pre-connected analyte sensor are shown in FIG. 57.

At block 5400, an analyte sensor such as analyte sensor 138 may be provided. As described herein the analyte sensor 138 may have an elongated body (e.g., an elongated conductive body with an elongated conductive core), and a working electrode on the elongated body (e.g., at a distal end of the elongated body). The analyte sensor may also include one or more electrical contacts at a proximal end or elsewhere along the elongated body and coupled, respectively, to the working electrode and/or the reference electrode.

At block 5402, a sensor carrier such as one of the implementations of sensor carrier 402 described herein may be attached, for example, to the proximal end of the elongated body. Attaching the sensor carrier includes coupling one or more contacts (e.g., on a substrate) of the sensor carrier to one or more corresponding electrical contacts on the elongated body.

At block 5403, a work station such as a manufacturing station is provided. As described herein, a manufacturing station can be configured to perform one or more dip coating processes to form the membrane 108 described above on the working electrode.

At block 5404, the analyte sensor may be coupled to at least one testing station (e.g., testing station 5002) by coupling the sensor carrier to circuitry of the at least one test station. Coupling the sensor carrier to the circuitry of the at least one test station may include mechanically coupling one or more anchoring features such as a substrate of the sensor carrier to a mating interface of the test station such that one or more external contacts on the substrate are coupled to one or more corresponding contacts at the test station. An identifier for the sensor on the sensor carrier may be read by the testing station. Test data obtained by the test station may be stored and/or transmitted, in association with the identifier, by the test station.

At block 5406, the analyte sensor may be coupled to at least one calibration station (e.g., calibration station 5004) by coupling the sensor carrier to circuitry of the at least one calibration station. Coupling the sensor carrier to the circuitry of the at least one calibration station may include mechanically coupling the one or more anchoring features such as the substrate of the sensor carrier to a mating interface of the calibration station such that one or more external contacts on the substrate is coupled to one or more corresponding contacts at the calibration station. An identifier for the sensor on the sensor carrier may be read by the calibration station. Calibration data obtained by the calibration station may be stored and/or transmitted, in association with the identifier, by the calibration station. Calibration data may be stored on the sensor carrier or transmitted for later use by an on-skin sensor assembly 600 during in vivo use of sensor 138.

Sensor carrier 402 may be coupled to one or more additional manufacturing stations as desired. The additional manufacturing stations may include potentiostat measurement stations, sensor straightening stations, membrane dipping stations, curing stations, analyte sensitivity measurement stations, and/or inspection stations.

At block 5408, the sensor carrier may be coupled to sensor electronics (e.g., sensor electronics 112 of electronics unit 500) of a wearable device such as on-skin sensor assembly 600. Coupling the sensor carrier to the sensor electronics may include coupling the one or more external contacts on the sensor carrier to corresponding contacts of the sensor electronics. In some embodiments, coupling the sensor carrier to the sensor electronics may include securing the sensor carrier between a base such as base 128 and electronics unit 500 as described herein. A reader in the on-skin sensor assembly 600 may obtain an identifier of the sensor from the sensor carrier. Calibration data for the sensor may be obtained based on the identifier.

At block 5410, in vivo signals from the working electrode (e.g., and a reference electrode) may be obtained and processed with the sensor electronics. The in vivo signals from the working electrode (e.g., and a reference electrode) may be received by the sensor electronics from the sensor through the circuitry of the sensor carrier.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims. For example, the operations described above in connection with blocks 5404 and 5406 may be reversed and/or may be performed in parallel.

In some scenarios, it may be desirable to couple sensor 138 to one or more contacts on a substrate in a preferred position and orientation. FIG. 58 shows an exemplary apparatus 5531 in which sensor 138 is oriented to substrate 5530 using an elastomeric tube. As shown in FIG. 58, apparatus 5531 may include a substrate 5530 having one or more conductive contacts such as contacts 5532 and 5534 (e.g., exposed copper pads on a printed circuit substrate), and an elastomeric tube 5500. Elastomeric tube 5500 may be formed from a non-conductive elastomer.

As shown, elastomeric tube 5500 may be formed with a "D", "0", oval, pyramidal, or hemispherical shaped cross-section having an elongated cutout 5503 in the bottom portion of the elastomeric tube 5500 within which sensor 138 is disposed. In this way, sidewalls of the elongated cutout of elastomeric tube 5500 can align sensor 138 relative to substrate 5530.

Bottom portions 5502 on either side of cutout 5503 may be attached to substrate 5530. The bottom portions 5502 may be attached to substrate using adhesive 5504 such as a pressure-sensitive adhesive. The elongated opening 5501 and cutout 5503 in the elastomeric tube 5500 provides sufficient space that, in order to assemble the apparatus, tube 5500 can be placed over sensor 138 while sensor 138 is in place on substrate 5530.

FIG. 59 shows an exploded perspective view of the apparatus of FIG. 55 in which contacts 5532 and 5534 can be seen on substrate 5530. Sensor 138 may be positioned over one or more contacts such as contacts 5532 and 5534.

Sensor 138 may be loosely held within opening 5501 of tube 5500 during initial placement of the tube over the sensor, and then be fixed to the substrate 5530 by the tube when the tube is compressed (e.g., by an upper housing of a wearable device). In this way, sensor 138 may be communicatively coupled and mechanically fixed to a substrate without soldering or other bonding operations.

During manufacturing operations and/or during in-vivo use of sensor 138, sensor 138 may be held in place on substrate 404 by external compression of tube 5500. FIG. 60 shows an example in which sensor 138 is held in place by compression of tube 5500 by a housing structure. For example, housing 5700 (e.g., a housing of a wearable device or a lid or clip for a manufacturing station) may include a protruding member 5702 that, in an assembled configuration, compresses tube 5500 to secure sensor 138.

As noted above in connection with, for example, FIGS. 35B, 43, 47A, 47B, 50, and 51, during manufacturing operations, multiple sensors 138 may be carried by a common sensor carrier. However, in some scenarios, a common carrier such as an intelligent carrier may be provided for manufacturing operations for multiple pre-connected sensors. FIG. 61 shows an example of a carrier for multiple pre-connected sensors. As shown in FIG. 58, a carrier 5800 may include a housing 5802 with interfaces 5804 for multiple pre-connected sensors. Housing 5802 may be a substantially solid substrate or may be a housing that forms an interior cavity within which other components are mounted and/or connected.

Each interface 5804 may be configured to receive a sensor carrier 402 in any of the implementations described herein. For example, each interface 5804 may include one or more features that interface with one or more corresponding anchoring features of a sensor carrier as described herein in accordance with various implementations. Carrier 5800 may include circuitry 5806 (e.g., one or more processors and/or memory) configured to communicate with sensors 138 and/or external computing equipment. Circuitry 5806 may include communications circuitry such as one or more antennas for transmitting and/or receiving data from external equipment. Housing 5802 may include one or more structures 5810 (e.g., clips, clasps, protrusions, recesses, notches, posts, or the like) for mechanically coupling carrier 5800 to manufacturing equipment. One or more conductive contacts 5808 may be provided on housing 5802 that communicatively couple manufacturing equipment to sensors 138 through the carrier.

As shown, each interface 5804 may be associated with a particular identification number (represented, as an example, in FIG. 58 as $I_1$, $I_2$ . . . $I_{N-1}$, and $I_N$). Circuitry 5806 may electronically identify sensors mounted in interfaces 5804 of carrier 5800 with the identification number associated with that interface. However, this is merely illustrative. In other implementations, sensors 138 may be uniquely identified by circuitry 5806 using a reader in each of interfaces 5804 that reads an identifier such as identifier 450 on the sensor carrier. Testing and/or calibration data may be gathered by processing circuitry 5806 and stored and/or transmitted along with an identifier for each sensor.

During manufacturing, one or more pre-connected sensors may be loaded carrier 5800. Carrier 5800 may secure the pre-connected sensors therein and perform potentiostat measurements for each sensor (e.g., using circuitry 5806). Sensors 138 may be secured to interfaces 5804 by individual mounting features or carrier 5800 may be provided with a locking mechanism such as a slidable bar 5812. Slidable bar 5812 may be slidable (e.g., by a handle 5814) between an open position as shown, in which sensor carriers can be inserted into and removed from interfaces 5804, to a closed position in which bar 5812 blocks removal of the sensor carriers from the interfaces.

In some scenarios, an initial measurement test may be performed by carrier 5800 to test the potentiostat connection through the sensor interconnect electrodes and the sensor surfaces. Manufacturing operations that may be performed for sensors 138 coupled to carrier 5800 may include physical manipulation of the sensor such as straightening of the sensors. Carrier 5800 may facilitate more efficient manufacturing by allowing multiple sensors to be straightened in a single operation using automated straightening equipment.

Carrier 5800 may facilitate potentiostat and/or other measurements at various stages of manufacturing for sensors 138. Potentiostat measurements may be performed before, during, and/or after straightening operations and information regarding sensor damage or any other mechanical stress that might be introduced by the straightening may be saved and/or transmitted along with associated sensor ID's.

Manufacturing operations that may be performed for sensors 138 coupled to carrier 5800 may also include a membrane process in which dipping operations are performed to form a membrane such as membrane 508 for each sensor. Straightened sensors 138 mounted in carrier 5800 may be concurrently dipped. Potentiostat measurements may be performed before, during, and/or after membrane operations and information associated with the electrochemistry of the sensors and dipping process may be gathered, processed, stored, and/or transmitted by carrier 5800.

Manufacturing operations that may be performed for sensors 138 coupled to carrier 5800 may also include a curing process. Performing curing for groups of sensors 138 mounted in carrier 5800 may allow the curing process to take less space, which can reduce the footprint of the manufacturing area used by curing equipment. Potentiostat measurements may be performed before, during, and/or after curing operations and information associated with the electrochemistry of the sensors and curing process may be gathered, processed, stored, and/or transmitted by carrier 5800.

Manufacturing operations that may be performed for sensors 138 coupled to carrier 5800 may also include calibration operations. Because carrier 5800 can perform connection testing early in the manufacturing process, improved analyte/electrochemical calibration can be performed by carrier 5800 itself and/or in cooperation with external manufacturing equipment. Calibration data may be gathered, processed, stored, and/or transmitted by carrier 5800.

Gathering calibration and/or testing data with carrier 5800 can save time in connecting and disconnecting additional external equipment. Gathering calibration and/or testing data with carrier 5800, particularly when data is gathered and stored automatically in connection with sensor ID's, can also reduce calibration/testing errors because the data is gathered by the same equipment throughout various processes.

Manufacturing operations that may be performed for sensors 138 coupled to carrier 5800 may also include analyte concentration measurements. For example, carrier 5800 may be moved by manufacturing equipment (e.g., a robotic arm) to expose the sensors 138 mounted in the carrier through various analyte baths (e.g., glucose baths). Carrier 5800 may gather electrical potential measurements during the various bath exposures. Information associated with the electrical potential measurements during the various bath exposures may be gathered, processed, stored, and/or transmitted by carrier 5800.

Manufacturing operations that may be performed for sensors 138 coupled to carrier 5800 may also include analyte sensitivity measurements. Sensitivity measurements that may be performed by carrier 5800 may include baseline measurements that indicate the signal from each sensor without analyte exposure, slope measurements that indicate the signal change for a given amount of an analyte, and/or noise measurements. These sensitivity measurements may be stored, and/or transmitted by carrier 5800.

Manufacturing operations that may be performed for sensors 138 coupled to carrier 5800 may also include visual inspection operations (e.g., by a technician). Providing a group of pre-connected sensors, mounted in carrier 5800, that have already been through all of the testing/calibration/manufacturing operations described above may allow a more efficient and/or more automated visual inspection and rejection (e.g., because the exact physical location of each sensor within carrier 5800 is known). Sensors 138 that have exhibited unusual electrochemistry or mechanical stress during manufacturing operations can be flagged by carrier 5800 (e.g., using a display, a visual indicator, or transmission of flag information to an external device) for retesting or rejection.

The connections between the elements shown in some figures illustrate exemplary communication paths. Additional communication paths, either direct or via an intermediary, may be included to further facilitate the exchange of information between the elements. The communication paths may be bi-directional communication paths allowing the elements to exchange information.

Various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIG. 2) may be implemented or performed with a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, various functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, WiFi, Bluetooth®, RFID, NFC, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,"desired," or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

Various system and methods described may be fully implemented and/or controlled in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where factory calibration schemes are contemplated, the plural inputs may allow plural users to input relevant data at the same time.

What is claimed is:

1. A system for measuring an analyte concentration in a host, the system comprising:

a transcutaneous analyte sensor;

a bottom housing;

a top housing;

sensor electronics configured to operatively connect to the transcutaneous analyte sensor, wherein the sensor electronics includes a substrate, wherein the sensor electronics are configured to be disposed between the bottom housing and the top housing;

wherein the bottom housing includes a floor and a plurality of locating pins, the plurality of locating pins extending from the floor;

wherein the plurality of locating pins are configured to extend into a plurality of holes in the substrate of the sensor electronics; and a conductive member configured to establish electrical connection between the sensor and the sensor electronics.

2. The system of claim 1, wherein the conductive member is a conductive foam.

3. The system of claim 1, wherein the conductive member is a conductive polymer.

4. The system of claim 3, wherein the conductive member is a conductive elastomer.

5. The system of claim 1, wherein the conductive member is a conductive fabric.

6. The system of claim 1, wherein the conductive member is a conductive wire.

7. The system of claim 1, wherein the conductive member is a metallic foil.

8. The system of claim 1, wherein the conductive member is a conductive strip.

9. The system of claim 1, wherein the plurality of locating pins consists of two locating pins.

10. The system of claim 1, wherein the plurality of locating pins consists of three locating pins.

11. The system of claim 1, wherein the plurality of locating pins are formed as an integral part of the floor.

12. The system of claim 1, wherein the sensor is pre-connected to the sensor electronics within the bottom housing and the top housing.

13. The system of claim 1, wherein the top housing and the bottom housing are assembled together to form a housing, the housing having an internal cavity.

14. The system of claim 13, wherein the top housing and the bottom housing are sealed together to prevent moisture ingress to the internal cavity.

15. The system of claim 14, wherein the sealing includes an encapsulating material.

\* \* \* \* \*